US010357036B2

(12) United States Patent
Harschneck et al.

(10) Patent No.: US 10,357,036 B2
(45) Date of Patent: Jul. 23, 2019

(54) COMPOUNDS FOR CONTROLLING ARTHROPODS

(71) Applicant: Bayer CropScience Aktiengesellschaft, Monheim am Rhein (DE)

(72) Inventors: Tobias Harschneck, Düsseldorf (DE); Michael Maue, Langenfeld (DE); Werner Hallenbach, Monheim (DE); Alexander Arlt, Köln (DE); Robert Velten, Langenfeld (DE); Reiner Fischer, Monheim (DE); Hans-Georg Schwarz, Dorsten (DE); Ulrich Görgens, Ratingen (DE); Kerstin Ilg, Köln (DE); Klaus Raming, Leverkusen (DE); Sebastian Horstmann, Leverkusen (DE); Daniela Portz, Vettweiß (DE); Johannes Köbberling, Neuss (DE); Andreas Turberg, Haan (DE); Hansjörg Dietrich, Liederbach am Taunus (DE)

(73) Assignee: Bayer CropScience Aktiengesellschaft, Monheim am Rhein (DE)

( * ) Notice: Subject to any disclaimer, the term of this patent is extended or adjusted under 35 U.S.C. 154(b) by 0 days.

(21) Appl. No.: 15/751,515

(22) PCT Filed: Aug. 11, 2016

(86) PCT No.: PCT/EP2016/069110
§ 371 (c)(1),
(2) Date: Feb. 9, 2018

(87) PCT Pub. No.: WO2017/025590
PCT Pub. Date: Feb. 16, 2017

(65) Prior Publication Data
US 2018/0289007 A1   Oct. 11, 2018

(30) Foreign Application Priority Data

Aug. 13, 2015 (EP) ..................................... 15180925

(51) Int. Cl.
*A01N 43/50* (2006.01)
*A01N 43/56* (2006.01)
*A01N 43/647* (2006.01)
*C07D 231/10* (2006.01)
*C07D 231/12* (2006.01)
*C07D 249/06* (2006.01)
*C07D 401/04* (2006.01)
*C07D 401/12* (2006.01)

(52) U.S. Cl.
CPC ............. *A01N 43/56* (2013.01); *A01N 43/50* (2013.01); *A01N 43/647* (2013.01); *C07D 231/10* (2013.01); *C07D 231/12* (2013.01); *C07D 249/06* (2013.01); *C07D 401/04* (2013.01); *C07D 401/12* (2013.01)

(58) Field of Classification Search
CPC ................ C07D 231/12; C07D 401/04; C07D 231/10; C07D 249/06; C07D 401/12; A01N 43/50; A01N 43/56; A01N 43/647
See application file for complete search history.

(56) References Cited

U.S. PATENT DOCUMENTS

2010/0120714 A1* 5/2010 Finkelstein ............ A01N 47/10
514/63

FOREIGN PATENT DOCUMENTS

| WO | 2000/07980 | A1 | 2/2000 |
| WO | 2010/051926 | A2 | 5/2010 |
| WO | 2011/113756 | A1 | 9/2011 |
| WO | 2012/069366 | A1 | 5/2012 |
| WO | 2012/080376 | A1 | 6/2012 |
| WO | 2012/107434 | A1 | 8/2012 |
| WO | 2012/175474 | A1 | 12/2012 |
| WO | 2015/067646 | A1 | 5/2015 |

OTHER PUBLICATIONS

International Search Report in corresponding application No. PCT/EP2016/069110 dated Nov. 7, 2016.

* cited by examiner

*Primary Examiner* — John Pak
(74) *Attorney, Agent, or Firm* — McBee Moore Woodard & Vanik IP, LLC

(57) ABSTRACT

The invention relates inter alia to compounds of the general formula (I). Also described are methods for preparing the compounds of the formula (I). The compounds according to the invention are especially suitable for controlling insects, arachnids and nematodes in agriculture, and ectoparasites in veterinary medicine and also as herbicides.

19 Claims, No Drawings

COMPOUNDS FOR CONTROLLING ARTHROPODS

CROSS REFERENCE TO RELATED APPLICATIONS

This application is a National Stage entry of International Application No. PCT/EP2016/069110 filed 11 Aug. 2016, which claims priority to European Patent Application No. 15180925.8, filed 13 Aug. 2015.

BACKGROUND

Field

The present application relates to novel compounds, to methods for preparation thereof and to use thereof for controlling animal pests, in particular arthropods and especially insects, arachnids and nematodes.

Description of Related Art

It is known that particular halogen-substituted compounds have insecticidal activity (EP 1 911 751, WO2012/069366, WO2012/080376, WO2012/107434 and WO2012/175474).

WO 2011/113756 discloses triazole derivatives having insecticidal activity.

In addition, it is known that certain halogen-substituted compounds have cytokine-inhibitory activities (WO 2000/07980).

Modern crop protection compositions have to meet many demands, for example in relation to the level, duration and spectrum of their action and possible use. Questions of toxicity and of combinability with other active ingredients or formulation auxiliaries play a role, as does the question of the cost and complexity involved in the synthesis of an active ingredient. In addition, resistances can occur. For all these reasons, the search for novel crop protection agents can never be considered to be complete, and there is a constant need for novel compounds having properties improved over the known compounds at least in relation to individual aspects.

SUMMARY

It was an object of the present invention to provide compounds which broaden the spectrum of the pesticides in various aspects and/or improve their activity.

It has now been found that, surprisingly, particular halogen-substituted compounds and salts thereof have biological properties and are especially suitable for controlling animal pests, and therefore have particularly good usability in the agrochemical sector and in the animal health sector.

Similar compounds have already become known from WO 2010/051926.

One aspect of the present invention relates to compounds of the general formula (I)

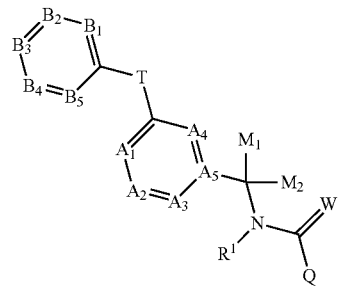

in which
R$^1$ is H, in each case optionally substituted C$_1$-C$_6$-alkyl, C$_2$-C$_6$-alkenyl, C$_2$-C$_6$-alkynyl, C$_3$-C$_7$-cycloalkyl, C$_1$-C$_6$-alkylcarbonyl, C$_1$-C$_6$-alkoxycarbonyl, aryl(C$_1$-C$_3$)-alkyl, heteroaryl(C$_1$-C$_3$)-alkyl, or
R$^1$ is H in each case optionally substituted C$_1$-C$_6$-alkyl, C$_2$-C$_6$-alkenyl, C$_2$-C$_6$-alkynyl, C$_3$-C$_7$-cycloalkyl, C$_1$-C$_6$-alkylcarbonyl, C$_1$-C$_6$-alkoxycarbonyl, C$_3$-C$_7$-cycloalkyl (C$_1$-C$_3$)-alkyl, aryl(C$_1$-C$_3$)-alkyl, heteroaryl(C$_1$-C$_3$)-alkyl,
the moieties are as follows:
A$_1$ is CR$^2$ or N,
A$_2$ is CR$^3$ or N,
A$_3$ is CR$^4$ or N,
A$_4$ is CR$^5$ or N,
A$_5$ is C,
B$_1$ is CR$^6$ or N,
B$_2$ is CR$^7$ or N,
B$_3$ is CR$^8$ or N,
B$_4$ is CR$^9$ or N, and
B$_5$ is CR$^{10}$ or N,
but not more than three of the A$_1$ to A$_4$ moieties are N and not more than three of the B$_1$ to B$_5$ moieties are simultaneously N;
M$_1$, M$_2$ are each independently H, in each case optionally substituted C$_1$-C$_6$-alkyl, C$_2$-C$_6$-alkenyl, C$_2$-C$_6$-alkynyl, C$_3$-C$_7$-cycloalkyl, C$_1$-C$_6$-alkylcarbonyl, C$_1$-C$_6$-alkoxycarbonyl, aryl(C$_1$-C$_3$)-alkyl, heteroaryl(C$_1$-C$_3$)-alkyl, or
M$_1$ and M$_2$ with the carbon atom to which they are attached form an optionally substituted 3-, 4-, 5- or 6-membered ring which optionally contains 0, 1 or 2 nitrogen atoms and/or 0, 1 or 2 oxygen atoms and/or 0, 1 or 2 sulfur atoms, or
M$^1$ or M$^2$ with R$^4$ from A$_3$, the carbon atom of A$_3$ and A$_5$ form a 5- or 6-membered ring optionally substituted by F, Cl, Br, I, C$_1$-C$_3$-alkyl, which may contain 0, 1 or 2 nitrogen atoms and/or 0, 1 or 2 oxygen atoms and/or 0, 1 or 2 sulfur atoms,
R$^2$, R$^3$, R$^4$, R$^5$, R$^6$, R$^7$, R$^9$ and R$^{10}$ are each independently H, halogen, cyano, nitro, in each case optionally substituted C$_1$-C$_6$-alkyl, C$_3$-C$_6$-cycloalkyl, C$_1$-C$_6$-alkoxy, N—C$_1$-C$_6$-alkoxyimino-C$_1$-C$_3$-alkyl, C$_1$-C$_6$-alkylsulfanyl, C$_1$-C$_6$-alkylsulfinyl, C$_1$-C$_6$-alkylsulfonyl, N—C$_1$-C$_6$-alkylamino or N,N-di-C$_1$-C$_6$-alkylamino,
if neither of the A$_2$ and A$_3$ moieties is N, R$^3$ and R$^4$ together with the carbon atom to which they are attached may form a 5- or 6-membered ring containing 0, 1 or 2 nitrogen atoms and/or 0 or 1 oxygen atom and/or 0 or 1 sulfur atom, or
if neither of the A$_1$ and A$_2$ moieties is N, R$^2$ and R$^3$ together with the carbon atom to which they are attached may form a 6-membered ring containing 0, 1 or 2 nitrogen atoms;

$R^8$ is halogen, cyano, nitro, in each case optionally substituted $C_1$-$C_6$-alkyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulfanyl, $C_1$-$C_6$-alkylsulfinyl, $C_1$-$C_6$-alkylsulfonyl, N—$C_1$-$C_6$-alkylamino or N,N-di-$C_1$-$C_6$-alkylamino, or is halogen, cyano, nitro, in each case optionally substituted $C_1$-$C_6$-alkyl, $C_3$-$C_6$-cycloalkyl, $C_3$-$C_6$-cycloalkyl($C_1$-$C_6$)alkyl, $C_1$-$C_6$-alkoxy, N—$C_1$-$C_6$-alkoxyimino-$C_1$-$C_3$-alkyl, $C_1$-$C_6$-alkylsulfanyl, $C_1$-$C_6$-alkylsulfinyl, $C_1$-$C_6$-alkylsulfonyl, N—$C_1$-$C_6$-alkylamino or N,N-di-$C_1$-$C_6$-alkylamino;

W is O or S,

Q is H, formyl, hydroxyl, amino or in each case optionally substituted $C_1$-$C_6$-alkyl, $C_2$-$C_6$-alkenyl, $C_2$-$C_6$-alkynyl, $C_3$-$C_6$-cycloalkyl, $C_1$-$C_5$-heterocycloalkyl, $C_1$-$C_4$-alkoxy, $C_1$-$C_6$-alkyl-$C_3$-$C_6$-cycloalkyl, $C_3$-$C_6$-cycloalkyl-$C_1$-$C_6$-alkyl, $C_6$-, $C_{10}$-$C_{14}$-aryl, $C_1$-$C_5$-heteroaryl, $C_6$-, $C_{10}$-, $C_{14}$-aryl-($C_1$-$C_3$)-alkyl, $C_1$-$C_5$-heteroaryl-($C_1$-$C_3$)-alkyl, N—$C_1$-$C_4$-alkylamino, N—$C_1$-$C_4$-alkylcarbonylamino, or N,N-di-$C_1$-$C_4$-alkylamino; or is an optionally poly-V-substituted unsaturated 6-membered carbocycle; or is an optionally poly-V-substituted unsaturated 4-, 5- or 6-membered heterocyclic ring, where V is independently halogen, cyano, nitro, in each case optionally substituted $C_1$-$C_6$-alkyl, $C_1$-$C_4$-alkenyl, $C_1$-$C_4$-alkynyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulfanyl, $C_1$-$C_6$-alkylsulfinyl, $C_1$-$C_6$-alkylsulfonyl, or N,N-di-($C_1$-$C_6$-alkyl)amino;

T is one of the 5-membered heteroaromatic systems T1-T8 shown below, where the bond to the ring (C—$B_1$—$B_2$—$B_3$—$B_4$—$B_5$) is marked with an asterisk *,

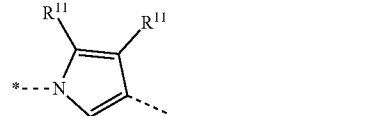

T1

T2

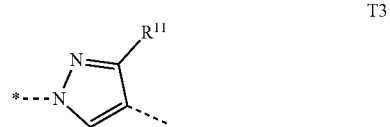

T3

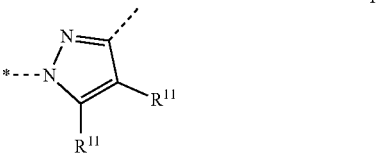

T4

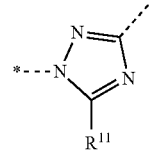

T5

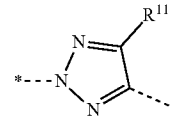

T6

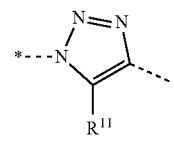

T7

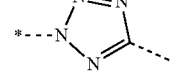

T8 where $R^{11}$ is in each case independently H, optionally halogenated $C_1$-$C_6$-alkyl or halogen, and salts, N-oxides and tautomeric forms of the compounds of the formula (I).

DETAILED DESCRIPTION OF A PREFERRED EMBODIMENT

A preferred embodiment of the present invention relates to compounds as described above, wherein $R^{11}$ in T is H.

A further preferred embodiment relates to compounds as described above, wherein T is T2, T3 or T7.

A further preferred embodiment relates to compounds as described above, wherein $A_1$ is $CR^2$, $A_2$ is $CR^3$, $A_3$ is $CR^4$, $A_4$ is $CR^5$, $A_5$ is C and $R^2$, $R^3$ and $R^5$ are in each case H.

A further preferred embodiment relates to compounds as described above, wherein $A_1$ is $CR^2$, $A_2$ is N, $A_3$ is $CR^4$, $A_4$ is $CR^5$, $A_5$ is C and $R^2$, $R^3$ and $R^5$ are in each case H.

A further preferred embodiment relates to compounds as described above, wherein $B_1$ is $CR^6$, $B_2$ is $CR^7$, $B_3$ is $CR^8$, $B_4$ is $CR^9$, and $B_5$ is $CR^{10}$.

A further preferred embodiment relates to compounds as described above, wherein $B_3$ is $CR^8$ and $R^8$ is halogenated $C_1$-$C_6$-alkyl and $B_2$ is $CR^7$ and $B_4$ is $CR^9$ and $R^7$ and $R^9$ are each H.

A further preferred embodiment relates to compounds as described above, wherein $B_1$ is $CR^6$ and $B_5$ is $CR^{10}$ and $R^6$ and $R^{10}$ are each optionally independently halogen, $C_1$-$C_6$-alkyl or $C_1$-$C_6$-alkyl substituted by halogen, $C_1$-$C_6$-alkoxy or $C_1$-$C_6$-alkoxy substituted by halogen.

A further preferred embodiment relates to compounds as described above, wherein $A_3$ is $CR^4$ and $R^4$ is H, halogen (preferably F or Cl, more preferably F) or $R^4$ together with the carbon atom of $CR^4$, $A_5$ and either C-$M_1$ or C-$M_2$ form a 5- or 6-membered ring optionally substituted by F, Cl, Br, I, $C_1$-$C_3$-alkyl, which may contain 0, 1 or 2 nitrogen atoms and/or 0, 1 or 2 oxygen atoms and/or 0, 1 or 2 sulfur atoms, more preferably form a 5-membered carbon ring.

A further preferred embodiment relates to compounds as described above, wherein $M_1$ and $M_2$ are each independently H or $C_1$-$C_6$-alkyl, more preferably H, or C-$M_1$ or C-$M_2$ together with $CR^4$ and $A_5$ form a 5- or 6-membered ring optionally substituted by F, Cl, Br, I, $C_1$-$C_3$-alkyl, which may contain 0, 1 or 2 nitrogen atoms and/or 0, 1 or 2 oxygen atoms and/or 0, 1 or 2 sulfur atoms, more preferably form a 5-membered carbon ring. By way of preference, in the case of ring formation by C-$M_1$ or C-$M_2$ with $CR^4$ and $A_5$, the other M in each case ($M_1$ if $M_2$ is involved in ring formation or $M_2$ if $M_1$ is involved in ring formation) is H.

A further preferred embodiment relates to compounds as described above, wherein $R^1$ is H and W is O.

A further preferred embodiment relates to compounds as described above, wherein Q is $C_1$-$C_6$-alkyl, $C_3$-$C_6$-cycloalkyl in each case optionally independently substituted by halogen, cyano; or 6-membered aromatic ring selected from phenyl or pyridyl optionally independently substituted by halogen, cyano.

A further aspect relates to an insecticidal composition comprising at least one compound of the formula (I) as described above and an extender and/or a surface-active substance.

A further aspect relates to a method for protecting transgenic or conventional seed and the plant that arises therefrom from infestation by pests, characterized in that the seed is treated with at least one compound as described above.

A further aspect relates to the use of compounds as described above, or to an insecticidal composition as described above for controlling pests.

A further aspect relates to seed, in which a compound as described above has been applied to the seed as a constituent of a coating or as a further layer or further layers in addition to a coating.

A further aspect relates to the use of a compound of the formula (I) as described above as a herbicide.

EMBODIMENTS OF THE COMPOUNDS ACCORDING TO THE INVENTION

Novel halogen-substituted compounds which have insecticidal, acaricidal and/or parasiticidal activity and are of the general formula (I) have been found:

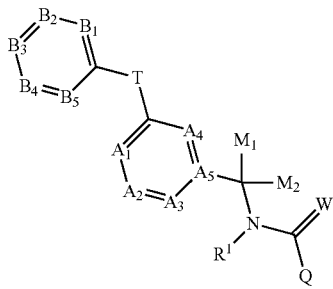

(I)

in which $R^1$ is H, in each case optionally substituted $C_1$-$C_6$-alkyl, $C_2$-$C_6$-alkenyl, $C_2$-$C_6$-alkynyl, $C_3$-$C_7$-cycloalkyl, $C_1$-$C_6$-alkylcarbonyl, $C_1$-$C_6$-alkoxycarbonyl, aryl($C_1$-$C_3$)-alkyl, heteroaryl($C_1$-$C_3$)-alkyl, or $R^1$ is H in each case optionally substituted $C_1$-$C_6$-alkyl, $C_2$-$C_6$-alkenyl, $C_2$-$C_6$-alkynyl, $C_3$-$C_7$-cycloalkyl, $C_1$-$C_6$-alkylcarbonyl, $C_1$-$C_6$-alkoxycarbonyl, $C_3$-$C_7$-cycloalkyl($C_1$-$C_3$)-alkyl, aryl($C_1$-$C_3$)-alkyl, heteroaryl($C_1$-$C_3$)-alkyl, the moieties are as follows:

$A_1$ is $CR^2$ or N,
$A_2$ is $CR^3$ or N,
$A_3$ is $CR^4$ or N,
$A_4$ is $CR^5$ or N,
$A_5$ is C,
$B_1$ is $CR^6$ or N,
$B_2$ is $CR^7$ or N,
$B_3$ is $CR^8$ or N,
$B_4$ is $CR^9$ or N, and
$B_5$ is $CR^{10}$ or N,
but not more than three of the $A_1$ to $A_4$ moieties are N and not more than three of the $B_1$ to $B_5$ moieties are simultaneously N;

$M_1$, $M_2$ are each independently H, in each case optionally substituted $C_1$-$C_6$-alkyl, $C_2$-$C_6$-alkenyl, $C_2$-$C_6$-alkynyl, $C_3$-$C_7$-cycloalkyl, $C_1$-$C_6$-alkylcarbonyl, $C_1$-$C_6$-alkoxycarbonyl, aryl($C_1$-$C_3$)-alkyl, heteroaryl($C_1$-$C_3$)-alkyl, or $M_1$ and $M_2$ with the carbon atom to which they are attached form an optionally substituted 3-, 4-, 5- or 6-membered ring which optionally contains 0, 1 or 2 nitrogen atoms and/or 0, 1 or 2 oxygen atoms and/or 0, 1 or 2 sulfur atoms, or $M^1$ or $M^2$ with $R^4$ from $A_3$, the carbon atom of $A_3$, $A_5$ and D form a 5- or 6-membered ring optionally substituted by $R^6$, preferably by F, Cl, Br, I, $C_1$-$C_3$-alkyl, which may contain 0, 1 or 2 nitrogen atoms and/or 0, 1 or 2 oxygen atoms and/or 0, 1 or 2 sulfur atoms, $R^2$, $R^3$, $R^4$, $R^5$, $R^6$, $R^7$, $R^9$ and $R^{10}$ are each independently H, halogen, cyano, nitro, in each case optionally substituted $C_1$-$C_6$-alkyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulfanyl, $C_1$-$C_6$-alkylsulfinyl, $C_1$-$C_6$-alkylsulfonyl, N—$C_1$-$C_6$-alkylamino or N,N-di-$C_1$-$C_6$-alkylamino, if neither of the $A_2$ and $A_3$ moieties is N, $R^3$ and $R^4$ together with the carbon atom to which they are attached may form a 5- or 6-membered ring containing 0, 1 or 2 nitrogen atoms and/or 0 or 1 oxygen atom and/or 0 or 1 sulfur atom, or if neither of the $A_1$ and $A_2$ moieties is N, $R^2$ and $R^3$ together with the carbon atom to which they are bonded may form a 6-membered ring containing 0, 1 or 2 nitrogen atoms;

$R^8$ is halogen, cyano, nitro, in each case optionally substituted $C_1$-$C_6$-alkyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulfanyl, $C_1$-$C_6$-alkylsulfinyl, $C_1$-$C_6$-alkylsulfonyl, N—$C_1$-$C_6$-alkylamino or N,N-di-$C_1$-$C_6$-alkylamino, or is halogen, cyano, nitro, in each case optionally substituted $C_1$-$C_6$-alkyl, $C_3$-$C_6$-cycloalkyl, $C_3$-$C_6$-cycloalkyl($C_1$-$C_6$)alkyl, $C_1$-$C_6$-alkoxy, N—$C_1$-$C_6$-alkoxyimino-$C_1$-$C_3$-alkyl, $C_1$-$C_6$-alkylsulfanyl, $C_1$-$C_6$-alkylsulfinyl, $C_1$-$C_6$-alkylsulfonyl, N—$C_1$-$C_6$-alkylamino or N,N-di-$C_1$-$C_6$-alkylamino;

W is O or S,

Q is H, formyl, hydroxyl, amino or in each case optionally substituted $C_1$-$C_6$-alkyl, $C_2$-$C_6$-alkenyl, $C_2$-$C_6$-alkynyl, $C_3$-$C_6$-cycloalkyl, $C_1$-$C_5$-heterocycloalkyl, $C_1$-$C_4$-alkoxy, $C_1$-$C_6$-alkyl-$C_3$-$C_6$-cycloalkyl, $C_3$-$C_6$-cycloalkyl-$C_1$-$C_6$-alkyl, $C_6$-, $C_{10}$-$C_{14}$-aryl, $C_1$-$C_5$-heteroaryl, $C_6$-, $C_{10}$-, $C_{14}$-aryl-($C_1$-$C_3$)-alkyl, $C_1$-$C_5$-heteroaryl-($C_1$-$C_3$)-alkyl, N—$C_1$-$C_3$-alkylamino, N—$C_1$-$C_4$-alkylcarbonylamino, or N,N-di-$C_1$-$C_4$-alkylamino; or is an optionally poly-V-substituted unsaturated 6-membered carbocycle; or is an optionally poly-V-substituted unsaturated 4-, 5- or 6-membered heterocyclic ring, where V is independently halogen, cyano, nitro, in each case optionally substituted $C_1$-$C_6$-alkyl, $C_1$-$C_4$-alkenyl, $C_1$-$C_4$-alkynyl, $C_3$-$C_6$-cycloalkyl, $C_1$-$C_6$-alkoxy, N—$C_1$-$C_6$- alkoxyimino-$C_1$-$C_3$-alkyl, $C_1$-$C_6$-alkylsulfanyl, $C_1$-$C_6$-alkylsulfinyl, $C_1$-$C_6$-alkylsulfonyl, or N,N-di-($C_1$-$C_6$-alkyl)amino;

T is one of the 5-membered heteroaromatic systems T1-T8 shown below, where the bond to the ring (C—B1-B2-B3-B4-B5) is indicated by an asterisk,

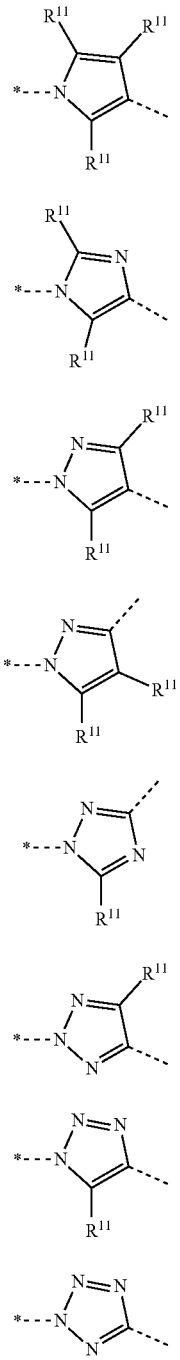

where $R^{11}$ is in each case independently H, optionally halogenated $C_1$-$C_6$-alkyl or halogen, and salts, N-oxides and tautomeric forms of the compounds of the formula (I).

$R^{11}$

Preference is given to compounds in which $R^{11}$ in T is H.

T

Preference is given to compounds of the formula (I) in which T is T3 or T4, particularly preferably T3.

Preference is given to compounds of the formula (I) in which T is T3 or T4, particularly preferably T3, and $R^6$ in T is in each case H.

Preference is further given to compounds in which T is T1.

Preference is given to compounds of the formula (I) in which T is T1 and $R^{11}$ in T1 is in each case H.

Preference is further given to compounds in which T is T2.

Preference is given to compounds of the formula (I) in which T is T2 and $R^{11}$ in T2 is in each case H. Preferably wherein $B_1$ is C—$R^6$, $B_5$ is C—$R^{10}$, $B_3$ is C—$R^8$, $R^8$ is heptafluoroisopropyl, $B_2$, $B_4$, $A_1$, $A_2$ and $A_4$ are CH, $M_1$ and $M_2$ are H, W is O, $R^6$ is halogen, preferably Cl or F, more preferably Cl, $R^{10}$ is halogen, preferably Cl or F, more preferably Cl, $A_3$ is C—$R^4$, $R^4$ is halogen, preferably F or Cl, more preferably F, or $C_1$-$C_3$-alkyl, preferably methyl, $R^{11}$ is in each case H and Q is $C_1$-$C_3$-alkyl, preferably methyl or ethyl, or $C_3$-$C_4$-cycloalkyl, preferably cyclopropyl.

Preference is given to compounds of the formula (I) in which T is T5, T6 or T7, particularly preferably T7.

Preference is given to compounds of the formula (I) in which T is T5, T6 or T7, particularly preferably T7, and $R^{11}$ in T5, T6 or T7 is in each case H. Preferably T is T7, $B_1$ is C—$R^6$, $B_5$ is C—$R^{10}$, $B_3$ is C—$R^8$, $R^8$ is heptafluoroisopropyl, $B_2$, $B_4$, $A_1$, $A_2$ and $A_4$ are CH, $M_1$ and $M_2$ are H, $R^{11}$ is H, W is O, $R^6$ is halogen, preferably Cl or F, more preferably Cl, $R^{10}$ is halogen, preferably Cl or F, more preferably Cl, $A_3$ is C—$R^4$, $R^4$ is halogen, preferably F or Cl, more preferably Cl, and Q is $C_1$-$C_3$-alkyl, preferably methyl or ethyl, or $C_3$-$C_4$-cycloalkyl, preferably cyclopropyl.

Preference is further given to compounds in which T is T8.

Preference is given to compounds of the formula (I) in which T is T8 and $R^{11}$ in T8 is in each case H.

A preferred embodiment of the present invention relates to compounds of the formula (I) in which T is T2, T3 or T7.

A

Preference is further given to compounds in which $A_1$ is $CR^2$, $A_2$ is $CR^3$, $A_3$ is $CR^4$, $A_4$ is $CR^5$, $A_5$ is C.

Preference is further given to compounds in which $A_1$ is $CR^2$, $A_2$ is N, $A_3$ is $CR^4$, $A_4$ is $CR^5$, $A_5$ is C.

B

Preference is further given to compounds in which $B_1$ is $CR^6$, $B_2$ is $CR^7$, $B_3$ is $CR^8$, $B_4$ is $CR^9$, and $B_5$ is $CR^1$.

Preference is further given to compounds in which $A_1$ is $CR^2$, $A_2$ is $CR^3$, $A_3$ is $CR^4$, $A^4$ is $CR^5$, $A_5$ is C and $B_1$ is $CR^6$, $B_2$ is $CR^7$, $B_3$ is $CR^8$, $B_4$ is $CR^9$, and $B_5$ is $CR^1$.

$R^8$

Preference is given to compounds of the formula (I) in which $B_3$ is $CR^8$ and $R^8$ is halogen, cyano, nitro, in each case halogen-substituted $C_1$-$C_4$-alkyl, $C_3$-$C_4$-cycloalkyl, $C_1$-$C_4$-alkoxy, N—$C_1$-$C_4$-alkoxyimino-$C_1$-$C_4$-alkyl, $C_1$-$C_4$-alkylsulfanyl, $C_1$-$C_4$-alkylsulfinyl, $C_1$-$C_4$-alkylsulfonyl, N—$C_1$-$C_4$-alkylamino or N,N-di-$C_1$-$C_4$-alkylamino or; $B_3$ is $CR^8$ and $R^8$ is halogen, cyano, nitro, in each case halogen-substituted $C_1$-$C_4$-alkyl, $C_3$-$C_4$-cycloalkyl, $C_1$-$C_4$-alkyl($C_3$-$C_4$)cycloalkyl, $C_1$-$C_4$-alkoxy, N—$C_1$-$C_4$-alkoxyimino-$C_1$-$C_4$-alkyl, $C_1$-$C_4$-alkylsulfanyl, $C_1$-$C_4$-alkylsulfinyl, $C_1$-$C_4$-alkylsulfonyl such as $SO_2CF_3$, N—$C_1$-$C_4$-alkylamino or N,N-di-$C_1$-$C_4$-alkylamino.

In a further preferred embodiment, $R^8$ is halogen such as fluorine, chlorine, bromine, iodine, or halogen-substituted $C_1$-$C_4$-alkyl, cyano, nitro, methyl, ethyl, difluoromethyl, trichloromethyl, chlorodifluoromethyl, dichlorofluoromethyl, trifluoromethyl, chloromethyl, bromomethyl, 1-fluoroethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, pentafluoro-tert-butyl, heptafluoro-n-propyl, heptafluoroisopropyl, nonafluoro-n-butyl, nonafluoro-sec-butyl, cyclopropyl, cyclobutyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methylsulfanyl, methylsulfonyl, methylsulfinyl, trifluoromethylsulfonyl, trifluoromethylsulfinyl, trifluoromethylsulfanyl, N,N-dimethylamino or is $SO_2CF_3$, halogen such as fluorine, chlorine, bromine, iodine, or halogen-substituted $C_1$-$C_4$-alkyl or $C_1$-$C_4$-alkyl-$C_3$-$C_4$-cycloalkyl, cyano, nitro, methyl, ethyl, difluoromethyl, trichloromethyl, chlorodifluoromethyl, dichlorofluoromethyl, trifluoromethyl, chloromethyl, bromomethyl, 1-fluoroethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, pentafluoro-tert-butyl, heptafluoro-n-propyl, heptafluoroisopropyl, nonafluoro-n-butyl, nonafluoro-sec-butyl, cyclopropyl, cyclobutyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, N-methoxyiminomethyl, 1-(N-methoxyimino)ethyl, methylsulfanyl, methylsulfonyl, methylsulfinyl, trifluoromethylsulfonyl, trifluoromethylsulfinyl, trifluoromethylsulfanyl, N,N-dimethylamino.

In a further more preferred embodiment, $R^8$ is halogenated, preferably perhalogenated, even more preferably perfluorinated $C_1$-$C_6$-alkyl, or is halogenated, preferably perhalogenated, even more preferably (perfluorinated $C_1$-$C_4$-alkyl)-$C_3$-$C_4$-cycloalkyl or is $SO_2CF_3$.

In a particularly preferred embodiment, $R^8$ is difluoromethyl, trichloromethyl, chlorodifluoromethyl, dichlorofluoromethyl, trifluoromethyl, 1-fluoroethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, pentafluoro-tert-butyl, heptafluoro-n-propyl, heptafluoroisopropyl, nonafluoro-n-butyl, nonafluoro-sec-butyl, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, trifluoromethylsulfonyl, trifluoromethylsulfinyl or trifluoromethylsulfanyl; or is $SO_2\ CF_3$, difluoromethyl, trichloromethyl, chlorodifluoromethyl, dichlorofluoromethyl, trifluoromethyl, 1-fluoroethyl, 2-fluoroethyl, 2,2-difluoroethyl, 2,2,2-trifluoroethyl, 1,2,2,2-tetrafluoroethyl, 1-chloro-1,2,2,2-tetrafluoroethyl, 2,2,2-trichloroethyl, 2-chloro-2,2-difluoroethyl, 1,1-difluoroethyl, pentafluoroethyl, pentafluoro-tert-butyl, heptafluoro-n-propyl, heptafluoroisopropyl, nonafluoro-n-butyl, nonafluoro-sec-butyl, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, trifluoromethylsulfonyl, trifluoromethylsulfinyl, trifluoromethylsulfanyl, trifluoromethylcyclopropyl, such as 1-trifluoromethylcyclopropyl.

In a particularly preferred embodiment, $R^8$ is perfluorinated $C_1$-$C_3$-alkyl such as perfluorinated n- or i-propyl (—$C_3F_7$), perfluorinated ethyl ($C_2F_5$) or perfluorinated methyl ($CF_3$), more preferably perfluorinated n- or i-propyl (—$C_3F_7$) or perfluorinated methyl; or is halogen-substituted $C_1$-$C_4$-alkyl-$C_3$-$C_4$-cycloalkyl, such as (perfluorinated $C_1$-$C_4$-alkyl)-$C_3$-$C_4$-cycloalkyl, preferably trifluoromethylcyclopropyl, such as 1-trifluoromethylcyclopropyl.

$R^7$, $R^9$

Preference is given to compounds in which $B_2$ is $CR^7$ and $B_4$ is $CR^9$ and $R^7$ and $R^9$ are in each case H.

$R^{10}$, $R^6$

Preference is given to the compounds in which $B_1$ is $CR^6$, and $B_5$ is $CR^{10}$ and $R^6$ and $R^{10}$ are each optionally independently halogen (preferably selected from the group consisting of F, Cl, Br and I; more preferably Cl), an optionally halogen-substituted (preferably selected from the group consisting of F, Cl, Br and I; more preferably F) group selected from $C_1$-$C_6$-alkyl (preferably $CH_3$), —S—$C_1$-$C_6$-alkyl (preferably S—$CH_3$), —SO—$C_1$-$C_6$-alkyl (preferably S(O)—$CH_3$), $SO_2$—$C_1$-$C_6$-alkyl (preferably $SO_2$—$CH_3$) and $C_1$-$C_6$-alkoxy (preferably —O—$CH_3$).

In a preferred embodiment, $R^6$ is Cl, —$CH_3$, —O—$CH_3$, —S—$CH_3$, —SO—$CH_3$, —$SO_2$—$CH_3$, —$CF_3$, —$CHF_2$, —$CH_2F$, —O—$CF_3$, —O—$CHF_2$, —O—$CH_2F$ or 1- to 3-fold fluorinated —S—$CH_3$ (=—S—$CH_2F$, —S—$CHF_2$ or —S—$CF_3$), —SO—$CH_3$, or —$SO_2$—$CH_3$.

In a preferred embodiment, $R^6$ is Cl, —$CH_3$, —O—$CH_3$, —S—$CH_3$, —SO—$CH_3$, —$SO_2$—$CH_3$, —$CF_3$, —$CHF_2$, —$CH_2F$, —O—$CF_3$, —O—$CHF_2$, —O—$CH_2F$.

In a preferred embodiment, $R^{10}$ is Cl, —$CH_3$, —O—$CH_3$, —S—$CH_3$, —SO—$CH_3$, —$SO_2$—$CH_3$, —$CF_3$, —$CHF_2$, —$CH_2F$, —O—$CF_3$, —O—$CHF_2$, —O—$CH_2F$ or 1- to 3-fold fluorinated —S—$CH_3$, —SO—$CH_3$ or —$SO_2$—$CH_3$.

In a preferred embodiment, $R^{10}$ is Cl, —$CH_3$, —O—$CH_3$, —S—$CH_3$, —SO—$CH_3$, —$SO_2$—$CH_3$, —$CF_3$, —$CHF_2$, —$CH_2F$, —O—$CF_3$, —O—$CHF_2$, —O—$CH_2F$.

In a further preferred embodiment, $R^6$ and $R^{10}$ are in each case —$CH_3$ or in each case Cl.

In a further preferred embodiment, $R^6$ is Cl and $R^{10}$ is Cl, —$CH_3$, —O—$CH_3$, —S—$CH_3$, —SO—$CH_3$, —$SO_2$—$CH_3$, —$CF_3$, —$CHF_2$, —$CH_2F$, —O—$CF_3$, —O—$CHF_2$, —O—$CH_2F$, 1- to 3-fold fluorinated —S—$CH_3$, —SO—$CH_3$, or —$SO_2$—$CH_3$ or $R^{10}$ is Cl and $R^6$ is Cl, —$CH_3$, —O—$CH_3$, —S—$CH_3$, —SO—$CH_3$, —$SO_2$—$CH_3$, —$CF_3$, —$CHF_2$, —$CH_2F$, —O—$CF_3$, —O—$CHF_2$, —O—$CH_2F$, 1- to 3-fold fluorinated —S—$CH_3$, —SO—$CH_3$, or —$SO_2$—$CH_3$.

In a further preferred embodiment, $R^6$ is Cl and $R^{10}$ is Cl, —$CH_3$, —O—$CH_3$, —S—$CH_3$, —SO—$CH_3$, —$SO_2$—$CH_3$, —$CF_3$, —$CHF_2$, —$CH_2F$, —O—$CF_3$, —O—$CHF_2$, —O—$CH_2F$, or $R^{10}$ is Cl and $R^6$ is Cl, —$CH_3$, —O—$CH_3$, —S—$CH_3$, —SO—$CH_3$, —$SO_2$—$CH_3$, —$CF_3$, —$CHF_2$, —$CH_2F$, —O—$CF_3$, —O—$CHF_2$, —O—$CH_2F$.

$R^2$, $R^3$, $R^5$

Preference is given to compounds in which $A_1$ is $CR^2$, $A_2$ is $CR^3$ and $A_4$ is $CR^5$ and $R^2$, $R^3$ and $R^5$ are in each case H.

$R^4$

Preference is given to compounds in which $A_3$ is $CR^4$ and $R^4$ is H, optionally halogenated $C_1$-$C_4$-alkyl or halogen (preferably Br, F or Cl, more preferably Cl or F, even more preferably F) or $R_4$ together with the carbon atom of $CR_4$, $A_5$ and either C-$M_1$ or C-$M_2$ form a 5- or 6-membered ring optionally substituted by F, Cl, Br, I, $C_1$-$C_3$-alkyl, which may contain 0, 1 or 2 nitrogen atoms and/or 0, 1 or 2 oxygen atoms and/or 0, 1 or 2 sulfur atoms, more preferably form a 5-membered carbon ring.

In a further preferred embodiment, $R^4$ is H, $C_1$-$C_4$-alkyl, fluorinated $C_1$-$C_4$-alkyl, Cl, or F, preferably $CH_3$, $CF_3$, H, Cl or F.

In a further preferred embodiment, $R^4$ is H, Cl, or F, preferably Cl or F. In a further preferred embodiment, $R^4$ is Cl.

$M_1$, $M_2$

Preference is given to compounds in which $M_1$ and $M_2$ are each independently H or $C_1$-$C_6$-alkyl, more preferably H, or $C$-$M_1$ or $C$-$M_2$ together with the carbon atom of $CR^4$ and $A_5$ form a 5- or 6-membered ring optionally substituted by F, Cl, Br, I, $C_1$-$C_3$-alkyl, which may contain 0, 1 or 2 nitrogen atoms and/or 0, 1 or 2 oxygen atoms and/or 0, 1 or 2 sulfur atoms, more preferably form a 5-membered carbon ring. By way of preference, in the case of ring formation by $C$-$M_1$ or $C$-$M_2$ with the carbon atom of $CR^4$ and As, the other M in each case ($M_1$ if $M_2$ is involved in ring formation or $M_2$ if $M_1$ is involved in ring formation) is H.

$R^1$

Preference is given to compounds in which $R^1$ is H.

Further preference is given to compounds in which $R^1$ is $C_1$-$C_4$-alkyl, preferably methyl, or $C_3$-$C_7$-cycloalkyl($C_1$-$C_3$)-alkyl, preferably cyclopropylmethylene.

W

In a preferred embodiment, W is O.

In a further preferred embodiment, W is S.

Q

Preference is given to compounds in which Q is $C_1$-$C_6$-alkyl, $C_3$-$C_6$-cycloalkyl in each case optionally independently substituted by halogen or cyano or a 6-membered aromatic ring such as phenyl or pyridyl, more preferably $C_1$-$C_6$-alkyl, $C_3$-$C_6$-cycloalkyl in each case optionally substituted by one or more substituents selected from halogen and cyano.

In a preferred embodiment, Q is optionally halogenated $C_1$-$C_4$-alkyl, more preferably $C_1$-$C_4$-alkyl.

In a further preferred embodiment, Q is cyclopropyl or 1-cyanocyclopropyl.

Preference is given to compounds of the formula (Ia)

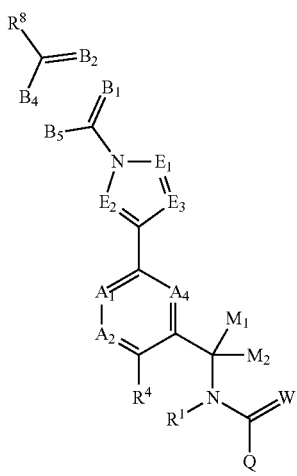

(Ia)

in which
$B_1$, $B_2$, $B_4$ and $B_5$, $A_1$, $A_2$, $A_4$, $R^1$, $R^4$, $R^8$, W, Q, $M_1$ and $M_2$ are as defined above and $E_1$, $E_2$, $E_3$ are each independently N or C—$R^6$ and together with the nitrogen between $E_1$ and $E_2$ and the carbon between $E_2$ and $E_3$ is a ring T selected from T1 to T8, preferably as described above. Particular preference is given to compounds of the formula (Ia), where $R^1$ is H. Preference is furthermore given to compounds of the formula (Ib), where $R^1$ is methyl. Preference is additionally given to compounds of the formula (Ia) in which $B_1$, $B_2$, $B_4$ and $B_5$, $A_1$, $A_2$, $A_4$, $R_1$, $R^4$, $R^8$, W, Q, $M_1$ and $M_2$ are as defined in Table 1.

Preference is furthermore given to compounds of the formula (Ib)

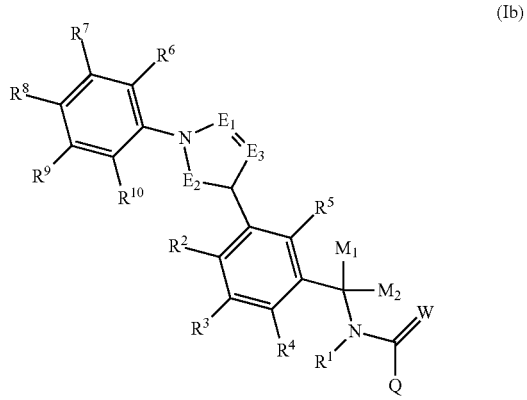

(Ib)

in which
$R^1$ to $R^{10}$, W, Q, $M_1$ and $M_2$ are as defined above and $E_1$, $E_2$, $E_3$ are each independently N or C—$R^6$ and together with the nitrogen between $E_1$ and $E_2$ and the carbon between $E_2$ and $E_3$ is a ring T selected from T1 to T8, preferably as described above. Particular preference is given to compounds of the formula (Ib), where $R^1$ is H. Preference is furthermore given to compounds of the formula (Ib), where $R^1$ is methyl.

Preference is furthermore given to compounds of the formula (I-T3)

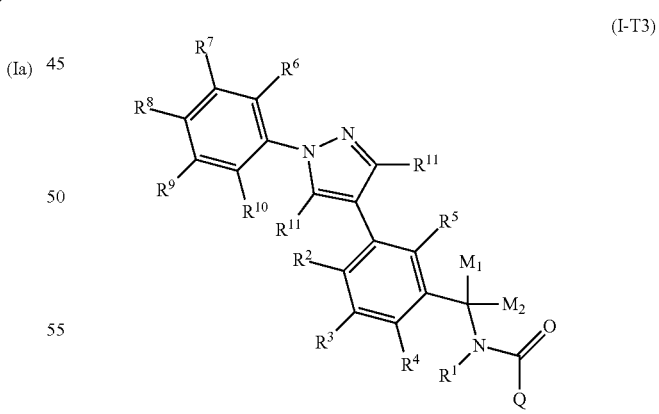

(I-T3)

in which
$R^1$ to $R^{10}$, W, Q, $M_1$ and $M_2$ are as defined above. Particular preference is given to compounds of the formula (I-T3), where $R^1$ is H. Preference is furthermore given to compounds of the formula (I-T3), where $R^1$ is methyl.

Preference is furthermore given to compounds of the formula (I-T1)

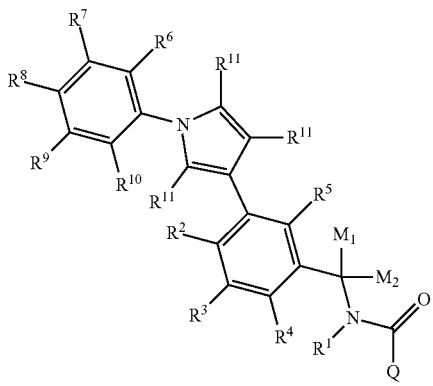
(I-T1)

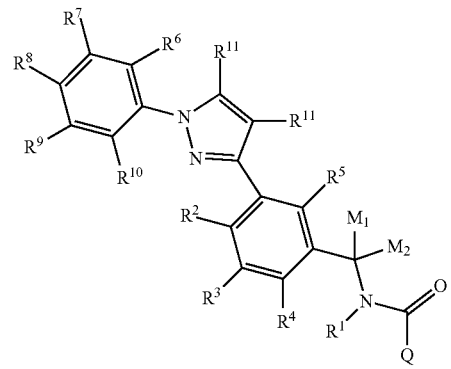
(I-T4)

in which
$R^1$ to $R^{10}$, W, Q, $M_1$ and $M_2$ are as defined above. Particular preference is given to compounds of the formula (I-T4), where $R^1$ is H. Preference is furthermore given to compounds of the formula (I-T4), where $R^1$ is methyl.

Preference is furthermore given to compounds of the formula (I-T5)

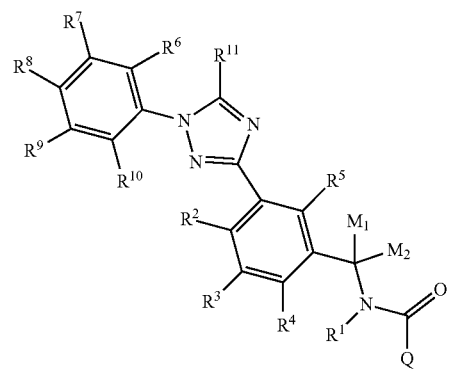
(I-T5)

in which
$R^1$ to $R^{10}$, W, Q, $M_1$ and $M_2$ are as defined above. Particular preference is given to compounds of the formula (I-T1), where $R^1$ is H. Preference is furthermore given to compounds of the formula (I-T1), where $R^1$ is methyl.

Preference is furthermore given to compounds of the formula (I-T2)

$R^1$ to $R^{10}$, W, Q, $M_1$ and $M_2$ are as defined above. Particular preference is given to compounds of the formula (I-T5), where $R^1$ is H. Preference is furthermore given to compounds of the formula (I-T5), where $R^1$ is methyl.

Preference is furthermore given to compounds of the formula (I-T6)

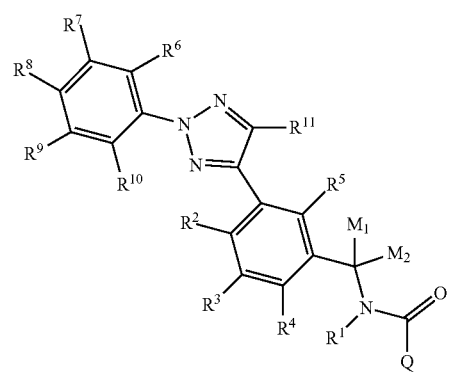
(I-T6)

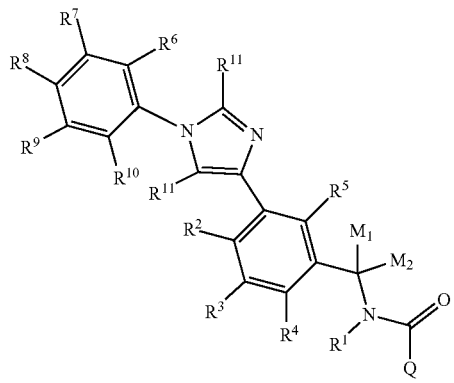
(I-T2)

in which
$R^1$ to $R^{10}$, W, Q, $M_1$ and $M_2$ are as defined above. Particular preference is given to compounds of the formula (I-T2), where $R^1$ is H. Preference is furthermore given to compounds of the formula (I-T2), where $R^1$ is methyl.

Preference is furthermore given to compounds of the formula (I-T4)

$R^1$ to $R^{10}$, W, Q, $M_1$ and $M_2$ are as defined above. Particular preference is given to compounds of the formula (I-T6), where $R^1$ is H. Preference is furthermore given to compounds of the formula (I-T6), where $R^1$ is methyl.

Preference is furthermore given to compounds of the formula (I-T7)

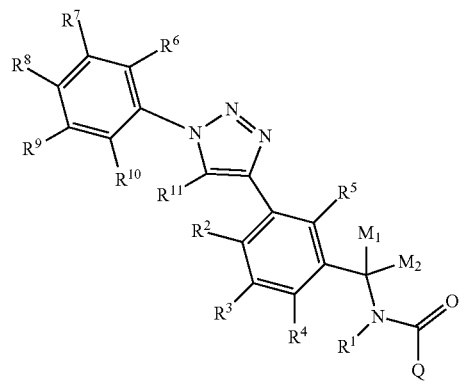

(I-T7)

$R^1$ to $R^{10}$, W, Q, $M_1$ and $M_2$ are as defined above. Particular preference is given to compounds of the formula (I-T7), where $R^1$ is H. Preference is furthermore given to compounds of the formula (I-T7), where $R^1$ is methyl.

Preference is furthermore given to compounds of the formula (I-T8)

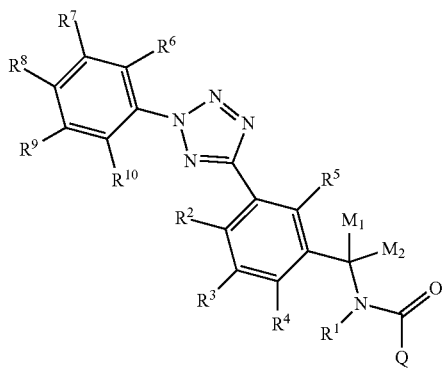

(I-T8)

$R^1$ to $R^{10}$, W, Q, $M_1$ and $M_2$ are as defined above. Particular preference is given to compounds of the formula (I-T8), where $R^1$ is H. Preference is furthermore given to compounds of the formula (I-T8), where $R^1$ is methyl.

Preference is furthermore given to compounds of the formula (I-T8)

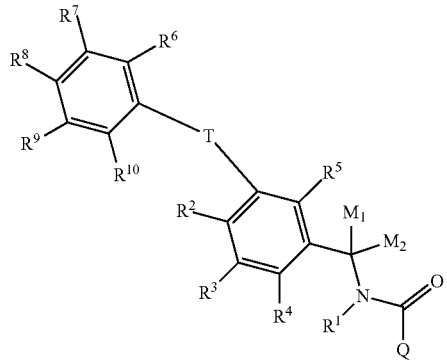

(I-Ta)

$R^1$ to $R^{10}$, W, Q, $M_1$ and $M_2$ are as defined above. Particular preference is given to compounds of the formula (I-T8), where $R^1$ is H. Preference is furthermore given to compounds of the formula (I-T8), where $R^1$ is methyl.

Preference is furthermore given to compounds of the formula (I-Tb)

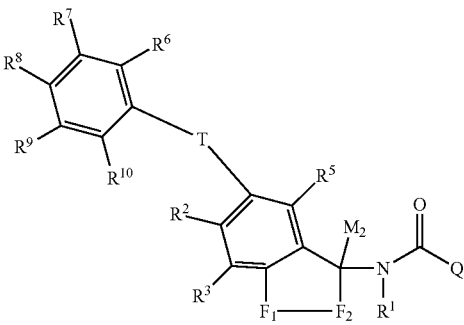

(I-Tb)

$R^1$, $R^2$, $R^3$, $R^5$ to $R^{10}$, T, Q and $M_2$ are as defined above, $F_1$ and $F_2$ are each independently C—$R^6$, N—$R^6$, O or S. In this case, T is particularly preferably T2, T7 or T3, especially preferably T3. Particular preference is given to compounds of the formula (I-Tb), where $R^1$ is H. Preference is furthermore given to compounds of the formula (I-Tb), where $R^1$ is methyl.

Preference is furthermore given to compounds of the formula (I-Tc)

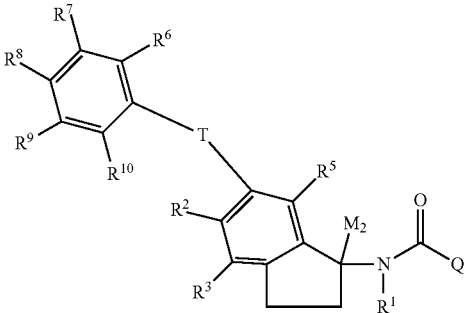

(I-Tc)

$R^1$, $R^2$, $R^3$, $R^5$ to $R^{10}$, T, Q and $M_2$ are as defined above. In this case, T is particularly preferably T2, T7 or T3, especially preferably T3. Particular preference is given to compounds of the formula (I-Tc), where $R^1$ is H. Preference is furthermore given to compounds of the formula (I-Tc), where $R^1$ is methyl. Preference is also given to compounds of the formula (I-Tc) where $R^1$, $R^2$, $R^3$, $R^5$, $R^7$, $R^9$ and $M_2$ are in each case H, $R^8$ is heptafluoroisopropyl, Q is $C_1$-$C_3$-alkyl, preferably methyl or ethyl, more preferably ethyl, $R^{10}$ is Halogen, preferably F or Cl, more preferably Cl, and $R^6$ is in each case halogenated, preferably fluorinated, $C_1$-$C_3$-alkyl or $C_1$-$C_3$-alkoxy, preferably $CF_3$, $OCF_3$ or $OCHF_2$.

Particular preference is given to compounds of the formula (Ia)

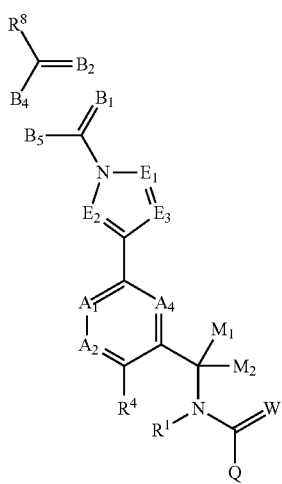

(Ia)

where $R^8$ is fluorinated $C_1$-$C_4$-alkyl, more preferably perfluorinated $C_1$-$C_4$-alkyl, particularly preferably heptafluoroisopropyl, $B_1$ is C—$R^6$ and $B_5$ is C—$R^{10}$, wherein $R^6$ and $R^{10}$ are each independently halogen, in each case optionally fluorinated $C_1$-$C_4$-alkyl, —S—$C_1$-$C_4$-alkyl, —SO—$C_1$-$C_4$-alkyl, —SO_2—$C_1$-$C_4$-alkyl, or $C_1$-$C_4$-alkoxy, more preferably each independently Cl, optionally fluorinated $C_1$-$C_4$-alkyl, —S—$C_1$-$C_4$-alkyl, —SO—$C_1$-$C_4$-alkyl, —SO_2—$C_1$-$C_4$-alkyl, or optionally fluorinated $C_1$-$C_4$-alkoxy, even more preferably each independently Cl, optionally fluorinated $C_1$-$C_4$-alkyl, —S—$C_1$-$C_4$-alkyl, —SO—$C_1$-$C_4$-alkyl, —SO_2—$C_1$-$C_4$-alkyl, or optionally perfluorinated $C_1$-$C_4$-alkoxy, especially preferably each independently $OCF_3$, $CHF_2$, Cl, methyl, —S— methyl, —SO-methyl, —SO2-methyl, $B_2$, $B_4$, $E_2$ and $E_3$, $A_1$ and $A_4$ are CH, $M_1$ is H, $E_1$ is N, $A_2$ is C—H or N, $R^4$ is H, F or Cl, $R^1$ is H, $C_1$-$C_4$-alkyl or cyclopropylcarbonyl ($C_3H_5$—C(=O)—, preferably H, methyl or cyclopropylcarbonyl, more preferably H or methyl, Q is optionally halogenated, preferably optionally fluorinated, $C_1$-$C_4$-alkyl or optionally halogenated cyclopropyl, more preferably methyl, ethyl, propyl, butyl, 2,2,2-trifluoroethyl or cyclopropyl, and W is O.

Preference is furthermore given to compounds of the formula (Ia) in which $R^8$ is fluorinated $C_1$-$C_4$-alkyl, more preferably perfluorinated $C_1$-$C_4$-alkyl, especially preferably heptafluoroisopropyl, $B_1$ is C—$R^6$ and $B_5$ is C—$R^{10}$, where $R^6$ and $R^{10}$ are each independently halogen, each optionally fluorinated $C_1$-$C_4$-alkyl, —S—$C_1$-$C_4$-alkyl, —SO—$C_1$-$C_4$-alkyl, —SO_2—$C_1$-$C_4$-alkyl, or $C_1$-$C_4$-alkoxy, more preferably each independently Cl, optionally fluorinated $C_1$-$C_4$-alkyl, —S—$C_1$-$C_4$-alkyl, —SO—$C_1$-$C_4$-alkyl, —SO_2—$C_1$-$C_4$-alkyl, or optionally fluorinated $C_1$-$C_4$-alkoxy, even more preferably each independently Cl, optionally fluorinated $C_1$-$C_4$-alkyl, —S—$C_1$-$C_4$-alkyl, —SO—$C_1$-$C_4$-alkyl, —SO_2—$C_1$-$C_4$-alkyl, or optionally perfluorinated $C_1$-$C_4$-alkoxy, especially preferably each independently $OCF_3$, $CHF_2$, Cl, methyl, S-methyl, —SO-methyl, —SO_2-methyl, $B_2$, $B_4$, $E_2$ and $E_3$, $A_1$ and $A_4$ are CH, $M_1$ is H, $E_1$ is N, $A_2$ is C—H or N, $R^4$ is H, F or Cl, $R^1$ is H, $C_1$-$C_4$-alkyl or cyclopropylcarbonyl ($C_3H_5$—C(=O)—, preferably H, methyl or cyclopropylcarbonyl, more preferably H or methyl, Q is optionally halogenated, preferably optionally fluorinated, $C_1$-$C_4$-alkyl or optionally halogenated cyclopropyl, more preferably methyl, ethyl, propyl, butyl, 2,2,2-trifluoroethyl or cyclopropyl, and W is S.

A further aspect of the present invention relates to compounds of the formula (Ic)

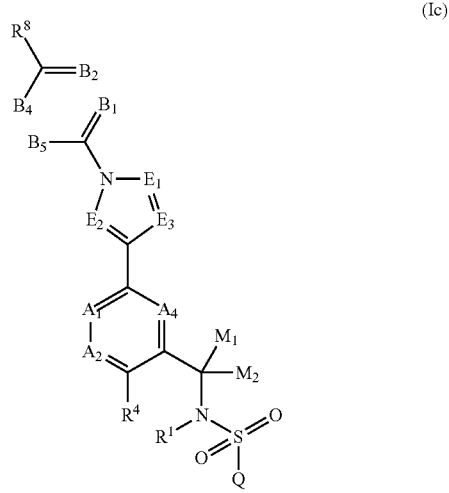

(Ic)

where an —S(O)_2— group is between Q and N. $B_1$, $B_2$, $B_4$ and $B_5$, $A_1$, $A_2$, $A_4$, $E_1$, $E_2$, $E_3$, $R^1$, $R^4$, $R^8$, Q, $M_1$ and $M_2$ have in this case the definition, preferred definition or particularly preferred definitions as described herein for compounds of the formulae (I), (Ia), (I-Ta), (I-Tb) and (I-Tc). By way of preference, $B_1$, $B_2$, $B_4$ and $B_5$ are C—$R^6$, C—$R^7$, C—$R^9$, C—$R^{10}$, and $A_1$, $A_2$, $A_4$ are C—$R^2$, C—$R^3$, C—$R^5$, and $R^2$, $R^3$, $R^5$, $R^7$, $R^9$, $M_1$ and $M_2$ are in each case H, and $R^8$ is heptafluoroisopropyl, and $R^6$ and $R^{10}$ are in each case each independently halogen, preferably F or Cl, more preferably Cl, and Q is $C_1$-$C_3$-alkyl, preferably methyl or ethyl, and $E_1$ is N, and $E_2$ and $E_3$ are C—H.

The present invention therefore also relates to compounds of the formula (I')

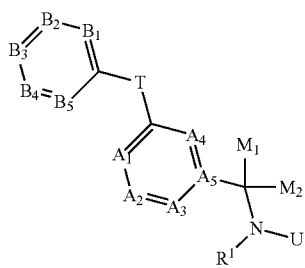

(I')

where U is —C(=W)-Q or —S(O)$_2$-Q and
B$_1$, B$_2$, B$_3$, B$_4$ and B$_5$, A$_1$, A$_2$, A$_3$, A$_4$ and A$_5$, T, R$^1$, M$_1$ and M$_2$ and Q may in each case have the definition specified in compounds of the formula (I) and preferred embodiments thereof and compounds of the formula (Ic) and preferred embodiments thereof.

The present invention therefore also relates to compounds of the formula (I")

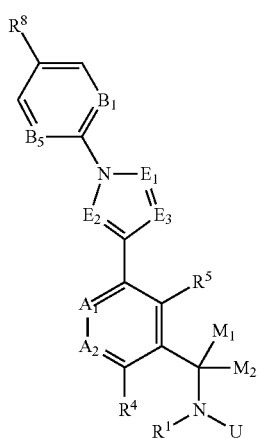

(I")

where U is —C(=W)-Q or —S(O)$_2$-Q and
B$_1$, and B$_5$, A$_1$, A$_2$, E$_1$, E$_2$, E$_3$, R$^1$, R$^4$, R$^5$, R$^8$ M$_1$, M$_2$ and Q may in each case have the meaning specified in the compounds of the formula (I') and preferred embodiments thereof. R$^8$ is preferably heptafluoroisopropyl.

A further aspect relates to a method for protecting transgenic or conventional seed and the plant that arises therefrom from infestation by pests, characterized in that the seed is treated with at least one compound of the formula (I) or a formula derived from formula (I) as described herein.

Yet a further aspect relates to the use of compounds of the formula (I) or a formula derived from formula (I) as described herein or of an insecticidal composition as described herein for controlling pests.

A further aspect relates to the use of compounds of the formula (I) or a formula derived from formula (I) as described herein in vector control.

Yet a further aspect relates to seed in which a compound of the formula (I) or a formula derived from formula (I) as described herein has been applied to the seed as a constituent of a coating or as a further layer or further layers in addition to a coating.

Accordingly, a further aspect relates to a method for applying a coating comprising at least one compounds of the formula (I) or a formula derived from formula (I) as described herein or for applying a compounds of the formula (I) or a formula derived from formula (I) as described herein, which is applied to seed as a layer or further layers in addition to a coating, comprising the steps of a) mixing seeds with a coating material consisting of or comprising a compounds of the formula (I) or a formula derived from formula (I) as described herein, b) enriching the coated seed composition obtained, c) drying the enriched seed composition obtained, d) dis- or deagglomerating the dried seed composition obtained.

Depending on the nature of the substituents, the compounds of the formula (I) or a formula derived from formula (I) described here may optionally be in the form of geometric and/or optically active isomers or corresponding isomer mixtures in different compositions. The invention relates both to the pure isomers and to the isomer mixtures.

The compounds according to the invention can also be present as metal complexes.

Definitions

The person skilled in the art is aware that, if not stated explicitly, the expressions "a" or "an" as used in the present application may, depending on the situation, mean "one (1)", "one (1) or more" or "at least one (1)".

For all the structures described herein, such as ring systems and groups, adjacent atoms must not be —O—O— or —O—S—.

Structures having a variable number of possible carbon atoms (C atoms) may be referred to in the present application as C$_{lower\ limit\ of\ carbon\ atoms}$-C$_{upper\ limit\ of\ carbon\ atoms}$ structures (C$_{LL}$—C$_{UL}$ structures), in order thus to be stipulated more specifically. Example: an alkyl group may consist of 3 to 10 carbon atoms and in that case corresponds to C$_3$-C$_{10}$-alkyl. Ring structures composed of carbon atoms and heteroatoms may be referred to as "LL- to UL-membered" structures. One example of a 6-membered ring structure is toluene (a 6-membered ring structure substituted by a methyl group).

If a collective term for a substituent, for example (C$_{LL}$—C$_{UL}$)-alkyl, is at the end of a composite substituent, for example (C$_{LL}$—C$_{UL}$)-cycloalkyl-(C$_{LL}$—C$_{UL}$)-alkyl, the constituent at the start of the composite substituent, for example the (C$_{LL}$—C$_{UL}$)-cycloalkyl, may be mono- or polysubstituted identically or differently and independently by the latter substituent, for example (C$_{LL}$—C$_{UL}$)-alkyl. All the collective terms used in this application for chemical groups, cyclic systems and cyclic groups can be stipulated more specifically through the addition "C$_{LL}$—C$_{UL}$" or "LL- to UL-membered".

Unless defined differently, the definition for collective terms also applies to these collective terms in composite substituents. Example: the definition of C$_{LL}$—C$_{UL}$-alkyl also applies to C$_{LL}$—C$_{UL}$-alkyl as part of a composite substituent, for example C$_L$L-C$_{UL}$-cycloalkyl-C$_{LL}$—C$_{UL}$-alkyl.

It is obvious to the person skilled in the art that examples given in the present application are not to be considered as limiting, but rather merely describe some embodiments in more detail.

In the definitions of the symbols given in the above formulae, collective terms which are generally representative of the following substituents were used:

Halogen refers to the elements of the 7th main group, preferably fluorine, chlorine, bromine and iodine, more preferably fluorine, chlorine and bromine and still more preferably fluorine and chlorine.

Examples of heteroatoms are N, O, S, P, B, Si. Preferably, the term "heteroatom" relates to N, S and O.

According to the invention, "alkyl"-on its own or as part of a chemical group—represents straight-chain or branched hydrocarbons preferably having 1 to 6 carbon atoms, for example methyl, ethyl, n-propyl, isopropyl, n-butyl, isobutyl, s-butyl, t-butyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, hexyl, 1-methylpentyl, 2-methylpentyl, 3-methylpentyl, 4-methylpentyl, 1,2-dimethylpropyl, 1,3-dimethylbutyl, 1,4-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl and 2-ethylbutyl. Preference is also given to alkyls having 1 to 4 carbon atoms such as, inter alia, methyl, ethyl, n-propyl, isopropyl, n-butyl, isobutyl, s-butyl or t-butyl. The alkyl groups according to the invention may be substituted by one or more identical or different radicals.

According to the invention, "alkenyl"—on its own or as part of a chemical group—represents straight-chain or branched hydrocarbons preferably having 2 to 6 carbon atoms and at least one double bond, for example vinyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-dimethyl-2-propenyl, 1-ethyl-1-methyl-2-propenyl and 1-ethyl-2-methyl-2-propenyl. Preference is also given to alkenyls having 2 to 4 carbon atoms such as, inter alia, 2-propenyl, 2-butenyl or 1-methyl-2-propenyl. The alkenyl groups according to the invention may be substituted by one or more identical or different radicals.

According to the invention, "alkynyl"—on its own or as part of a chemical group—represents straight-chain or branched hydrocarbons preferably having 2 to 6 carbon atoms and at least one triple bond, for example 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-3-butynyl, 1,2-dimethyl-3-butynyl, 2,2-dimethyl-3-butynyl, 1-ethyl-3-butynyl, 2-ethyl-3-butynyl, 1-ethyl-1-methyl-2-propynyl and 2,5-hexadiynyl. Preference is also given to alkynyls having 2 to 4 carbon atoms such as, inter alia, ethynyl, 2-propynyl or 2-butynyl-2-propenyl. The alkynyl groups according to the invention may be substituted by one or more identical or different radicals.

According to the invention, "cycloalkyl"—alone or as part of a chemical group—represents mono-, bi- or tricyclic hydrocarbons, preferably having 3 to 10 carbons, for example cyclopropyl, cyclobutyl, cyclopentyl, cyclohexyl, cycloheptyl, cyclooctyl, bicyclo[2.2.1]heptyl, bicyclo[2.2.2] octyl or adamantyl. Preference is also given to cycloalkyls having 3, 4, 5, 6 or 7 carbon atoms such as, inter alia, cyclopropyl or cyclobutyl. The cycloalkyl groups according to the invention may be substituted by one or more identical or different radicals.

According to the invention, "alkylcycloalkyl" represents mono-, bi- or tricyclic alkylcycloalkyl preferably having 4 to 10 or 4 to 7 carbon atoms, for example methylcyclopropyl, ethylcyclopropyl, isopropylcyclobutyl, 3-methylcyclopentyl and 4-methylcyclohexyl. Preference is also given to alkylcycloalkyls having 4, 5 or 7 carbon atoms such as, inter alia, ethylcyclopropyl or 4-methylcyclohexyl.

The alkylcycloalkyl groups according to the invention may be substituted by one or more identical or different radicals.

According to the invention, "cycloalkylalkyl" represents mono-, bi- or tricyclic cycloalkylalkyl preferably having 4 to 10 or 4 to 7 carbon atoms such as, for example, cyclopropylmethyl, cyclobutylmethyl, cyclopentylmethyl, cyclohexylmethyl and cyclopentylethyl. Preference is also given to cycloalkylalkyls having 4, 5 or 7 carbon atoms such as, inter alia, cyclopropylmethyl or cyclobutylmethyl. The cycloalkylalkyl groups according to the invention may be substituted by one or more identical or different radicals.

According to the invention, "hydroxyalkyl" represents a straight-chain or branched alcohol preferably having 1 to 6 carbon atoms such as, for example, methanol, ethanol, n-propanol, isopropanol, n-butanol, isobutanol, s-butanol and t-butanol. Preference is also given to hydroxyalkyl groups having 1 to 4 carbon atoms. The hydroxyalkyl groups according to the invention may be substituted by one or more identical or different radicals.

According to the invention, "alkoxy" represents a straight-chain or branched O-alkyl preferably having 1 to 6 carbon atoms such as, for example, methoxy, ethoxy, n-propoxy, isopropoxy, n-butoxy, isobutoxy, s-butoxy and t-butoxy. Preference is also given to alkoxy groups having 1 to 4 carbon atoms. The alkoxy groups according to the invention may be substituted by one or more identical or different radicals.

According to the invention, "alkylsulfanyl" represents straight-chain or branched S-alkyl preferably having 1 to 6 carbon atoms such as, for example, methylthio, ethylthio, n-propylthio, isopropylthio, n-butylthio, isobutylthio, s-butylthio and t-butylthio. Preference is also given to alkylsulfanyl groups having 1 to 4 carbon atoms. The alkylsulfanyl groups according to the invention may be substituted by one or more identical or different radicals.

According to the invention, "alkylsulfinyl" represents straight-chain or branched alkylsulfinyl preferably having 1 to 6 carbon atoms such as, for example, methylsulfinyl, ethylsulfinyl, n-propylsulfinyl, isopropylsulfinyl, n-butylsulfinyl, isobutylsulfinyl, s-butylsulfinyl and t-butylsulfinyl. Preference is also given to alkylsulfinyl groups having 1 to 4 carbon atoms. The alkylsulfinyl groups according to the invention may be substituted by one or more identical or different radicals.

According to the invention, "alkylsulfonyl" represents straight-chain or branched alkylsulfonyl preferably having 1 to 6 carbon atoms such as, for example, methylsulfonyl, ethylsulfonyl, n-propylsulfonyl, isopropylsulfonyl, n-butylsulfonyl, isobutylsulfonyl, s-butylsulfonyl and t-butylsulfonyl. Preference is also given to alkylsulfonyl groups having 1 to 4 carbon atoms. The alkylsulfonyl groups according to the invention may be substituted by one or more identical or different radicals.

According to the invention, "alkylcarbonyl" represents straight-chain or branched alkyl-C(=O) preferably having 2 to 7 carbon atoms such as methylcarbonyl, ethylcarbonyl, n-propylcarbonyl, isopropylcarbonyl, s-butylcarbonyl and t-butylcarbonyl. Preference is also given to alkylcarbonyls having 1 to 4 carbon atoms. The alkylcarbonyls according to the invention may be substituted by one or more identical or different radicals.

According to the invention, "cycloalkylcarbonyl" represents straight-chain or branched cycloalkylcarbonyl preferably having 3 to 10 carbon atoms in the cycloalkyl moiety such as, for example, cyclopropylcarbonyl, cyclobutylcarbonyl, cyclopentylcarbonyl, cyclohexylcarbonyl, cycloheptylcarbonyl, cyclooctylcarbonyl, bicyclo[2.2.1]heptyl, bicyclo[2.2.2]octylcarbonyl and adamantylcarbonyl. Preference is also given to cycloalkylcarbonyl having 3, 5 or 7 carbon atoms in the cycloalkyl moiety. The cycloalkylcarbonyl groups according to the invention may be substituted by one or more identical or different radicals.

According to the invention, "alkoxycarbonyl"—alone or as a constituent of a chemical group—represents straight-chain or branched alkoxycarbonyl, preferably having 1 to 6 carbon atoms or having 1 to 4 carbon atoms in the alkoxy moiety such as, for example, methoxycarbonyl, ethoxycarbonyl, n-propoxycarbonyl, isopropoxycarbonyl, s-butoxycarbonyl and t-butoxycarbonyl. The alkoxycarbonyl groups according to the invention may be substituted by one or more identical or different radicals.

According to the invention, "alkylaminocarbonyl" represents straight-chain or branched alkylaminocarbonyl having preferably 1 to 6 carbon atoms or 1 to 4 carbon atoms in the alkyl moiety, for example methylaminocarbonyl, ethylaminocarbonyl, n-propylaminocarbonyl, isopropylaminocarbonyl, s-butylaminocarbonyl and t-butylaminocarbonyl. The alkylaminocarbonyl groups according to the invention may be substituted by one or more identical or different radicals.

According to the invention, "N,N-dialkylaminocarbonyl" represents straight-chain or branched N,N-dialkylaminocarbonyl having preferably 1 to 6 carbon atoms or 1 to 4 carbon atoms in the alkyl moiety, such as, for example, N,N-dimethylaminocarbonyl, N,N-diethylaminocarbonyl, N,N-di(n-propylamino)carbonyl, N,N-di(isopropylamino)carbonyl and N,N-di-(s-butylamino)carbonyl. The N,N-dialkylaminocarbonyl groups according to the invention may be substituted by one or more identical or different radicals.

According to the invention, "aryl" represents a mono-, bi- or polycyclic aromatic system having preferably 6 to 14, in particular 6 to 10 ring carbon atoms such as, for example, phenyl, naphthyl, anthryl, phenanthrenyl, preferably phenyl. In addition, aryl also represents polycyclic systems such as tetrahydronaphthyl, indenyl, indanyl, fluorenyl, biphenyl, where the bonding site is on the aromatic system. The aryl groups according to the invention may be substituted by one or more identical or different radicals.

Examples of substituted aryls are the arylalkyls, which may likewise be substituted by one or more identical or different radicals in the $C_1$-$C_4$-alkyl and/or $C_6$-$C_{14}$-aryl moiety. Examples of such arylalkyls include benzyl and 1-phenylethyl.

According to the invention, "heterocycle", "heterocyclic ring" or "heterocyclic ring system" represents a carbocyclic ring system having at least one ring in which at least one carbon atom is replaced by a heteroatom, preferably by a heteroatom from the group consisting of N, O, S, P, B, Si, Se, and which is saturated, unsaturated or heteroaromatic and may this be unsubstituted or substituted, where the bonding site is on a ring atom. Unless defined differently, the heterocyclic ring contains preferably 3 to 9 ring atoms, especially 3 to 6 ring atoms, and one or more, preferably 1 to 4, especially 1, 2 or 3, heteroatoms in the heterocyclic ring, preferably from the group consisting of N, O, and S, although no two oxygen atoms should be directly adjacent. The heterocyclic rings usually contain not more than 4 nitrogen atoms and/or not more than 2 oxygen atoms and/or not more than 2 sulfur atoms. If the heterocyclyl radical or the heterocyclic ring is optionally substituted, it may be fused to other carbocyclic or heterocyclic rings. In the case of optionally substituted heterocyclyl, the invention also embraces polycyclic systems, for example 8-azabicyclo [3.2.1]octanyl or 1-azabicyclo[2.2.1]heptyl. In the case of optionally substituted heterocyclyl, the invention also embraces spirocyclic systems, for example 1-oxa-5-azaspiro [2.3]hexyl.

Heterocyclyl groups according to the invention are, for example, piperidinyl, piperazinyl, morpholinyl, thiomorpholinyl, dihydropyranyl, tetrahydropyranyl, dioxanyl, pyrrolinyl, pyrrolidinyl, imidazolinyl, imidazolidinyl, thiazolidinyl, oxazolidinyl, dioxolanyl, dioxolyl, pyrazolidinyl, tetrahydrofuranyl, dihydrofuranyl, oxetanyl, oxiranyl, azetidinyl, aziridinyl, oxazetidinyl, oxaziridinyl, oxazepanyl, oxazinanyl, azepanyl, oxopyrrolidinyl, dioxopyrrolidinyl, oxomorpholinyl, oxopiperazinyl and oxepanyl.

Heteroarylene, i.e. heteroaromatic systems, has a particular meaning. According to the invention, the expression "heteroaryl" represents heteroaromatic compounds, i.e. fully unsaturated aromatic heterocyclic compounds covered by the above definition of heterocycles, preferably 5- to 7-membered rings having 1 to 3, preferably 1 or 2, identical or different heteroatoms from the abovementioned group. Heteroaryls according to the invention are, for example, furyl, thienyl, pyrazolyl, imidazolyl, 1,2,3- and 1,2,4-triazolyl, isoxazolyl, thiazolyl, isothiazolyl, 1,2,3-, 1,3,4-, 1,2,4- and 1,2,5-oxadiazolyl, azepinyl, pyrrolyl, pyridyl, pyridazinyl, pyrimidinyl, pyrazinyl, 1,3,5-, 1,2,4- and 1,2,3-triazinyl, 1,2,4-, 1,3,2-, 1,3,6- and 1,2,6-oxazinyl, oxepinyl, thiepinyl, 1,2,4-triazolonyl and 1,2,4-diazepinyl. The heteroaryl groups according to the invention may also be substituted by one or more identical or different radicals.

The expression "(optionally) substituted" groups/substituents, such as a substituted alkyl, alkenyl, alkynyl, alkoxy, alkylsulfanyl, alkylsulfinyl, alkylsulfonyl, cycloalkyl, aryl, phenyl, benzyl, heterocyclyl and heteroaryl radical, signify for example a substituted radical derived from an unsubstituted base structure, wherein the substituents are for example one (1) substituent or more than one substituents, preferably 1, 2, 3, 4, 5, 6, or 7, selected from a group consisting of amino, hydroxy, halogen, nitro, cyano, isocyano, mercapto, isothiocyanato, $C_1$-$C_4$-carboxy, carbonamide, $SF_5$, aminosulfonyl, $C_1$-$C_4$-alkyl, $C_3$-$C_4$-cycloalkyl, $C_2$-$C_4$-alkenyl, $C_3$-$C_4$-cycloalkenyl, $C_2$-$C_4$-alkynyl, N-mono-$C_1$-$C_4$-alkylamino, N,N-di-$C_1$-$C_4$-alkylamino, N—$C_1$-$C_4$-alkanoylamino, $C_1$-$C_4$-alkoxy, $C_2$-$C_4$-alkenyloxy, $C_2$-$C_4$-alkynyloxy, $C_3$-$C_4$-cycloalkoxy, $C_3$-$C_4$-cycloalkenyloxy, $C_1$-$C_4$-alkoxycarbonyl, $C_2$-$C_4$—$C_2$-$C_4$-alkenyloxycarbonyl, $C_2$-$C_4$-alkynyloxycarbonyl, $C_6$-, $C_{10}$-, $C_{14}$-aryloxycarbonyl, $C_1$-$C_4$-alkanoyl, $C_2$-$C_4$-alkenylcarbonyl, $C_2$-$C_4$-alkynylcarbonyl, $C_6$-, $C_{10}$-, $C_{14}$-arylcarbonyl, $C_1$-$C_4$-alkylsulfanyl, $C_3$-$C_4$-cycloalkylsulfanyl, $C_1$-$C_4$-alkylthio, $C_2$-$C_4$-alkenylthio, $C_3$-$C_4$-cycloalkenylthio, $C_2$-$C_4$-alkynylthio, $C_1$-$C_4$-alkylsulfenyl and $C_1$-$C_4$-alkylsulfinyl, wherein both enantiomers of the $C_1$-$C_4$-alkylsulfinyl group are included, $C_1$-$C_4$-alkylsulfonyl, N-mono-$C_1$-$C_4$-alkylaminosulfonyl, N,N-di-$C_1$-$C_4$-alkylaminosulfonyl, $C_1$-$C_4$-alkylphosphinyl, $C_1$-$C_4$-alkylphosphonyl, wherein for $C_1$-$C_4$-alkylphosphinyl and $C_1$-$C_4$-alkylphosphonyl both enantiomers are included, N—$C_1$-$C_4$-alkylaminocarbonyl, N,N-di-$C_1$-$C_4$-alkylaminocarbonyl, N—$C_1$-$C_4$-alkanoylaminocarbonyl, N—$C_1$-$C_4$-alkanoyl-N—$C_1$-$C_4$-alkylaminocarbonyl, $C_6$-, $C_{10}$-, $C_{14}$-aryl, $C_6$-, $C_{10}$-, $C_{14}$-aryloxy, benzyl, benzyloxy, benzylthio, $C_6$-, $C_{10}$-, $C_{14}$-arylthio, $C_6$-, $C_{10}$-, $C_{14}$-arylamino, benzylamino, heterocyclyl and trialkylsilyl, substituents attached by a double bond such as $C_1$-$C_4$-alkylidene (e.g. methylidene or ethylidene), an oxo group, an imino group and also a substituted imino group. Particularly preferred substituted groups are halogenated groups. If two or more radicals form one or more rings, these may be carbocyclic, heterocyclic, saturated, partially saturated, unsaturated, for example also aromatic and further-substituted.

The substituents mentioned by way of example ("first substituent level") may, if they contain hydrocarbonaceous components, optionally be further substituted therein ("second substituent level"), for example by one or more of the substituents each independently selected from halogen, hydroxyl, amino, nitro, cyano, isocyano, azido, acylamino, an oxo group and an imino group. The term "(optionally) substituted" group preferably embraces just one or two substituent levels.

The inventive halogen-substituted chemical groups or halogenated groups (for example alkyl or alkoxy) are mono- or polysubstituted by halogen up to the maximum possible number of substituents. Such groups are also referred to as halo groups (for example haloalkyl). In the case of polysubstitution by halogen, the halogen atoms may be identical or different, and may all be bonded to one carbon atom or may be bonded to a plurality of carbon atoms. Here, halogen represents in particular fluorine, chlorine, bromine or iodine, preferably fluorine, chlorine or bromine and more preferably fluorine or Cl. More particularly, halogen-substituted groups are monohalocycloalkyl such as 1-fluorocyclopropyl, 2-fluorocyclopropyl or 1-fluorocyclobutyl, monohaloalkyl such as 2-chloroethyl, 2-fluoroethyl, 1-chloroethyl, 1-fluoroethyl, chloromethyl, or fluoromethyl; perhaloalkyl such as trichloromethyl or trifluoromethyl or $CF_2CF_3$, polyhaloalkyl such as difluoromethyl, 2-fluoro-2-chloroethyl, dichloromethyl, 1,1,2,2-tetrafluoroethyl or 2,2,2-trifluoroethyl. Further examples of haloalkyls are trichloromethyl, chlorodifluoromethyl, dichlorofluoromethyl, chloromethyl, bromomethyl, 1-fluoroethyl, 2-fluoroethyl, 2,2-difluoroethyl, 2,2,2-trifluoroethyl, 2,2,2-trichloroethyl, 2-chloro-2,2-difluoroethyl, pentafluoroethyl, 3,3,3-trifluoropropyl and pentafluoro-t-butyl. Preference is given to haloalkyl groups having 1 to 4 carbon atoms and 1 to 9, preferably 1 to 5, identical or different halogen atoms selected from fluorine, chlorine and bromine. Particular preference is given to haloalkyls having 1 or 2 carbon atoms and 1 to 5 identical or different halogen atoms selected from fluorine and chlorine, such as, inter alia, difluoromethyl, trifluoromethyl or 2,2-difluoroethyl. Further examples of compounds substituted by halogen are haloalkoxy such as $OCF_3$, $OCHF_2$, $OCH_2F$, $OCF_2CF_3$, $OCH_2CF_3$, $OCH_2CHF_2$ and $OCH_2CH_2Cl$, haloalkylsulfanyls such as difluoromethylthio, trifluoromethylthio, trichloromethylthio, chlorodifluoromethylthio, 1-fluoroethylthio, 2-fluoroethylthio, 2,2-difluoroethylthio, 1,1,2,2-tetrafluoroethylthio, 2,2,2-trifluoroethylthio or 2-chloro-1,1,2-trifluoroethylthio, haloalkylsulfinyls such as difluoromethylsulfinyl, trifluoromethylsulfinyl, trichloromethylsulfinyl, chlorodifluoromethylsulfinyl, 1-fluoroethylsulfinyl, 2-fluoroethylsulfinyl, 2,2-difluoroethylsulfinyl, 1,1,2,2-tetrafluoroethylsulfinyl, 2,2,2-trifluorethylsulfinyl and 2-chloro-1,1,2-difluoroethylsulfinyl, haloalkylsulfinyls such as difluoromethylsulfinyl, trifluoromethylsulfinyl, trichloromethylsulfinyl, chlorodifluoromethylsulfinyl, 1-fluoroethylsulfinyl, 2-fluoroethylsulfinyl, 2,2-difluoroethylsulfinyl, 1,1,2,2-tetrafluoroethylsulfinyl, 2,2,2-trifluoroethylsulfinyl and 2-chloro-1,1,2-trifluoroethylsulfinyl, haloalkylsulfonyl groups such as difluoromethylsulfonyl, trifluoromethylsulfonyl, trichloromethylsulfonyl, chlorodifluoromethylsulfonyl, 1-fluoroethylsulfonyl, 2-fluoroethylsulfonyl, 2,2-difluoroethylsulfonyl, 1,1,2,2-tetrafluoroethylsulfonyl, 2,2,2-trifluoroethylsulfonyl and 2-chloro-1,1,2-trifluoroethylsulfonyl.

In the case of radicals having carbon atoms, preference is given to those having 1 to 4 carbon atoms, especially 1 or 2 carbon atoms. Preference is generally given to substituents from the group of halogen, for example fluorine and chlorine, ($C_1$-$C_4$)alkyl, preferably methyl or ethyl, ($C_1$-$C_4$)haloalkyl, preferably trifluoromethyl, ($C_1$-$C_4$)alkoxy, preferably methoxy or ethoxy, ($C_1$-$C_4$)haloalkoxy, nitro and cyano. Particular preference is given here to the substituents methyl, methoxy, fluorine and chlorine.

Substituted amino such as mono- or disubstituted amino is a radical from the group of the substituted amino radicals N-substituted, for example, by one or two identical or different radicals from the group of alkyl, hydroxyl, amino, alkoxy, acyl and aryl; preferably N-mono- and N,N-dialkylamino (e.g. methylamino, ethylamino, N,N-dimethylamino, N,N-diethylamino, N,N-di-n-propylamino, N,N-diisopropylamino or N,N-dibutylamino), N-mono- or N,N-dialkoxyalkylamino groups (e.g. N-methoxymethylamino, N-methoxyethylamino, N,N-di(methoxymethyl)amino or N,N-di(methoxyethyl)amino), N-mono- and N,N-diarylamino, such as optionally substituted anilines, acylamino, N,N-diacylamino, N-alkyl-N-arylamino, N-alkyl-N-acylamino and saturated N-heterocycles; preference is given to alkyl radicals having 1 to 4 carbon atoms; aryl is preferably phenyl or substituted phenyl; acyl is as defined further down, preferably ($C_1$-$C_4$)alkanoyl. The same applies to substituted hydroxylamino or hydrazino.

According to the invention, the term "cyclic amino groups" embraces heteroaromatic or aliphatic ring systems having one or more nitrogen atoms. The heterocycles are saturated or unsaturated, consist of one or more optionally fused ring systems and optionally include further heteroatoms, for example one or two nitrogen, oxygen and/or sulfur atoms. In addition, the term also embraces groups having a Spiro ring or a bridged ring system. The number of atoms which form the cyclic amino group is not limited and may be, for example, in the case of a one-ring system 3 to 8 ring atoms, and in the case of a two-ring system 7 to 11 atoms.

Examples of cyclic amino groups having saturated and unsaturated monocyclic groups having a nitrogen atom as heteroatom include 1-azetidinyl, pyrrolidino, 2-pyrrolidin-1-yl, 1-pyrrolyl, piperidino, 1,4-dihydropyrazin-1-yl, 1,2,5,6-tetrahydropyrazin-1-yl, 1,4-dihydropyridin-1-yl, 1,2,5,6-tetrahydropyridin-1-yl, homopiperidinyl; examples of cyclic amino groups having saturated and unsaturated monocyclic groups having two or more nitrogen atoms as heteroatoms include 1-imidazolidinyl, 1-imidazolyl, 1-pyrazolyl, 1-triazolyl, 1-tetrazolyl, 1-piperazinyl, 1-homopiperazinyl, 1,2-dihydropiperazin-1-yl, 1,2-dihydropyrimidin-1-yl, perhydropyrimidin-1-yl, 1,4-diazacycloheptan-1-yl; examples of cyclic amino groups having saturated and unsaturated monocyclic groups having one or two oxygen atoms and one to three nitrogen atoms as heteroatoms, for example oxazolidin-3-yl, 2,3-dihydroisoxazol-2-yl, isoxazol-2-yl, 1,2,3-oxadiazin-2-yl, morpholino, examples of cyclic amino groups having saturated and unsaturated monocyclic groups having one to three nitrogen atoms and one to two sulfur atoms as heteroatoms include thiazolidin-3-yl, isothiazolin-2-yl, thiomorpholino, or dioxothiomorpholino; examples of cyclic amino groups having saturated and unsaturated fused cyclic groups include indol-1-yl, 1,2-dihydrobenzimidazol-1-yl, perhydropyrrolo[1.2-a]pyrazin-2-yl; examples of cyclic amino groups having spirocyclic groups include 2-azaspiro [4.5]decan-2-yl; examples of cyclic amino groups having bridged heterocyclic groups include 2-azabicyclo[2.2.1]heptan-7-yl.

Substituted amino also includes quaternary ammonium compounds (salts) having four organic substituents on the nitrogen atom.

Optionally substituted phenyl is preferably phenyl which is unsubstituted or mono- or polysubstituted, preferably up to trisubstituted, by identical or different radicals from the group of halogen, ($C_1$-$C_4$)-alkyl, ($C_1$-$C_4$)-alkoxy, ($C_1$-$C_4$)-alkoxy-($C_1$-$C_4$)-alkoxy, ($C_1$-$C_4$)-alkoxy-($C_1$-$C_4$)-alkyl, ($C_1$-$C_4$)-haloalkyl, ($C_1$-$C_4$)-haloalkoxy, ($C_1$-$C_4$)-alkylsulfanyl, ($C_1$-$C_4$)-haloalkylsulfanyl, cyano, isocyano and nitro, for example o-, m- and p-tolyl, dimethylphenyls, 2-, 3- and 4-chlorophenyl, 2-, 3- and 4-fluorophenyl, 2-, 3- and 4-trifluoromethyl- and -trichloromethylphenyl, 2,4-, 3,5-, 2,5- and 2,3-dichlorophenyl, o-, m- and p-methoxyphenyl, 4-heptafluorophenyl.

Optionally substituted cycloalkyl is preferably cycloalkyl, which is unsubstituted or mono- or polysubstituted, preferably up to trisubstituted, by identical or different radicals from the group of halogen, cyano, $C_1$-$C_4$-alkyl, $C_1$-$C_4$-alkoxy, $C_1$-$C_4$-alkoxy-$C_1$-$C_4$-alkoxy, $C_1$-$C_4$-alkoxy-$C_1$-$C_4$-alkyl, $C_1$-$C_4$-haloalkyl and $C_1$-$C_4$-haloalkoxy, especially substituted by one or two $C_1$-$C_4$-alkyl radicals.

Optionally substituted heterocyclyl is preferably heterocyclyl which is unsubstituted or mono- or polysubstituted, preferably up to trisubstituted, by identical or different radicals from the group of halogen, cyano, $C_1$-$C_4$-alkyl, $C_1$-$C_4$-alkoxy, $C_1$-$C_4$-alkoxy-$C_1$-$C_4$-alkoxy, $C_1$-$C_4$-alkoxy-$C_1$-$C_4$-alkyl, $C_1$-$C_4$-haloalkyl, $C_1$-$C_4$-haloalkoxy, nitro and oxo, especially mono- or polysubstituted by radicals from the group of halogen, $C_1$-$C_4$-alkyl, $C_1$-$C_4$-alkoxy, $C_1$-$C_4$-haloalkyl and oxo, most preferably substituted by one or two $C_1$-$C_4$-alkyl radicals.

Examples of alkyl-substituted heteroaryl groups are furylmethyl, thienylmethyl, pyrazolylmethyl, imidazolylmethyl, 1,2,3- and 1,2,4-triazolylmethyl, isoxazolylmethyl, thiazolylmethyl, isothiazolylmethyl, 1,2,3-, 1,3,4-, 1,2,4- and 1,2,5-oxadiazolylmethyl, azepinylmethyl, pyrrolylmethyl, pyridylmethyl, pyridazinylmethyl, pyrimidinylmethyl, pyrazinylmethyl, 1,3,5-, 1,2,4- and 1,2,3-triazinylmethyl, 1,2,4-, 1,3,2-, 1,3,6- and 1,2,6-oxazinylmethyl, oxepinylmethyl, thiepinylmethyl and 1,2,4-diazepinylmethyl.

Inventive compounds may occur in preferred embodiments. Individual embodiments described herein may be combined with one another. Not included are combinations which contravene the laws of nature and which the person skilled in the art would therefore rule out on the basis of his/her expert knowledge. Ring structures having three or more adjacent oxygen atoms, for example, are excluded.

Isomers

Depending on the nature of the substituents, the compounds of the formula (I) may take the form of geometric and/or optically active isomers or corresponding isomer mixtures in different compositions. These stereoisomers are, for example, enantiomers, diastereomers, atropisomers or geometric isomers. The invention therefore encompasses pure stereoisomers and any desired mixtures of these isomers.

Methods and Uses

The invention also relates to methods for controlling animal pests, in which compounds of the formula (I) are allowed to act on animal pests and/or their habitat. The control of the animal pests is preferably carried out in agriculture and forestry, and in material protection. This preferably excludes methods for surgical or therapeutic treatment of the human or animal body and diagnostic methods carried out on the human or animal body.

The invention further relates to the use of the compounds of the formula (I) as pesticides, especially crop protection agents.

In the context of the present application, the term "pesticide" also always encompasses the term "crop protection agent".

The compounds of the formula (I), given good plant tolerance, favourable homeotherm toxicity and good environmental compatibility, are suitable for protecting plants and plant organs against biotic and abiotic stress factors, for increasing harvest yields, for improving the quality of the harvested material and for controlling animal pests, especially insects, arachnids, helminths, nematodes and molluscs, which are encountered in agriculture, in horticulture, in animal husbandry, in aquatic cultures, in forests, in gardens and leisure facilities, in the protection of stored products and of materials, and in the hygiene sector.

In the context of the present patent application, the term "hygiene" is understood as meaning the entirety of all measures, processes and procedures whose aim it is to prevent disorders—in particular infective diseases—and to serve to keep humans, animals and/or the environment healthy and/or to maintain cleanliness. According to the invention, this includes in particular measures for cleaning, disinfecting and sterilizing, for example, textiles or hard surfaces, mainly made of glass, wood, concrete, porcelain, ceramic, plastic or else of metal(s), and keeping them clean of hygiene pests and/or their faeces. Excluded according to the invention are in this respect again processes for the surgical or therapeutic treatment of the human or animal body and diagnostic processes undertaken on the human or animal body.

The term "hygiene sector" thus includes all areas, technical fields and commercial utilizations in which such hygiene measures, processes and procedures are of importance, for example hygiene in kitchens, bakeries, airports, baths, swimming pools, shopping centres, hotels, hospitals, stables, etc.

Accordingly, the term "hygiene pest" is understood as meaning one or more animal pests whose presence in the hygiene sector is problematic, in particular for health reasons. Accordingly, the main aim is to minimize or prevent hygiene pests or contact therewith in the hygiene sector. This can be effected, in particular, by using a pesticide, where the agent can be employed both prophylactically and only in the case of infestation to control the pest. It is also possible to use agents which act by avoiding or reducing contact with the pest. Hygiene pests are, for example, the organisms mentioned below.

Thus, the term "hygiene protection" includes all actions which serve to maintain and/or improve such hygiene measures, processes and procedures.

The compounds of the formula (I) can preferably be used as pesticides. They are active against normally sensitive and resistant species and also against all or specific stages of development. The abovementioned pests include:

Pests from the phylum of the Arthropoda, especially from the class of the Arachnida, for example *Acarus* spp., for example *Acarus siro, Aceria kuko, Aceria sheldoni, Aculops* spp., *Aculus* spp., for example *Aculus fockeui, Aculus schlechtendali, Amblyomma* spp., *Amphitetranychus viennensis, Argas* spp., *Boophilus* spp., *Brevipalpus* spp., for example *Brevipalpus phoenicis, Bryobia graminum, Bryobia praetiosa, Centruroides* spp., *Chorioptes* spp., *Dermanyssus gallinae, Dermatophagoides pteronyssinus, Dermatophagoides farinae, Dermacentor* spp., *Eotetranychus* spp., for example *Eotetranychus hicoriae, Epitrimerus pyri, Eutetranychus* spp., for example *Eutetranychus banksi, Eriophyes* spp., for example *Eriophyes pyri, Glycyphagus domesticus, Halotydeus destructor, Hemitarsonemus* spp., for example *Hemitarsonemus latus (=Polyphagotarsonemus latus), Hyalomma* spp., *Ixodes* spp., *Latrodectus* spp., *Loxosceles* spp., *Neutrombicula autumnalis, Nuphersa* spp., *Oligonychus* spp., for example *Oligonychus coffeae, Oligonychus coniferarum, Oligonychus ilicis, Oligonychus indicus, Oligonychus mangiferus, Oligonychus pratensis, Oligonychus punicae, Oligonychus yothersi, Ornithodorus* spp., *Ornithonyssus* spp., *Panonychus* spp., for example *Panonychus citri (=Metatetranychus citri), Panonychus ulmi (=Metatetranychus ulmi), Phyllocoptruta oleivora, Platytetranychus multidigituli, Polyphagotarsonemus latus, Psoroptes* spp., *Rhipicephalus* spp., *Rhizoglyphus* spp., *Sarcoptes* spp., *Scorpio maurus, Steneotarsonemus* spp., *Steneotarsonemus spinki, Tarsonemus* spp., for example *Tarsonemus confusus, Tarsonemus pallidus, Tetranychus* spp., for example *Tetranychus canadensis, Tetranychus cinnabarinus, Tetranychus turkestani, Tetranychus urticae, Trombicula alfreddugesi, Vaejovis* spp., *Vasates lycopersici;* from the class of the Chilopoda, for example *Geophilus* spp., *Scutigera* spp.;

from the order or the class of the Collembola, for example *Onychiurus armatus; Sminthurus viridis;* from the class of the Diplopoda, for example *Blaniulus guttulatus;* from the class of the Insecta, for example from the order of the Blattodea, for example *Blatta orientalis, Blattella asahinai, Blattella germanica, Leucophaea maderae, Loboptera decipiens, Neostylopyga rhombifolia, Panchlora* spp., *Parcoblatta* spp., *Periplaneta* spp., for example *Periplaneta americana, Periplaneta australasiae, Pycnoscelus surinamensis, Supella longipalpa;* from the order of the Coleoptera, for example *Acalymma vittatum, Acanthoscelides obtectus, Adoretus* spp., *Aethina tumida, Agelastica alni, Agriotes* spp., for example *Agriotes linneatus, Agriotes mancus, Alphitobius diaperinus, Amphimallon solstitialis, Anobium punctatum, Anoplophora* spp., *Anthonomus* spp., for example *Anthonomus grandis, Anthrenus* spp., *Apion* spp., *Apogonia* spp., *Atomaria* spp., for example *Atomaria linearis, Attagenus* spp., *Buis caerulescens, Bruchidius obtectus, Bruchus* spp., for example *Bruchus pisorum, Bruchus rufimanus, Cassida* spp., *Cerotoma trifurcata, Ceutorrhynchus* spp., for example *Ceutorrhynchus assimilis, Ceutorrhynchus quadridens, Ceutorrhynchus rapae, Chaetocnema* spp., for example *Chaetocnema confinis, Chaetocnema denticulata, Chaetocnema ectypa, Cleonus mendicus, Conoderus* spp., *Cosmopolites* spp., for example *Cosmopolites sordidus, Costelytra zealandica, Ctenicera* spp., *Curculio* spp., for example *Curculio caryae, Curculio caryatrypes, Curculio obtusus, Curculio sayi, Cryptolestes ferrugineus, Cryptolestes pusillus, Cryptorhynchus lapathi, Cryptorhynchus mangiferae, Cylindrocopturus* spp., *Cylindrocopturus adspersus, Cylindrocopturus furnissi, Dermestes* spp., *Diabrotica* spp., for example *Diabrotica balteata, Diabrotica barberi, Diabrotica undecimpunctata howardi, Diabrotica undecimpunctata undecimpunctata, Diabrotica virgifera virgifera, Diabrotica virgifera zeae, Dichocrocis* spp., *Dicladispa armigera, Diloboderus* spp., *Epicaerus* spp., *Epilachna* spp., for example *Epilachna borealis, Epilachna varivestis, Epitrix* spp., for example *Epitrix cucumeris, Epitrix furcula, Epitrix hirtipennis, Epitrix subcrinita, Epitrix tuberis, Faustinus* spp., *Gibbium psylloides, Gnathocerus cornutus, Hellula undalis, Heteronychus arator, Heteronyx* spp., *Hylamorpha elegans, Hylotrupes bajulus, Hypera postica, Hypomeces squamosus, Hypothenemus* spp., for example *Hypothenemus hampei, Hypothenemus obscurus, Hypothenemus pubescens, Lachnosterna consanguinea, Lasioderma serricorne, Latheticus oryzae, Lathridius* spp., *Lema* spp., *Leptinotarsa decemlineata, Leucoptera* spp., for example *Leucoptera coffeella, Lissorhoptrus oryzophilus, Listronotus (=Hyperodes)* spp., *Lixus* spp., *Luperodes* spp., *Luperomorpha xanthodera, Lyctus* spp., *Megascelis* spp., *Melanotus* spp., for example *Melanotus longulus oregonensis, Meligethes aeneus, Melolontha* spp., for example *Melolontha melolontha, Migdolus* spp., *Monochamus* spp., *Naupactus xanthographus, Necrobia* spp., *Neogalerucella* spp., *Niptus hololeucus, Oryctes rhinoceros, Oryzaephilus surinamensis, Oryzaphagus oryzae, Otiorhynchus* spp., for example *Otiorhynchus cribricollis, Otiorhynchus ligustici, Otiorhynchus ovatus, Otiorhynchus rugosostriarus, Otiorhynchus sulcatus, Oulema* spp., for example *Oulema melanopus, Oulema oryzae, Oxycetonia jucunda, Phaedon cochleariae, Phyllophaga* spp., *Phyllophaga helleri, Phyllotreta* spp., for example *Phyllotreta armoraciae, Phyllotreta pusilla, Phyllotreta ramosa, Phyllotreta striolata, Popillia japonica, Premnotrypes* spp., *Prostephanus truncatus, Psylliodes* spp., for example *Psylliodes affinis, Psylliodes chrysocephala, Psylliodes punctulata, Ptinus* spp., *Rhizobius ventralis, Rhizopertha dominica, Rhynchophorus* spp., *Rhynchophorus ferrugineus, Rhynchophorus palmarum, Sinoxylon perforans, Sitophilus* spp., for example *Sitophilus granarius, Sitophilus linearis, Sitophilus oryzae, Sitophilus zeamais, Sphenophorus* spp., *Stegobium paniceum, Sternechus* spp., for example *Sternechus paludatus, Symphyletes* spp., *Tanymecus* spp., for example *Tanymecus dilaticollis, Tanymecus indicus, Tanymecus palliatus, Tenebrio molitor, Tenebrioides mauretanicus, Tribolium* spp., for example *Tribolium audax, Tribolium castaneum, Tribolium confusum, Trogoderma* spp., *Tychius* spp., *Xylotrechus* spp., *Zabrus* spp., for example *Zabrus tenebrioides;* from the order of the Dermaptera, for example *Anisolabis maritime, Forficula auricularia, Labidura riparia;* from the order of the Diptera, for example *Aedes* spp., for example *Aedes aegypti, Aedes albopictus, Aedes sticticus, Aedes vexans, Agromyza* spp., for example *Agromyza frontella, Agromyza parvicornis, Anastrepha* spp., *Anopheles* spp., for example *Anopheles quadrimaculatus, Anopheles gambiae, Asphondylia* spp., *Bactrocera* spp., for example *Bactrocera cucurbitae, Bactrocera dorsalis, Bactrocera oleae, Bibio hortulanus, Calliphora erythrocephala, Calliphora vicina, Ceratitis capitata, Chironomus* spp., *Chrysomya* spp., *Chrysops* spp., *Chrysozona pluvialis, Cochliomya* spp., *Contarinia* spp., for example *Contarinia johnsoni, Contarinia nasturtii, Contarinia pyrivora, Contarinia schulzi, Contarinia sorghicola, Contarinia tritici, Cordylobia anthropophaga, Cricotopus sylvestris, Culex* spp., for example *Culex pipiens, Culex quinquefasciatus, Culicoides* spp., *Culiseta* spp., *Cuterebra* spp., *Dacus oleae, Dasineura* spp., for example *Dasineura brassicae, Delia* spp., for example *Delia antiqua, Delia coarctata, Delia florilega, Delia platura, Delia radicum, Dermatobia hominis, Drosophila* spp., for example *Drosphila melanogaster, Drosophila*

*suzukii, Echinocnemus* spp., *Euleia heraclei, Fannia* spp., *Gasterophilus* spp., *Glossina* spp., *Haematopota* spp., *Hydrellia* spp., *Hydrellia griseola, Hylemya* spp., *Hippobosca* spp., *Hypoderma* spp., *Liriomyza* spp., for example *Liriomyza brassicae, Liriomyza huidobrensis, Liriomyza sativae, Lucilia* spp., for example *Lucilia cuprina, Lutzomyia* spp., *Mansonia* spp., *Musca* spp., for example *Musca domestica, Musca domestica vicina, Oestrus* spp., *Oscinella frit, Paratanytarsus* spp., *Paralauterborniella subcincta, Pegomya* or *Pegomyia* spp., for example *Pegomya betae, Pegomya hyoscyami, Pegomya rubivora, Phlebotomus* spp., *Phorbia* spp., *Phormia* spp., *Piophila casei, Platyparea poeciloptera, Prodiplosis* spp., *Psila rosae, Rhagoletis* spp., for example *Rhagoletis cingulata, Rhagoletis completa, Rhagoletis fausta, Rhagoletis indifferens, Rhagoletis mendax, Rhagoletis pomonella, Sarcophaga* spp., *Simulium* spp., for example *Simulium meridionale, Stomoxys* spp., *Tabanus* spp., *Tetanops* spp., *Tipula* spp., for example *Tipula paludosa, Tipula simplex, Toxotrypana curvicauda;* from the order of the Hemiptera for example *Acizzia acaciaebaileyanae, Acizzia dodonaeae, Acizzia uncatoides, Acrida turrita, Acyrthosiphon* spp., for example *Acyrthosiphon pisum, Acrogonia* spp., *Aeneolamia* spp., *Agonoscena* spp., *Aleurocanthus* spp., *Aleyrodes proletella, Aleurolobus barodensis, Aleurothrixus floccosus, Allocaridara malayensis, Amrasca* spp., for example *Amrasca bigutulla, Amrasca devastans, Anuraphis cardui, Aonidiella* spp., for example *Aonidiella aurantii, Aonidiella citrina, Aonidiella inornata, Aphanostigma piri, Aphis* spp., for example *Aphis citricola, Aphis craccivora, Aphis fabae, Aphis forbesi, Aphis glycines, Aphis gossypii, Aphis hederae, Aphis illinoisensis, Aphis middletoni, Aphis nasturtii, Aphis nerii, Aphis pomi, Aphis spiraecola, Aphis viburniphila, Arboridia apicalis, Arytainilla* spp., *Aspidiella* spp., *Aspidiotus* spp., for example *Aspidiotus nerii, Atanus* spp., *Aulacorthum solani, Bemisia tabaci, Blastopsylla occidentalis, Boreioglycaspis melaleucae, Brachycaudus helichrysi, Brachycolus* spp., *Brevicoryne brassicae, Cacopsylla* spp., for example *Cacopsylla pyricola, Calligypona marginata, Capulinia* spp., *Carneocephala fulgida, Ceratovacuna lanigera, Cercopidae, Ceroplastes* spp., *Chaetosiphon fragaefolii, Chionaspis tegalensis, Chlorita onukii, Chondracris rosea, Chromaphis juglandicola, Chrysomphalus aonidum, Chrysomphalus ficus, Cicadulina mbila, Coccomytilus halli, Coccus* spp., for example *Coccus hesperidum, Coccus longulus, Coccus pseudomagnoliarum, Coccus viridis, Cryptomyzus ribis, Cryptoneossa* spp., *Ctenarytaina* spp., *Dalbulus* spp., *Dialeurodes chittendeni, Dialeurodes citri, Diaphorina citri, Diaspis* spp., *Diuraphis* spp., *Doralis* spp., *Drosicha* spp., *Dysaphis* spp., for example *Dysaphis apiifolia, Dysaphis plantaginea, Dysaphis tulipae, Dysmicoccus* spp., *Empoasca* spp., for example *Empoasca abrupta, Empoasca fabae, Empoasca maligna, Empoasca solana, Empoasca stevensi, Eriosoma* spp., for example *Eriosoma americanum, Eriosoma lanigerum, Eriosoma pyricola, Erythroneura* spp., *Eucalyptolyma* spp., *Euphyllura* spp., *Euscelis bilobatus, Ferrisia* spp., *Fiorinia* spp., *Furcaspis oceanica, Geococcus coffeae, Glycaspis* spp., *Heteropsylla cubana, Heteropsylla spinulosa, Homalodisca coagulata, Hyalopterus arundinis, Hyalopterus pruni, Icerya* spp., for example *Icerya purchasi, Idiocerus* spp., *Idioscopus* spp., *Laodelphax striatellus, Lecanium* spp., for example *Lecanium corni (=Parthenolecanium corni), Lepidosaphes* spp., for example *Lepidosaphes ulmi, Lipaphis erysimi, Lopholeucaspis japonica, Lycorma delicatula, Macrosiphum* spp., for example *Macrosiphum euphorbiae, Macrosiphum lilii, Macrosiphum rosae, Macrosteles facifrons, Mahanarva* spp., *Melanaphis sacchari, Metcalfiella* spp., *Metcalfa pruinosa, Metopolophium dirhodum, Monellia costalis, Monelliopsis pecanis, Myzus* spp., for example *Myzus ascalonicus, Myzus cerasi, Myzus ligustri, Myzus ornatus, Myzus persicae, Myzus nicotianae, Nasonovia ribisnigri, Neomaskellia* spp., *Nephotettix* spp., for example *Nephotettix cincticeps, Nephotettix nigropictus, Nettigoniclla spectra, Nilaparvata lugens, Oncometopia* spp., *Orthezia praelonga, Oxya chinensis, Pachypsylla* spp., *Parabemisia myricae, Paratrioza* spp., for example *Paratrioza cockerelli, Parlatoria* spp., *Pemphigus* spp., for example *Pemphigus bursarius, Pemphigus populivenae, Peregrinus maidis, Perkinsiella* spp., *Phenacoccus* spp., for example *Phenacoccus madeirensis, Phloeomyzus passerinii, Phorodon humuli, Phylloxera* spp., for example *Phylloxera devastatrix, Phylloxera notabilis, Pinnaspis aspidistrae, Planococcus* spp., for example *Planococcus citri, Prosopidopsylla flava, Protopulvinaria pyriformis, Pseudaulacaspis pentagona, Pseudococcus* spp., for example *Pseudococcus calceolariae, Pseudococcus comstocki, Pseudococcus longispinus, Pseudococcus maritimus, Pseudococcus viburni, Psyllopsis* spp., *Psylla* spp., for example *Psylla buxi, Psylla mali, Psylla pyri, Pteromalus* spp., *Pulvinaria* spp., *Pyrilla* spp., *Quadraspidiotus* spp., for example *Quadraspidiotus juglansregiae, Quadraspidiotus ostreaeformis, Quadraspidiotus perniciosus, Quesada gigas, Rastrococcus* spp., *Rhopalosiphum* spp., for example *Rhopalosiphum maidis, Rhopalosiphum oxyacanthae, Rhopalosiphum padi, Rhopalosiphum rufiabdominale, Saissetia* spp., for example *Saissetia coffeae, Saissetia miranda, Saissetia neglecta, Saissetia oleae, Scaphoideus titanus, Schizaphis graminum, Selenaspidus articulatus, Sipha flava, Sitobion avenae, Sogata* spp., *Sogatella furcifera, Sogatodes* spp., *Stictocephala festina, Siphoninus phillyreae, Tenalaphara malayensis, Tetragonocephela* spp., *Tinocallis caryaefoliae, Tomaspis* spp., *Toxoptera* spp., for example *Toxoptera aurantii, Toxoptera citricidus, Trialeurodes vaporariorum, Trioza* spp., for example *Trioza diospyri, Typhlocyba* spp., *Unaspis* spp., *Viteus vitifolii, Zygina* spp.;

from the suborder of the Heteroptera, for example *Aelia* spp., *Anasa tristis, Antestiopsis* spp., *Boisea* spp., *Blissus* spp., *Calocoris* spp., *Campylomma livida, Cavelerius* spp., *Cimex* spp., for example *Cimex adjunctus, Cimex hemipterus, Cimex lectularius, Cimex pilosellus, Collaria* spp., *Creontiades dilutus, Dasynus piperis, Dichelops furcatus, Diconocoris hewetti, Dysdercus* spp., *Euschistus* spp., for example *Euschistus heros, Euschistus servus, Euschistus tristigmus, Euschistus variolarius, Eurydema* spp., *Eurygaster* spp., *Halyomorpha halys, Heliopeltis* spp., *Horcias nobilellus, Leptocorisa* spp., *Leptocorisa varicornis, Leptoglossus occidentalis, Leptoglossus phyllopus, Lygocoris* spp., for example *Lygocoris pabulinus, Lygus* spp., for example *Lygus elisus, Lygus hesperus, Lygus lineolaris, Macropes excavatus, Megacopta cribraria, Miridae, Monalonion atratum, Nezara* spp., for example *Nezara viridula, Nysius* spp., *Oebalus* spp., *Pentomidae, Piesma quadrata, Piezodorus* spp., for example *Piezodorus guildinii, Psallus* spp., *Pseudacysta persea, Rhodnius* spp., *Sahlbergella singularis, Scaptocoris castanea, Scotinophora* spp., *Stephanitis nashi, Tibraca* spp., *Triatoma* spp.;

from the order of the Hymenoptera, for example *Acromyrmex* spp., *Athalia* spp., for example *Athalia rosae, Atta* spp., *Camponotus* spp., *Dolichovespula* spp., *Diprion* spp., for example *Diprion similis, Hoplocampa* spp., for example *Hoplocampa cookei, Hoplocampa testudinea, Lasius* spp., *Linepithema (Iridiomyrmex) humile, Monomorium pharaonis, Paratrechina* spp., *Paravespula* spp., *Plagiolepis* spp.,

*Sirex* spp., *Solenopsis invicta*, *Tapinoma* spp., *Technomyrmex albipes*, *Urocerus* spp., *Vespa* spp., for example *Vespa crabro*, *Wasmannia auropunctata*, *Xeris* spp.;

from the order of the Isopoda, for example *Armadillidium vulgare*, *Oniscus asellus*, *Porcellio scaber*;

from the order of the Isoptera, for example *Coptotermes* spp., for example *Coptotermes formosanus*, *Cornitermes cumulans*, *Cryptotermes* spp., *Incisitermes* spp., *Kalotermes* spp., *Microtermes obesi*, *Nasutitermes* spp., *Odontotermes* spp., *Porotermes* spp., *Reticulitermes* spp., for example *Reticulitermes flavipes*, *Reticulitermes hesperus*;

from the order of the Lepidoptera, for example *Achroia grisella*, *Acronicta major*, *Adoxophyes* spp., for example *Adoxophyes orana*, *Aedia leucomelas*, *Agrotis* spp., for example *Agrotis segetum*, *Agrotis ipsilon*, *Alabama* spp., for example *Alabama argillacea*, *Amyelois transitella*, *Anarsia* spp., *Anticarsia* spp., for example *Anticarsia gemmatalis*, *Argyroploce* spp., *Autographa* spp., *Barathra brassicae*, *Blastodacna atra*, *Borbo cinnara*, *Bucculatrix thurberiella*, *Bupalus piniarius*, *Busseola* spp., *Cacoecia* spp., *Caloptilia theivora*, *Capua reticulana*, *Carpocapsa pomonella*, *Carposina niponensis*, *Cheimatobia brumata*, *Chilo* spp., for example *Chilo plejadellus*, *Chilo suppressalis*, *Choreutis pariana*, *Choristoneura* spp., *Chrysodeixis chalcites*, *Clysia ambiguella*, *Cnaphalocerus* spp., *Cnaphalocrocis medinalis*, *Cnephasia* spp., *Conopomorpha* spp., *Conotrachelus* spp., *Copitarsia* spp., *Cydia* spp., for example *Cydia nigricana*, *Cydia pomonella*, *Dalaca noctuides*, *Diaphania* spp., *Diparopsis* spp., *Diatraea saccharalis*, *Earias* spp., *Ecdytolopha aurantium*, *Elasmopalpus lignosellus*, *Eldana saccharina*, *Ephestia* spp., for example *Ephestia elutella*, *Ephestia kuehniella*, *Epinotia* spp., *Epiphyas postvittana*, *Erannis* spp., *Erschoviella musculana*, *Etiella* spp., *Eudocima* spp., *Eulia* spp., *Eupoecilia ambiguella*, *Euproctis* spp., for example *Euproctis chrysorrhoea*, *Euxoa* spp., *Feltia* spp., *Galleria mellonella*, *Gracillaria* spp., *Grapholitha* spp., for example *Grapholita molesta*, *Grapholita prunivora*, *Hedylepta* spp., *Helicoverpa* spp., for example *Helicoverpa armigera*, *Helicoverpa zea*, *Heliothis* spp., for example *Heliothis virescens*, *Hofmannophila pseudospretella*, *Homoeosoma* spp., *Homona* spp., *Hyponomeuta padella*, *Kakivoria flavofasciata*, *Lampides* spp., *Laphygma* spp., *Laspeyresia molesta*, *Leucinodes orbonalis*, *Leucoptera* spp., for example *Leucoptera coffeella*, *Lithocolletis* spp., for example *Lithocolletis blancardella*, *Lithophane antennata*, *Lobesia* spp., for example *Lobesia botrana*, *Loxagrotis albicosta*, *Lymantria* spp., for example *Lymantria dispar*, *Lyonetia* spp., for example *Lyonetia clerkella*, *Malacosoma neustria*, *Maruca testulalis*, *Mamestra brassicae*, *Melanitis leda*, *Mocis* spp., *Monopis obviella*, *Mythimna separata*, *Nemapogon cloacellus*, *Nymphula* spp., *Oiketicus* spp., *Omphisa* spp., *Operophtera* spp., *Oria* spp., *Orthaga* spp., *Ostrinia* spp., for example *Ostrinia nubilalis*, *Panolis flammea*, *Parnara* spp., *Pectinophora* spp., for example *Pectinophora gossypiella*, *Perileucoptera* spp., *Phthorimaea* spp., for example *Phthorimaea operculella*, *Phyllocnistis citrella*, *Phyllonorycter* spp., for example *Phyllonorycter blancardella*, *Phyllonorycter crataegella*, *Pieris* spp., for example *Pieris rapae*, *Platynota stultana*, *Plodia interpunctella*, *Plusia* spp., *Plutella xylostella* (=*Plutella maculipennis*), *Prays* spp., *Prodenia* spp., *Protoparce* spp., *Pseudaletia* spp., for example *Pseudaletia unipuncta*, *Pseudoplusia includens*, *Pyrausta nubilalis*, *Rachiplusia nu*, *Schoenobius* spp., for example *Schoenobius bipunctifer*, *Scirpophaga* spp., for example *Scirpophaga innotata*, *Scotia segetum*, *Sesamia* spp., for example *Sesamia inferens*, *Sparganothis* spp., *Spodoptera* spp., for example *Spodoptera eradiana*, *Spodoptera exigua*, *Spodoptera frugiperda*, *Spodoptera praefica*, *Stathmopoda* spp., *Stenoma* spp., *Stomopteryx subsecivella*, *Synanthedon* spp., *Tecia solanivora*, *Thaumetopoea* spp., *Thermesia gemmatalis*, *Tinea cloacella*, *Tinea pellionella*, *Tineola bisselliella*, *Tortrix* spp., *Trichophaga tapetzella*, *Trichoplusia* spp., for example *Trichoplusia ni*, *Tryporyza incertulas*, *Tuta absoluta*, *Virachola* spp.;

from the order of the Orthoptera or Saltatoria, for example *Acheta domesticus*, *Dichroplus* spp., *Gryllotalpa* spp., for example *Gryllotalpa gryllotalpa*, *Hieroglyphus* spp., *Locusta* spp., for example *Locusta migratoria*, *Melanoplus* spp., for example *Melanoplus devastator*, *Paratlanticus ussuriensis*, *Schistocerca gregaria*;

from the order of the Phthiraptera, for example *Damalinia* spp., *Haematopinus* spp., *Linognathus* spp., *Pediculus* spp., *Phylloxera vastatrix*, *Phthirus pubis*, *Trichodectes* spp.;

from the order of the Psocoptera, for example *Lepinotus* spp., *Liposcelis* spp.;

from the order of the Siphonaptera, for example *Ceratophyllus* spp., *Ctenocephalides* spp., for example *Ctenocephalides canis*, *Ctenocephalides felis*, *Pulex irritans*, *Tunga penetrans*, *Xenopsylla cheopis*;

from the order of the Thysanoptera, for example *Anaphothrips obscurus*, *Baliothrips biformis*, *Chaetanaphothrips leeuweni*, *Drepanothrips reuteri*, *Enneothrips flavens*, *Frankliniella* spp., for example *Frankliniella fusca*, *Frankliniella occidentalis*, *Frankliniella schultzei*, *Frankliniella tritici*, *Frankliniella vaccinii*, *Frankliniella williamsi*, *Haplothrips* spp., *Heliothrips* spp., *Hercinothrips femoralis*, *Kakothrips* spp., *Rhipiphorothrips cruentatus*, *Scirtothrips* spp., *Taeniothrips cardamomi*, *Thrips* spp., for example *Thrips palmi*, *Thrips tabaci*;

from the order of the Zygentoma (=Thysanura), for example *Ctenolepisma* spp., *Lepisma saccharina*, *Lepismodes inquilinus*, *Thermobia domestica*;

from the class of the Symphyla, for example *Scutigerella* spp., for example *Scutigerella immaculata*; pests from the phylum of the Mollusca, in particular from the class of the Bivalvia, for example *Dreissena* spp.;

and also from the class of the Gastropoda, for example *Arion* spp., for example *Arion ater rufus*, *Biomphalaria* spp., *Bulinus* spp., *Deroceras* spp., for example *Deroceras laeve*, *Galba* spp., *Lymnaea* spp., *Oncomelania* spp., *Pomacea* spp., *Succinea* spp.;

Animal and human parasites from the phyla of the Platyhelminthes and Nematoda, for example *Aelurostrongylus* spp., *Amidostomum* spp., *Ancylostoma* spp, for example *Ancylostoma duodenale*, *Ancylostoma ceylanicum*, *Acylostoma braziliensis*, *Angiostrongylus* spp., *Anisakis* spp., *Anoplocephala* spp., *Ascaris* spp., *Ascaridia* spp., *Baylisascaris* spp., *Brugia* spp., for example *Brugia malayi*, *Brugia timori*, *Bunostomum* spp., *Capillaria* spp., *Chabertia* spp., *Clonorchis* spp., *Cooperia* spp., *Crenosoma* spp., *Cyathostoma* spp., *Dicrocoelium* spp., *Dictyocaulus* spp., foer example *Dictyocaulus filaria*, *Diphyllobothrium* spp., for example *Diphyllobothrium latum*, *Dipylidium* spp., *Dirofilaria* spp., *Dracunculus* spp., for example *Dracunculus medinensis*, *Echinococcus* spp., for example *Echinococcus granulosus*, *Echinococcus multilocularis*, *Echinostoma* spp., *Enterobius* spp., for example *Enterobius vermicularis*, *Eucoleus* spp., *Fasciola* spp., *Fascioloides* spp., *Fasciolopsis* spp., *Filaroides* spp., *Gongylonema* spp., *Gyrodactylus* spp., *Habronema* spp., *Haemonchus* spp., *Heligmosomoides* spp., *Heterakis* spp., *Hymenolepis* spp., for example *Hymenolepis nana*, *Hyostrongylus* spp., *Litomosoides* spp., *Loa* spp., for example *Loa Loa*, *Metastrongylus* spp., *Metorchis* spp., *Mesocestoides* spp., *Moniezia* spp., *Muellerius* spp., *Necator* spp., *Nematodirus* spp., *Nippostrongylus* spp., *Oesophagostomum* spp., *Ollulanus* spp., *Onchocerca* spp, for example *Onchocerca volvulus*, *Opisthorchis* spp., *Oslerus* spp., *Ostertagia* spp., *Oxyuris* spp., *Paracapillaria* spp., *Parafilaria* spp., *Paragonimus* spp., *Paramphistomum* spp., *Paranoplocephala* spp., *Parascaris* spp., *Passalurus* spp., *Protostrongylus* spp., *Schistosoma* spp., *Setaria* spp., *Spirocerca* spp., *Stephanofilaria* spp., *Stephanurus* spp., *Strongyloides* spp., for example *Strongyloides fuelleborni*, *Strongyloides stercoralis*, *Strongylus* spp., *Syngamus* spp., *Taenia* spp., for example *Taenia saginata*, *Taenia solium*, *Teladorsagia* spp., *Thelazia* spp., *Toxascaris* spp., *Toxocara* spp., *Trichinella* spp., for example *Trichinella spiralis*, *Trichinella nativa*, *Trichinella britovi*, *Trichinella nelsoni*, *Trichinella pseudopsiralis*, *Trichobilharzia* spp., *Trichostrongylus* spp., *Trichuris* spp., for example *Trichuris trichiura*, *Uncinaria* spp., *Wuchereria* spp., for example *Wuchereria bancrofti*; Plant pests from the phylum of the Nematoda, i.e. plant-parasitic nematodes, in particular *Aglenchus* spp., for example *Aglenchus agricola*, *Anguina* spp., for example *Anguina tritici*, *Aphelenchoides* spp., for example *Aphelenchoides arachidis*, *Aphelenchoides fragariae*, *Belonolaimus* spp., for example *Belonolaimus gracilis*, *Belonolaimus longicaudatus*, *Belonolaimus nortoni*, *Bursaphelenchus* spp., for example *Bursaphelenchus cocophilus*, *Bursaphelenchus eremus*, *Bursaphelenchus xylophilus*, *Cacopaurus* spp., for example *Cacopaurus pestis*, *Criconemella* spp., for example *Criconemella curvata*, *Criconemella onoensis*, *Criconemella ornata*, *Criconemella rusium*, *Criconemella xenoplax* (=*Mesocriconema xenoplax*), *Criconemoides* spp., for example *Criconemoides ferniae*, *Criconemoides onoense*, *Criconemoides ornatum*, *Ditylenchus* spp., for example *Ditylenchus dipsaci*, *Dolichodorus* spp., *Globodera* spp., for example *Globodera pallida*, *Globodera rostochiensis*, *Helicotylenchus* spp., for example *Helicotylenchus dihystera*, *Hemicriconemoides* spp., *Hemicycliophora* spp., *Heterodera* spp., for example *Heterodera avenae*, *Heterodera glycines*, *Heterodera schachtii*, *Hirschmaniella* spp., *Hoplolaimus* spp., *Longidorus* spp., for example *Longidorus africanus*, *Meloidogyne* spp., for example *Meloidogyne chitwoodi*, *Meloidogyne fallax*, *Meloidogyne hapla*, *Meloidogyne incognita*, *Meloinema* spp., *Nacobbus* spp., *Neotylenchus* spp., *Paralongidorus* spp., *Paraphelenchus* spp., *Paratrichodorus* spp., for example *Paratrichodorus minor*, *Paratylenchus* spp., *Pratylenchus* spp., for example *Pratylenchus penetrans*, *Pseudohalenchus* spp., *Psilenchus* spp., *Punctodera* spp., *Quinisulcius* spp., *Radopholus* spp., for example *Radopholus citrophilus*, *Radopholus similis*, *Rotylenchulus* spp., *Rotylenchus* spp., *Scutellonema* spp., *Subanguina* spp., *Trichodorus* spp., for example *Trichodorus obtusus*, *Trichodorus primitivus*, *Tylenchorhynchus* spp., for example *Tylenchorhynchus annulatus*, *Tylenchulus* spp., for example *Tylenchulus semipenetrans*, *Xiphinema* spp., for example *Xiphinema index*.

In addition, it is possible to control, from the sub-kingdom of the Protozoa, the order of the Coccidia, for example *Eimeria* spp.

Nematodes

In the present context, the term "nematodes" comprises all species of the phylum Nematoda and here in particular species that act as parasites on plants or fungi (for example species of the order Aphelenchida, *Meloidogyne*, Tylenchida and others) or else on humans and animals (for example species of the orders Trichinellida, Tylenchida, Rhabditida and Spirurida) or cause damage in or on these living organisms, and also other parasitic helminths.

A nematicide in crop protection, as described herein, is capable of controlling nematodes.

The term "controlling nematodes" means killing the nematodes or preventing or impeding their development or their growth or preventing or impeding their penetration into or their sucking on plant tissue.

Here, the efficacy of the compounds is determined by comparing mortalities, gall formation, cyst formation, nematode density per volume of soil, nematode density per root, number of nematode eggs per volume of soil, mobility of the nematodes between a plant or plant part treated with the compound of the formula (I) or the treated soil and an untreated plant or plant part or the untreated soil (100%). Preferably, the reduction achieved is 25-50% in comparison to an untreated plant, plant part or the untreated soil, more preferably 51-79% and most preferably the complete eradication or the complete prevention of development and growth of the nematodes by a reduction of 80 to 100% is achieved. The control of nematodes as described herein also comprises the control of proliferation of the nematodes (development of cysts and/or eggs). Compounds of the formula (I) can also be used to keep the plants or animals healthy, and they can be employed curatively, preventatively or systemically for the control of nematodes.

The person skilled in the art knows methods for determining mortalities, gall formation, cyst formation, nematode density per volume of soil, nematode density per root, number of nematode eggs per volume of soil, mobility of the nematodes.

The use of a compound of the formula (I) may keep the plant healthy and also comprises a reduction of the damage caused by nematodes and an increase of the harvest yield.

In the present context, the term "nematodes" refers to plant nematodes which comprise all nematodes which damage plants. Plant nematodes comprise phytoparasitic nematodes and soil-borne nematodes. The phytoparasitic nematodes include ectoparasites such as *Xiphinema* spp., *Longidorus* spp. and *Trichodorus* spp.; semiparasites such as *Tylenchulus* spp.; migratory endoparasites such as *Pratylenchus* spp., *Radopholus* spp. and *Scutellonema* spp.; non-migratory parasites such as *Heterodera* spp., *Globodera* spp. and *Meloidogyne* spp., and also stem and leaf endoparasites such as *Ditylenchus* spp., *Aphelenchoides* spp. and *Hirschmaniella* spp. Particularly damaging root-parasitic soil nematodes are, for example, cyst-forming nematodes of the genera *Heterodera* or *Globodera*, and/or root gall nematodes of the genus *Meloidogyne*. Damaging species of these genera are, for example, *Meloidogyne incognita*, *Heterodera glycines* (soya bean cyst nematode), *Globodera pallida* and *Globodera rostochiensis* (potato cyst nematode), these species being controlled effectively by the compounds described in the present text. However, the use of the compounds described in the present text is by no means restricted to these genera or species, but also extends in the same manner to other nematodes.

The plant nematodes include, for example, *Aglenchus agricola*, *Anguina tritici*, *Aphelenchoides arachidis*, *Aphelenchoides fragaria*, and the stem and leaf endoparasites *Aphelenchoides* spp., *Belonolaimus gracilis*, *Belonolaimus longicaudatus*, *Belonolaimus nortoni*, *Bursaphelenchus cocophilus*, *Bursaphelenchus eremus*, *Bursaphelenchus xylophilus* and *Bursaphelenchus* spp., *Cacopaurus pestis*, *Criconemella curvata*, *Criconemella onoensis*, *Criconemella ornata*, *Criconemella rusium*, *Criconemella xenoplax* (=*Mesocriconema xenoplax*) and *Criconemella* spp., *Cri-* conemoides ferniae, Criconemoides onoense, Criconemoides ornatum and Criconemoides spp., Ditylenchus destructor, Ditylenchus dipsaci, Ditylenchus myceliophagus and also the stem and leaf endoparasites Ditylenchus spp., Dolichodorus heterocephalus, Globodera pallida (=Heterodera pallida), Globodera rostochiensis (potato cyst nematode), Globodera solanacearum, Globodera tabacum, Globodera virginia and the non-migratory cyst-forming parasites Globodera spp., Helicotylenchus digonicus, Helicotylenchus dihystera, Helicotylenchus erythrine, Helicotylenchus multicinctus, Helicotylenchus nannus, Helicotylenchus pseudorobustus and Helicotylenchus spp., Hemicriconemoides, Hemicycliophora arenaria, Hemicycliophora nudata, Hemicycliophora parvana, Heterodera avenae, Heterodera cruciferae, Heterodera glycines (soya bean cyst nematode), Heterodera oryzae, Heterodera schachtii, Heterodera zeae and the non-migratory cyst-forming parasites Heterodera spp., Hirschmaniella gracilis, Hirschmaniella oryzae, Hirschmaniella spinicaudata and the stem and leaf endoparasites Hirschmaniella spp., Hoplolaimus aegyptii, Hoplolaimus californicus, Hoplolaimus columbus, Hoplolaimus galeatus, Hoplolaimus indicus, Hoplolaimus magnistylus, Hoplolaimus pararobustus, Longidorus africanus, Longidorus breviannulatus, Longidorus elongatus, Longidorus laevicapitatus, Longidorus vineacola and the ectoparasites Longidorus spp., Meloidogyne acronea, Meloidogyne africana, Meloidogyne arenaria, Meloidogyne arenaria thamesi, Meloidogyne artiella, Meloidogyne chitwoodi, Meloidogyne coffeicola, Meloidogyne ethiopica, Meloidogyne exigua, Meloidogyne fallax, Meloidogyne graminicola, Meloidogyne graminis, Meloidogyne hapla, Meloidogyne incognita, Meloidogyne incognita acrita, Meloidogyne javanica, Meloidogyne kikuyensis, Meloidogyne minor, Meloidogyne naasi, Meloidogyne paranaensis, Meloidogyne thamesi and the non-migratory parasites Meloidogyne spp., Meloinema spp., Nacobbus aberrans, Neotylenchus vigissi, Paraphelenchus pseudoparietinus, Paratrichodorus allius, Paratrichodorus lobatus, Paratrichodorus minor, Paratrichodorus nanus, Paratrichodorus porosus, Paratrichodorus teres and Paratrichodorus spp., Paratylenchus hamatus, Paratylenchus minutus, Paratylenchus projectus and Paratylenchus spp., Pratylenchus agilis, Pratylenchus alleni, Pratylenchus andinus, Pratylenchus brachyurus, Pratylenchus cerealis, Pratylenchus coffeae, Pratylenchus crenatus, Pratylenchus delattrei, Pratylenchus giibbicaudatus, Pratylenchus goodeyi, Pratylenchus hamatus, Pratylenchus hexincisus, Pratylenchus loosi, Pratylenchus neglectus, Pratylenchus penetrans, Pratylenchus pratensis, Pratylenchus scribneri, Pratylenchus teres, Pratylenchus thornei, Pratylenchus vulnus, Pratylenchus zeae and the migratory endoparasites Pratylenchus spp., Pseudohalenchus minutus, Psilenchus magnidens, Psilenchus tumidus, Punctodera chalcoensis, Quinisulcius acutus, Radopholus citrophilus, Radopholus similis, the migratory endoparasites Radopholus spp., Rotylenchulus borealis, Rotylenchulus parvus, Rotylenchulus reniformis and Rotylenchulus spp., Rotylenchus laurentinus, Rotylenchus macrodoratus, Rotylenchus robustus, Rotylenchus uniformis and Rotylenchus spp., Scutellonema brachyurum, Scutellonema bradys, Scutellonema clathricaudatum and the migratory endoparasites Scutellonema spp., Subanguina radiciola, Tetylenchus nicotianae, Trichodorus cylindricus, Trichodorus minor, Trichodorus primitivus, Trichodorus proximus, Trichodorus similis, Trichodorus sparsus and the ectoparasites Trichodorus spp., Tylenchorhynchus agri, Tylenchorhynchus brassicae, Tylenchorhynchus clarus, Tylenchorhynchus claytoni, Tylenchorhynchus digitatus, Tylenchorhynchus ebriensis, Tylenchorhynchus maximus, Tylenchorhynchus nudus, Tylenchorhynchus vulgaris and Tylenchorhynchus spp., Tylenchulus semipenetrans and the semiparasites Tylenchulus spp., Xiphinema americanum, Xiphinema brevicolle, Xiphinema dimorphicaudatum, Xiphinema index and the ectoparasites Xiphinema spp.

Nematodes for the control of which a compound of the formula (I) may be used include nematodes of the genus Meloidogyne such as the Southern root-knot nematode (Meloidogyne incognita), the Javanese root-knot nematode (Meloidogyne javanica), the Northern root-knot nematode (Meloidogyne hapla) and the peanut root-knot nematode (Meloidogyne arenaria); nematodes of the genus Ditylenchus such as the potato rot nematode (Ditylenchus destructor) and stem and bulb eelworm (Ditylenchus dipsaci); nematodes of the genus Pratylenchus such as the cob root-lesion nematode (Pratylenchus penetrans), the chrysanthemum root-lesion nematode (Pratylenchus fallax), the coffee root nematode (Pratylenchus coffeae), the tea root nematode (Pratylenchus loosi) and the walnut root-lesion nematode (Pratylenchus vulnus); nematodes of the genus Globodera such as the yellow potato cyst nematode (Globodera rostochiensis) and the white potato cyst nematode (Globodera pallida); nematodes of the genus Heterodera such as the soya bean cyst nematode (Heterodera glycines) and the beet cyst eelworm (Heterodera schachtii); nematodes of the genus Aphelenchoides such as the rice white-tip nematode (Aphelenchoides besseyi), the chrysanthemum nematode (Aphelenchoides ritzemabosi) and the strawberry nematode (Aphelenchoides fragariae); nematodes of the genus Aphelenchus such as the fungivorous nematode (Aphelenchus avenae); nematodes of the genus Radopholus, such as the burrowing nematode (Radopholus similis); nematodes of the genus Tylenchulus such as the citrus root nematode (Tylenchulus semipenetrans); nematodes of the genus Rotylenchulus such as the reniform nematode (Rotylenchulus reniformis); tree-dwelling nematodes such as the pine wood nematode (Bursaphelenchus xylophilus) and the red ring nematode (Bursaphelenchus cocophilus) and the like.

Plants for the protection of which a compound of the formula (I) can be used include plants such as cereals (for example rice, barley, wheat, rye, oats, maize and the like), beans (soya bean, azuki bean, bean, broadbean, peas, peanuts and the like), fruit trees/fruits (apples, citrus species, pears, grapevines, peaches, Japanese apricots, cherries, walnuts, almonds, bananas, strawberries and the like), vegetable species (cabbage, tomato, spinach, broccoli, lettuce, onions, spring onion, pepper and the like), root crops (carrot, potato, sweet potato, radish, lotus root, turnip and the like), plants for industrial raw materials (cotton, hemp, paper mulberry, mitsumata, rape, beet, hops, sugar cane, sugar beet, olive, rubber, palm trees, coffee, tobacco, tea and the like), cucurbits (pumpkin, cucumber, watermelon, melon and the like), meadow plants (cocksfoot, sorghum, timothy-grass, clover, alfalfa and the like), lawn grasses (mascarene grass, bentgrass and the like), spice plants etc. (lavender, rosemary, thyme, parsley, pepper, ginger and the like) and flowers (chrysanthemums, rose, orchid and the like).

The compounds of the formula (I) are particularly suitable for controlling coffee nematodes, in particular Pratylenchus brachyurus, Pratylenchus coffeae, Meloidogyne exigua, Meloidogyne incognita, Meloidogyne coffeicola, Helicotylenchus spp. and also Meloidogyne paranaensis, Rotylenchus spp., Xiphinema spp., Tylenchorhynchus spp. and Scutellonema spp.

The compounds of the formula (I) are particularly suitable for controlling potato nematodes, in particular *Pratylenchus brachyurus, Pratylenchus pratensis, Pratylenchus scribneri, Pratylenchus penetrans, Pratylenchus coffeae, Ditylenchus dipsaci* and also *Pratylenchus alleni, Pratylenchus andinus, Pratylenchus cerealis, Pratylenchus crenatus, Pratylenchus hexincisus, Pratylenchus loosi, Pratylenchus neglectus, Pratylenchus teres, Pratylenchus thornei, Pratylenchus vulnus, Belonolaimus longicaudatus, Trichodorus cylindricus, Trichodorus primitivus, Trichodorus proximus, Trichodorus similis, Trichodorus sparsus, Paratrichodorus minor, Paratrichodorus allius, Paratrichodorus nanus, Paratrichodorus teres, Meloidogyne arenaria, Meloidogyne fallax, Meloidogyne hapla, Meloidogyne thamesi, Meloidogyne incognita, Meloidogyne chitwoodi, Meloidogyne javanica, Nacobbus aberrans, Globodera rostochiensis, Globodera pallida, Ditylenchus destructor, Radopholus similis, Rotylenchulus reniformis, Neotylenchus vigissi, Paraphelenchus pseudoparietinus, Aphelenchoides fragariae* and *Meloinema* spp.

The compounds of the formula (I) are particularly suitable for controlling tomato nematodes, in particular *Meloidogyne arenaria, Meloidogyne hapla, Meloidogyne javanica, Meloidogyne incognita, Pratylenchus penetrans* and also *Pratylenchus brachyurus, Pratylenchus coffeae, Pratylenchus scribneri, Pratylenchus vulnus, Paratrichodorus minor, Meloidogyne exigua, Nacobbus aberrans, Globodera solanacearum, Dolichodorus heterocephalus* and *Rotylenchulus reniformis*.

The compounds of the formula (I) are particularly suitable for controlling cucumber plant nematodes, in particular *Meloidogyne arenaria, Meloidogyne hapla, Meloidogyne javanica, Meloidogyne incognita, Rotylenchulus reniformis* and *Pratylenchus thornei*.

The compounds of the formula (I) are particularly suitable for controlling cotton nematodes, in particular *Belonolaimus longicaudatus, Meloidogyne incognita, Hoplolaimus columbus, Hoplolaimus galeatus* and *Rotylenchulus reniformis*.

The compounds of the formula (I) are particularly suitable for controlling maize nematodes, in particular *Belonolaimus longicaudatus, Paratrichodorus minor* and also *Pratylenchus brachyurus, Pratylenchus delattrei, Pratylenchus hexincisus, Pratylenchus penetrans, Pratylenchus zeae,* (*Belonolaimus gracilis*), *Belonolaimus nortoni, Longidorus breviannulatus, Meloidogyne arenaria, Meloidogyne arenaria thamesi, Meloidogyne graminis, Meloidogyne incognita, Meloidogyne incognita acrita, Meloidogyne javanica, Meloidogyne naasi, Heterodera avenae, Heterodera oryzae, Heterodera zeae, Punctodera chalcoensis, Ditylenchus dipsaci, Hoplolaimus aegyptii, Hoplolaimus magnistylus, Hoplolaimus galeatus, Hoplolaimus indicus, Helicotylenchus digonicus, Helicotylenchus dihystera, Helicotylenchus pseudorobustus, Xiphinema americanum, Dolichodorus heterocephalus, Criconemella ornata, Criconemella onoensis, Radopholus similis, Rotylenchulus borealis, Rotylenchulus parvus, Tylenchorhynchus agri, Tylenchorhynchus clarus, Tylenchorhynchus claytoni, Tylenchorhynchus maximus, Tylenchorhynchus nudus, Tylenchorhynchus vulgaris, Quinisulcius acutus, Paratylenchus minutus, Hemicycliophora parvana, Aglenchus agricola, Anguina tritici, Aphelenchoides arachidis, Scutellonema brachyurum* and *Subanguina radiciola*.

The compounds of the formula (I) are particularly suitable for controlling soya bean nematodes, in particular *Pratylenchus brachyurus, Pratylenchus pratensis, Pratylenchus penetrans, Pratylenchus scribneri, Belonolaimus longicaudatus, Heterodera glycines, Hoplolaimus columbus* and also *Pratylenchus coffeae, Pratylenchus hexincisus, Pratylenchus neglectus, Pratylenchus crenatus, Pratylenchus alleni, Pratylenchus agilis, Pratylenchus zeae, Pratylenchus vulnus,* (*Belonolaimus gracilis*), *Meloidogyne arenaria, Meloidogyne incognita, Meloidogyne javanica, Meloidogyne hapla, Hoplolaimus columbus, Hoplolaimus galeatus* and *Rotylenchulus reniformis*.

The compounds of the formula (I) are particularly suitable for controlling tobacco nematodes, in particular *Meloidogyne incognita, Meloidogyne javanica* and also *Pratylenchus brachyurus, Pratylenchus pratensis, Pratylenchus hexincisus, Pratylenchus penetrans, Pratylenchus neglectus, Pratylenchus crenatus, Pratylenchus thornei, Pratylenchus vulnus, Pratylenchus zeae, Longidorus elongatu, Paratrichodorus lobatus, Trichodorus* spp., *Meloidogyne arenaria, Meloidogyne hapla, Globodera tabacum, Globodera solanacearum, Globodera virginiae, Ditylenchus dipsaci, Rotylenchus* spp., *Helicotylenchus* spp., *Xiphinema americanum, Criconemella* spp., *Rotylenchulus reniformis, Tylenchorhynchus claytoni, Paratylenchus* spp. and *Tetylenchus nicotianae*.

The compounds of the formula (I) are particularly suitable for controlling citrus nematodes, in particular *Pratylenchus coffeae* and also *Pratylenchus brachyurus, Pratylenchus vulnus, Belonolaimus longicaudatus, Paratrichodorus minor, Paratrichodorus porosus, Trichodorus, Meloidogyne incognita, Meloidogyne incognita acrita, Meloidogyne javanica, Rotylenchus macrodoratus, Xiphinema americanum, Xiphinema brevicolle, Xiphinema index, Criconemella* spp., *Hemicriconemoides, Radopholus similis* and *Radopholus citrophilus, Hemicycliophora arenaria, Hemicycliophora nudata* and *Tylenchulus semipenetrans*.

The compounds of the formula (I) are particularly suitable for controlling banana nematodes, in particular *Pratylenchus coffeae, Radopholus similis* and also *Pratylenchus giibbicaudatus, Pratylenchus loosi, Meloidogyne* spp., *Helicotylenchus multicinctus, Helicotylenchus dihystera* and *Rotylenchulus* spp.

The compounds of the formula (I) are particularly suitable for controlling pineapple nematodes, in particular *Pratylenchus zeae, Pratylenchus pratensis, Pratylenchus brachyurus, Pratylenchus goodeyi., Meloidogyne* spp., *Rotylenchulus reniformis* and also *Longidorus elongatus, Longidorus laevicapitatus, Trichodorus primitivus, Trichodorus minor, Heterodera* spp., *Ditylenchus myceliophagus, Hoplolaimus californicus, Hoplolaimus pararobustus, Hoplolaimus indicus, Helicotylenchus dihystera, Helicotylenchus nannus, Helicotylenchus multicinctus, Helicotylenchus erythrine, Xiphinema dimorphicaudatum, Radopholus similis, Tylenchorhynchus digitatus, Tylenchorhynchus ebriensis, Paratylenchus minutus, Scutellonema clathricaudatum, Scutellonema bradys, Psilenchus tumidus, Psilenchus magnidens, Pseudohalenchus minutus, Criconemoides ferniae, Criconemoides onoense* and *Criconemoides ornatum*.

The compounds of the formula (I) are particularly suitable for controlling grapevine nematodes, in particular *Pratylenchus vulnus, Meloidogyne arenaria, Meloidogyne incognita, Meloidogyne javanica, Xiphinema americanum, Xiphinema index* and also *Pratylenchus pratensis, Pratylenchus scribneri, Pratylenchus neglectus, Pratylenchus brachyurus, Pratylenchus thornei* and *Tylenchulus semipenetrans*.

The compounds of the formula (I) are particularly suitable for controlling nematodes in tree crops—pome fruit, in particular *Pratylenchus penetrans* and from *Pratylenchus vulnus, Longidorus elongatus, Meloidogyne incognita* and *Meloidogyne hapla*.

The compounds of the formula (I) are particularly suitable for controlling nematodes in tree crops—stone fruit, in particular *Pratylenchus penetrans, Pratylenchus vulnus, Meloidogyne arenaria, Meloidogyne hapla, Meloidogyne javanica, Meloidogyne incognita, Criconemella xenoplax* and from *Pratylenchus brachyurus, Pratylenchus coffeae, Pratylenchus scribneri, Pratylenchus zeae, Belonolaimus longicaudatus, Helicotylenchus dihystera, Xiphinema americanum, Criconemella curvata, Tylenchorhynchus claytoni, Paratylenchus hamatus, Paratylenchus projectus, Scutellonema brachyurum* and *Hoplolaimus galeatus.*

The compounds of the formula (I) are particularly suitable for controlling nematodes in tree crops, sugar cane and rice, in particular *Trichodorus* spp., *Criconemella* spp. and from *Pratylenchus* spp., *Paratrichodorus* spp., *Meloidogyne* spp., *Helicotylenchus* spp., *Tylenchorhynchus* spp., *Aphelenchoides* spp., *Heterodera* spp., *Xiphinema* spp. and *Cacopaurus pestis.*

In the present context, the term "nematodes" also refers to nematodes damaging humans or animals.

Specific nematode species harmful to humans or to animals are:

Trichinellida, for example: *Trichuris* spp., *Capillaria* spp., *Paracapillaria* spp., *Eucoleus* spp., *Trichomosoides* spp., *Trichinella* spp.

from the order of Tylenchida, for example: *Micronema* spp., *Strongyloides* spp.

from the order of Rhabditida, for example: *Strongylus* spp., *Triodontophorus* spp., *Oesophagodontus* spp., *Trichonema* spp., *Gyalocephalus* spp., *Cylindropharynx* spp., *Poteriostomum* spp., *Cyclococercus* spp., *Cylicostephanus* spp., *Oesophagostomum* spp., *Chabertia* spp., *Stephanurus* spp., *Ancylostoma* spp., *Uncinaria* spp., *Necator* spp., *Bunostomum* spp., *Globocephalus* spp., *Syngamus* spp., *Cyathostoma* spp., *Metastrongylus* spp., *Dictyocaulus* spp., *Muellerius* spp., *Protostrongylus* spp., *Neostrongylus* spp., *Cystocaulus* spp., *Pneumostrongylus* spp., *Spicocaulus* spp., *Elaphostrongylus* spp., *Parelaphostrongylus* spp., *Crenosoma* spp., *Paracrenosoma* spp., *Oslerus* spp., *Angiostrongylus* spp., *Aelurostrongylus* spp., *Filaroides* spp., *Parafilaroides* spp., *Trichostrongylus* spp., *Haemonchus* spp., *Ostertagia* spp., *Teladorsagia* spp., *Marshallagia* spp., *Cooperia* spp., *Nippostrongylus* spp., *Heligmosomoides* spp., *Nematodirus* spp., *Hyostrongylus* spp., *Obeliscoides* spp., *Amidostomum* spp., *Ollulanus* spp.

From the order of Spirurida, for example: *Oxyuris* spp., *Enterobius* spp., *Passalurus* spp., *Syphacia* spp., *Aspiculuris* spp., *Heterakis* spp.; *Ascaris* spp., *Toxascaris* spp., *Toxocara* spp., *Baylisascaris* spp., *Parascaris* spp., *Anisakis* spp., *Ascaridia* spp.; *Gnathostoma* spp., *Physaloptera* spp., *Thelazia* spp., *Gongylonema* spp., *Habronema* spp., *Parabronema* spp., *Draschia* spp., *Dracunculus* spp.; *Stephanofilaria* spp., *Parafilaria* spp., *Setaria* spp., *Loa* spp., *Dirofilaria* spp., *Litomosoides* spp., *Brugia* spp., *Wuchereria* spp., *Onchocerca* spp., *Spirocerca* spp.;

Many known nematicides also act against other parasitic helminths and are therefore used for controlling worms—not necessarily belonging to the group Nematoda—which are parasites in humans and animals.

The present invention also relates to the use of the compounds of the formula (I) as anthelmintic medicaments. The pathogenic endoparasitic helminths include Platyhelmintha (e.g. Monogenea, cestodes and trematodes), Acanthocephala and Pentastoma. The following helminths may be mentioned as being preferred:

Monogenea: for example: *Gyrodactylus* spp., *Dactylogyrus* spp., *Polystoma* spp.

Cestodes: from the order of the Pseudophyllidea, for example: *Diphyllobothrium* spp., *Spirometra* spp., *Schistocephalus* spp., *Ligula* spp., *Bothridium* spp., *Diphlogonoporus* spp.

from the order of Cyclophyllida, for example: *Mesocestoides* spp., *Anoplocephala* spp., *Paranoplocephala* spp., *Moniezia* spp., *Thysanosoma* spp., *Thysaniezia* spp., *Avitellina* spp., *Stilesia* spp., *Cittotaenia* spp., *Andyra* spp., *Bertiella* spp., *Taenia* spp., *Echinococcus* spp., *Hydatigera* spp., *Davainea* spp., *Raillietina* spp., *Hymenolepis* spp., *Echinolepis* spp., *Echinocotyle* spp., *Diorchis* spp., *Dipylidium* spp., *Joyeuxiella* spp., *Diplopylidium* spp.

Trematodes: from the class of the Digenea, for example: *Diplostomum* spp., *Posthodiplostomum* spp., *Schistosoma* spp., *Trichobilharzia* spp., *Ornithobilharzia* spp., *Austrobilharzia* spp., *Gigantobilharzia* spp., *Leucochloridium* spp., *Brachylaima* spp., *Echinostoma* spp., *Echinoparyphium* spp., *Echinochasmus* spp., *Hypoderaeum* spp., *Fasciola* spp., *Fascioloides* spp., *Fasciolopsis* spp., *Cyclocoelum* spp., *Typhlocoelum* spp., *Paramphistomum* spp., *Calicophoron* spp., *Cotylophoron* spp., *Gigantocotyle* spp., *Fischoederius* spp., *Gastrothylacus* spp., *Notocotylus* spp., *Catatropis* spp., *Plagiorchis* spp., *Prosthogonimus* spp., *Dicrocoelium* spp., *Eurytrema* spp., *Troglotrema* spp., *Paragonimus* spp., *Collyriclum* spp., *Nanophyetus* spp., *Opisthorchis* spp., *Clonorchis* spp., *Metorchis* spp., *Heterophyes* spp., *Metagonimus* spp.

Acanthocephala: from the order of the Oligacanthorhynchida, for example: *Macracanthorhynchus* spp., *Prosthenorchis* spp.; from the order Polymorphida for example: *Filicollis* spp.; from the order Moniliformida for example: *Moniliformis* spp.

From the order of the Echinorhynchida, for example, *Acanthocephalus* spp., *Echinorhynchus* spp., *Leptorhynchoides* spp.

Pentastoma: from the order of the Porocephalida, for example, *Linguatula* spp.

In the veterinary field and in animal husbandry, the administration of the compounds of the formula (I) is carried out in a known manner, directly or enterally, parenterally, dermally or nasally in the form of suitable use forms. Administration may be prophylactic or therapeutic.

The compounds of the formula (I) can, as the case may be, at certain concentrations or application rates, also be used as herbicides, safeners, growth regulators or agents to improve plant properties, as microbicides or gametocides, for example as fungicides, antimycotics, bactericides, virucides (including agents against viroids) or as agents against MLO (*mycoplasma*-like organisms) and RLO (*rickettsia*-like organisms). They can, as the case may be, also be used as intermediates or precursors for the synthesis of further active compounds.

Formulations

The present invention further relates to formulations and use forms prepared therefrom as pesticides, for example drench, drip and spray liquors, comprising at least one compound of the formula (I). Optionally, the use forms comprise further pesticides and/or adjuvants which improve action, such as penetrants, e.g. vegetable oils, for example rapeseed oil, sunflower oil, mineral oils, for example paraffin oils, alkyl esters of vegetable fatty acids, for example rapeseed oil methyl ester or soya oil methyl ester, or alkanol alkoxylates and/or spreaders, for example alkylsiloxanes and/or salts, for example organic or inorganic ammonium or phosphonium salts, for example ammonium sulfate or diammonium hydrogenphosphate and/or retention promoters, for example dioctyl sulfosuccinate or hydroxypropylguar polymers and/or humectants, for example glycerol and/or fertilizers, for example ammonium-, potassium- or phosphorus-containing fertilizers.

Customary formulations are, for example, water-soluble liquids (SL), emulsion concentrates (EC), emulsions in water (EW), suspension concentrates (SC, SE, FS, OD), water-dispersible granules (WG), granules (GR) and capsule concentrates (CS); these and further possible formulation types are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations, in addition to one or more compounds of the formula (I), optionally comprise further agrochemically active ingredients.

Preference is given to formulations or use forms comprising auxiliaries, for example extenders, solvents, spontaneity promoters, carriers, emulsifiers, dispersants, frost protection agents, biocides, thickeners and/or further auxiliaries, for example adjuvants. An adjuvant in this context is a component which enhances the biological effect of the formulation, without the component itself having any biological effect. Examples of adjuvants are agents which promote retention, spreading, attachment to the leaf surface or penetration.

These formulations are prepared in a known way, for example by mixing the compounds of the formula (I) with auxiliaries such as, for example, extenders, solvents and/or solid carriers and/or other auxiliaries such as, for example, surfactants. The formulations are produced either in suitable facilities or else before or during application.

The auxiliaries used may be substances suitable for imparting special properties, such as certain physical, technical and/or biological properties, to the formulation of the compounds of the formula (I), or to the use forms prepared from these formulations (for example ready-to-use pesticides such as spray liquors or seed dressing products).

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the simple and substituted amines, amides, lactams (such as N-alkylpyrrolidones) and lactones, the sulfones and sulfoxides (such as dimethyl sulfoxide).

If the extender utilized is water, it is also possible to use, for example, organic solvents as auxiliary solvents. Liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulfoxide, and water.

In principle, it is possible to use all suitable solvents. Examples of suitable solvents are aromatic hydrocarbons, such as xylene, toluene or alkylnaphthalenes, chlorinated aromatic or aliphatic hydrocarbons, such as chlorobenzene, chloroethylene or methylene chloride, aliphatic hydrocarbons, such as cyclohexane, paraffins, mineral oil fractions, mineral and vegetable oils, alcohols, such as methanol, ethanol, isopropanol, butanol or glycol and their ethers and esters, ketones such as acetone, methyl ethyl ketone, methyl isobutyl ketone or cyclohexanone, strongly polar solvents, such as dimethyl sulfoxide, and also water.

In principle, it is possible to use all suitable carriers. Useful carriers especially include: for example ammonium salts and ground natural minerals such as kaolins, clays, talc, chalk, quartz, attapulgite, montmorillonite or diatomaceous earth, and synthetic minerals such as finely divided silica, alumina and natural or synthetic silicates, resins, waxes and/or solid fertilizers. It is likewise possible to use mixtures of such carriers. Useful carriers for granules include: for example crushed and fractionated natural rocks such as calcite, marble, pumice, sepiolite, dolomite, and synthetic granules of inorganic and organic flours, and also granules of organic material such as sawdust, paper, coconut shells, maize cobs and tobacco stalks.

It is also possible to use liquefied gaseous extenders or solvents. Especially suitable are those extenders or carriers which are gaseous at standard temperature and under atmospheric pressure, for example aerosol propellants such as halogenated hydrocarbons, and also butane, propane, nitrogen and carbon dioxide.

Examples of emulsifiers and/or foam formers, dispersants or wetting agents having ionic or nonionic properties or mixtures of these surface-active substances are salts of polyacrylic acid, salts of lignosulfonic acid, salts of phenolsulfonic acid or naphthalenesulfonic acid, polycondensates of ethylene oxide with fatty alcohols or with fatty acids or with fatty amines, with substituted phenols (preferably alkylphenols or arylphenols), salts of sulfosuccinic esters, taurine derivatives (preferably alkyl taurates), phosphoric esters of polyethoxylated alcohols or phenols, fatty acid esters of polyols, and derivatives of the compounds containing sulfates, sulfonates and phosphates, for example alkylaryl polyglycol ethers, alkylsulfonates, alkyl sulfates, arylsulfonates, protein hydrolysates, lignosulfite waste liquors and methylcellulose. The presence of a surfactant is advantageous if one of the compounds of the formula (I) and/or one of the inert carriers is insoluble in water and if the application takes place in water.

Further auxiliaries which may be present in the formulations and the use forms derived therefrom are dyes such as inorganic pigments, for example iron oxide, titanium oxide and Prussian Blue, and organic dyes such as alizarin dyes, azo dyes and metal phthalocyanine dyes, and nutrients and trace nutrients such as salts of iron, manganese, boron, copper, cobalt, molybdenum and zinc.

Additional components which may be present are stabilizers, such as cold stabilizers, preservatives, antioxidants, light stabilizers, or other agents which improve chemical and/or physical stability. Foam generators or antifoams may also be present.

In addition, the formulations and the use forms derived therefrom may also comprise, as additional auxiliaries, stickers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids. Further auxiliaries may be mineral and vegetable oils.

It is possible if appropriate for still further auxiliaries to be present in the formulations and the use forms derived therefrom. Examples of such additives are fragrances, protective colloids, binders, adhesives, thickeners, thixotropic agents, penetrants, retention promoters, stabilizers, sequestrants, complexing agents, humectants, spreaders. In general, the compounds of the formula (I) can be combined with any solid or liquid additive commonly used for formulation purposes.

Useful retention promoters include all those substances which reduce dynamic surface tension, for example dioctyl sulfosuccinate, or increase viscoelasticity, for example hydroxypropylguar polymers.

Useful penetrants in the present context are all those substances which are typically used to improve the penetration of agrochemically active compounds into plants. Penetrants are defined in this context by their ability to penetrate from the (generally aqueous) application liquor and/or from the spray coating into the cuticle of the plant and hence increase the mobility of the active ingredients in the cuticle. The method described in the literature (Baur et al., 1997, Pesticide Science 51, 131-152) can be used for determining this property. Examples include alcohol alkoxylates such as coconut fatty ethoxylate (10) or isotridecyl ethoxylate (12), fatty acid esters, for example rapeseed oil methyl ester or soya oil methyl ester, fatty amine alkoxylates, for example tallowamine ethoxylate (15), or ammonium and/or phosphonium salts, for example ammonium sulfate or diammonium hydrogenphosphate.

The formulations preferably comprise between 0.00000001% and 98% by weight of the compound of the formula (I), more preferably between 0.01% and 95% by weight of the compound of the formula (I), most preferably between 0.5% and 90% by weight of the compound of the formula (I), based on the weight of the formulation.

The content of the compound of the formula (I) in the use forms prepared from the formulations (in particular pesticides) may vary within wide ranges. The concentration of the compound of the formula (I) in the use forms may typically be between 0.00000001% and 95% by weight of the compound of the formula (I), preferably between 0.00001% and 1% by weight, based on the weight of the use form. Application is accomplished in a customary manner appropriate for the use forms.

Mixtures

The compounds of the formula (I) can also be used in a mixture with one or more suitable fungicides, bactericides, acaricides, molluscicides, nematicides, insecticides, microbiological agents, beneficial organisms, herbicides, fertilizers, bird repellents, phytotonics, sterilants, safeners, semiochemicals and/or plant growth regulators, in order thus, for example, to broaden the spectrum of action, prolong the period of action, enhance the rate of action, prevent repellency or prevent evolution of resistance. In addition, active ingredient combinations of this kind can improve plant growth and/or tolerance to abiotic factors, for example high or low temperatures, to drought or to elevated water content or soil salinity. It is also possible to improve flowering and fruiting performance, optimize germination capacity and root development, facilitate harvesting and improve yields, influence maturation, improve the quality and/or the nutritional value of the harvested products, prolong storage life and/or improve the processibility of the harvested products.

In addition, the compounds of the formula (I) may be present in a mixture with other active ingredients or semiochemicals such as attractants and/or bird repellents and/or plant activators and/or growth regulators and/or fertilizers. Likewise, the compounds of the formula (I) can be used in mixtures with agents to improve plant properties, for example growth, yield and quality of the harvested material.

In a particular embodiment according to the invention, the compounds of the formula (I) are present in formulations or in the use forms prepared from these formulations in a mixture with further compounds, preferably those as described below.

If one of the compounds mentioned below can occur in different tautomeric forms, these forms are also included even if not explicitly mentioned in each case.

Insecticides/Acaricides/Nematicides

The active ingredients specified here with their common names are known and are described for example in "The Pesticide Manual", 16th ed., British Crop Protection Council 2012, or can be searched for on the Internet (e.g. http//www.alanwood.net/pesticides).

(1) Acetylcholinesterase (AChE) inhibitors, for example carbamates, e.g. alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, e.g. acephate, azamethiphos, azinphos-ethyl, azinphos-methyl, cadusafos, chlorethoxyfos, chlorfenvinphos, chlormephos, chloropyrifos, chloropyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel antagonists, for example cyclodiene-organochlorines, e.g. chlordane and endosulfan or phenylpyrazoles (fiproles), e.g. ethiprole and fipronil.

(3) Sodium channel modulators/voltage-gated sodium channel blockers, for example pyrethroids, e.g. acrinathrin, allethrin, d-cis-trans allethrin, d-trans allethrin, bifenthrin, bioallethrin, bioallethrin S-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans isomers], deltamethrin, empenthrin [(EZ)-(1R) isomers], esfenvalerate, etofenprox, fenpropathrin, fenvalerate, flucythrinate, flumethrin, tau-fluvalinate, halfenprox, imiprothrin, kadethrin, momfluorothrin, permethrin, phenothrin [(1R)-trans isomer], prallethrin, pyrethrins (pyrethrum), resmethrin, silafluofen, tefluthrin, tetramethrin, tetramethrin [(1R) isomers)], tralomethrin and transfluthrin or DDT or methoxychlor.

(4) Nicotinergic acetylcholine receptor (nAChR) agonists, for example neonicotinoids, e.g. acetamiprid, clothianidin, dinotefuran, imidacloprid, nitenpyram, thiacloprid and thiamethoxam or nicotine or sulfoxaflor or flupyradifurone.

(5) Nicotinergic acetylcholine receptor (nAChR) allosteric activators, for example spinosyns, e.g. spinetoram and spinosad.

(6) Chloride channel activators, for example avermectins/milbemycins, e.g. abamectin, emamectin benzoate, lepimectin and milbemectin.

(7) Juvenile hormone mimics, for example, juvenile hormone analogues, e.g. hydroprene, kinoprene and methoprene or fenoxycarb or pyriproxyfen.
(8) Active ingredients having unknown or nonspecific mechanisms of action, for example alkyl halides, e.g. methyl bromide and other alkyl halides; or chloropicrin or sulfuryl fluoride or borax or tartar emetic.
(9) Selective antifeedants, e.g. pymetrozine or flonicamid.
(10) Mite growth inhibitors, e.g. clofentezine, hexythiazox and diflovidazin or etoxazole.
(11) Microbial disruptors of insect midgut membranes, e.g. *Bacillus thuringiensis* subspecies *israelensis*, *Bacillus sphaericus*, *Bacillus thuringiensis* subspecies *aizawai*, *Bacillus thuringiensis* subspecies *kurstaki*, *Bacillus thuringiensis* subspecies *tenebrionis*, and BT plant proteins: Cry1Ab, Cry1Ac, Cry1Fa, Cry2Ab, mCry3A, Cry3Ab, Cry3Bb, Cry34/35Ab1.
(12) Oxidative phosphorylation inhibitors, ATP disruptors, for example diafenthiuron or organotin compounds, e.g. azocyclotin, cyhexatin and fenbutatin oxide or propargite or tetradifon.
(13) Uncouplers of oxidative phosphorylation via disruption of the H proton gradient, for example chlorfenapyr, DNOC and sulfluramid.
(14) Nicotinic acetylcholine receptor antagonists, for example bensultap, cartap hydrochloride, thiocyclam, and thiosultap-sodium.
(15) Inhibitors of chitin biosynthesis, type 0, for example bistrifluron, chlorfluazuron, diflubenzuron, flucycloxuron, flufenoxuron, hexaflumuron, lufenuron, novaluron, noviflumuron, teflubenzuron and triflumuron.
(16) Inhibitors of chitin biosynthesis, type 1, for example buprofezin.
(17) Moulting disruptors (especially for Diptera, i.e. dipterans), for example cyromazine.
(18) Ecdysone receptor agonists, for example chromafenozide, halofenozide, methoxyfenozide and tebufenozide.
(19) Octopaminergic agonists, for example amitraz.
(20) Complex III electron transport inhibitors, for example hydramethylnon or acequinocyl or fluacrypyrim.
(21) Complex I electron transport inhibitors, for example METI acaricides, e.g. fenazaquin, fenpyroximate, pyrimidifen, pyridaben, tebufenpyrad and tolfenpyrad or rotenone (Derris).
(22) Voltage-gated sodium channel blockers, for example indoxacarb or metaflumizone.
(23) Inhibitors of acetyl-CoA carboxylase, for example tetronic and tetramic acid derivatives, e.g. spirodiclofen, spiromesifen and spirotetramat.
(24) Complex IV electron transport inhibitors, for example phosphines, e.g. aluminium phosphide, calcium phosphide, phosphine and zinc phosphide or cyanide.
(25) Complex II electron transport inhibitors, for example cyenopyrafen and cyflumetofen.
(28) Ryanodine receptor effectors, for example diamides, e.g. chlorantraniliprole, cyantraniliprole and flubendiamide.
Further active compounds having an unknown or unclear mechanism of action, for example afidopyropen, afoxolaner, azadirachtin, benclothiaz, benzoximate, bifenazate, broflanilide, bromopropylate, quinomethionate, cryolite, cyclaniliprole, cycloxaprid, cyhalodiamide, dicloromezotiaz, dicofol, diflovidazin, flometoquin, fluazaindolizine, fluensulfone, flufenerim, flufenoxystrobin, flufiprole, fluhexafon, fluopyram, fluralaner, fluxametamide, fufenozide, guadipyr, heptafluthrin, imidaclothiz, iprodione, lotilaner, meperfluthrin, paichongding, pyflubumide, pyridalyl, pyrifluquinazon, pyriminostrobin, sarolaner, tetramethylfluthrin, tetraniliprole, tetrachlorantraniliprole, tioxazafen, thiofluoximate, triflumezopyrim and iodomethane; and additionally preparations based on *Bacillus firmus* (1-1582, BioNeem, Votivo), and the following known active compounds: 1-{2-fluoro-4-methyl-5-[(2,2,2-trifluoroethyl)sulfinyl]phenyl}-3-(trifluoromethyl)-1H-1,2,4-triazole-5-amine (known from WO2006/043635), {1'-[(2E)-3-(4-chlorophenyl)prop-2-en-1-yl]-5-fluorospiro[indole-3,4'-piperidin]-1(2H)-yl}(2-chloropyridin-4-yl)methanone (known from WO2003/106457), 2-chloro-N-[2-{1-[(2E)-3-(4-chlorophenyl)prop-2-en-1-yl]piperidin-4-yl}-4-(trifluoromethyl)phenyl]isonicotinamide (known from WO2006/003494), 3-(2,5-dimethylphenyl)-4-hydroxy-8-methoxy-1,8-diazaspiro[4.5]dec-3-en-2-one (known from WO2009/049851), 3-(2,5-dimethylphenyl)-8-methoxy-2-oxo-1,8-diazaspiro[4.5]dec-3-en-4-yl ethyl carbonate (known from WO2009/049851), 4-(but-2-yn-1-yloxy)-6-(3,5-dimethylpiperidin-1-yl)-5-fluoropyrimidine (known from WO2004/099160), 4-(but-2-yn-1-yloxy)-6-(3-chlorophenyl)pyrimidine (known from WO2003/076415), PF1364 (CAS Reg.No. 1204776-60-2), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-methylhydrazinecarboxylate (known from WO2005/085216), methyl 2-[3,5-dibromo-2-({[3-bromo-1-(3-chloropyridin-2-yl)-1H-pyrazol-5-yl]carbonyl}amino)benzoyl]-2-ethylhydrazinecarboxylate (known from WO2005/085216), N-[2-(5-amino-1,3,4-thiadiazol-2-yl)-4-chloro-6-methylphenyl]-3-bromo-1-(3-chloropyridin-2-yl)-1H-pyrazole-5-carboxamide (known from CN102057925), 4-[5-(3,5-dichlorophenyl)-5-(trifluoromethyl)-4,5-dihydro-1,2-oxazol-3-yl]-2-methyl-N-(1-oxidothietan-3-yl)benzamide (known from WO2009/080250), N-[(2E)-1-[(6-chloropyridin-3-yl)methyl]pyridin-2(1H)-ylidene]-2,2,2-trifluoroacetamide (known from WO2012/029672), 1-[(2-chloro-1,3-thiazol-5-yl)methyl]-4-oxo-3-phenyl-4H-pyrido[1,2-a]pyrimidin-1-ium-2-olate (known from WO2009/099929), 1-[(6-chloropyridin-3-yl)methyl]-4-oxo-3-phenyl-4H-pyrido[1,2-a]pyrimidin-1-ium-2-olate (known from WO2009/099929), 4-(3-{2,6-dichloro-4-[(3,3-dichloroprop-2-en-1-yl)oxy]phenoxy}propoxy)-2-methoxy-6-(trifluoromethyl)pyrimidine (known from CN101337940), N-[2-(tert-butylcarbamoyl)-4-chloro-6-methylphenyl]-1-(3-chloropyridin-2-yl)-3-(fluoromethoxy)-1H-pyrazole-5-carboxamide (known from WO2008/134969, butyl [2-(2,4-dichlorophenyl)-3-oxo-4-oxaspiro[4.5]dec-1-en-1-yl]carbonate (known from CN 102060818), 3E)-3-[1-[(6-chloro-3-pyridyl)methyl]-2-pyridylidene]-1,1,1-trifluoropropan-2-one (known from WO2013/144213, N-(methylsulfonyl)-6-[2-(pyridin-3-yl)-1,3-thiazol-5-yl]pyridine-2-carboxamide (known from WO2012/000896), N-[3-(benzylcarbamoyl)-4-chlorophenyl]-1-methyl-3-(pentafluoroethyl)-4-(trifluoromethyl)-1H-pyrazole-5-carboxamide (known from WO2010/051926), 5-bromo-4-chloro-N-[4-chloro-2-methyl-6-(methylcarbamoyl)phenyl]-2-(3-chloro-2-pyridyl)pyrazole-3-carboxamide (known from CN103232431).

Fungicides

The active ingredients specified herein by their common name are known and described, for example, in the "Pesticide Manual" or on the Internet (for example: http://www.alanwood.net/pesticides).

All the fungicidal mixing components listed in classes (1) to (15) may optionally form salts with corresponding bases or acids if suitable functional groups are present. In addition, the fungicidal mixing components listed in classes (1) to (15) also include tautomeric forms if tautomerism is possible.

1) Inhibitors of the ergosterol biosynthesis, for example (1.01) aldimorph, (1.02) azaconazole, (1.03) bitertanol, (1.04) bromuconazole, (1.05) cyproconazole, (1.06) diclobutrazole, (1.07) difenoconazole, (1.08) diniconazole, (1.09) diniconazole-M, (1.10) dodemorph, (1.11) dodemorph acetate, (1.12) epoxiconazole, (1.13) etaconazole, (1.14) fenarimol, (1.15) fenbuconazole, (1.16) fenhexamide, (1.17) fenpropidin, (1.18) fenpropimorph, (1.19) fluquinconazole, (1.20) flurprimidol, (1.21) flusilazole, (1.22) flutriafol, (1.23) furconazole, (1.24) furconazole-cis, (1.25) hexaconazole, (1.26) imazalil, (1.27) imazalil sulfate, (1.28) imibenconazole, (1.29) ipconazole, (1.30) metconazole, (1.31) myclobutanil, (1.32) naftifine, (1.33) nuarimol, (1.34) oxpoconazole, (1.35) paclobutrazole, (1.36) pefurazoate, (1.37) penconazole, (1.38) piperalin, (1.39) prochloraz, (1.40) propiconazole, (1.41) prothioconazole, (1.42) pyributicarb, (1.43) pyrifenox, (1.44) quinconazole, (1.45) simeconazole, (1.46) spiroxamine, (1.47) tebuconazole, (1.48) terbinafin, (1.49) tetraconazole, (1.50) triadimefon, (1.51) triadimenol, (1.52) tridemorph, (1.53) triflumizole, (1.54) triforin, (1.55) triticonazole, (1.56) uniconazole, (1.57) uniconazole-p, (1.58) viniconazole, (1.59) voriconazole, (1.60) 1-(4-chlorophenyl)-2-(1H-1,2,4-triazol-1-yl)cycloheptanol, (1.61) 1-(2,2-dimethyl-2,3-dihydro-1H-inden-1-yl)-1H-imidazole-5-carboxylic acid methyl ester, (1.62) N'-{5-(difluoromethyl)-2-methyl-4-[3-(trimethylsilyl)propoxy]phenyl}-N-ethyl-N-methylimidoformamide, (1.63) N-ethyl-N-methyl-N'-{2-methyl-5-(trifluoromethyl)-4-[3-(trimethylsilyl)propoxy]phenyl}imidoformamide, (1.64) O-[1-(4-methoxyphenoxy)-3,3-dimethylbutan-2-yl]-1H-imidazole-1-carbothioate, (1.65) pyrisoxazole, (1.66) 2-{[3-(2-chlorophenyl)-2-(2,4-difluorophenyl)oxiran-2-yl]methyl}-2,4-dihydro-3H-1,2,4-triazole-3-thione, (1.67) 1-{[3-(2-chlorophenyl)-2-(2,4-difluorophenyl)oxiran-2-yl]methyl}-1H-1,2,4-triazol-5-ylthiocyanate, (1.68) 5-(allylsulfanyl)-1-{[3-(2-chlorophenyl)-2-(2,4-difluorophenyl)oxiran-2-yl]methyl}-1H-1,2,4-triazole, (1.69) 2-[1-(2,4-dichlorophenyl)-5-hydroxy-2,6,6-trimethylheptan-4-yl-2,4-dihydro-3H-1,2,4-triazole-3-thione, (1.70) 2-{[rel(2R,3S)-3-(2-chlorophenyl)-2-(2,4-difluorophenyfloxiran-2-yl]methyl}-2,4-dihydro-3H-1,2,4-triazole-3-thione, (1.71) 2-{[rel(2R,3R)-3-(2-chlorophenyl)-2-(2,4-difluorophenyl)oxiran-2-yl]methyl}-2,4-dihydro-3H-1,2,4-triazole-3-thione, (1.72) 1-{[rel(2R,3S)-3-(2-chlorophenyl)-2-(2,4-difluorophenyl)oxiran-2-yl]methyl}-1H-1,2,4-triazol-5-ylthiocyanate, (1.73) 1-{[rel(2R,3R)-3-(2-chlorophenyl)-2-(2,4-difluorophenyl)oxiran-2-yl]methyl}-1H-1,2,4-triazol-5-ylthiocyanate, (1.74) 5-(allylsulfanyl)-1-{[rel(2R,3S)-3-(2-chlorophenyl)-2-(2,4-difluorophenyl)oxiran-2-yl]methyl}-1H-1,2,4-triazole, (1.75) 5-(allylsulfanyl)-1-{[rel(2R,3R)-3-(2-chlorophenyl)-2-(2,4-difluorophenyl)oxiran-2-yl]methyl}-1H-1,2,4-triazole, (1.76) 2-[(2S,4S,5S)-1-(2,4-dichlorophenyl)-5-hydroxy-2,6,6-trimethylheptan-4-yl]-2,4-dihydro-3H-1,2,4-triazole-3-thione, (1.77) 2-[(2R,4S,5S)-1-(2,4-dichlorophenyl)-5-hydroxy-2,6,6-trimethylheptan-4-yl]-2,4-dihydro-3H-1,2,4-triazole-3-thione, (1.78) 2-[(2R,4R,5R)-1-(2,4-dichlorophenyl)-5-hydroxy-2,6,6-trimethylheptan-4-yl]-2,4-dihydro-3H-1,2,4-triazole-3-thione, (1.79) 2-[(2S,4R,5R)-1-(2,4-dichlorophenyl)-5-hydroxy-2,6,6-trimethylheptan-4-yl]-2,4-dihydro-3H-1,2,4-triazole-3-thione, (1.80) 2-[(2S,4S,5R)-1-(2,4-dichlorophenyl)-5-hydroxy-2,6,6-trimethylheptan-4-yl]-2,4-dihydro-3H-1,2,4-triazole-3-thione, (1.81) 2-[(2R,4S,5R)-1-(2,4-dichlorophenyl)-5-hydroxy-2,6,6-trimethylheptan-4-yl]-2,4-dihydro-3H-1,2,4-triazole-3-thione, (1.82) 2-[(2R,4R,5S)-1-(2,4-dichlorophenyl)-5-hydroxy-2,6,6-trimethylheptan-4-yl]-2,4-dihydro-3H-1,2,4-triazole-3-thione, (1.83) 2-[(2S,4R,5S)-1-(2,4-dichlorophenyl)-5-hydroxy-2,6,6-trimethylheptan-4-yl]-2,4-dihydro-3H-1,2,4-triazole-3-thione, (1.84) 2-[4-(4-chlorophenoxy)-2-(trifluoromethyl)phenyl]-1-(1H-1,2,4-triazol-1-yl)propan-2-ol, (1.85) 2-[4-(4-chlorophenoxy)-2-(trifluoromethyl)phenyl]-1-(1H-1,2,4-triazol-1-yl)butan-2-ol, (1.86) 2-[4-(4-chlorophenoxy)-2-(trifluoromethyl)phenyl]-1-(1H-1,2,4-triazol-1-yl)pentan-2-ol, (1.87) 2-[2-chloro-4-(4-chlorophenoxy)phenyl]-1-(1H-1,2,4-triazol-1-yl)butan-2-ol, (1.88) 2-[2-chloro-4-(2,4-dichlorophenoxy)phenyl]-1-(1H-1,2,4-triazol-1-yl)propan-2-ol, (1.89) (2R)-2-(1-chlorocyclopropyl)-4-[(1R)-2,2-dichlorocyclopropyl]-1-(1H-1,2,4-triazol-1-yl)butan-2-ol, (1.90) (2R)-2-(1-chlorocyclopropyl)-4-[(1S)-2,2-dichlorocyclopropyl]-1-(1H-1,2,4-triazol-1-yl)butan-2-ol, (1.91) (2S)-2-(1-chlorocyclopropyl)-4-[(1S)-2,2-dichlorocyclopropyl]-1-(1H-1,2,4-triazol-1-yl)butan-2-01, (1.92) (2S)-2-(1-chlorocyclopropyl)-4-[(1R)-2,2-dichlorocyclopropyl]-1-(1H-1,2,4-triazol-1-yl)butan-2-ol, (1.93) (1S,2R,5R)-5-(4-chlorobenzyl)-2-(chloromethyl)-2-methyl-1-(1H-1,2,4-triazol-1-ylmethyl)cyclopentanol, (1.94) (1R,2S,5S)-5-(4-chlorobenzyl)-2-(chloromethyl)-2-methyl-1-(1H-1,2,4-triazol-1-ylmethyl)cyclopentanol, (1.95) 5-(4-chlorobenzyl)-2-(chloromethyl)-2-methyl-1-(1H-1,2,4-triazol-1-ylmethyl)cyclopentanol.

2) Inhibitors of complex I or II of the respiratory chain, for example (2.01) bixafen, (2.02) boscalid, (2.03) carboxin, (2.04) diflumetorim, (2.05) fenfuram, (2.06) fluopyram, (2.07) flutolanil, (2.08) fluxapyroxad, (2.09) furametpyr, (2.10) furmecyclox, (2.11) isopyrazam (mixture of syn-epimeric racemate 1RS,4SR,9RS and anti-epimeric racemate 1RS,4SR,9SR), (2.12) isopyrazam (anti-epimeric racemate 1RS,4SR,9SR), (2.13) isopyrazam (anti-epimeric enantiomer 1R,4S,9S), (2.14) isopyrazam (anti-epimeric enantiomer 1S,4R,9R), (2.15) isopyrazam (syn-epimeric racemate 1RS,4SR,9RS), (2.16) isopyrazam (syn-epimeric enantiomer 1R,4S,9R), (2.17) isopyrazam (syn-epimeric enantiomer 1S,4R,9S), (2.18) mepronil, (2.19) oxycarboxin, (2.20) penflufen, (2.21) penthiopyrad, (2.22) sedaxane, (2.23) thifluzamide, (2.24) 1-methyl-N-[2-(1,1,2,2-tetrafluoroethoxy)phenyl]-3-(trifluoromethyl)-1H-pyrazole-4-carboxamide, (2.25) 3-(difluoromethyl)-1-methyl-N-[2-(1,1,2,2-tetrafluoroethoxy)phenyl]-1H-pyrazole-4-carboxamide, (2.26) 3-(difluoromethyl)-N-[4-fluoro-2-(1,1,2,3,3,3-hexafluoropropoxy)phenyl]-1-methyl-1H-pyrazole-4-carboxamide, (2.27) N-[1-(2,4-dichlorophenyl)-1-methoxypropan-2-yl]-3-(difluoromethyl)-1-methyl-1H-pyrazole-4-carboxamide, (2.28) 5,8-difluoro-N-[2-(2-fluoro-4-{[4-(trifluoromethyl)pyridin-2-yl]oxy}phenyl)ethyl]quinazolin-4-amine, (2.29) benzovindiflupyr, (2.30) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide, (2.31) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.32) 3-(difluoromethyl)-1-methyl-N-(1,1,3-trimethyl-2,3-dihydro-1H-inden-4-yl)-1H-pyrazole-4-carboxamide, (2.33) 1,3,5-trimethyl-N-(1,1,3-trimethyl-2,3-dihydro-1H-inden-4-yl)-1H-pyrazole-4-carboxamide, (2.34) 1-methyl-3-(trifluoromethyl)-N-(1,1,3-trimethyl-2,3-dihydro-1H-inden-4-yl)-1H-pyrazole-4- carboxamide, (2.35) 1-methyl-3-(trifluoromethyl)-N-[(3R)-1,1,3-trimethyl-2,3-dihydro-1H-inden-4-yl]-1H-pyrazole-4-carboxamide, (2.36) 1-methyl-3-(trifluoromethyl)-N-[(3S)-1,1,3-trimethyl-2,3-dihydro-1H-inden-4-yl]-1H-pyrazole-4-carboxamide, (2.37) 3-(difluoromethyl)-1-methyl-N-[(3S)-1,1,3-trimethyl-2,3-dihydro-1H-inden-4-yl]-1H-pyrazole-4-carboxamide, (2.38) 3-(difluoromethyl)-1-methyl-N-[(3R)-1,1,3-trimethyl-2,3-dihydro-1H-inden-4-yl]-1H-pyrazole-4-carboxamide, (2.39) 1,3,5-trimethyl-N-[(3R)-1,1,3-trimethyl-2,3-dihydro-1H-inden-4-yl]-1H-pyrazole-4-carboxamide, (2.40) 1,3,5-trimethyl-N-[(3S)-1,1,3-trimethyl-2,3-dihydro-1H-inden-4-yl]-1H-pyrazole-4-carboxamide, (2.41) benodanil, (2.42) 2-chloro-N-(1,1,3-trimethyl-2,3-dihydro-1H-inden-4-yl)pyridine-3-carboxamide, (2.43) isofetamide, (2.44) 1-methyl-3-(trifluoromethyl)-N-[2'-(trifluoromethyl)biphenyl-2-yl]-1H-pyrazole-4-carboxamide, (2.45) N-(4'-chlorobiphenyl-2-yl)-3-(difluoromethyl)-1-methyl-1H-pyrazole-4-carboxamide, (2.46) N-(2',4'-dichlorobiphenyl-2-yl)-3-(difluoromethyl)-1-methyl-1H-pyrazole-4-carboxamide, (2.47) 3-(difluoromethyl)-1-methyl-N-[4'-(trifluoromethyl)biphenyl-2-yl]-1H-pyrazole-4-carboxamide, (2.48) N-(2',5'-difluorobiphenyl-2-yl)-1-methyl-3-(trifluoromethyl)-1H-pyrazole-4-carboxamide, (2.49) 3-(difluoromethyl)-1-methyl-N-[4'-(prop-1-yn-1-yl)biphenyl-2-yl]-1H-pyrazole-4-carboxamide, (2.50) 5-fluoro-1,3-dimethyl-N-[4'-(prop-1-yn-1-yl)biphenyl-2-yl]-1H-pyrazole-4-carboxamide, (2.51) 2-chloro-N-[4'-(prop-1-yn-1-yl)biphenyl-2-yl]nicotinamide, (2.52) 3-(difluoromethyl)-N-[4'-(3,3-dimethylbut-1-yn-1-yl)biphenyl-2-yl]-1-methyl-1H-pyrazole-4-carboxamide, (2.53) N-[4'-(3,3-dimethylbut-1-yn-1-yl)biphenyl-2-yl]-5-fluoro-1,3-dimethyl-1H-pyrazole-4-carboxamide, (2.54) 3-(difluoromethyl)-N-(4'-ethynylbiphenyl-2-yl)-1-methyl-1H-pyrazole-4-carboxamide, (2.55) N-(4'-ethynylbiphenyl-2-yl)-5-fluoro-1,3-dimethyl-1H-pyrazole-4-carboxamide, (2.56) 2-chloro-N-(4'-ethynylbiphenyl-2-yl)nicotinamide, (2.57) 2-chloro-N-[4'-(3,3-dimethylbut-1-yn-1-yl)biphenyl-2-yl]nicotinamide, (2.58) 4-(difluoromethyl)-2-methyl-N-[4'-(trifluoromethyl)biphenyl-2-yl]-1,3-thiazole-5-carboxamide, (2.59) 5-fluoro-N-[4'-(3-hydroxy-3-methylbut-1-yn-1-yl)biphenyl-2-yl]-1,3-dimethyl-1H-pyrazole-4-carboxamide, (2.60) 2-chloro-N-[4'-(3-hydroxy-3-methylbut-1-yn-1-yl)biphenyl-2-yl]nicotinamide, (2.61) 3-(difluoromethyl)-N-[4'-(3-methoxy-3-methylbut-1-yn-1-yl)biphenyl-2-yl]-1-methyl-1H-pyrazole-4-carboxamide, (2.62) 5-fluoro-N-[4'-(3-methoxy-3-methylbut-1-yn-1-yl)biphenyl-2-yl]-1,3-dimethyl-1H-pyrazole-4-carboxamide, (2.63) 2-chloro-N-[4'-(3-methoxy-3-methylbut-1-yn-1-yl)biphenyl-2-yl]nicotinamide, (2.64) 1,3-dimethyl-N-(1,1,3-trimethyl-2,3-dihydro-1H-inden-4-yl)-1H-pyrazole-4-carboxamide, (2.65) 1,3-dimethyl-N-[(3R)-1,1,3-trimethyl-2,3-dihydro-1H-inden-4-yl]-1H-pyrazole-4-carboxamide, (2.66) 1,3-dimethyl-N-[(3S)-1,1,3-trimethyl-2,3-dihydro-1H-inden-4-yl]-1H-pyrazole-4-carboxamide, (2.67) 3-(difluoromethyl)-N-methoxy-1-methyl-N-[1-(2,4,6-trichlorophenyl)propan-2-yl]-1H-pyrazole-4-carboxamide, (2.68) 3-(difluoromethyl)-N-(7-fluoro-1,1,3-trimethyl-2,3-dihydro-1H-inden-4-yl)-1-methyl-1H-pyrazole-4-carboxamide, (2.69) 3-(difluoromethyl)-N-[(3R)-7-fluoro-1,1,3-trimethyl-2,3-dihydro-1H-inden-4-yl]-1-methyl-1H-pyrazole-4-carboxamide, (2.70) 3-(difluoromethyl)-N-[(3S)-7-fluoro-1,1,3-trimethyl-2,3-dihydro-1H-inden-4-yl]-1-methyl-1H-pyrazole-4-carboxamide.

3) Inhibitors of the respiratory chain on complex III, for example (3.01) ametoctradin, (3.02) amisulbrom, (3.03) azoxystrobin, (3.04) cyazofamid, (3.05) coumethoxystrobin, (3.06) coumoxystrobin, (3.07) dimoxystrobin, (3.08) enoxastrobin, (3.09) famoxadon, (3.10) fenamidon, (3.11) flufenoxystrobin, (3.12) fluoxastrobin, (3.13) kresoxim-methyl, (3.14) metominostrobin, (3.15) orysastrobin, (3.16) picoxystrobin, (3.17) pyraclostrobin, (3.18) pyrametostrobin, (3.19) pyraoxystrobin, (3.20) pyribencarb, (3.21) triclopyricarb, (3.22) trifloxystrobin, (3.23) (2E)-2-(2-{[6-(3-chloro-2-methylphenoxy)-5-fluoropyrimidin-4-yl]oxy}phenyl)-2-(methoxyimino)-N-methylacetamide, (3.24) (2E)-2-(methoxyimino)-N-methyl-2-(2-{[({(1E)-1-[3-(trifluoromethyl)phenyl]ethyliden}amino)oxy]methyl}phenyl)acetamide, (3.25) (2E)-2-(methoxyimino)-N-methyl-2-{2-[(E)-({1-[3-(trifluoromethyl)phenyl]ethoxy}imino)methyl]phenyl}acetamide, (3.26) (2E)-2-{2-[({[(1E)-1-(3-{[(E)-1-fluoro-2-phenylvinyl]oxy}phenyl)ethyliden]amino}oxy)methyl]phenyl}-2-(methoxyimino)-N-methylacetamide, (3.27) fenaminostrobin, (3.28) 5-methoxy-2-methyl-4-(2-{[({(1E)-1-[3-(trifluoromethyl)phenyl]ethyliden}amino)oxy]methyl}phenyl)-2,4-dihydro-3H-1,2,4-triazol-3-one, (3.29) (2E)-2-{2-[({cyclopropyl[(4-methoxyphenyl)imino]methyl}sulfanyl)methyl]phenyl}-3-methoxyacrylic acid methyl ester, (3.30) N-(3-ethyl-3,5,5-trimethylcyclohexyl)-3-formamido-2-hydroxybenzamide, (3.31) 2-{2-[(2,5-dimethylphenoxy)methyl]phenyl}-2-methoxy-N-methylacetamide, (3.32) 2-{2-[(2,5-dimethylphenoxy)methyl]phenyl}-2-methoxy-N-methylacetamide, (3.33) (2E,3Z)-5-{[1-(4-chlorophenyl)-1H-pyrazol-3-yl]oxy}-2-(methoxyimino)-N,3-dimethylpent-3-enamide.

4) Mitosis and cell division inhibitors, for example (4.01) benomyl, (4.02) carbendazim, (4.03) chlorfenazole, (4.04) diethofencarb, (4.05) ethaboxam, (4.06) fluopicolide, (4.07) fuberidazole, (4.08) pencycuron, (4.09) thiabendazole, (4.10) thiophanate-methyl, (4.11) thiophanate, (4.12) zoxamide, (4.13) 5-chloro-7-(4-methylpiperidin-1-yl)-6-(2,4,6-trifluorophenyl)[1,2,4]triazolo[1,5-a]pyrimidine, (4.14) 3-chloro-5-(6-chloropyridin-3-yl)-6-methyl-4-(2,4,6-trifluorophenyl)pyridazine.

5) Compounds capable of having multisite action, for example (5.01) Bordeaux mixture, (5.02) captafol, (5.03) captan, (5.04) chlorothalonil, (5.05) copper hydroxide, (5.06) copper naphthenate, (5.07) copper oxide, (5.08) copper oxychloride, (5.09) copper(2+) sulfate, (5.10) dichlofluanid, (5.11) dithianon, (5.12) dodine, (5.13) dodine free base, (5.14) ferbam, (5.15) fluorofolpet, (5.16) folpet, (5.17) guazatine, (5.18) guazatine acetate, (5.19) iminoctadine, (5.20) iminoctadine albesilate, (5.21) iminoctadine triacetate, (5.22) mancopper, (5.23) mancozeb, (5.24) maneb, (5.25) metiram, (5.26) metiram zinc, (5.27) oxine-copper, (5.28) propamidine, (5.29) propineb, (5.30) sulfur and sulfur preparations including calcium polysulfide, (5.31) thiram, (5.32) tolylfluanid, (5.33) zineb, (5.34) ziram, (5.35) anilazine.

6) Compounds capable of inducing host defence, for example (6.01) acibenzolar-S-methyl, (6.02) isotianil, (6.03) probenazole, (6.04) tiadinil, (6.05) laminarin.

7) Amino acid and/or protein biosynthesis inhibitors, for example (7.01) andoprim, (7.02) blasticidin-S, (7.03) cyprodinil, (7.04) kasugamycin, (7.05) kasugamycin hydrochloride hydrate, (7.06) mepanipyrim, (7.07) pyrimethanil, (7.08) 3-(5-fluoro-3,3,4,4-tetramethyl-3,4-dihydroisoquinolin-1-yl)quinoline, (7.09) oxytetracycline, (7.10) streptomycin.

8) ATP production inhibitors, for example (8.01) fentin acetate, (8.02) fentin chloride, (8.03) fentin hydroxide, (8.04) silthiofam.

9) Cell wall synthesis inhibitors, for example (9.01) benthiavalicarb, (9.02) dimethomorph, (9.03) flumorph, (9.04) iprovalicarb, (9.05) mandipropamide, (9.06) polyoxins, (9.07) polyoxorim, (9.08) validamycin A, (9.09) valifenalate, (9.10) polyoxin B, (9.11) (2E)-3-(4-tert-butylphenyl)-3-(2-chloropyridin-4-yl)-1-(morpholin-4-yl)prop-2-en-1-one, (9.12) (2Z)-3-(4-tert-butylphenyl)-3-(2-chloropyridin-4-yl)-1-(morpholin-4-yl)prop-2-en-1-one.

10) Lipid and membrane synthesis inhibitors, for example (10.01) biphenyl, (10.02) chloroneb, (10.03) dicloran, (10.04) edifenphos, (10.05) etridiazole, (10.06) iodocarb, (10.07) iprobenfos, (10.08) isoprothiolane, (10.09) propamocarb, (10.10) propamocarb hydrochloride, (10.11) prothiocarb, (10.12) pyrazophos, (10.13) quintozene, (10.14) tecnazene, (10.15) tolclofos-methyl.

11) Melanin biosynthesis inhibitors, for example (11.01) carpropamide, (11.02) diclocymet, (11.03) fenoxanil, (11.04) phthalide, (11.05) pyroquilon, (11.06) tricyclazole, (11.07) 2,2,2-trifluoroethyl {3-methyl-1-[(4-methylbenzoyl)amino]butan-2-yl}carbamate.

12) Nucleic acid synthesis inhibitors, for example (12.01) benalaxyl, (12.02) benalaxyl-M (kiralaxyl), (12.03) bupirimate, (12.04) clozylacon, (12.05) dimethirimol, (12.06) ethirimol, (12.07) furalaxyl, (12.08) hymexazole, (12.09) metalaxyl, (12.10) metalaxyl-M (mefenoxam), (12.11) ofurace, (12.12) oxadixyl, (12.13) oxolinic acid, (12.14) octhilinone.

13) Signal transduction inhibitors, for example (13.01) chlozolinate, (13.02) fenpiclonil, (13.03) fludioxonil, (13.04) iprodione, (13.05) procymidone, (13.06) quinoxyfen, (13.07) vinclozolin, (13.08) proquinazid.

14) Compounds capable of acting as uncouplers, for example (14.01) binapacryl, (14.02) dinocap, (14.03) ferimzone, (14.04) fluazinam, (14.05) meptyldinocap.

15) Further compounds, for example (15.001) benthiazole, (15.002) bethoxazin, (15.003) capsimycin, (15.004) carvone, (15.005) quinomethionate, (15.006) pyriofenone (chlazafenone), (15.007) cufraneb, (15.008) cyflufenamid, (15.009) cymoxanil, (15.010) cyprosulfamide, (15.011) dazomet, (15.012) debacarb, (15.013) dichlorophen, (15.014) diclomezin, (15.015) difenzoquat, (15.016) difenzoquat metilsulfate, (15.017) diphenylamine, (15.018) ecomate, (15.019) fenpyrazamine, (15.020) flumetover, (15.021) fluoroimide, (15.022) flusulfamide, (15.023) flutianil, (15.024) fosetyl-aluminium, (15.025) fosetyl-calcium, (15.026) fosetyl-sodium, (15.027) hexachlorobenzene, (15.028) irumamycin, (15.029) methasulfocarb, (15.030) methyl isothiocyanate, (15.031) metrafenone, (15.032) mildiomycin, (15.033) natamycin, (15.034) nickel dimethyldithiocarbamate, (15.035) nitrothal-isopropyl, (15.036) oxamocarb, (15.037) oxyfenthiin, (15.038) pentachlorophenol and salts, (15.039) phenothrin, (15.040) phosphorous acid and salts thereof, (15.041) propamocarb-fosetylate, (15.042) propanosin-sodium, (15.043) pyrimorph, (15.044) pyrrolnitrin, (15.045) tebufloquin, (15.046) tecloftalam, (15.047) tolnifanid, (15.048) triazoxide, (15.049) trichlamid, (15.050) zarilamid, (15.051) 2-methylpropanoic acid (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl ester, (15.052) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.053) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.054) oxathiapiproline, (15.055) 1H-imidazole-1-carboxylic acid 1-(4-methoxyphenoxy)-3,3-dimethylbutan-2-yl ester, (15.056) 2,3,5,6-tetrachloro-4-(methylsulfonyl)pyridine, (15.057) 2,3-dibutyl-6-chlorothieno[2,3-d]pyrimidin-4 (3H)-one, (15.058) 2,6-dimethyl-1H,5H-[1,4]dithiino[2,3-c:5,6-c']dipyrrole-1,3,5,7 (2H,6H)-tetrone, (15.059) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, (15.060) 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, (15.061) 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, (15.062) 2-butoxy-6-iodo-3-propyl-4H-chromen-4-one, (15.063) 2-chloro-5-[2-chloro-1-(2,6-difluoro-4-methoxyphenyl)-4-methyl-1H-imidazol-5-yl]pyridine, (15.064) 2-phenylphenol and salts, (15.065) 3-(4,4,5-trifluoro-3,3-dimethyl-3,4-dihydroisoquinolin-1-yl)quinoline, (15.066) 3,4,5-trichloropyridine-2,6-dicarboxylic acid nitrile, (15.067) 3-chloro-5-(4-chlorophenyl)-4-(2,6-difluorophenyl)-6-methylpyridazine, (15.068) 4-(4-chlorophenyl)-5-(2,6-difluorophenyl)-3,6-dimethylpyridazine, (15.069) 5-amino-1,3,4-thiadiazole-2-thiol, (15.070) 5-chloro-N'-phenyl-N'-(prop-2-in-1-yl)thiophene-2-sulfonohydrazide, (15.071) 5-fluoro-2-[(4-fluorobenzyl)oxy]pyrimidin-4-amine, (15.072) 5-fluoro-2-[(4-methylbenzyl)oxy]pyrimidin-4-amin, (15.073) 5-methyl-6-octyl[1,2,4]triazolo[1,5-a]pyrimidin-7-amin, (15.074) (2Z)-3-amino-2-cyano-3-phenylacrylic acid ethyl ester, (15.075) N'-(4-{[3-(4-chlorobenzyl)-1,2,4-thiadiazol-5-yl]oxy}-2,5-dimethylphenyl)-N-ethyl-N-methylimidoformamide, (15.076) N-(4-chlorobenzyl)-3-[3-methoxy-4-(prop-2-in-1-yloxy)phenyl]propanamide, (15.077) N-[(4-chlorophenyl)(cyano)methyl]-3-[3-methoxy-4-(prop-2-in-1-yloxy)phenyl]propanamide, (15.078) N-[(5-bromo-3-chloropyridin-2-yl)methyl]-2,4-dichloronicotinamide, (15.079) N-[1-(5-bromo-3-chloropyridin-2-yl)ethyl]-2,4-dichloronicotinamide, (15.080) N-[1-(5-bromo-3-chloropyridin-2-yl)ethyl]-2-fluoro-4-iodonicotinamide, (15.081) N-{(E)-[(cyclopropylmethoxy)imino][6-(difluoromethoxy)-2,3-difluorophenyl]methyl}-2-phenylacetamide, (15.082) N—{(Z)-[(cyclopropylmethoxy)imino][6-(difluoromethoxy)-2,3-difluorophenyl]methyl}-2-phenylacetamide, (15.083) N'-{4-[(3-tert-butyl-4-cyano-1,2-thiazol-5-yl)oxy]-2-chloro-5-methylphenyl}-N-ethyl-N-methylimidoformamide, (15.084) N-methyl-2-(1-{[5-methyl-3-(trifluoromethyl)-1H-pyrazol-1-yl]acetyl}piperidin-4-yl)-N-(1,2,3,4-tetrahydronaphthalin-1-yl)-1,3-thiazole-4-carboxamide, (15.085) N-methyl-2-(1-{[5-methyl-3-(trifluoromethyl)-1H-pyrazol-1-yl]acetyl}piperidin-4-yl)-N-[(1R)-1,2,3,4-tetrahydronaphthalin-1-yl]-1,3-thiazole-4-carboxamide, (15.086) N-methyl-2-(1-{[5-methyl-3-(trifluoromethyl)-1H-pyrazol-1-yl]acetyl}piperidin-4-yl)-N-[(1S)-1,2,3,4-tetrahydronaphthalin-1-yl]-1,3-thiazole-4-carboxamide, (15.087) {6-[({[(1-methyl-1H-tetrazol-5-yl)(phenyl)methylen]amino}oxy)methyl]pyridin-2-yl}carbamic acid pentyl ester, (15.088) phenazine-1-carboxylic acid, (15.089) quinolin-8-ol, (15.090) quinolin-8-ol sulfate (2:1), (15.091) {6-[({[(1-methyl-1H-tetrazol-5-yl)(phenyl)methylen]amino}oxy)methyl]pyridin-2-yl}carbamic acid tert-butyl ester, (15.092) (5-bromo-2-methoxy-4-methylpyridin-3-yl)(2,3,4-trimethoxy-6-methylphenyl)methanone, (15.093) N-[2-(4-{[3-(4-chlorophenyl)prop-2-yn-1-yl]oxy}-3-methoxyphenyl)ethyl]-N2-(methylsulfonyl)valinamide, (15.094) 4-oxo-4-[(2-phenylethyl)amino]butanoic acid, (15.095) {6-[({[(Z)-(1-methyl-1H-tetrazol-5-yl)(phenyl)methylen]amino}oxy)methyl]pyridin-2-yl}carbamic acid but-3-yn-1-yl ester, (15.096) 4-amino-5-fluoropyrimidin-2-ol (tautomeric form: 4-amino-5-fluoropyrimidin-2 (1H)- one), (15.097) propyl 3,4,5-trihydroxybenzoate, (15.098) [3-(4-chloro-2-fluorophenyl)-5-(2,4-difluorophenyl)-1,2-oxazol-4-yl](pyridin-3-yl)methanol, (15.099) (S)-[3-(4-chloro-2-fluorophenyl)-5-(2,4-difluorophenyl)-1,2-oxazol-4-yl](pyridin-3-yl)methanol, (15.100) (R)-[3-(4-chloro-2-fluorophenyl)-5-(2,4-difluorophenyl)-1,2-oxazol-4-yl](pyridin-3-yl)methanol, (15.101) 2-fluoro-6-(trifluoromethyl)-N-(1,1,3-trimethyl-2,3-dihydro-1H-inden-4-yl)benzamide, (15.102) 2-(6-benzylpyridin-2-yl)quinazoline, (15.103) 2-[6-(3-fluoro-4-methoxyphenyl)-5-methylpyridin-2-yl]quinazoline, (15.104) 3-(4,4-difluoro-3,3-dimethyl-3,4-dihydroisoquinolin-1-yl)quinoline, (15.105) abscisic acid, (15.106) N'-[5-bromo-6-(2,3-dihydro-1H-inden-2-yloxy)-2-methylpyridin-3-yl]-N-ethyl-N-methylimidoformamide, (15.107) N'-{5-bromo-6-[1-(3,5-difluorophenyl)ethoxy]-2-methylpyridin-3-yl}-N-ethyl-N-methylimidoformamide, (15.108) N'-{5-bromo-6-[(1R)-1-(3,5-difluorophenyl)ethoxy]-2-methylpyridin-3-yl}-N-ethyl-N-methylimidoformamide, (15.109) N'-{5-bromo-6-[(1S)-1-(3,5-difluorophenyl)ethoxy]-2-methylpyridin-3-yl}-N-ethyl-N-methylimidoformamide, (15.110) N'-{5-bromo-6-[(cis-4-isopropylcyclohexyl)oxy]-2-methylpyridin-3-yl}-N-ethyl-N-methylimidoformamide, (15.111) N'-{5-bromo-6-[(trans-4-isopropylcyclohexyl)oxy]-2-methylpyridin-3-yl}-N-ethyl-N-methylimidoformamide, (15.112) N-cyclopropyl-3-(difluoromethyl)-5-fluoro-N-(2-isopropylbenzyl)-1-methyl-1H-pyrazole-4-carboxamide, (15.113) N-cyclopropyl-N-(2-cyclopropylbenzyl)-3-(difluoromethyl)-5-fluoro-1-methyl-1H-pyrazole-4-carboxamide, (15.114) N-(2-tert-butylbenzyl)-N-cyclopropyl-3-(difluoromethyl)-5-fluoro-1-methyl-1H-pyrazole-4-carboxamide, (15.115) N-(5-chloro-2-ethylbenzyl)-N-cyclopropyl-3-(difluoromethyl)-5-fluoro-1-methyl-1H-pyrazole-4-carboxamide, (15.116) N-(5-chloro-2-isopropylbenzyl)-N-cyclopropyl-3-(difluoromethyl)-5-fluoro-1-methyl-1H-pyrazole-4-carboxamide, (15.117) N-cyclopropyl-3-(difluoromethyl)-N-(2-ethyl-5-fluorobenzyl)-5-fluoro-1-methyl-1H-pyrazole-4-carboxamide, (15.118) N-cyclopropyl-3-(difluoromethyl)-5-fluoro-N-(5-fluoro-2-isopropylbenzyl)-1-methyl-1H-pyrazole-4-carboxamide, (15.119) N-cyclopropyl-N-(2-cyclopropyl-5-fluorobenzyl)-3-(difluoromethyl)-5-fluoro-1-methyl-1H-pyrazole-4-carboxamide, (15.120) N-(2-cyclopentyl-5-fluorobenzyl)-N-cyclopropyl-3-(difluoromethyl)-5-fluoro-1-methyl-1H-pyrazole-4-carboxamide, (15.121) N-cyclopropyl-3-(difluoromethyl)-5-fluoro-N-(2-fluoro-6-isopropylbenzyl)-1-methyl-1H-pyrazole-4-carboxamide, (15.122) N-cyclopropyl-3-(difluoromethyl)-N-(2-ethyl-5-methylbenzyl)-5-fluoro-1-methyl-1H-pyrazole-4-carboxamide, (15.123) N-cyclopropyl-3-(difluoromethyl)-5-fluoro-N-(2-isopropyl-5-methylbenzyl)-1-methyl-1H-pyrazole-4-carboxamide, (15.124) N-cyclopropyl-N-(2-cyclopropyl-5-methylbenzyl)-3-(difluoromethyl)-5-fluoro-1-methyl-1H-pyrazole-4-carboxamide, (15.125) N-(2-tert-butyl-5-methylbenzyl)-N-cyclopropyl-3-(difluoromethyl)-5-fluoro-1-methyl-1H-pyrazole-4-carboxamide, (15.126) N-[5-chloro-2-(trifluoromethyl)benzyl]-N-cyclopropyl-3-(difluoromethyl)-5-fluoro-1-methyl-1H-pyrazole-4-carboxamide, (15.127) N-cyclopropyl-3-(difluoromethyl)-5-fluoro-1-methyl-N-[5-methyl-2-(trifluoromethyl)benzyl]-1H-pyrazole-4-carboxamide, (15.128) N-[2-chloro-6-(trifluoromethyl)benzyl]-N-cyclopropyl-3-(difluoromethyl)-5-fluoro-1-methyl-1H-pyrazole-4-carboxamide, (15.129) N-[3-chloro-2-fluoro-6-(trifluoromethyl)benzyl]-N-cyclopropyl-3-(difluoromethyl)-5-fluoro-1-methyl-1H-pyrazole-4-carboxamide, (15.130) N-cyclopropyl-3-(difluoromethyl)-N-(2-ethyl-4,5-dimethylbenzyl)-5-fluoro-1-methyl-1H-pyrazole-4-carboxamide, (15.131) N-cyclopropyl-3-(difluoromethyl)-5-fluoro-N-(2-isopropylbenzyl)-1-methyl-1H-pyrazole-4-carbothioamide, (15.132) N'-(2,5-dimethyl-4-phenoxyphenyl)-N-ethyl-N-methylimidoformamide, (15.133) N'-{4-[(4,5-dichloro-1,3-thiazol-2-yl)oxy]-2,5-dimethylphenyl}-N-ethyl-N-methylimidoformamide, (15.134) N-(4-chloro-2,6-difluorophenyl)-4-(2-chloro-4-fluorophenyl)-1,3-dimethyl-1H-pyrazol-5-amine, (15.135) 9-fluoro-2,2-dimethyl-5-(quinolin-3-yl)-2,3-dihydro-1,4-benzoxazepine, (15.136) 2-{2-fluoro-6-[(8-fluoro-2-methylquinolin-3-yl)oxy]phenyl}propan-2-ol, (15.137) 2-{2-[(7,8-difluoro-2-methylquinolin-3-yl)oxy]-6-fluorophenyl}propan-2-ol, (15.138) 4-(2-chloro-4-fluorophenyl)-N-(2-fluorophenyl)-1,3-dimethyl-1H-pyrazol-5-amine, (15.139) 4-(2-chloro-4-fluorophenyl)-N-(2,6-difluorophenyl)-1,3-dimethyl-1H-pyrazol-5-amine, (15.140) 4-(2-chloro-4-fluorophenyl)-N-(2-chloro-6-fluorophenyl)-1,3-dimethyl-1H-pyrazol-5-amine, (15.141) 4-(2-bromo-4-fluorophenyl)-N-(2-chloro-6-fluorophenyl)-1,3-dimethyl-1H-pyrazol-5-amine, (15.142) N-(2-bromo-6-fluorophenyl)-4-(2-chloro-4-fluorophenyl)-1,3-dimethyl-1H-pyrazol-5-amine, (15.143) 4-(2-bromo-4-fluorophenyl)-N-(2-bromophenyl)-1,3-dimethyl-1H-pyrazol-5-amine, (15.144) 4-(2-bromo-4-fluorophenyl)-N-(2-bromo-6-fluorophenyl)-1,3-dimethyl-1H-pyrazol-5-amine, (15.145) 4-(2-bromo-4-fluorophenyl)-N-(2-chlorophenyl)-1,3-dimethyl-1H-pyrazol-5-amine, (15.146) N-(2-bromophenyl)-4-(2-chloro-4-fluorophenyl)-1,3-dimethyl-1H-pyrazol-5-amine, (15.147) 4-(2-chloro-4-fluorophenyl)-N-(2-chlorophenyl)-1,3-dimethyl-1H-pyrazol-5-amine, (15.148) 4-(2-bromo-4-fluorophenyl)-N-(2,6-difluorophenyl)-1,3-dimethyl-1H-pyrazol-5-amine, (15.149) 4-(2-bromo-4-fluorophenyl)-N-(2-fluorophenyl)-1,3-dimethyl-1H-pyrazol-5-amine, (15.150) N'-(4-{3-[(difluoromethyl)sulfanyl]phenoxy}-2,5-dimethylphenyl)-N-ethyl-N-methylimidoformamide, (15.151) N'-(2,5-dimethyl-4-{3-[(1,1,2,2-tetrafluoroethyl)sulfanyl]phenoxy}phenyl)-N-ethyl-N-methylimidoformamide, (15.152) N'-(2,5-dimethyl-4-{3-[(2,2,2-trifluoroethyl)sulfanyl]phenoxy}phenyl)-N-ethyl-N-methylimidoformamide, (15.153) N'-(2,5-dimethyl-4-{3-[(2,2,3,3-tetrafluoropropyl)sulfanyl]phenoxy}phenyl)-N-ethyl-N-methylimidoformamide, (15.154) N'-(2,5-dimethyl-4-{3-[(pentafluoroethyl)sulfanyl]phenoxy}phenyl)-N-ethyl-N-methylimidoformamide, (15.155) N'-(4-{[3-(difluoromethoxy)phenyl]sulfanyl}-2,5-dimethylphenyl)-N-ethyl-N-methylimidoformamide, (15.156) N'-(2,5-dimethyl-4-{[3-(1,1,2,2-tetrafluoroethoxy)phenyl]sulfanyl}phenyl)-N-ethyl-N-methylimidoformamide, (15.157) N'-(2,5-dimethyl-4-{[3-(2,2,2-trifluoroethoxy)phenyl]sulfanyl}phenyl)-N-ethyl-N-methylimidoformamide, (15.158) N'-(2,5-dimethyl-4-{[3-(2,2,3,3-tetrafluoropropoxy)phenyl]sulfanyl}phenyl)-N-ethyl-N-methylimidoformamide, (15.159) N'-(2,5-dimethyl-4-{[3-(pentafluoroethoxy)phenyl]sulfanyl}phenyl)-N-ethyl-N-methylimidoformamide, (15.160) 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, (15.161) 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.162) 2-[3,5-bis(difluorpmethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone, (15.163) 2-{3-[2-(1-{[3,5-bis(difluoromethyl)-1H-pyrazol-1-yl]

acetyl}piperidin-4-yl)-1,3-thiazol-4-yl]-4,5-dihydro-1,2-oxazol-5-yl}phenyl methanesulfonate, (15.164) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.165) 2-[3,5-bis(difluoromethyl)-1H-pyrazol-1-yl]-1-[4-(4-{(5S)-5-[2-(prop-2-yn-1-yloxy)phenyl]-4,5-dihydro-1,2-oxazol-3-yl}-1,3-thiazol-2-yl)piperidin-1-yl]ethanone, (15.166) 2-[3,5-bis(difluoromethyl)-1H-pyrazol-1-yl]-1-[4-(4-{(5R)-5-[2-(prop-2-yn-1-yloxy)phenyl]-4,5-dihydro-1,2-oxazol-3-yl}-1,3-thiazol-2-yl)piperidin-1-yl]ethanone, (15.167) 2-[3,5-bis(difluoromethyl)-1H-pyrazol-1-yl]-1-[4-(4-{(5S)-5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.168) 2-[3,5-bis(difluoromethyl)-1H-pyrazol-1-yl]-1-[4-(4-{(5R)-5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.169) 2-[3,5-bis(difluoromethyl)-1H-pyrazol-1-yl]-1-[4-(4-{(5S)-5-[2-chloro-6-(prop-2-yn-1-yloxy)phenyl]-4,5-dihydro-1,2-oxazol-3-yl}-1,3-thiazol-2-yl)piperidin-1-yl]ethanone, (15.170) 2-[3,5-bis(difluoromethyl)-1H-pyrazol-1-yl]-1-[4-(4-{(5R)-5-[2-chloro-6-(prop-2-yn-1-yloxy)phenyl]-4,5-dihydro-1,2-oxazol-3-yl}-1,3-thiazol-2-yl)piperidin-1-yl]ethanone, (15.171) 2-{(5S)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate, (15.172) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate, (15.173) 2-{(5S)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.174) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate.

Biological Pesticides as Mixing Components

The compounds of the formula (I) can be combined with biological pesticides.

Biological pesticides include especially bacteria, fungi, yeasts, plant extracts and products formed by microorganisms, including proteins and secondary metabolites.

Biological pesticides include bacteria such as spore-forming bacteria, root-colonizing bacteria and bacteria which act as biological insecticides, fungicides or nematicides.

Examples of such bacteria which are used or can be used as biological pesticides are:

*Bacillus amyloliquefaciens*, strain FZB42 (DSM 231179), or *Bacillus cereus*, especially *B. cereus* strain CNCM 1-1562 or *Bacillus firmus*, strain 1-1582 (Accession number CNCM 1-1582) or *Bacillus pumilus*, especially strain GB34 (Accession No. ATCC 700814) and strain QST2808 (Accession No. NRRL B-30087), or *Bacillus subtilis*, especially strain GB03 (Accession No. ATCC SD-1397), or *Bacillus subtilis* strain QST713 (Accession No. NRRL B-21661) or *Bacillus subtilis* strain OST 30002 (Accession No. NRRL B-50421) *Bacillus thuringiensis*, especially *B. thuringiensis* subspecies *israelensis* (serotype H-14), strain AM65-52 (Accession No. ATCC 1276), or *B. thuringiensis* subsp. *aizawai*, especially strain ABTS-1857 (SD-1372), or *B. thuringiensis* subsp. *kurstaki* strain HD-1, or *B. thuringiensis* subsp. *tenebrionis* strain NB 176 (SD-5428), *Pasteuria penetrans, Pasteuria* spp. (*Rotylenchulus reniformis* nematode)-PR3 (Accession Number ATCC SD-5834), *Streptomyces microflavus* strain AQ6121 (=QRD 31.013, NRRL B-50550), *Streptomyces galbus* strain AQ 6047 (Accession Number NRRL 30232).

Examples of fungi and yeasts which are used or can be used as biological pesticides are:

*Beauveria bassiana*, in particular strain ATCC 74040, *Coniothyrium minitans*, in particular strain CON/M/91-8 (Accession No. DSM-9660), *Lecanicillium* spp., in particular strain HRO LEC 12, *Lecanicillium lecanii* (formerly known as *Verticillium lecanii*), in particular strain KVO1, *Metarhizium anisopliae*, in particular strain F52 (DSM3884/ATCC 90448), *Metschnikowia fructicola*, in particular strain NRRL Y-30752, *Paecilomyces fumosoroseus* (new: *Isaria fumosorosea*), in particular strain IFPC 200613, or strain Apopka 97 (Accession No. ATCC 20874), *Paecilomyces lilacinus*, in particular *P. lilacinus* strain 251 (AGAL 89/030550), *Talaromyces flavus*, in particular strain V117b, *Trichoderma atroviride*, in particular strain SC1 (Accession Number CBS 122089), *Trichoderma harzianum*, in particular *T. harzianum rifai* T39 (Accession Number CNCM 1-952).

Examples of viruses which are used or can be used as biological pesticides are:

*Adoxophyes orana* (summer fruit *tortrix*) granulosis virus (GV), *Cydia pomonella* (codling moth) granulosis virus (GV), *Helicoverpa armigera* (cotton bollworm) nuclear polyhedrosis virus (NPV), *Spodoptera exigua* (beet armyworm) mNPV, *Spodoptera frugiperda* (fall armyworm) mNPV, *Spodoptera littoralis* (African cotton leafworm) NPV.

Also included are bacteria and fungi which are added as 'inoculant' to plants or plant parts or plant organs and which, by virtue of their particular properties, promote plant growth and plant health. Examples include:

*Agrobacterium* spp., *Azorhizobium caulinodans, Azospirillum* spp., *Azotobacter* spp., *Bradyrhizobium* spp., *Burkholderia* spp., especially *Burkholderia cepacia* (formerly known as *Pseudomonas cepacia*), *Gigaspora* spp., or *Gigaspora monosporum, Glomus* spp., *Laccaria* spp., *Lactobacillus buchneri, Paraglomus* spp., *Pisolithus tinctorus, Pseudomonas* spp., *Rhizobium* spp., especially *Rhizobium trifolii, Rhizopogon* spp., *Scleroderma* spp., *Suillus* spp., *Streptomyces* spp.

Examples of plant extracts and products formed by microorganisms, including proteins and secondary metabolites, which are used or can be used as biological pesticides are:

*Allium sativum, Artemisia absinthium,* azadirachtin, Biokeeper WP, *Cassia nigricans, Celastrus angulatus, Chenopodium anthelminticum,* chitin, Armour-Zen, *Dryopteris filix-mas, Equisetum arvense,* Fortune Aza, Fungastop, Heads Up (*Chenopodium quinoa* saponin extract), pyrethrum/pyrethrins, *Quassia amara, Quercus, Quillaja,* Regalia, "Requiem™ Insecticide", rotenone, ryania/ryanodine, *Symphytum officinale, Tanacetum vulgare,* thymol, Triact 70, TriCon, *Tropaeolum majus, Urtica dioica,* Veratrin, *Viscum album,* Brassicaceae extract, especially oilseed rape powder or mustard powder.

Safeners as Mixing Components

The compounds of the formula (I) can be combined with safeners, for example benoxacor, cloquintocet (-mexyl), cyometrinil, cyprosulfamide, dichlormid, fenchlorazole (-ethyl), fenclorim, flurazole, fluxofenim, furilazole, isoxadifen (-ethyl), mefenpyr (-diethyl), naphthalic anhydride, oxabetrinil, 2-methoxy-N-({4-[(methylcarbamoyl)amino]phenyl}sulfonyl)benzamide (CAS 129531-12-0), 4-(dichloroacetyl)-1-oxa-4-azaspiro[4.5]decane (CAS 71526-07-3), 2,2,5-trimethyl-3-(dichloroacetyl)-1,3-oxazolidine (CAS 52836-31-4).

Plants and Plant Parts

All plants and plant parts can be treated in accordance with the invention. Plants are understood here to mean all plants and populations of plants, such as desirable and undesirable wild plants or crop plants (including naturally occurring crop plants), for example cereals (wheat, rice, triticale, barley, rye, oats), maize, soya bean, potato, sugar beet, sugar cane, tomatoes, bell peppers and chilli peppers, cucumbers, melons, carrots, water melons, onions, lettuce, spinach, leeks, beans, *Brassica oleracea* (e.g. cabbage) and other vegetable species, cotton, tobacco, oilseed rape, and also fruit plants (with the fruits apples, pears, citrus fruits and grapes). Crop plants may be plants which can be obtained by conventional breeding and optimization methods or by biotechnological and genetic engineering methods or combinations of these methods, including the transgenic plants and including the plant cultivars which are protectable or non-protectable by plant breeders' rights. Plants shall be understood to mean all developmental stages of the plants, for example seeds, cuttings and young (immature) plants up to mature plants. Plant parts shall be understood to mean all parts and organs of the plants above and below ground, such as shoot, leaf, flower and root, examples given being leaves, needles, stalks, stems, flowers, fruit bodies, fruits and seeds, and also roots, tubers and rhizomes. Plant parts also include harvested material (harvested plants or plant parts) and vegetative and generative propagation material, for example cuttings, tubers, rhizomes, slips and seeds.

Treatment according to the invention of the plants and plant parts with the compounds of the formula (I) is carried out directly or by allowing the compounds to act on their surroundings, habitat or storage space by the customary treatment methods, for example by immersion, spraying, evaporation, fogging, scattering, painting on, injection and, in the case of propagation material, in particular in the case of seeds, also by applying one or more coats.

As already mentioned above, it is possible to treat all plants and parts thereof in accordance with the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The term "parts" or "parts of plants" or "plant parts" has been explained above. Particular preference is given in accordance with the invention to treating plants of the respective commercially customary plant cultivars or those that are in use. Plant cultivars are understood to mean plants having new properties ("traits") which have been grown by conventional breeding, by mutagenesis or by recombinant DNA techniques. They may be cultivars, varieties, biotypes or genotypes.

Transgenic Plants, Seed Treatment and Integration Events

The preferred transgenic plants or plant cultivars (those obtained by genetic engineering) which are to be treated in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher harvest yields, higher quality and/or higher nutritional value of the harvested products, better capability for storage and/or processability of the harvested products. Further and particularly emphasized examples of such properties are increased resistance of the plants against animal and microbial pests, such as insects, arachnids, nematodes, mites, slugs and snails owing, for example, to toxins formed in the plants, in particular those produced in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof), and also increased resistance of the plants against phytopathogenic fungi, bacteria and/or viruses caused, for example, by systemic acquired resistance (SAR), systemin, phytoalexins, elicitors and resistance genes and correspondingly expressed proteins and toxins, and also increased tolerance of the plants to certain herbicidally active compounds, for example imidazolinones, sulfonylureas, glyphosates or phosphinothricin (for example the "PAT" gene). The genes which impart the desired properties ("traits") in question may also be present in combinations with one another in the transgenic plants. Examples of transgenic plants mentioned include the important crop plants, such as cereals (wheat, rice, triticale, barley, rye, oats), maize, soybeans, potatoes, sugar beet, sugar cane, tomatoes, peas and other types of vegetable, cotton, tobacco, oilseed rape and also fruit plants (with the fruits apples, pears, citrus fruits and grapevines), particular emphasis being given to maize, soybeans, wheat, rice, potatoes, cotton, sugar cane, tobacco and oilseed rape. Properties ("traits") which are particularly emphasized are the increased resistance of the plants to insects, arachnids, nematodes and slugs and snails.

Crop Protection—Types of Treatment

The plants and plant parts are treated with the compounds of the formula (I) directly or by action on their surroundings, habitat or storage space using customary treatment methods, for example by dipping, spraying, atomizing, irrigating, evaporating, dusting, fogging, broadcasting, foaming, painting, spreading-on, injecting, watering (drenching), drip irrigating and, in the case of propagation material, in particular in the case of seed, additionally by dry seed treatment, liquid seed treatment, slurry treatment, by incrusting, by coating with one or more coats, etc. It is furthermore possible to apply the compounds of the formula (I) by the ultra-low volume method or to inject the application form or the compound of the formula (I) itself into the soil.

A preferred direct treatment of the plants is foliar application, i.e. compounds of the formula (I) are applied to the foliage, where treatment frequency and the application rate should be adjusted according to the level of infestation with the pest in question.

In the case of systemically active compounds, the compounds of the formula (I) also access the plants via the root system. The plants are then treated by the action of the compounds of the formula (I) on the habitat of the plant. This can be accomplished, for example, by drenching, or by mixing into the soil or the nutrient solution, meaning that the locus of the plant (e.g. soil or hydroponic systems) is impregnated with a liquid form of the compounds of the formula (I), or by soil application, meaning that the compounds of the formula (I) are introduced in solid form (e.g. in the form of granules) into the locus of the plants. In the case of paddy rice crops, this can also be accomplished by metering the compound of the formula (I) in a solid application form (for example as granules) into a flooded paddy field.

Seed Treatment

The control of animal pests by the treatment of the seed of plants has long been known and is the subject of constant improvements. Nevertheless, the treatment of seed entails a series of problems which cannot always be solved in a satisfactory manner. Thus, it is desirable to develop methods for protecting the seed and the germinating plant which dispense with, or at least reduce considerably, the additional application of pesticides during storage, after sowing or after emergence of the plants. It is additionally desirable to optimize the amount of active ingredient used so as to provide optimum protection for the seed and the germinating plant from attack by animal pests, but without damage to the plant itself by the active ingredient used. In particular, methods for the treatment of seed should also take account of the intrinsic insecticidal or nematicidal properties of pest-resistant or -tolerant transgenic plants in order to achieve optimal protection of the seed and the germinating plant with a minimum expenditure on pesticides.

The present invention therefore in particular also relates to a method for the protection of seed and germinating plants from attack by pests, by treating the seed with one of the compounds of the formula (I). The method according to the invention for protecting seed and germinating plants against attack by pests further comprises a method in which the seed is treated simultaneously in one operation or sequentially with a compound of the formula (I) and a mixing component. It further also comprises a method where the seed is treated at different times with a compound of the formula (I) and a mixing component.

The invention likewise relates to the use of the compounds of the formula (I) for the treatment of seed for protecting the seed and the resulting plant from animal pests.

The invention further relates to seed which has been treated with a compound of the formula (I) for protection from animal pests. The invention also relates to seed which has been treated simultaneously with a compound of the formula (I) and a mixing component. The invention further relates to seed which has been treated at different times with a compound of the formula (I) and a mixing component. In the case of seed which has been treated at different times with a compound of the formula (I) and a mixing component, the individual substances may be present on the seed in different layers. In this case, the layers comprising a compound of the formula (I) and a mixing component may optionally be separated by an intermediate layer. The invention also relates to seed in which a compound of the formula (I) and a mixing component have been applied as part of a coating or as a further layer or further layers in addition to a coating.

The invention further relates to seed which, after the treatment with a compound of the formula (I), is subjected to a film-coating process to prevent dust abrasion on the seed.

One of the advantages encountered with a systemically acting compound of the formula (I) is the fact that, by treating the seed, not only the seed itself but also the plants resulting therefrom are, after emergence, protected against animal pests. In this way, the immediate treatment of the crop at the time of sowing or shortly thereafter can be dispensed with.

A further advantage is that the treatment of the seed with a compound of the formula (I) can enhance germination and emergence of the treated seed.

It is likewise considered to be advantageous that compounds of the formula (I) can especially also be used for transgenic seed.

Furthermore, compounds of the formula (I) can be employed in combination with compositions of signalling technology, leading to better colonization by symbionts such as, for example, rhizobia, mycorrhizae and/or endophytic bacteria or fungi, and/or to optimized nitrogen fixation.

The compounds of the formula (I) are suitable for the protection of seed of any plant variety which is used in agriculture, in greenhouses, in forests or in horticulture. More particularly, this includes seed of cereals (for example wheat, barley, rye, millet and oats), maize, cotton, soya beans, rice, potatoes, sunflowers, coffee, tobacco, canola, oilseed rape, beet (for example sugar beet and fodder beet), peanuts, vegetables (for example tomatoes, cucumbers, beans, cruciferous vegetables, onions and lettuce), fruit plants, lawns and ornamental plants. Of particular significance is the treatment of the seed of cereals (such as wheat, barley, rye and oats), maize, soya beans, cotton, canola, oilseed rape, vegetables and rice.

As already mentioned above, the treatment of transgenic seed with a compound of the formula (I) is also of particular importance. This involves the seed of plants which generally contain at least one heterologous gene which controls the expression of a polypeptide having insecticidal and/or nematicidal properties in particular. The heterologous genes in transgenic seed may originate in this case from microorganisms such as *Bacillus, Rhizobium, Pseudomonas, Serratia, Trichoderma, Clavibacter, Glomus* or *Gliocladium*. The present invention is particularly suitable for the treatment of transgenic seed containing at least one heterologous gene originating from *Bacillus* sp. The heterologous gene is more preferably derived from *Bacillus thuringiensis*.

In the context of the present invention, the compound of the formula (I) is applied to the seed. The seed is preferably treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. Thus, for example, it is possible to use seed which has been harvested, cleaned and dried down to a moisture content which allows storage. Alternatively, it is also possible to use seed which, after drying, has been treated with, for example, water and then dried again, for example priming. In the case of rice seed, it is also possible to use seed which has been imbibed in water up to a certain stage (pigeon breast stage) for example, which leads to improved germination and more uniform emergence.

When treating the seed, care must generally be taken that the amount of the compound of the formula (I) applied to the seed and/or the amount of further additives is chosen in such a way that the germination of the seed is not adversely affected, or that the resulting plant is not damaged. This has to be ensured particularly in the case of active ingredients which can exhibit phytotoxic effects at certain application rates.

In general, the compounds of the formula (I) are applied to the seed in the form of a suitable formulation. Suitable formulations and processes for seed treatment are known to the person skilled in the art.

The compounds of the formula (I) can be converted to the customary seed-dressing formulations, such as solutions, emulsions, suspensions, powders, foams, slurries or other coating compositions for seed, and also ULV formulations.

These formulations are produced in a known manner, by mixing compounds of the formula (I) with customary additives, for example customary extenders and solvents or diluents, dyes, wetters, dispersants, emulsifiers, antifoams, preservatives, secondary thickeners, stickers, gibberellins and also water.

Dyes which may be present in the seed-dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed-dressing formulations usable in accordance with the invention are all substances which promote wetting and which are customary for the formulation of agrochemically active ingredients. Alkyl naphthalenesulfonates, such as diisopropyl or diisobutyl naphthalenesulfonates, can be used with preference.

Suitable dispersants and/or emulsifiers which may be present in the seed-dressing formulations usable in accordance with the invention are all nonionic, anionic and cationic dispersants customary for the formulation of agrochemically active ingredients. Nonionic or anionic dispersants or mixtures of nonionic or anionic dispersants can be used with preference. Suitable nonionic dispersants especially include ethylene oxide/propylene oxide block polymers, alkylphenol polyglycol ethers and tristyrylphenol polyglycol ethers, and the phosphated or sulfated derivatives thereof. Suitable anionic dispersants are especially lignosulfonates, polyacrylic acid salts and arylsulfonate-formaldehyde condensates.

Antifoams which may be present in the seed-dressing formulations usable in accordance with the invention are all foam-inhibiting substances customary for the formulation of agrochemically active ingredients. Silicone antifoams and magnesium stearate can be used with preference.

Preservatives which may be present in the seed-dressing formulations usable in accordance with the invention are all substances usable for such purposes in agrochemical compositions. Examples include dichlorophene and benzyl alcohol hemiformal.

Secondary thickeners which may be present in the seed-dressing formulations usable in accordance with the invention are all substances which can be used for such purposes in agrochemical compositions. Preferred examples include cellulose derivatives, acrylic acid derivatives, xanthan, modified clays and finely divided silica.

Useful stickers which may be present in the seed-dressing formulations usable in accordance with the invention are all customary binders usable in seed-dressing products. Preferred examples include polyvinylpyrrolidone, polyvinyl acetate, polyvinyl alcohol and tylose.

Gibberellins which may be present in the seed-dressing formulations usable in accordance with the invention are preferably the gibberellins A1, A3 (=gibberellic acid), A4 and A7; particular preference is given to using gibberellic acid. The gibberellins are known (cf. R. Wegler "Chemie der Pflanzenschutz-und Schädlingsbekämpfungsmittel", vol. 2, Springer Verlag, 1970, pp. 401-412).

The seed-dressing formulations usable in accordance with the invention can be used to treat a wide variety of different kinds of seed, either directly or after prior dilution with water. For instance, the concentrates or the preparations obtainable therefrom by dilution with water can be used to dress the seed of cereals, such as wheat, barley, rye, oats and triticale, and also the seed of maize, rice, oilseed rape, peas, beans, cotton, sunflowers, soya beans and beets, or else a wide variety of different vegetable seed. The seed-dressing formulations usable with the invention, or the dilute use forms thereof, can also be used to dress seed of transgenic plants.

For the treatment of seed with the seed-dressing formulations usable in accordance with the invention, or use forms prepared therefrom, all mixing units usable customarily for the seed dressing are useful. Specifically, the procedure in seed dressing is to place the seed into a mixer in batchwise or continuous operation, to add the particular desired amount of seed-dressing formulations, either as such or after prior dilution with water, and to mix until the formulation is distributed homogeneously on the seed. If appropriate, this is followed by a drying operation.

The application rate of the seed dressing formulations usable in accordance with the invention can be varied within a relatively wide range. It is guided by the particular content of the compounds of the formula (I) in the formulations and by the seed. The application rates of the compound of the formula (I) are generally between 0.001 and 50 g per kilogram of seed, preferably between 0.01 and 15 g per kilogram of seed.

Animal Health

In the animal health field, i.e. the field of veterinary medicine, the compounds of the formula (I) are active against animal parasites, in particular ectoparasites or endoparasites. The term "endoparasites" includes especially helminths and protozoa, such as coccidia. Ectoparasites are typically and preferably arthropods, especially insects and acarids.

In the field of veterinary medicine, the compounds of the formula (I) having favourable endotherm toxicity are suitable for controlling parasites which occur in animal breeding and animal husbandry in livestock, breeding animals, zoo animals, laboratory animals, experimental animals and domestic animals. They are active against all or specific stages of development of the parasites.

Agricultural livestock include, for example, mammals such as sheep, goats, horses, donkeys, camels, buffalo, rabbits, reindeer, fallow deer, and particularly cattle and pigs; poultry such as turkeys, ducks, geese, and particularly chickens; fish and crustaceans, for example in aquaculture, and also insects such as bees.

Domestic animals include, for example, mammals, such as hamsters, guinea pigs, rats, mice, chinchillas, ferrets, and particularly dogs, cats, caged birds, reptiles, amphibians and aquarium fish.

In a preferred embodiment, the compounds of the formula (I) are administered to mammals.

In another preferred embodiment, the compounds of the formula (I) are administered to birds, namely caged birds and particularly poultry.

Use of the compounds of the formula (I) for the control of animal parasites is intended to reduce or prevent illness, cases of death and reductions in performance (in the case of meat, milk, wool, hides, eggs, honey and the like), such that more economical and simpler animal husbandry is enabled and better animal well-being is achievable.

In relation to the field of animal health, the term "control" or "controlling" means that the compounds of the formula (I) are effective in reducing the incidence of the particular parasite in an animal infected with such parasites to an innocuous degree. More specifically, "controlling" in the present context means that the compound of the formula (I) can kill the respective parasite, inhibit its growth, or inhibit its proliferation.

Arthropods Include:

from the order Anoplurida, for example *Haematopinus* spp., *Linognathus* spp., *Pediculus* spp., *Phtirus* spp., *Solenopotes* spp.; from the order Mallophagida and the suborders Amblycerina and Ischnocerina, for example *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; from the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; from the order Siphonapterida, for example *Pulex* spp., *Ctenocephalides* spp., *Tunga* spp., *Xenopsylla* spp., *Ceratophyllus* spp.;

from the order Heteropterida, for example *Cimex* spp., *Triatoma* spp., *Rhodnius* spp., *Panstrongylus* spp.; and also nuisance and hygiene pests from the order Blattarida.

Arthropods Further Include:

from the subclass Acari (Acarina) and the order Metastigmata, for example from the family Argasidae like *Argas* spp., *Ornithodorus* spp., *Otobius* spp., from the family Ixodidae like *Ixodes* spp., *Amblyomma* spp., *Rhipicephalus* (*Boophilus*) spp., *Dermacentor* spp., *Haemophysalis* spp., *Hyalomma* spp., *Rhipicephalus* spp. (the original genus of multi-host ticks); from the order Mesostigmata like *Dermanyssus* spp., *Ornithonyssus* spp., *Pneumonyssus* spp., *Raillietia* spp., *Pneumonyssus* spp., *Sternostoma* spp., *Varroa* spp., *Acarapis* spp.; from the order Actinedida (Prostigmata), for example *Acarapis* spp., *Cheyletiella* spp., *Ornithocheyletia* spp., *Myobia* spp., *Psorergates* spp., *Demodex* spp., *Trombicula* spp., *Neotrombiculla* spp., *Listrophorus* spp.; and from the order Acaridida (Astigmata), for example *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

Parasitic Protozoa Include:

Mastigophora (Flagellata), for example Trypanosomatidae, for example *Trypanosoma b. brucei*, *T.b. gambiense*, *T.b. rhodesiense*, *T. congolense*, *T. cruzi*, *T. evansi*, *T. equinum*, *T. lewisi*, *T. percae*, *T. simiae*, *T. vivax*, *Leishmania brasiliensis*, *L. donovani*, *L. tropica*, for example Trichomonadidae, for example *Giardia lamblia*, *G. canis*;

Sarcomastigophora (Rhizopoda) such as Entamoebidae, for example *Entamoeba histolytica*, Hartmanellidae, for example *Acanthamoeba* sp., *Harmanella* sp.;

Apicomplexa (Sporozoa) such as Eimeridae, for example *Eimeria acervulina*, *E. adenoides*, *E. alabamensis*, *E. anatis*, *E. anserina*, *E. arloingi*, *E. ashata*, *E. auburnensis*, *E. bovis*, *E. brunetti*, *E. canis*, *E. chinchillae*, *E. clupearum*, *E. columbae*, *E. contorta*, *E. crandalis*, *E. debliecki*, *E. dispersa*, *E. ellipsoidales*, *E. falciformis*, *E. faurei*, *E. flavescens*, *E. gallopavonis*, *E. hagani*, *E. intestinalis*, *E. iroquoina*, *E. irresidua*, *E. labbeana*, *E. leucarti*, *E. magna*, *E. maxima*, *E. media*, *E. meleagridis*, *E. meleagrimitis*, *E. mitis*, *E. necatrix*, *E. ninakohlyakimovae*, *E. ovis*, *E. parva*, *E. pavonis*, *E. perforans*, *E. phasani*, *E. piriformis*, *E. praecox*, *E. residua*, *E. scabra*, *E. spec.*, *E. stiedai*, *E. suis*, *E. tenella*, *E. truncata*, *E. truttae*, *E. zuernii*, *Globidium* spec., *Isospora belli*, *I. canis*, *I. felis*, *I. ohioensis*, *I. rivolta*, *I. spec.*, *I. suis*, *Cystisospora* spec., *Cryptosporidium* spec., in particular *C. parvum*; such as Toxoplasmadidae, for example *Toxoplasma gondii*, *Hammondia heydornii*, *Neospora caninum*, *Besnoitia besnoitii*; such as Sarcocystidae, for example *Sarcocystis bovicanis*, *S. bovihominis*, *S. ovicanis*, *S. ovifelis*, *S. neurona*, *S. spec.*, *S. suihominis*, such as Leucozoidae, for example *Leucozytozoon simondi*, such as Plasmodiidae, for example *Plasmodium berghei*, *P. falciparum*, *P. malariae*, *P. ovale*, *P. vivax*, *P. spec.*, such as Piroplasmea, for example *Babesia argentina*, *B. bovis*, *B. canis*, *B. spec.*, *Theileria parva*, *Theileria spec.*, such as Adeleina, for example *Hepatozoon canis*, *H. spec.*

Pathogenic endoparasites which are helminths include Platyhelmintha (e.g. Monogenea, cestodes and trematodes), nematodes, Acanthocephala, and Pentastoma. These include:

Monogenea: for example: *Gyrodactylus* spp., *Dactylogyrus* spp., *Polystoma* spp.;

Cestodes: from the order of Pseudophyllidea, for example: *Diphyllobothrium* spp., *Spirometra* spp., *Schistocephalus* spp., *Ligula* spp., *Bothridium* spp., *Diphlogonoporus* spp.; from the order Cyclophyllida, for example: *Mesocestoides* spp., *Anoplocephala* spp., *Paranoplocephala* spp., *Moniezia* spp., *Thysanosoma* spp., *Thysaniezia* spp., *Avitellina* spp., *Stilesia* spp., *Cittotaenia* spp., *Andyra* spp., *Bertiella* spp., *Taenia* spp., *Echinococcus* spp., *Hydatigera* spp., *Davainea* spp., *Raillietina* spp., *Hymenolepis* spp., *Echinolepis* spp., *Echinocotyle* spp., *Diorchis* spp., *Dipylidium* spp., *Joyeuxiella* spp., *Diplopylidium* spp.

Trematodes: from the class of Digenea, for example: *Diplostomum* spp., *Posthodiplostomum* spp., *Schistosoma* spp., *Trichobilharzia* spp., *Ornithobilharzia* spp., *Austrobilharzia* spp., *Gigantobilharzia* spp., *Leucochloridium* spp., *Brachylaima* spp., *Echinostoma* spp., *Echinoparyphium* spp., *Echinochasmus* spp., *Hypoderaeum* spp., *Fasciola* spp., *Fascioloides* spp., *Fasciolopsis* spp., *Cyclocoelum* spp., *Typhlocoelum* spp., *Paramphistomum* spp., *Calicophoron* spp., *Cotylophoron* spp., *Gigantocotyle* spp., *Fischoederius* spp., *Gastrothylacus* spp., *Notocotylus* spp., *Catatropis* spp., *Plagiorchis* spp., *Prosthogonimus* spp., *Dicrocoelium* spp., *Eurytrema* spp., *Troglotrema* spp., *Paragonimus* spp., *Collyriclum* spp., *Nanophyetus* spp., *Opisthorchis* spp., *Clonorchis* spp., *Metorchis* spp., *Heterophyes* spp., *Metagonimus* spp.;

Nematodes: Trichinellida, for example: *Trichuris* spp., *Capillaria* spp., *Paracapillaria* spp., *Eucoleus* spp., *Trichomosoides* spp., *Trichinella* spp.;

from the order Tylenchida, for example: *Micronema* spp., *Strongyloides* spp.;

from the order Rhabditida, for example: *Strongylus* spp., *Triodontophorus* spp., *Oesophagodontus* spp., *Trichonema* spp., *Gyalocephalus* spp., *Cylindropharynx* spp., *Poteriostomum* spp., *Cyclococercus* spp., *Cylicostephanus* spp., *Oesophagostomum* spp., *Chabertia* spp., *Stephanurus* spp., *Ancylostoma* spp., *Uncinaria* spp., *Necator* spp., *Bunostomum* spp., *Globocephalus* spp., *Syngamus* spp., *Cyathostoma* spp., *Metastrongylus* spp., *Dictyocaulus* spp., *Muellerius* spp., *Protostrongylus* spp., *Neostrongylus* spp., *Cystocaulus* spp., *Pneumostrongylus* spp., *Spicocaulus* spp., *Elaphostrongylus* spp., *Parelaphostrongylus* spp., *Crenosoma* spp., *Paracrenosoma* spp., *Oslerus* spp., *Angiostrongylus* spp., *Aelurostrongylus* spp., *Filaroides* spp., *Parafilaroides* spp., *Trichostrongylus* spp., *Haemonchus* spp., *Ostertagia* spp., *Teladorsagia* spp., *Marshallagia* spp., *Cooperia* spp., *Nippostrongylus* spp., *Heligmosomoides* spp., *Nematodirus* spp., *Hyostrongylus* spp., *Obeliscoides* spp., *Amidostomum* spp., *Ollulanus* spp.;

from the order Spirurida, for example: *Oxyuris* spp., *Enterobius* spp., *Passalurus* spp., *Syphacia* spp., *Aspiculuris* spp., *Heterakis* spp.; *Ascaris* spp., *Toxascaris* spp., *Toxocara* spp., *Baylisascaris* spp., *Parascaris* spp., *Anisakis* spp., *Ascaridia* spp.; *Gnathostoma* spp., *Physaloptera* spp., *Thelazia* spp., *Gongylonema* spp., *Habronema* spp., *Parabronema* spp., *Draschia* spp., *Dracunculus* spp.; *Stephanofilaria* spp., *Parafilaria* spp., *Setaria* spp., *Loa* spp., *Dirofilaria* spp., *Litomosoides* spp., *Brugia* spp., *Wuchereria* spp., *Onchocerca* spp., *Spirocerca* spp.;

Acanthocephala: from the order of Oligacanthorhynchida, for example: *Macracanthorhynchus* spp., *Prosthenorchis* spp.; from the order Polymorphida for example: *Filicollis* spp.; from the order Moniliformida for example: *Moniliformis* spp.;

from the order Echinorhynchida, for example *Acanthocephalus* spp., *Echinorhynchus* spp., *Leptorhynchoides* spp.;

Pentastoma: from the order Porocephalida, for example *Linguatula* spp.

In the veterinary field and in animal husbandry, the compounds of the formula (I) are administered by methods generally known in the art, such as via the enteral, parenteral, dermal or nasal route in the form of suitable preparations. Administration may be prophylactic or therapeutic.

Thus, one embodiment of the present invention refers to the use of a compound of the formula (I) as a medicament.

A further aspect refers to the use of a compound of the formula (I) as an antiendoparasitic agent, in particular a helminthicidal agent or antiprotozoic agent. Compounds of the formula (I) are suitable for use as an antiendoparasitic agent, especially as a helminthicidal agent or antiprotozoic agent, for example in animal breeding, in animal husbandry, in animal houses and in the hygiene sector.

A further aspect in turn relates to the use of a compound of the formula (I) as an antiectoparasitic agent, in particular an arthropodicide such as an insecticide or an acaricide. A further aspect relates to the use of a compound of the formula (I) as an antiectoparasitic agent, in particular an arthropodicide such as an insecticide or an acaricide, for example in animal husbandry, in animal breeding, in animal houses or in the hygiene sector.

Anthelmintic Mixing Components

The following anthelmintic mixing components may be mentioned by way of example:

anthelmintically active compounds including trematicidally and cestocidally active compounds:

from the class of the macrocyclic lactones, for example: abamectin, doramectin, emamectin, eprinomectin, ivermectin, milbemycin, moxidectin, nemadectin, selamectin;

from the class of the benzimidazoles and probenzimidazoles, for example: albendazole, albendazole-sulfoxide, cambendazole, cyclobendazole, febantel, fenbendazole, flubendazole, mebendazole, netobimin, oxfendazole, oxibendazole, parbendazole, thiabendazole, thiophanate, triclabendazole;

from the class of the cyclooctadepsipeptides, for example: emodepside, PF1022;

from the class of the aminoacetonitrile derivatives, for example: monepantel;

from the class of the tetrahydropyrimidines, for example: morantel, pyrantel, oxantel;

from the class of the imidazothiazoles, for example: butamisole, levamisole, tetramisole;

from the class of the salicylanilides, for example: bromoxanide, brotianide, clioxanide, closantel, niclosamide, oxyclozanide, rafoxanide, tribromsalan;

from the class of the paraherquamides, for example: derquantel, paraherquamide;

from the class of the aminophenylamidines, for example: amidantel, deacylated amidantel (dAMD), tribendimidine;

from the class of the organophosphates, for example: coumaphos, crufomate, dichlorvos, haloxone, naphthalofos, trichlorfon;

from the class of the substituted phenols, for example: bithionol, disophenol, hexachlorophene, niclofolan, meniclophotan, nitroxynil;

from the class of the piperazinones, for example: praziquantel, epsiprantel;

from various other classes, for example: amoscanate, bephenium, bunamidine, clonazepam, clorsulon, diamfenetid, dichlorophen, diethylcarbamazine, emetine, hetolin, hycanthone, lucanthone, Miracil, mirasan, niclosamide, niridazole, nitroxynil, nitroscanate, oltipraz, omphalotin, oxamniquin, paromomycin, piperazine, resorantel.

Vector Control

The compounds of the formula (I) can also be used in vector control. In the context of the present invention, a vector is an arthropod, especially an insect or arachnid, capable of transmitting pathogens, for example viruses, worms, single-cell organisms and bacteria, from a reservoir (plant, animal, human, etc.) to a host. The pathogens can be transmitted either mechanically (for example trachoma by non-stinging flies) to a host or after injection (for example malaria parasites by mosquitoes) into a host.

Examples of vectors and the diseases or pathogens they transmit are:

1) Mosquitoes
   *Anopheles*: malaria, filariasis;
   *Culex*: Japanese encephalitis, filariasis, other viral diseases, transmission of worms;
   *Aedes*: yellow fever, dengue fever, filariasis, other viral diseases;
   Simuliidae: transmission of worms, in particular *Onchocerca volvulus;*
2) Lice: skin infections, epidemic typhus;
3) Fleas: plague, endemic typhus;
4) Flies: sleeping sickness (trypanosomiasis); cholera, other bacterial diseases;
5) Mites: acariosis, epidemic typhus, rickettsialpox, tularaemia, Saint Louis encephalitis, tick-borne encephalitis (TBE), Crimean-Congo haemorrhagic fever, borreliosis;
6) Ticks: borellioses such as *Borrelia duttoni*, tick-borne encephalitis, Q fever (*Coxiella burnetii*), babesioses (*Babesia canis canis*).

Examples of vectors in the context of the present invention are insects, such as aphids, flies, leafhoppers or thrips, which can transmit plant viruses to plants. Other vectors capable of transmitting plant viruses are spider mites, lice, beetles and nematodes.

Further examples of vectors in the context of the present invention are insects and arachnids such as mosquitoes, especially of the genera *Aedes, Anopheles*, for example *A. gambiae, A. arabiensis, A. funestus, A. dirus* (malaria) and *Culex*, lice, fleas, flies, mites and ticks, which can transmit pathogens to animals and/or humans.

Vector control is also possible if the compounds of the formula (I) are resistance-breaking.

Compounds of the formula (I) are suitable for use in the prevention of diseases and/or pathogens transmitted by vectors. Thus, a further aspect of the present invention is the use of compounds of the formula (I) for vector control, for example in agriculture, in horticulture, in forests, in gardens and in leisure facilities, and also in the protection of materials and stored products.

Protection of Industrial Materials

The compounds of the formula (I) are suitable for protecting industrial materials against attack or destruction by insects, for example from the orders Coleoptera, Hymenoptera, Isoptera, Lepidoptera, Psocoptera and Zygentoma.

Industrial materials in the present context are understood to mean inanimate materials, such as preferably plastics, adhesives, sizes, papers and cards, leather, wood, processed wood products and coating compositions. The use of the invention for protection of wood is particularly preferred.

In a further embodiment, the compounds of the formula (I) are used together with at least one further insecticide and/or at least one fungicide.

In a further embodiment, the compounds of the formula (I) are present as a ready-to-use pesticide, i.e. it can be applied to the material in question without further modifications. Suitable further insecticides or fungicides are in particular those mentioned above.

Surprisingly, it has also been found that the compounds of the formula (I) can be employed for protecting objects which come into contact with saltwater or brackish water, in particular hulls, screens, nets, buildings, moorings and signalling systems, against fouling. It is equally possible to use the compounds of the formula (I), alone or in combinations with other active ingredients, as antifouling agents.

Control of Animal Nests in the Hygiene Sector

The compounds of the formula (I) are suitable for controlling animal pests in the hygiene sector. More particularly, the invention can be used in the domestic protection sector, in the hygiene protection sector and in the protection of stored products, particularly for control of insects, arachnids and mites encountered in enclosed spaces, for example dwellings, factory halls, offices, vehicle cabins. For controlling animal pests, the compounds of the formula (I) are used alone or in combination with other active ingredients and/or auxiliaries. They are preferably used in domestic insecticide products. The compounds of the formula (I) are effective against sensitive and resistant species, and against all developmental stages.

These pests include, for example, pests from the class Arachnida, from the orders Scorpiones, Araneae and Opiliones, from the classes Chilopoda and Diplopoda, from the class Insecta the order Blattodea, from the orders Coleoptera, Dermaptera, Diptera, Heteroptera, Hymenoptera, Isoptera, Lepidoptera, Phthiraptera, Psocoptera, Saltatoria or Orthoptera, Siphonaptera and Zygentoma and from the class Malacostraca the order Isopoda.

Application is carried out, for example, in aerosols, unpressurized spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or bait stations.

A further aspect of the invention is the use of a compound of the formula (I) as a herbicide.

Preparation Methods

The compounds according to the invention can be prepared by customary methods known to those skilled in the art.

Reaction scheme 1 shows a general preparation method for the compounds (Ia) according to the invention.

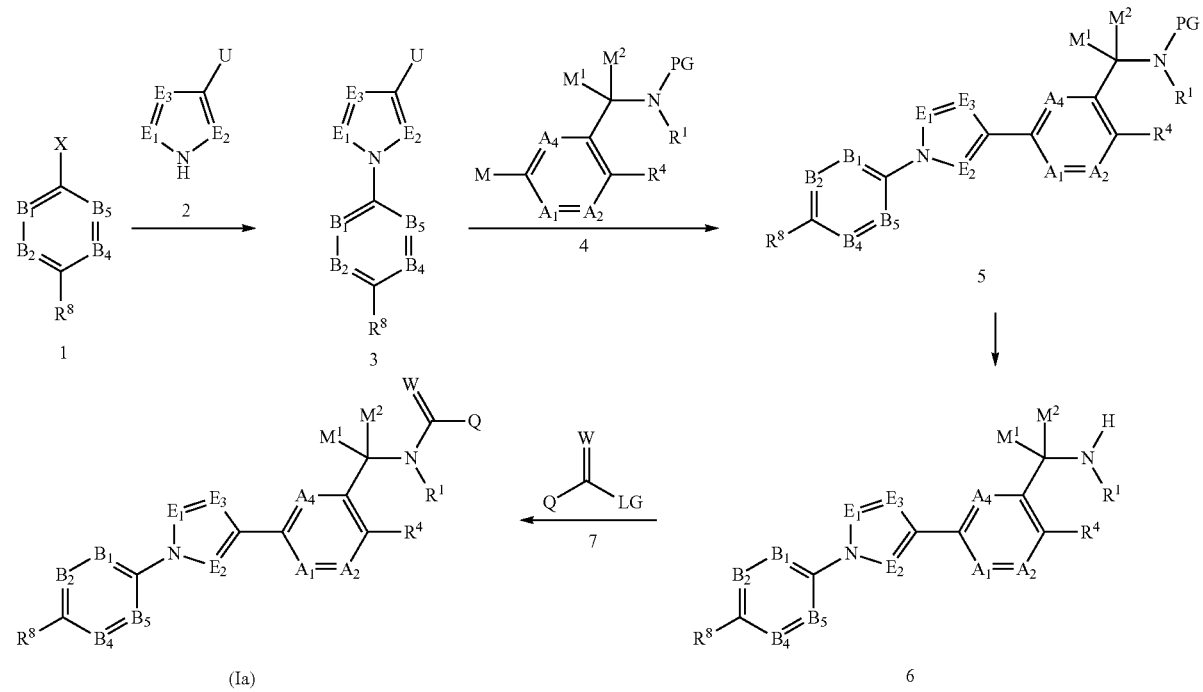

The radicals $A_1$, $A_2$, $A_4$, $B_1$, $B_2$, $B_4$, $B_5$, $R^1$, $M^1$, $M^2$, Q, $R^4$ and $R^8$ are defined as described above. W is oxygen. PG represents a suitable protective group, e.g. t-butoxycarbonyl. LG represents a leaving group, e.g. chlorine. The five-membered rings of $E_1$-$E_3$, carbon and nitrogen represent the 5-membered heterocycles defined under T. X represents a halogen, e.g. fluorine. U represents bromine, iodine or triflate when M represents a boronic acid, boronic ester or trifluoroboronate. U is a boronic acid, boronic ester, trifluoroboronate or ZnCl, when M is bromine, iodine or triflate.

Compounds according to the invention of the general structure (Ia) can be prepared by methods known to those skilled in the art by reacting intermediate 6 with acylating agents of the general structure 7. Intermediates of the general structure 6 can be prepared from N-protected derivatives of the general structure 5 [see e.g. Greene-Wuts T. W. (2006) Protection for the Amino Group, in Greene's Protective Groups in Organic Synthesis, Fourth Edition, John Wiley & Sons, Inc., Hoboken, N.J., USA, S. 706 ff.]. Compounds of the general structure 5 can be prepared by means of palladium-catalysed reactions from the co-reactants 3 and 4 [e.g. WO 2005/040110; WO 2009/089508, WO 2015/067647]. The compounds of the general structure 4 are either commercially available or can be prepared by processes known to the person skilled in the art (see e.g. WO2006/053166, US 2012/0088764, WO 2008/70447). The compounds of the general structure 3 can be prepared from the corresponding starting materials 1 and 2 by methods known from literature either by a nucleophilic substitution of the aromatic system (X=chlorine or fluorine) [see e.g. WO 2007/107470; Tetrahedron Letters 2003, 44, 7629-7632] or by a transition metal-catalysed reaction (X=bromine or iodine) [see e.g. WO 2012/003405; WO 2009/158371]. Further methods for preparing compounds of the general structure 3 are described in the literature [see e.g. WO 2015/067647].

Reaction scheme 1a shows a general preparation method for the compounds (Ic) according to the invention.

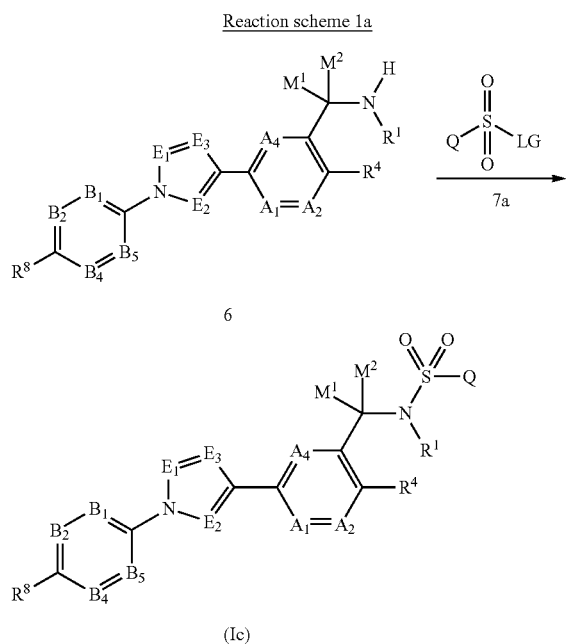

The radicals $A_1$, $A_2$, $A_4$, $B_1$, $B_2$, $B_4$, $B_5$, $R^1$, $M^1$, $M^2$, Q, $R^4$ and $R^8$ are as defined above. LG is a leaving group, for example chlorine. The five-membered ring of $E_1$-$E_3$, carbon and nitrogen are the 5-membered heterocycles defined under T.

Compounds of the general structure (Ic) according to the invention may be prepared by methods known to those skilled in the art by reacting intermediate 6 with sulfonylating reagents of the general structure 7a.

Reaction scheme 2 shows a further general preparation method for the compounds (Ia) according to the invention.

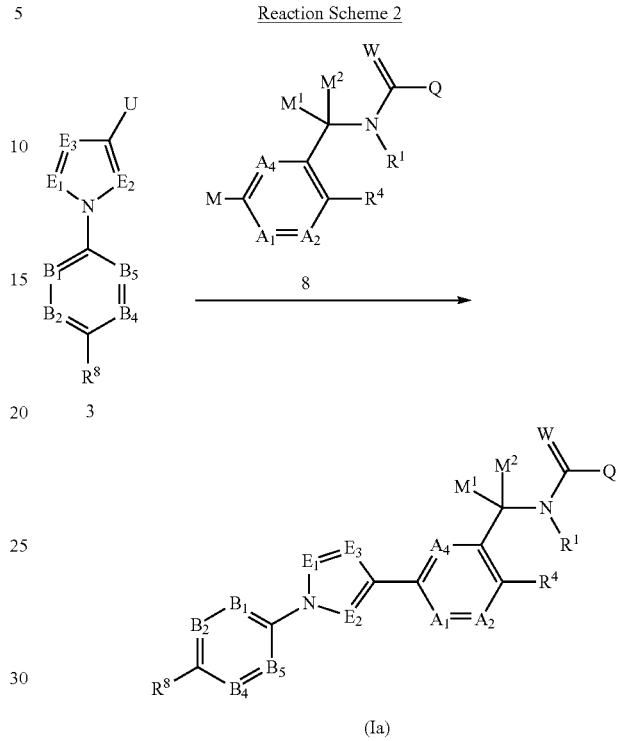

The radicals $A_1$, $A_2$, $A_4$, $B_1$, $B_2$, $B_4$, $B_5$, $R^1$, $M^1$, $M^2$, Q, $R^4$ and $R^8$ are defined as described above. W is oxygen. The five-membered rings of $E_1$-$E_3$, carbon and nitrogen represent the 5-membered heterocycles defined under T. U represents bromine, iodine or triflate when M represents a boronic acid, boronic ester or trifluoroboronate. U is a boronic acid, boronic ester or trifluoroboronate when M is bromine, iodine or triflate.

Compounds according to the invention of the general structure (Ia) can be prepared by means of palladium-catalysed reactions from the co-reactants 3 and 8 [see e.g. WO 2005/040110; WO 2009/089508, WO 2015/067647]. The preparation of compounds of the general structure 3 has already been described above.

Reaction scheme 3 shows a general preparation method for the intermediate 6.

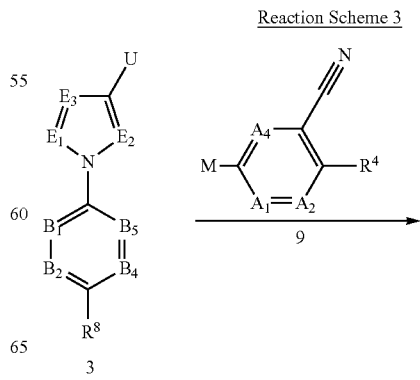

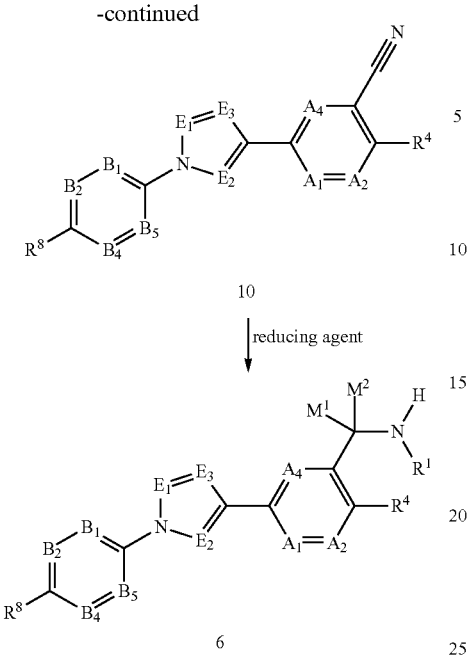

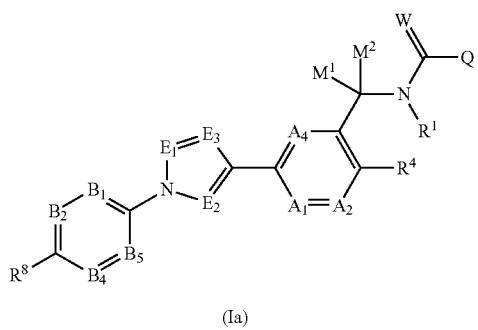

(Ia)

The radicals $A_1$, $A_2$, $A_4$, $B_1$, $B_2$, $B_4$, $B_5$, $R^1$, Q, $R^4$ and $R^8$ are defined as described above. $M_1$, $M_2$ and $R_1$ in reaction scheme 3 are hydrogen. The five-membered rings of E1-E3, carbon and nitrogen represent the 5-membered heterocycles defined under T. U represents bromine, iodine or triflate when M represents a boronic acid, boronic ester or trifluoroboronate. U is a boronic acid, boronic ester or trifluoroboronate when M is bromine, iodine or triflate.

The intermediate of the general structure 6 can be prepared from compounds of the structure 10 by reaction with a suitable reducing agent, for example NaBH$_4$, in the presence of trifluoroacetic acid [see e.g. Houben-Weyl, *Methoden der Organischen Chemie* [*Methods of Organic Chemistry*], Volume E16d/2 (Georg Thieme Verlag Stuttgart), p. 1006 ff.]. Compounds of the general structure 10 can be prepared by means of palladium-catalysed reactions from the co-reactants 3 and 9 [see e.g. WO 2003/087061; US 2009-0203690]. The compounds of the general structure 9 are either commercially available or can be prepared by processes known to the person skilled in the art.

Compounds of the formula (Ia) in which $R^1$ is not H, for example methyl, can be prepared according to reaction scheme 4.

The radicals $A_1$, $A_2$, $A_4$, $B_1$, $B_2$, $B_4$, $B_5$, $M^1$, $M^2$, Q, $R^4$ and $R^8$ are defined as described above and $R^1$ in this case is in each case optionally substituted $C_1$-$C_6$-alkyl, $C_2$-$C_6$-alkenyl, $C_2$-$C_6$-alkynyl, $C_1$-$C_6$-alkylcarbonyl, $C_1$-$C_6$-alkoxycarbonyl, $C_3$-$C_7$-cycloalkyl($C_1$-$C_3$)-alkyl, aryl($C_1$-$C_3$)-alkyl, heteroaryl($C_1$-$C_3$)-alkyl, in each case preferably optionally substituted $C_1$-$C_4$-alkyl or cyclopropylcarbonyl, more preferably methyl. W is oxygen. LG represents a leaving group, e.g. iodine. The five-membered cycles of E1-E3, carbon and nitrogen represent the 5-membered heterocycles defined under T.

Compounds of the general structure Ia' ($R^1$=H) according to the invention may in correspondence with reaction scheme 4 be converted to compounds of the general structure Ia according to the invention by deprotonation with a suitable base and reaction with a suitable electrophile in which R' corresponds by definition to another radical [see e.g. WO 2001/96283; Journal of the American Chemical Society (2009), 131, 10253; Organic Letters (2011), 13, 5920; e.g. synthesis example Ia-24].

Reaction scheme 4a shows a general preparation method for compounds of the formula (Ia) in which W is sulfur.

Reaction Scheme 4

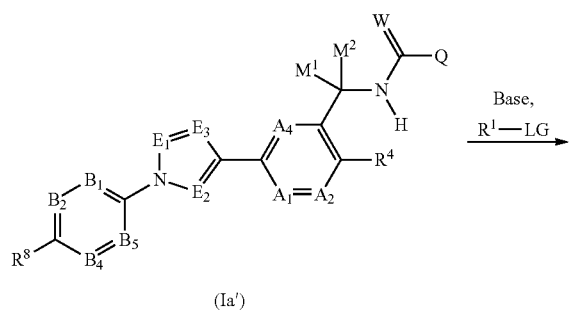

(Ia')

Base, $R^1$—LG →

Reaction scheme 4a

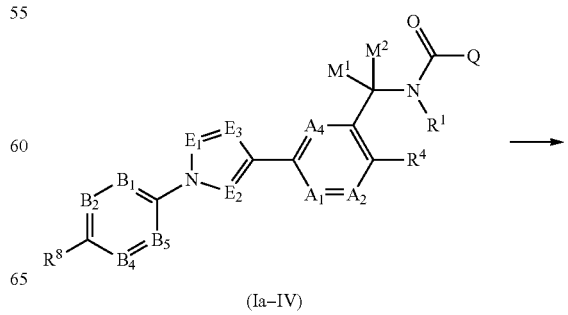

(Ia-IV)

→

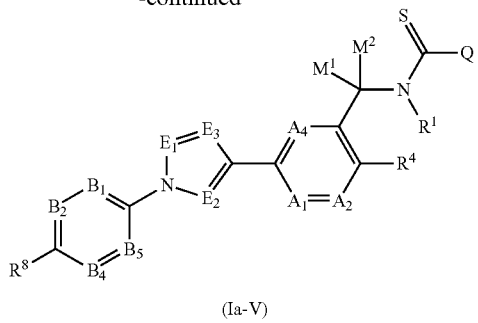

(Ia-V)

The radicals $A_1$, $A_2$, $A_4$, $B_1$, $B_2$, $B_4$, $B_5$, $M^1$, $M^2$, Q, $R^4$ and $R^8$ are as defined above and $R^1$ is H, in each case optionally substituted $C_1$-$C_6$-alkyl, $C_2$-$C_6$-alkenyl, $C_2$-$C_6$-alkynyl, $C_1$-$C_6$-alkoxycarbonyl, $C_3$-$C_7$-cycloalkyl($C_1$-$C_3$)-alkyl, aryl($C_1$-$C_3$)-alkyl, heteroaryl($C_1$-$C_3$)-alkyl, preferably H, in each case optionally substituted $C_1$-$C_4$-alkyl, more preferably H and methyl. The five-membered rings of $E_1$-$E_3$, carbon and nitrogen are the 5-membered heterocycles defined under T.

Compounds of the general structure Ia-IV according to the invention may be converted to compounds of the general structure Ia-V according to the invention according to reaction scheme 4a by thiation with a suitable reagent, e.g. Lawesson's reagent or $P_4S_{10}$ [see e.g. US 2012/0165339; WO 2004/018411; e.g. synthesis example Ia-162]

Compounds of the formula (Ic) in which $R^1$ is not H, for example methyl, can be prepared by according to reaction scheme 4b.

Reaction scheme 4b

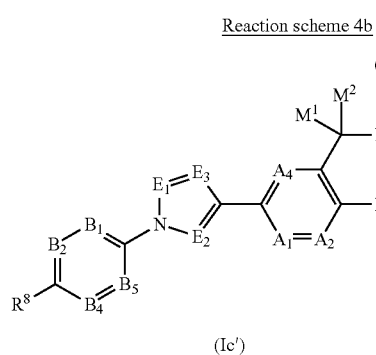

(Ic')

$\xrightarrow{\text{Base,} \atop R^1\text{—LG}}$

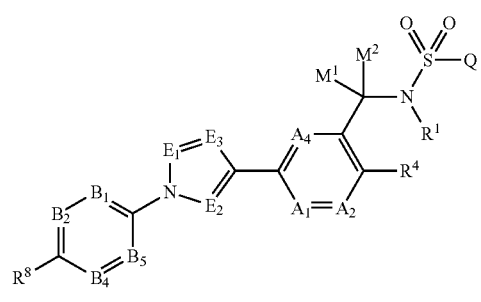

(Ic)

The radicals $A_1$, $A_2$, $A_4$, $B_1$, $B_2$, $B_4$, $B_5$, $M^1$, $M^2$, Q, $R^4$, $R^8$ and $R^{11}$ are as defined above and $R^1$ in this case is in each case optionally substituted $C_1$-$C_6$-alkyl, $C_2$-$C_6$-alkenyl, $C_2$-$C_6$-alkynyl, $C_1$-$C_6$-alkylcarbonyl, $C_1$-$C_6$-alkoxycarbonyl, $C_3$-$C_7$-cycloalkyl($C_1$-$C_3$)-alkyl, aryl($C_1$-$C_3$)-alkyl, heteroaryl($C_1$-$C_3$)-alkyl, preferably in each case optionally substituted $C_1$-$C_4$-alkyl or cyclopropylcarbonyl, more preferably methyl. LG is a leaving group, for example iodine. The five-membered rings of E1-E3, carbon and nitrogen are the 5-membered heterocycles defined under T.

Compounds of the general structure Ic' ($R^1$=H) according to the invention may be converted to compounds of the general structure Ic according to the invention, in which $R^1$ corresponds to another radical by definition, in accordance with reaction scheme 4b by deprotonation with a suitable base and reaction with a suitable electrophile [see e.g. WO 2001/96283; Journal of the American Chemical Society (2009), 131, 10253; Organic Letters (2011), 13, 5920; e.g. synthesis example Ic-03].

Reaction scheme 5 shows a general preparation method for the compounds (Ia-I to Ia-III) according to the invention.

Reaction Scheme 5

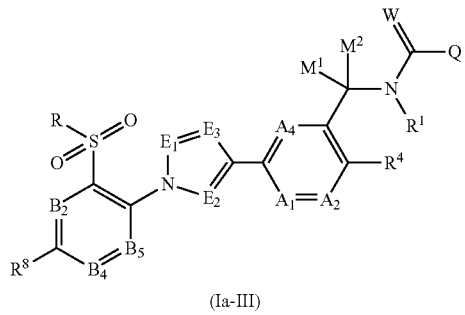

(Ia-III)

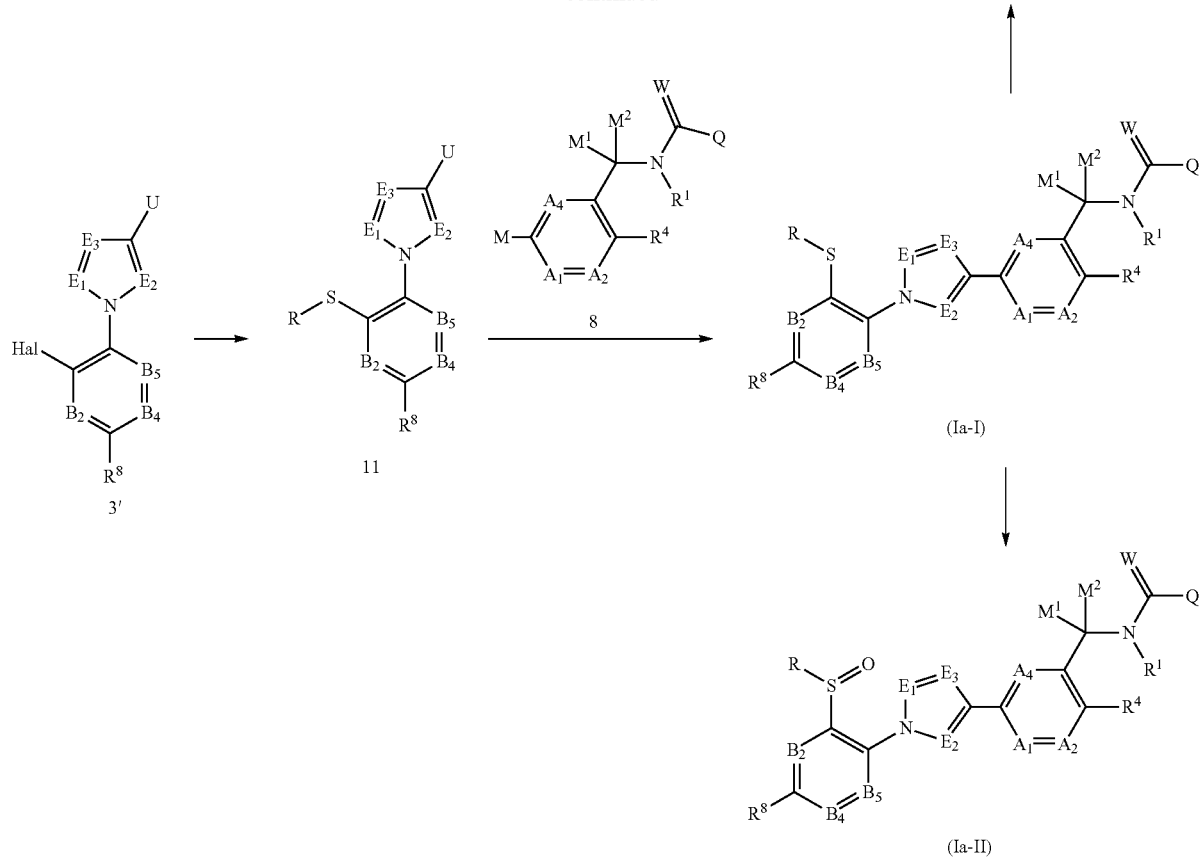

(Ia-I)

(Ia-II)

The radicals $A_1$, $A_2$, $A_4$, $B_2$, $B_4$, $B_5$, $B_5$, $R^1$, $M^1$, $M^2$, Q, $R^4$ and $R^8$ are defined as described above. W is oxygen. Hal is F, Cl, Br or I, preferably Cl. The five-membered rings of $E_1$-$E_3$, carbon and nitrogen represent the 5-membered heterocycles defined under T. R is optionally substituted $C_1$-$C_6$-alkyl. U represents bromine, iodine or triflate when M represents a boronic acid, boronic ester or trifluoroboronate. U is a boronic acid, boronic ester or trifluoroboronate when M is bromine, iodine or triflate.

Compounds of the general structure 11 can be prepared from intermediates of the general structure 3' by reaction with suitable nucleophiles, e.g. sodium thiomethoxide (see synthesis example below). Compounds of the general structure (Ia-I) can be prepared by means of palladium-catalysed reactions from the co-reactants 11 and 8 [see e.g. WO 2005/040110; WO 2009/089508, WO 2015/067647]. Compounds of the general structure (Ia-II, Ia-III) according to the invention can be prepared by methods known to those skilled in the art by reacting compounds (Ia-I) according to the invention with suitable oxidizing agents, for example m-chloroperbenzoic acid or $H_2O_2$ (see synthesis example below).

Reaction scheme 6 shows a general preparation method for the starting materials 8.

Reaction Scheme 6

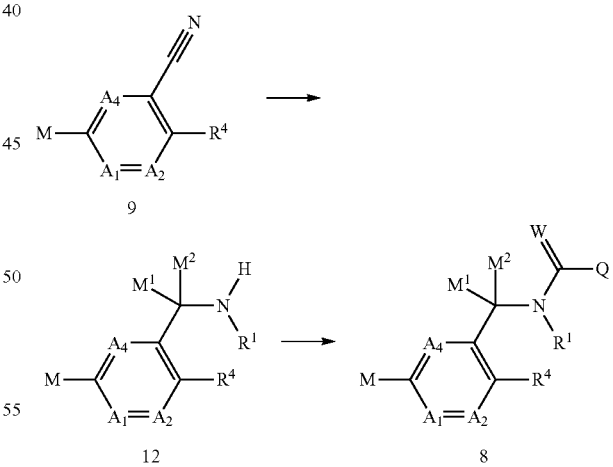

The radicals $A_1$, $A_2$, $A_4$, $R^1$, $M^1$, $M^2$, Q and $R^4$ are as defined described above. W is oxygen. M is a boronic acid, a boronic ester, a trifluoroboronate, bromine, iodine or triflate.

Compounds of the general structure 8 can be prepared from intermediates 12 by methods known to those skilled in the art by reaction with acylating reagents. If M is a boronic acid, a boronic ester or a trifluoroboronate and $M^1$ and $M^2$ are each hydrogen, compounds of the general structure 12 can be obtained by hydrogenation starting from intermediates 9 [see for example WO 2015/81280]. If M is bromine, iodine or triflate and either $M^1$ or $M^2$ is a group which is not hydrogen, compounds of the general structure 12 can be obtained by addition of a suitable nucleophile, methylmagnesium bromide for example, starting from intermediates 9 [see for example WO 2011/054436]. Compounds of the general structure 9 are commercially available or can be prepared by methods known to those skilled in the art.

Reaction scheme 7 shows a general preparation method for the starting materials 12.

Reaction scheme 7

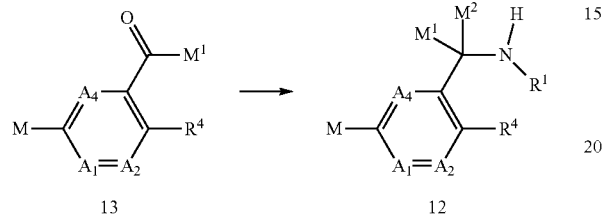

13   12

The radicals $A_1$, $A_2$, $A_4$, $R^1$, $M^1$, $M^2$, Q and $R^4$ are as defined above. W is oxygen. M is bromine, iodine or triflate.

If either $M^1$ or $M^2$ is a group that is not hydrogen, compounds of the general structure 12 may be obtained starting from ketones of the general structure 13 by reductive amination using sodium cyanoborohydride as reducing agent for example [see e.g. WO 2010/132437, WO2014/089048]. Compounds of the general structure 13 are commercially available or can be prepared by methods known to those skilled in the art.

Reaction scheme 8 shows a general preparation method for starting materials 12.

Reaction scheme 8

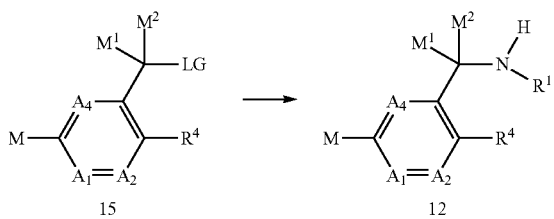

15   12

The radicals $A_1$, $A_2$, $A_4$, $R^1$, $M^1$, $M^2$, Q and $R^4$ are as defined above. W is oxygen. M is bromine, iodine or triflate.

If not more than one of the groups $M^1$ or $M^2$ is a substituent not equal to hydrogen, compounds of the general structure 12 may be obtained starting from compounds of the general structure 14. For this purpose, the hydroxyl function in the compounds of the general structure 14 is converted into a suitable leaving group (LG), for example a methanesulfonate, and as a result the intermediate of the general structure 15 is obtained. Substitution of the leaving group with a suitable nitrogen nucleophile, ammonia for example, leads to compounds of the general structure 12. When using certain nitrogen nucleophiles, such as azides or phthalimides for example, an additional stage is required to obtain compounds of the general structure 12. The steps necessary for this purpose are known to those skilled in the art. [see e.g. WO 2015/009977, WO 2011/124998, WO 2013/045451]. The compounds of the general structure 14 are commercially available or can be prepared by methods known to those skilled in the art.

Reaction scheme 9 shows a general preparation method for compounds of the formula I-T7.

Reaction scheme 9

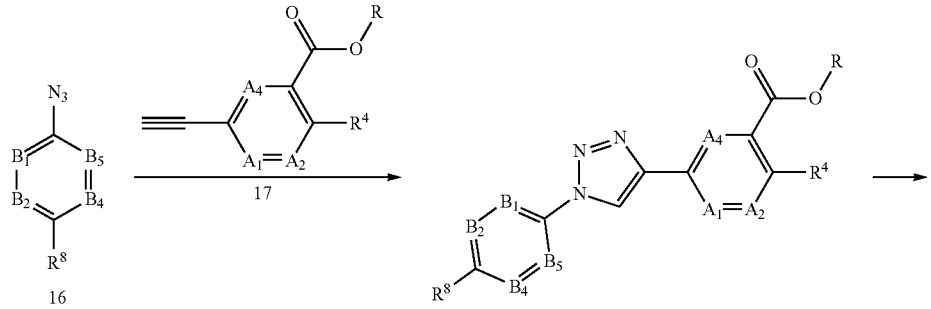

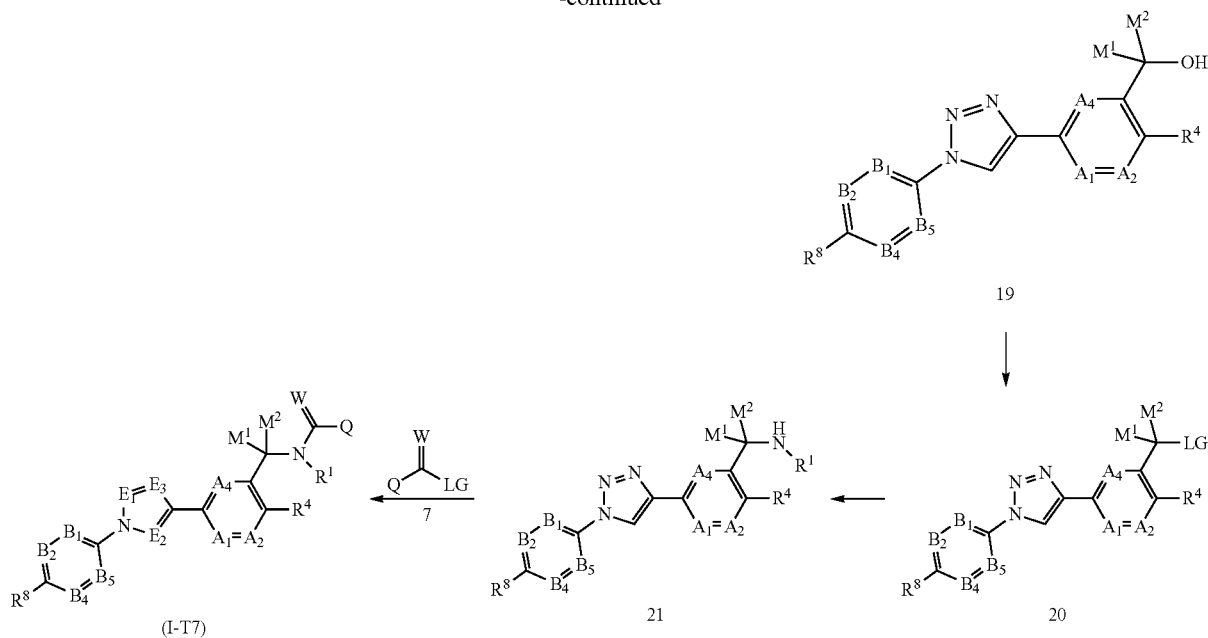

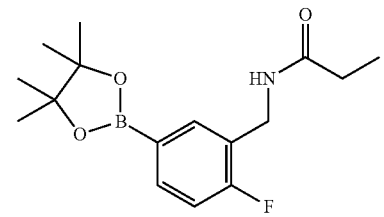

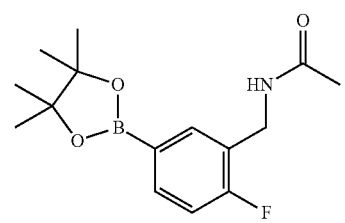

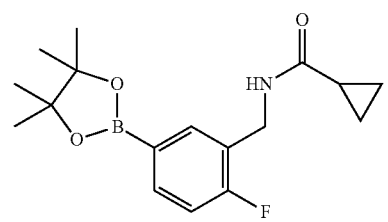

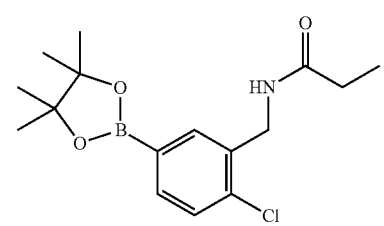

The radicals $A_1$, $A_2$, $A_4$, $B_1$, $B_2$, $B_4$, $B_5$, $R^1$, $M^1$, $M^2$, Q, $R^4$ and $R^8$ are as defined above. W is oxygen. R is alkyl, for example methyl or ethyl and LG is a leaving group, for example chlorine or a methanesulfonate.

Compounds of the general structure (I-T7) according to the invention may be prepared by methods known to those skilled in the art by reacting intermediate 21 with acylating reagents of the general structure 7. If not more than one of the groups $M^1$ or $M^2$ is a substituent that is not hydrogen, intermediates of the general structure 21 may be obtained from compounds of the general structure 19. For this purpose, the hydroxyl function in compounds of the general structure 19 is firstly converted into a leaving group, a methanesulfonate for example, by methods known to those skilled in the art and as a result intermediates of the general structure 20 are obtained. Substitution of the leaving group with a suitable nitrogen nucleophile, ammonia for example, leads to compounds of the general structure 21 [see e.g. WO 2009/097992]. Compounds of the general structure 19 may be obtained by reduction with suitable reducing agents, for example DIBAL-H, by methods known to those skilled in the art, starting from intermediates of the general structure 18 [see e.g. WO 2012/138648]. Compounds of the general structure 18 may be obtained by cycloaddition of intermediates of the general structure 16 with intermediates of the general structure 17, for example under Cu catalysis (see e.g. Med. Chem. Commun. 2011, 2, 638.). Intermediates of the general structures 16 and 17 are commercially available or can be prepared by methods known to those skilled in the art.

Furthermore, one embodiment refers to the following intermediates for preparing compounds of the formula I in which Q is methyl, ethyl, cycloalkyl, $R^4$ is F, Cl or methyl and $A_1$, $A_2$ and $A_3$ are C—H.

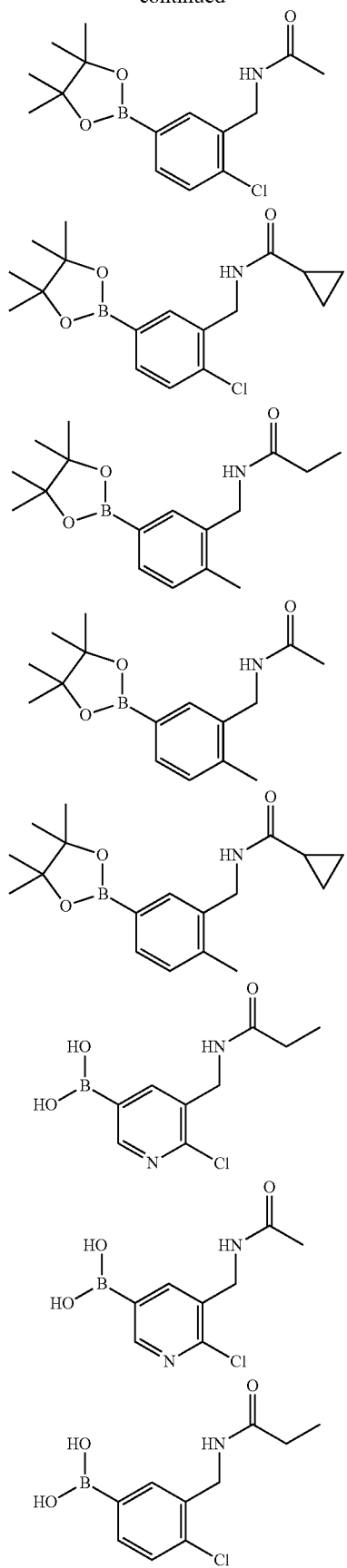
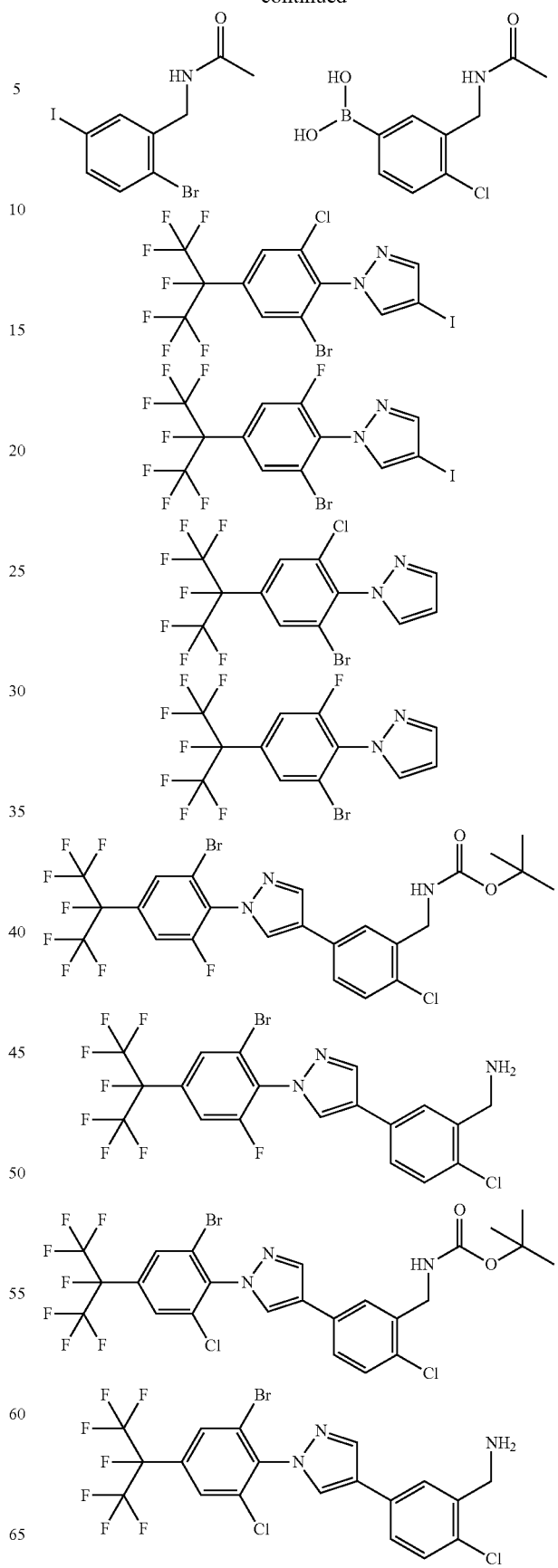

85
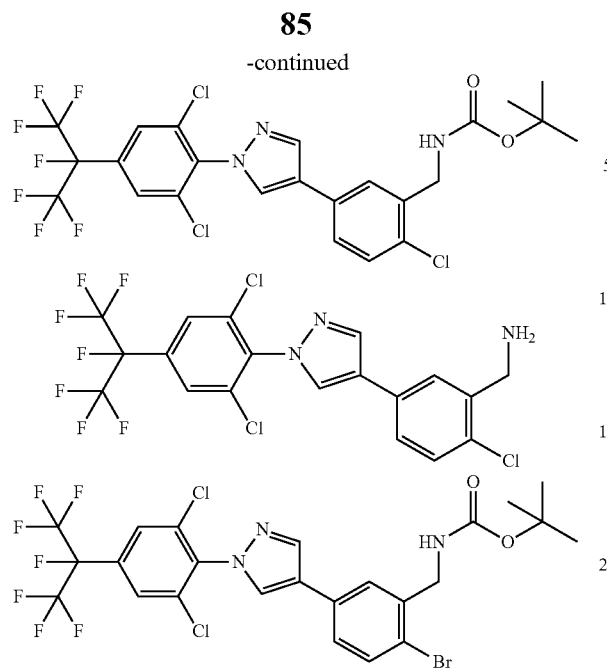
86
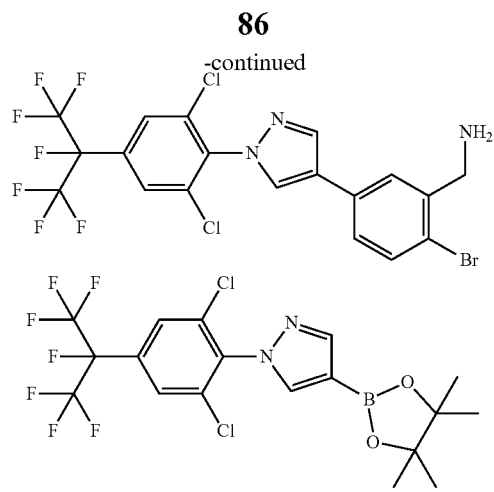
EXPERIMENTAL SECTION
Preparation of N-(6-{1-[2-chloro-4-(1,1,1,2,3,3,3-heptafluoropropan-2-yl)-6-(trifluoromethoxy)phenyl]-1H-pyrazol-4-yl}-2,3-dihydro-1H-inden-1-yl)propanamide (I-Tc-01)
Reaction Scheme 10
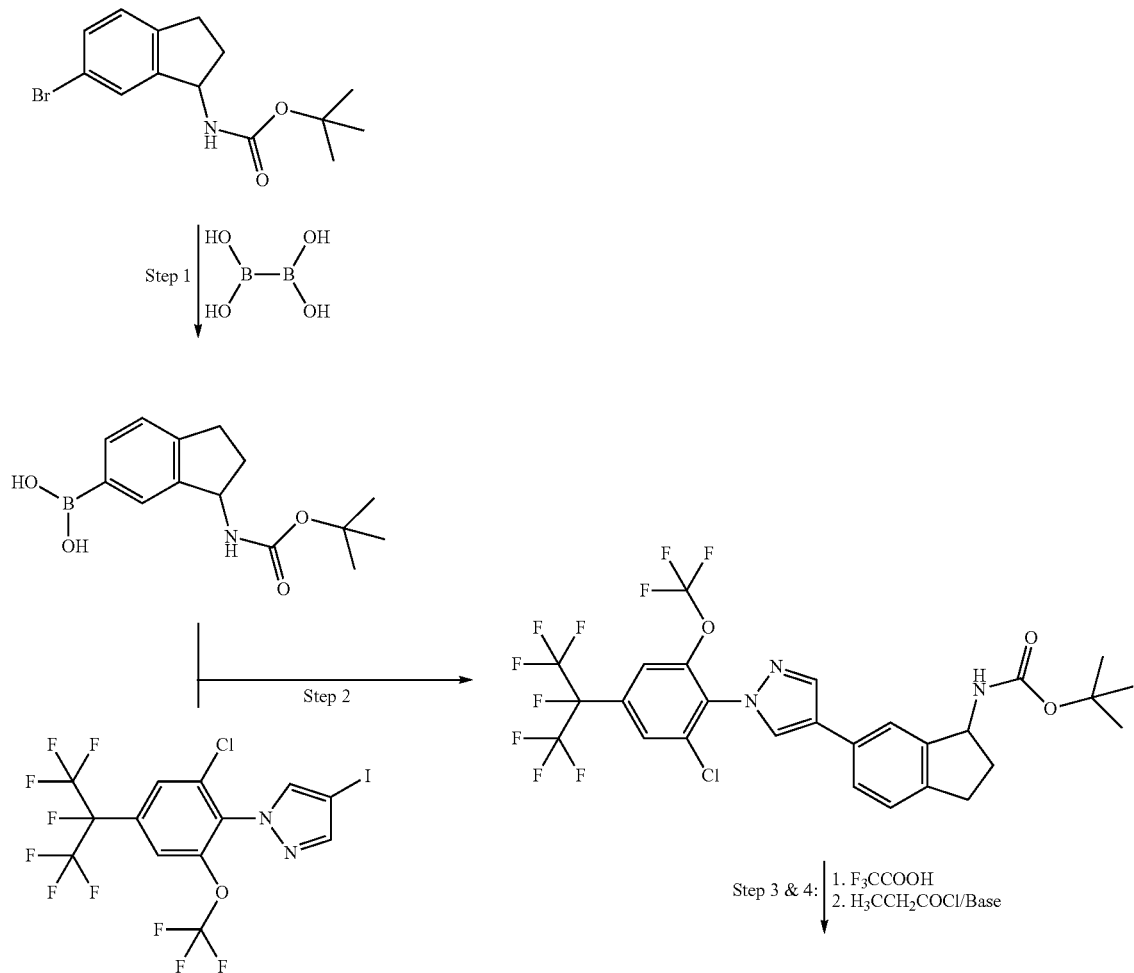

-continued

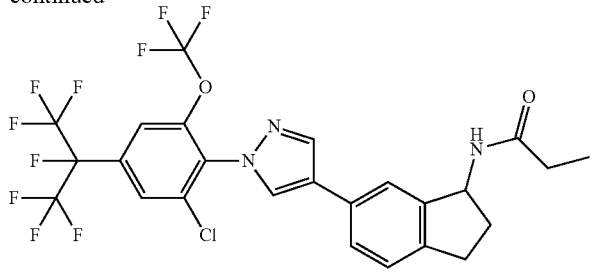

Step 1: Preparation of {3-[(tert-butoxycarbonyl)amino]-2,3-dihydro-1H-inden-5-yl}boric acid 836 mg (2.68 mmol) of tert-butyl-(6-bromo-2,3-dihydro-1H-inden-1-yl)carbamate (commercially available), 480 mg (5.35 mmol) of tetrahydroxydiborane and 89.4 mg (0.134 mmol) of Cataxium A Pd G2 were initially charged in a 100 ml flask under argon. Subsequently, 11 ml of methanol degassed with argon and 1.038 g (8.03 mmol, 1.4 ml) of diisopropylethylamine were added and the mixture was heated to 50° C. for 60 minutes. The mixture was cooled and the solvent was removed on a rotary evaporator under reduced pressure. The residue was dissolved in ethyl acetate, the organic phase washed successively with saturated aqueous sodium hydrogencarbonate solution, 5% aqueous sodium dihydrogen phosphate solution and twice with aqueous saturated sodium chloride solution, dried with sodium sulfate and evaporated on a rotary evaporator under reduced pressure. The residue was stirred with petroleum ether with addition of a little dichloromethane. The solid was filtered off with suction and dried under reduced pressure. 473 mg of {3-[(tert-butoxycarbonyl)amino]-2,3-dihydro-1H-inden-5-yl}boronic acid were obtained.

HPLC-MS[a]: log P=2.1, mass (m/z)=222 [(M+H)−57]+.
$^1$H-NMR (400 MHz, $d_3$-acetonitrile): δ (ppm): 7.64 (s, 1H), 7.61 (d, J=7.5 Hz, 1H), 7.23 (d, J=7.5 Hz, 1H), 6.02 (s, 2H (broad)), 5.59 (s, 1H (broad)), 5.05-5.12 (m, 1H), 2.9-2.95 (m, 1H), 2.76-2.86 (m, 1H), 2.41-2.5 (m, 1H), 1.71-1.82 (m, 1H), 1.45 (s, 9H).

Step 2: Preparation of tert-butyl (6-{1-[2-chloro-4-(1,1,1,2,3,3,3-heptafluoropropan-2-yl)-6-(trifluoromethoxy)phenyl]-1H-pyrazol-4-yl}-2,3-dihydro-1H-inden-1-yl)carbamate 293 mg (0.472 mmol) and 137.416 mg (0.496 mmol) {3-[(tert-butoxycarbonyl)amino]-2,3-dihydro-1H-inden-5-yl}boronic acid in 10.6 ml of isopropanol were initially charged in a 100 ml flask under argon, and 1.44 ml of degassed 1 molar aqueous potassium carbonate solution and 27.286 mg (0.05 mmol) of tetrakis(triphenylphosphine)palladium(0) were added. The mixture was then heated to 65° C. with stirring for 3 hours. For the work-up, the mixture was cooled and the solvent was evaporated on a rotary evaporator under reduced pressure. The residue was partitioned between ethyl acetate and water, the organic phase was washed twice with saturated aqueous sodium chloride solution, dried over sodium sulfate, and evaporated. The residue was purified on a cartridge containing 40 g of silica gel using a gradient from pure cyclohexane to cyclohexane/ethyl acetate 80:20 (v/v). 323 mg of tert-butyl (6-{1-[2-chloro-4-(1,1,1,2,3,3,3-heptafluoropropan-2-yl)-6-(trifluoromethoxy)phenyl]-1H-pyrazol-4-yl}-2,3-dihydro-1H-inden-1-yl)carbamate were obtained with a purity of 95% (LC/MS area).

HPLC-MS[a]: log P=6.1, mass (m/z)=662 [(M+H)]+.
$^1$H-NMR (400 MHz, $d_3$-acetonitrile): δ (ppm): 8.13 (s, 1H), 8.09 (s, 1H), 7.96 (s, 1H), 7.75 (s, 1H), 7.45-7.51 (m, 2H), 7.27 (d, J=8.1 Hz, 1H), 5.65 (s, 1H (broad)), 5.02-5.18 (m, 1H), 2.9-3.0 (m, 1H), 2.76-2.88 (m, 1H), 2.42-2.53 (m, 1H), 1.73-1.89 (m, 1H), 1.46 (s, 9H).

Step 3: Preparation of 6-{1-[2-chloro-4-(1,1,1,2,3,3,3-heptafluoropropan-2-yl)-6-(trifluoromethoxy)phenyl]-1H-pyrazol-4-yl}indan-1-amine 323 mg (0.488 mmol) of tert-butyl (6-{1-[2-chloro-4-(1,1,1,2,3,3,3-heptafluoropropan-2-yl)-6-(trifluoromethoxy)phenyl]-1H-pyrazol-4-yl}-2,3-dihydro-1H-inden-1-yl)carbamate in 4 ml of dichloromethane were initially charged in a 25 ml flask and subsequently 0.75 ml of trifluoroacetic acid was added dropwise. After the addition was complete, the mixture was stirred at room temperature for 30 minutes. For the work-up, the mixture was evaporated on a rotary evaporator under reduced pressure. The residue was taken up in 3 ml of dichloromethane and rendered alkaline with 4.63 ml of 10% aqueous NaOH. The organic phase was separated and the aqueous phase was re-extracted twice with 5 ml of dichloromethane each time. The combined extracts were then washed with saturated aqueous sodium chloride solution, dried with sodium sulfate and evaporated. 172 mg of 6-{1-[2-chloro-4-(1,1,1,2,3,3,3-heptafluoropropan-2-yl)-6-(trifluoromethoxy)phenyl]-1H-pyrazol-4-yl}indan-1-amine were obtained.

HPLC-MS[a]: log P=2.43, mass (m/z)=545 [(M+H)−17]+.
$^1$H-NMR (400 MHz, $d_3$-acetonitrile): δ (ppm): 8.15 (s, 1H), 8.09 (s, 1H), 7.97 (s, 1H), 7.75 (s, 1H), 7.58 (s, 1H), 7.43 (d, J=7.7 Hz, 1H), 7.24 (d, J=7.7 Hz, 1H), 4.25-4.39 (m, 1H), 2.88-3.0 (m, 1H), 2.72-2.82 (m, 1H), 2.38-2.50 (m, 1H), 1.59-1.70 (m, 1H).

Step 4: Preparation of N-(6-{1-[2-chloro-4-(1,1,1,2,3,3,3-heptafluoropropan-2-yl)-6-(trifluoromethoxy)phenyl]-1H-pyrazol-4-yl}-2,3-dihydro-1H-inden-1-yl)propanamide (I-Tc-01)

172 mg (0.306 mmol) of 6-{1-[2-chloro-4-(1,1,1,2,3,3,3-heptafluoropropan-2-yl)-6-(trifluoromethoxy)phenyl]-1H-pyrazol-4-yl}indan-1-amine were dissolved in 5 ml of dichloromethane and 93 mg (128 μl, 0.919 mmol) of triethylamine were then added. The solution was cooled to 0° C. and then 32.142 mg (30 μl, 0.337 mmol) of propionyl chloride, dissolved in 2 ml of dichloromethane, were added dropwise. The mixture was then further stirred at room temperature for 2 hours. Then the mixture was washed first with 5% aqueous sodium dihydrogenphosphate solution and then with saturated aqueous sodium chloride solution, dried with sodium sulfate and evaporated on a rotary evaporator under reduced pressure. The residue was purified by chromatography using a 15 g cartridge containing silica and a gradient from pure cyclohexane to 55:45 (v/v) cyclohexane/ethyl acetate. 134 mg of N-(6-{1-[2-chloro-4-(1,1,1,2,3,3,3-heptafluoropropan-2-yl)-6-(trifluoromethoxy)phenyl]-1H-pyrazol-4-yl}-2,3-dihydro-1H-inden-1-yl)propanamide (I-Tc-01) were obtained.

HPLC-MS[a)]: log P=4.84, mass (m/z)=618 [(M+H)]+.

¹H-NMR of (I-Tc-01): (400 MHz, d₃-acetonitrile): δ (ppm): 8.14 (s, 1H), 8.09 (s, 1H), 7.96 (s, 1H), 7.75 (s, 1H), 7.45-7.5 (m, 2H), 7.28 (d, J=7.7 Hz, 1H), 6.58-6.68 (m, 1H (broad)), 5.39 (q, J=7.9 Hz, 1H), 2.91-3.1 (m, 1H), 2.80-2.90 (m, 1H), 2.43-2.53 (m, 1H), 2.18-2.23 (m, 2H), 1.72-1.88 (m, 1H), 1.15 (t, J=7.6 Hz, 3H).

Preparation of N-(2-chloro-5-{1-[2,6-dichloro-4-(1,1,1,2,3,3,3-heptafluoropropan-2-yl)phenyl]-1H-pyrazol-4-yl}benzyl)cyclopropanecarboxamide (Ia-25)

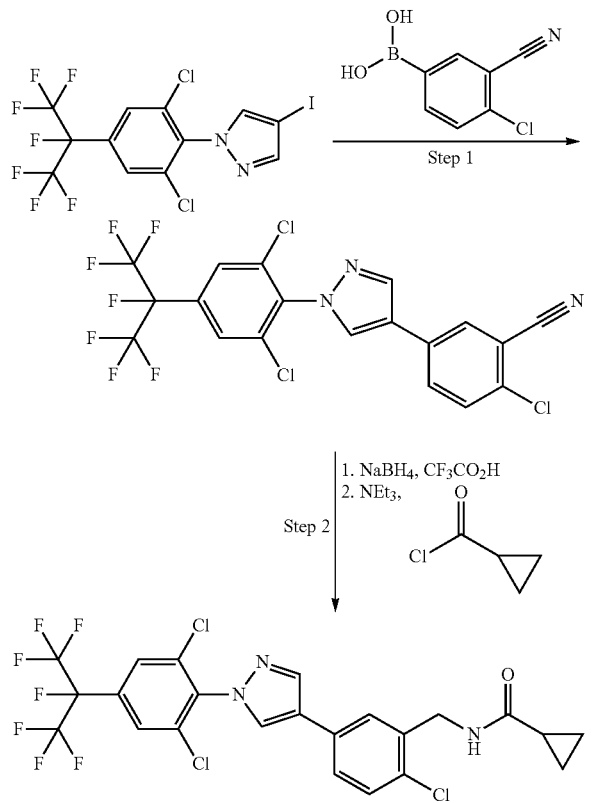

Reaction Scheme 11

Step 1: Preparation of 2-chloro-5-{1-[2,6-dichloro-4-(1,1,2,3,3,3-heptafluoropropan-2-yl)phenyl]-1H-pyrazol-4-yl}benzonitrile 21.7 ml of a saturated aqueous sodium hydrogencarbonate solution were added to a solution of 2.0 g (3.9 mmol) of 1-[2,6-dichloro-4-(1,1,1,2,3,3,3-heptafluoropropan-2-yl)phenyl]-4-iodo-1H-pyrazole and 0.83 g (4.6 mmol) of (4-chloro-3-cyanophenyl)boric acid in 65 mL of dioxane under argon. The reaction mixture was stirred at 80° C. for 16 h. The organic solvent was removed under reduced pressure and the aqueous phase was extracted repeatedly with ethyl acetate. The combined organic phases were dried with sodium sulfate, filtered and the solvent was removed under reduced pressure. The residue was separated chromatographically by MPLC on silica gel (gradient: ethyl acetate/cyclohexane 0:100→20:80). 1.57 g of 2-chloro-5-{1-[2,6-dichloro-4-(1,1,1,2,3,3,3-heptafluoropropan-2-yl)phenyl]-1H-pyrazol-4-yl}benzonitrile were thus obtained.

HPLC-MS[a)]: log P=5.3, mass (m/z)=518 [(M+H)]+.

¹H-NMR (400 MHz, d₆-DMSO): 8.107 (9.7); 7.886 (10.1); 7.842 (5.8); 7.837 (6.2); 7.751 (16.0); 7.722 (2.9); 7.717 (2.7); 7.701 (3.8); 7.696 (3.6); 7.570 (6.3); 7.548 (4.7); 7.263 (15.7); 5.301 (0.6); 2.045 (0.6); 1.592 (20.7); 1.259 (0.4); 0.000 (14.8); −0.001 (14.2).

Step 2: Preparation of N-(2-chloro-5-{1-[2,6-dichloro-4-(1,1,1,2,3,3,3-heptafluoropropan-2-yl)phenyl]-1H-pyrazol-4-yl}benzyl)cyclopropanecarboxamide (Ia-25)

A solution of 0.06 g (0.8 mmol) of trifluoroacetic acid in 1 ml of THF was added dropwise at room temperature to a suspension of 31 mg (0.83 mmol) of sodium borohydride in 2 ml of THF. After 2 mins, a solution of 86 mg (0.17 mmol) of 2-chloro-5-{1-[2,6-dichloro-4-(1,1,1,2,3,3,3-heptafluoropropan-2-yl)phenyl]-1H-pyrazol-4-yl}benzonitrile in 1 mL of THF was added dropwise to this mixture. The reaction was stirred at room temperature for 40 h, then cooled to below 10° C. and 1 mL of water was added. The organic solvent was removed under reduced pressure, water was added and the aqueous phase was extracted repeatedly with dichloromethane. The combined organic phases were dried with sodium sulfate, filtered and the solvent was removed under reduced pressure.

The residue (89 mg) was dissolved in 3 mL of THF and, at 0° C., 13 µL (0.14 mmol) of cyclopropanoyl chloride and 25 µL (0.18 mmol) of triethylamine were added. The solution was stirred at room temperature for 16 h and the solvent was then removed under reduced pressure. The residue was taken up in ethyl acetate and washed with water. The organic phase was dried over sodium sulfate and filtered, and the solvent was removed under reduced pressure. The crude product was separated chromatographically by HPLC (gradient: H₂O/acetonitrile). 28 mg of N-(2-chloro-5-{1-[2,6-dichloro-4-(1,1,1,2,3,3,3-heptafluoropropan-2-yl)phenyl]-1H-pyrazol-4-yl}benzyl)cyclopropanecarboxamide (Ia-25) were thus obtained.

HPLC-MS[a)]: log P=4.80, mass (m/z)=590 [(M+H)]+.

¹H-NMR (400 MHz, d₆-DMSO): s. see NMR peak list

Preparation of preparation of N-(2-chloro-5-{1-[2,6-dichloro-4-(1,1,1,2,3,3,3-heptafluoropropan-2-yl)phenyl]-1H-pyrazol-4-yl}benzyl)-N-methylpropanamide (Ia-22)

Reaction Scheme 12

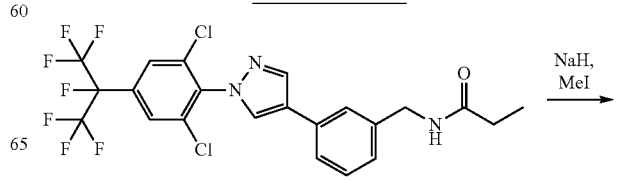

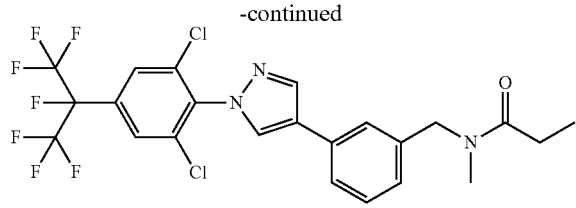

To a solution of 64 mg (0.12 mmol) of N-(2-chloro-5-{1-[2,6-dichloro-4-(1,1,1,2,3,3,3-heptafluoropropan-2-yl)phenyl]-1H-pyrazol-4-yl}benzyl)propanamide in 3.2 mL of THF at 0° C. was added 8 mg (0.2 mmol) of sodium hydride (55% dispersion in mineral oil). After 10 min at 0° C., 11 μL (0.18 mmol) of iodomoethane were added dropwise. Subsequently, the ice bath was removed. After 16 h at room temperature, the solvent was removed under reduced pressure and water was added to the residue. The phases were separated and the aqueous phase was extracted repeatedly with ethyl acetate. The combined organic phases were dried with sodium sulfate, filtered and the solvent was removed under reduced pressure. The residue was separated chromatographically by MPLC on silica gel (gradient: ethyl acetate/cyclohexane 0:100→30:70). 47 mg of N-(2-chloro-5-{1-[2,6-dichloro-4-(1,1,1,2,3,3,3-heptafluoropropan-2-yl)phenyl]-1H-pyrazol-4-yl}benzyl)-N-methylpropanamide (Ia-22) were thus obtained.

HPLC-MS[a]: log P=4.72, mass (m/z)=556 [(M+H)]+.

$^1$H-NMR of (I-a-25) (400 MHz, d$_6$-DMSO): s. see NMR peak list

Preparation of Preparation of N-(5-{1-[2-chloro-4-(1,1,1,2,3,3,3-heptafluoropropan-2-yl)-6-(methylsulfanyl)phenyl]-1H-pyrazol-4-yl}-2-fluorobenzyl) propanamide (Ia-10), N-(5-{1-[2-chloro-4-(1,1,1,2,3,3,3-heptafluoropropan-2-yl)-6-(methylsulfinyl)phenyl]-1H-pyrazol-4-yl}-2-fluorobenzyl)propanamide (I-a-45) and N-(5-{1-[2-chloro-4-(1,1,1,2,3,3,3-heptafluoropropan-2-yl)-6-(methylsulfonyl) phenyl]-1H-pyrazol-4-yl}-2-fluorobenzyl)propanamide (I-a-46)

Reaction Scheme 13
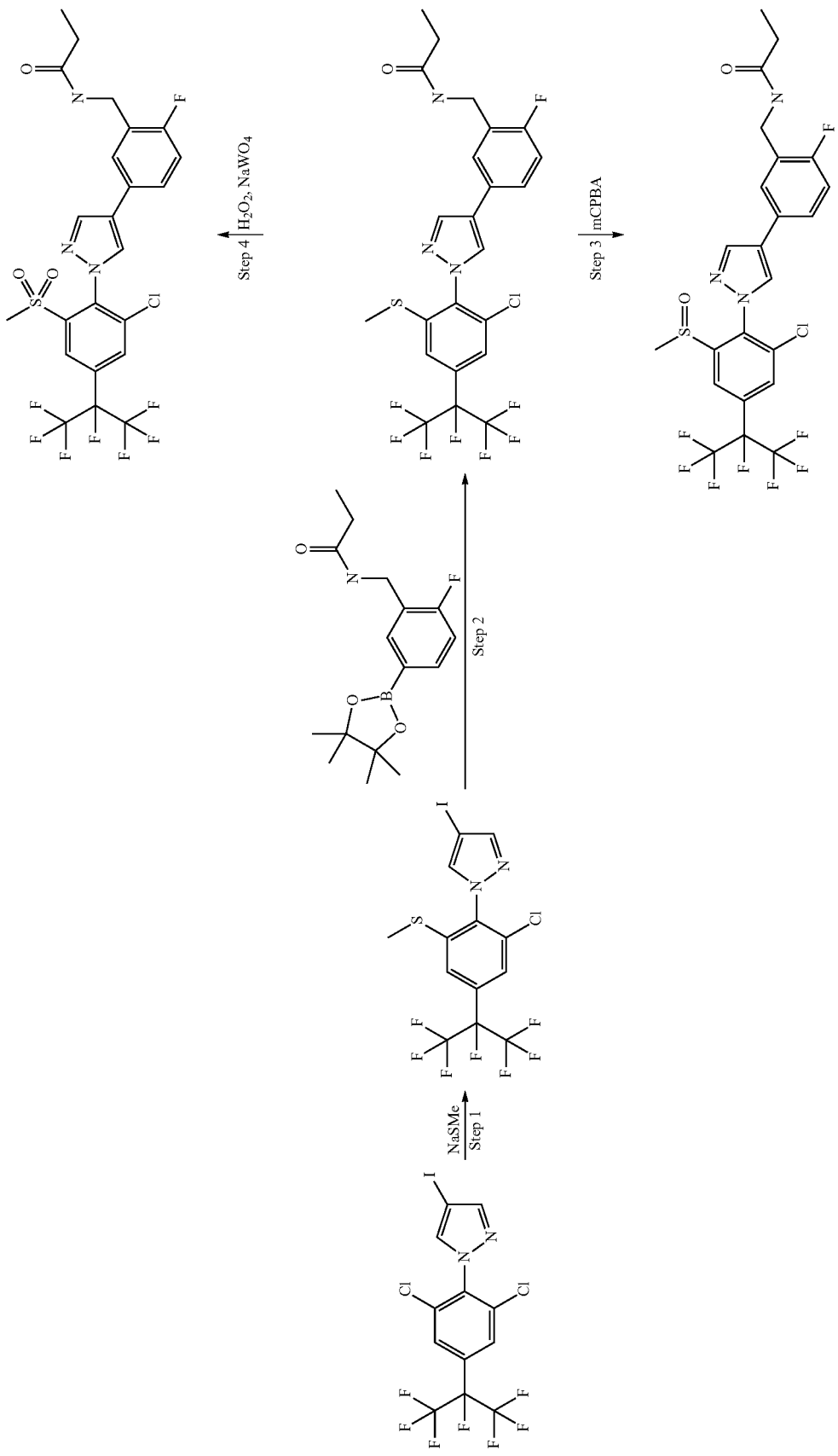

Step 1: Preparation of 1-[2-chloro-4-(1,1,1,2,3,3,3-heptafluoropropan-2-yl)-6-(methylsulfanyl) phenyl]-4-iodo-1H-pyrazole To a solution of 2.1 g (4.14 mmol) of 1-[2,6-dichloro-4-(1,1,1,2,3,3,3-heptafluoropropan-2-yl)phenyl]-4-iodo-1H-pyrazole in 7.6 ml DMF was added dropwise at 0° C. 367 mg (4.97 mmol) of sodium thiomethoxide in 2 ml of DMF. The reaction mixture was stirred at RT for 2 h. EtOAc was added to the mixture and washed repeatedly with $H_2O$. The organic phase was dried over $MgSO_4$ and the solvent removed under reduced pressure. The residue was purified by column chromatography (EtOAc/c-hex). 1.91 g of 1-[2-chloro-4-(1,1,1,2,3,3,3-heptafluoropropan-2-yl)-6-(methylsulfanyl)phenyl]-4-iodo-1H-pyrazole were obtained.

HPLC-MS[a)]: log P=5.19, mass (m/z)=518 [(M+H)]$^+$.
$^1$H-NMR (400 MHz, $d_6$-DMSO): δ (ppm): 8.30 (s, 1H), 7.93 (s, 1H), 7.73 (s, 1H), 7.46 (s, 1H), 2.50 (s, 3H)

Step 2: Preparation of N-(5-{1-[2-chloro-4-(1,1,1,2,3,3,3-heptafluoropropan-2-yl)-6-(methylsulfanyl)phenyl]-1H-pyrazol-4-yl}-2-fluorobenzyl)propanamide (Ia-10)

300 mg (0.57 mmol) of 1-[2-chloro-4-(1,1,1,2,3,3,3-heptafluoropropan-2-yl)-6-(methylsulfanyl)phenyl]-4-iodo-1H-pyrazole, 206 mg (0.67 mmol) of N-[2-fluoro-5-(4,4,5,5-tetramethyl-1,3,2-dioxaborolan-2-yl)benzyl]propanamide and 27 mg (0.02 mmol) of tetrakis(triphenylphosphine)palladium(0) were dissolved in 5 ml of dioxane and 2 ml of saturated aqueous $NaHCO_3$ solution were added. The mixture was stirred at 80° C. overnight. The reaction mixture was cooled to RT and filtered over silica gel. The filtrate was concentrated, and the residue was purified by HPLC (MeCN/$H_2O$). 87 mg of N-(5-{1-[2-chloro-4-(1,1,1,2,3,3,3-heptafluoropropan-2-yl)-6-(methylsulfanyl)phenyl]-1H-pyrazol-4-yl}-2-fluorobenzyl)propanamide (Ia-10) were obtained.

HPLC-MS[a)]: log P=4.29, mass (m/z)=572 [(M+H)]$^+$.
$^1$H-NMR (400 MHz, $d_6$-DMSO): s. see NMR peak list Step 3: Preparation of N-(5-{1-[2-chloro-4-(1,1,1,2,3,3,3-heptafluoropropan-2-yl)-6-(methylsulfinyl)phenyl]-1H-pyrazol-4-yl}-2-fluorobenzyl)propanamide (Ia-45)

34 mg (0.05 mmol) of N-(5-{1-[2-chloro-4-(1,1,1,2,3,3,3-heptafluoropropan-2-yl)-6-(methylsulfanyl)phenyl]-1H-pyrazol-4-yl}-2-fluorobenzyl)propanamide were dissolved in 10 ml of $CH_2Cl_2$ and 13 g (0.05 mmol) of m-chloroperbenzoic acid were added at 0° C. The reaction mixture was stirred at 0° C. for 2 h. The reaction was terminated by adding 1M NaOH. The phases were separated and the organic phase was concentrated. The residue was purified by column chromatography (EtOAc/c-hex). 18 mg of N-(5-{1-[2-chloro-4-(1,1,1,2,3,3,3-heptafluoropropan-2-yl)-6-(methylsulfinyl)phenyl]-1H-pyrazol-4-yl}-2-fluorobenzyl)propanamide (Ia-45) were obtained.

HPLC-MS[a)]: log P=3.52, mass (m/z)=588 [(M+H)]$^+$.
$^1$H-NMR (Ia-45) (400 MHz, $d_6$-DMSO): δ (ppm): 8.74 (s, 1H), 8.34 (s, 1H), 8.28-8.24 (m, 2H), 8.16 (s, 1H), 7.64-7.57 (m, 2H), 7.25 (t, 1H), 4.32 (d, 2H), 2.68 (s, 3H), 2.17 (q, 2H), 1.03 (t, 3H).

Step 4: Preparation of N-(5-{1-[2-chloro-4-(1,1,1,2,3,3,3-heptafluoropropan-2-yl)-6-(methylsulfonyl)phenyl]-1H-pyrazol-4-yl}-2-fluorobenzyl)propanamide (Ia-46)

34 mg (0.05 mmol) of N-(5-{-[2-chloro-4-(1,1,1,2,3,3,3-heptafluoropropan-2-yl)-6-(methylsulfanyl)phenyl]-1H-pyrazol-4-yl}-2-fluorobenzyl)propanamide and 1 mg of $Na_2WO_4$ were dissolved in 3 ml of acetic acid. The reaction mixture was heated to 40° C. and 15 µl (0.17 mmol) of 35% $H_2O_2$ were added. The reaction was stirred at 50° C. for 2 h. The mixture was cooled to RT, $CH_2Cl_2$ was added and washed successively with saturated aqueous $NaHCO_3$ and NaCl solution. The organic phase was dried over $MgSO_4$ and the solvent removed under reduced pressure. The residue was purified by column chromatography (EtOAc/c-hex). 11 mg of N-(5-{1-[2-chloro-4-(1,1,1,2,3,3,3-heptafluoropropan-2-yl)-6-(methylsulfonyl)phenyl]-1H-pyrazol-4-yl}-2-fluorobenzyl)propanamide (Ia-46) were obtained.

HPLC-MS[a)]: log P=3.65, mass (m/z)=603 [(M)]$^+$.
$^1$H-NMR (Ia-46) (400 MHz, $d_6$-DMSO): δ (ppm): 8.60 (s, 1H), 8.51 (d, 1H), 8.34 (s, 1H), 8.26-8.24 (m, 2H), 7.62-7.57 (m, 2H), 7.23 (t, 1H), 4.32 (d, 2H), 3.36 (s, 3H), 2.17 (q, 2H), 1.02 (t, 3H)

Preparation of N-[2-fluoro-5-(4,4,5,5-tetramethyl-1,3,2-dioxaborolan-2-yl)benzyl]propanamide

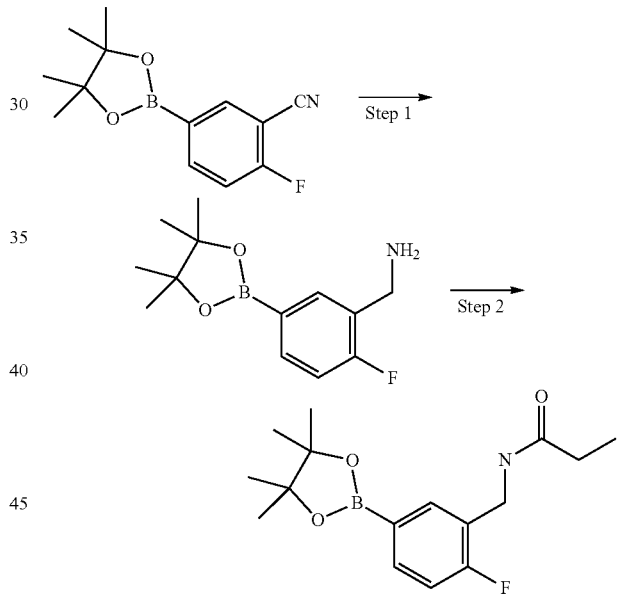

Reaction Scheme 14

Step 1: Preparation of 1-[2-fluoro-5-(4,4,5,5-tetramethyl-1,3,2-dioxaborolan-2-yl)phenyl]methanamine 2.30 g (9.03 mmol) of 2-fluoro-5-(4,4,5,5-tetramethyl-1,3,2-dioxaborolan-2-yl)benzonitrile were dissolved in 46 mL of 7M methanolic ammonia solution, Raney nickel was added and the mixture was stirred at 5 bar $H_2$ pressure and 40° C. for 2 h. The reaction solution was cooled to RT and filtered off. The filtrate was concentrated. 2.77 g of 1-[2-fluoro-5-(4,4,5,5-tetramethyl-1,3,2-dioxaborolan-2-yl)phenyl]methanamine were obtained.

HPLC-MS[a)]: log P=1.15 mass (m/z)=252 [(M+H)]$^+$.
$^1$H-NMR (400 MHz, $d_6$-DMSO): δ (ppm): 7.82 (d, 1H), 7.58-7.50 (m, 1H), 7.12-7.05 (m, 1H), 3.72 (s, 2H), 1.72 (s, 2H), 1.28 (s, 12H)

Step 2: Preparation of N-[2-fluoro-5-(4,4,5,5-tetramethyl-1,3,2-dioxaborolan-2-yl)benzyl]propanamide 510 mg (2.03 mmol) of 1-[2-fluoro-5-(4,4,5,5-tetramethyl-1,3,2-dioxaborolan-2-yl)phenyl]methanamine were dissolved in $CH_2Cl_2$ and at 0° C. added dropwise to a solution of 0.56 ml (4.06 mmol) of $NEt_3$ and 0.19 ml of propionyl chloride in $CH_2Cl_2$. The reaction mixture was stirred at RT for 2 h. IM HCl was added to the mixture and extracted with $CH_2Cl_2$. The combined organic phases were dried over $MgSO_4$ and the solvent was removed under reduced pressure. 626 mg of N-[2-fluoro-5-(4,4,5,5-tetramethyl-1,3,2-dioxaborolan-2-yl)benzyl]propanamide were obtained.

HPLC-MS[a]: log P=2.70 mass (m/z)=308 [(M+H)]+.

$^1$H-NMR (400 MHz, $d_6$-DMSO): δ (ppm): 8.30 (t, 1H), 7.65-7.60 (m, 2H), 7.19-7.14 (m, 1H), 4.28 (d, 2H), 8.52 (q, 2H), 1.29 (s, 12H), 1.01 (t, 3H)

Preparation of [5-(acetamidomethyl)-6-chloropyridin-3-yl]boronic acid

Reaction scheme 15

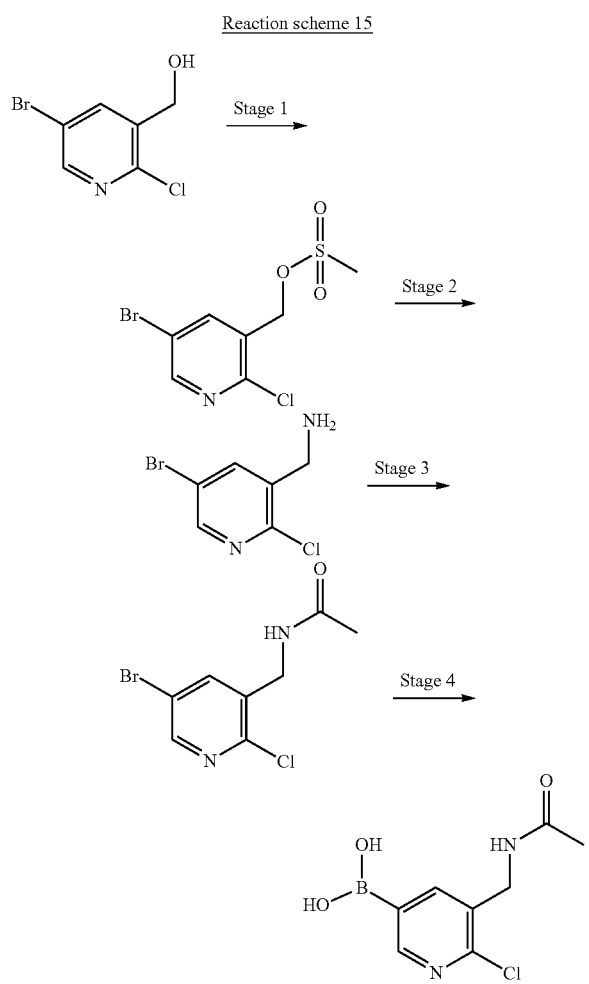

Stage 1: Preparation of (5-bromo-2-chloropyridin-3-yl)methyl methanesulfonate

A solution of 5.00 g (19.1 mmol, 85% purity) of (5-bromo-2-chloropyridin-3-yl)methanol and 10 mL (57 mmol) of N,N-diisopropylethylamine in 150 mL of THF was cooled to 0° C. and 1.5 mL (19 mmol) of methanesulfonyl chloride were added. The reaction solution was stirred for 60 min and dichloromethane was then added. The solution was washed with water, saturated sodium hydrogencarbonate solution and saturated sodium chloride solution and dried with sodium sulfate. The solvents were removed under reduced pressure and 6.50 g of (5-bromo-2-chloropyridin-3-yl)methyl methanesulfonate were thus obtained.

HPLC-MS[a]: log P=1.95, mass (m/z)=302 [(M+H)]+

$^1$H-NMR (400 MHz, $d_6$-DMSO): δ=8.645 (4.9); 8.638 (5.0); 8.396 (0.3); 8.314 (4.8); 8.307 (4.6); 5.376 (0.5); 5.318 (16.0); 4.808 (1.0); 3.339 (31.4); 3.320 (11.3); 2.525 (0.6); 2.511 (11.4); 2.507 (22.9); 2.502 (31.2); 2.498 (23.7); 2.494 (11.8); 2.294 (2.2); 1.356 (1.2); 1.275 (0.6); 1.259 (0.9); 1.244 (0.9); 0.000 (0.7).

Stage 2: Preparation of 1-(5-bromo-2-chloropyridin-3-yl)methanamine

To a mixture of 135 mL of 25% aqueous ammonia solution and 163 mL of ethanol were added 7.00 g (23.3 mmol) of (5-bromo-2-chloropyridin-3-yl)methyl methanesulfonate at 0° C. The solution was stirred at room temperature overnight and then concentrated under reduced pressure. 140 mL of 2M aqueous sodium hydroxide solution were added to the residue and this mixture was extracted exhaustively with dichloromethane. The combined organic phases were dried with sodium sulfate, filtered and the solvent was removed under reduced pressure. 4.78 g of 1-(5-bromo-2-chloropyridin-3-yl)methanamine were thus obtained.

HPLC-MS[a]: mass (m/z)=223 [(M+H)]+

$^1$H-NMR (400 MHz, $d_6$-DMSO): δ=8.426 (4.8); 8.420 (5.1); 8.208 (5.1); 8.202 (4.8); 3.747 (16.0); 3.321 (2.9); 2.526 (0.6); 2.512 (10.7); 2.508 (21.7); 2.503 (29.8); 2.499 (22.6); 2.494 (11.4); 2.293 (0.6); 2,000 (4.1); 0.008 (0.7); 0.000 (18.6); −0.008 (0.8).

Stage 3: Preparation of N-[(5-bromo-2-chloropyridin-3-yl)methyl]acetamide

To a solution of 2.50 g (11.3 mmol) of 1-(5-bromo-2-chloropyridin-3-yl)methanamine in 50 mL of $CH_2Cl_2$ were added 0.87 g (11 mmol) of acetyl chloride and 3.46 mL (24.8 mmol) of trimethylamine and the mixture was stirred overnight at room temperature. Dichloromethane was added and the solution was then washed with water and dried with sodium sulfate. The solvents were removed under reduced pressure and 2.88 g of N-[(5-bromo-2-chloropyridin-3-yl)methyl]acetamide were thus obtained.

HPLC-MS[a]: log P=1.15, mass (m/z)=265 [(M+H)]+

$^1$H-NMR (400 MHz, $d_6$-DMSO): δ=8.491 (2.4); 8.484 (2.4); 8.456 (0.4); 8.442 (0.7); 7.939 (2.2); 7.933 (2.2); 4.289 (3.3); 4.274 (3.3); 3.320 (18.3); 2.524 (0.3); 2.511 (9.4); 2.507 (20.4); 2.502 (29.0); 2.498 (21.8); 2.493 (10.5); 2.124 (0.3); 1.920 (16.0); 0.000 (2.5).

Stage 4: Preparation of [5-(acetamidomethyl)-6-chloropyridin-3-yl]boric acid

To 40 mL of oxygen-free methanol were added 2.15 g (8.16 mmol) of (N-[(5-bromo-2-chloropyridin-3-yl)methyl]acetamide, 2.19 g (24.5 mmol) of tetrahydroxydiboron, 273 mg (0.41 mmol) of chloro[(di(1-adamantyl)-N-butylphosphine)-2-(2-aminobiphenyl)]palladium(II) and 3.80 mL (24.5 mmol) of N,N-diethylisopropylamine. The reaction solution was heated to 40° C. for 5 h and subsequently stirred overnight at room temperature. 1 M aqueous sodium hydroxide solution was added and the organic solvent removed under reduced pressure. Further 1 M aqueous sodium hydroxide solution and methyl tert-butyl ether were then added and insoluble constituents were filtered off. The filtrate was separated into organic and aqueous phases. The aqueous phase was repeatedly extracted with methyl tert-butyl ether and the organic phase repeatedly extracted with 1 M aqueous sodium hydroxide solution. The combined aqueous phases were acidified to pH 0 with concentrated hydrochloric acid, saturated sodium chloride solution was added and the mixture repeatedly extracted with methyl ethyl ketone. The combined methyl ethyl ketone extracts were washed with saturated sodium chloride solution, dried with sodium sulfate and the solvent was then removed under reduced pressure. 2.05 g of [5-(acetamidomethyl)-6-chloro-pyridin-3-yl]boronic acid were thus obtained.

HPLC-MS$^{a)}$: mass (m/z)=229 [(M+H)]$^+$ $^1$H-NMR (400 MHz. d$_6$-DMSO): δ=8.577 (2.7); 8.572 (2.8); 8.453 (0.5); 8.432 (0.8); 8.417 (1.3); 8.404 (0.7); 8.036 (2.4); 8.03 (2.4); 8.031 (2.4); 4.293 (3.6); 4.279 (3.6); 2.520 (0.5); 2.511 (14.9); 2.507 (33.1); 2.502 (47.7); 2.498 (36.9); 2.493 (18.8); 2.456 (0.6); 2.438 (1.4); 2.420 (1.4); 2.402 (0.5); 2.067 (5.7); 1.917 (16.0); 1.909 (1.5); 1.892 (1.2); 0.925 (1.8); 0.907 (3.5); 0.888 (1.7); 0.000 (5.9); −0.008 (0.3).

Preparation of tert-butyl [2-chloro-5-(4,4,5,5-tetramethyl-1,3,2-dioxaborolan-2-yl)benzyl]carbamate

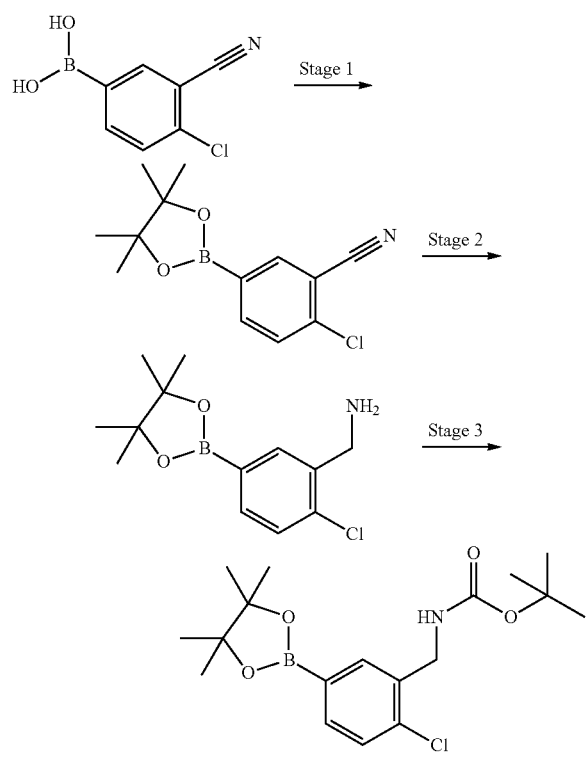

Reaction scheme 16

Stage 1: 2-Chloro-5-(4,4,5,5-tetramethyl-1,3,2-dioxaborolan-2-yl)benzonitrile

A suspension of 10.0 g (55.1 mmol) of (4-chloro-3-cyanophenyl)boronic acid, 6.52 g (55.1 mmol) of pinacol and molecular sieves were stirred at room temperature for 24 h. The reaction solution was filtered over celite and the solvent was removed under reduced pressure. The residue was purified chromatographically by MPLC on silica gel (gradient: ethyl acetate/cyclohexane 0:100→50:50). 12.6 g of 2-chloro-5-(4,4,5,5-tetramethyl-1,3,2-dioxaborolan-2-yl)benzonitrile were thus obtained.

HPLC-MS$^{a)}$: log P=4.19, mass (m/z)=264 [(M+H)]$^+$ $^1$H-NMR (400 MHz. d$_6$-DMSO): δ=8.065 (0.8); 8.062 (0.9); 7.953 (0.5); 7.950 (0.4); 7.933 (0.6); 7.929 (0.6); 7.786 (0.9); 7.765 (0.7); 3.320 (8.9); 2.512 (3.7); 2.507 (8.0); 2.503 (11.4); 2.498 (8.7); 2.494 (4.3); 1.311 (16.0); 0.000 (0.7).

Stage 2: 1-[2-Chloro-5-(4,4,5,5-tetramethyl-1,3,2-dioxaborolan-2-yl)phenyl]methanamine To a solution of 12.0 g (45.5 mmol) of 2-chloro-5-(4,4,5,5-tetramethyl-1,3,2-dioxaborolan-2-yl)benzonitrile in 450 mL of 7 M methanolic ammonia solution were added 6 g of Raney cobalt and the reaction solution was stirred at room temperature under 20 bar hydrogen pressure for 16 h. The reaction mixture was filtered and the filtrate was concentrated under reduced pressure. 13.9 g of a pale yellow-green solid were obtained.

HPLC-MS$^{a)}$: log P=1.27, mass (m/z)=268 [(M+H)]$^+$

Stage 3: tert-Butyl [2-chloro-5-(4,4,5,5-tetramethyl-1,3,2-dioxaborolan-2-yl)benzyl]carbamate To a solution of 2.00 g of the crude product from stage 2 and 2.13 g (9.75 mmol) of di-tert-butyl dicarbonate in 20 mL of CH$_2$Cl$_2$ were added 1.31 mL (9.43 mmol) of trimethylamine at 0° C. The reaction mixture was stirred at room temperature overnight, water was added and the mixture extracted with CH$_2$Cl$_2$. The combined organic phases were washed with saturated brine, dried with sodium sulfate and the solvent removed under reduced pressure. The residue was separated chromatographically by MPLC on silica gel (gradient: ethyl acetate/cyclohexane 0:100→100:0). 0.81 g of tert-butyl [2-chloro-5-(4,4,5,5-tetramethyl-1,3,2-dioxaborolan-2-yl)benzyl]carbamate and 0.73 g of a mixed fraction of the desired product with a secondary product were obtained. This mixture was again separated chromatographically. The separation was effected by HPLC (gradient: H$_2$O/acetonitrile) and gave a further 0.45 g of tert-butyl [2-chloro-5-(4,4,5,5-tetramethyl-1,3,2-dioxaborolan-2-yl)benzyl]carbamate.

HPLC-MS$^{a)}$: log P=4.73, mass (m/z)=312 [(M+H)−56]$^+$ $^1$H-NMR (400 MHz. d$_6$-DMSO): δ=7.637 (0.6); 7.542 (0.4); 7.539 (0.4); 7.523 (0.6); 7.519 (0.6); 7.433 (1.1); 7.414 (0.8); 4.198 (0.7); 4.183 (0.7); 3.318 (15.8); 2.510 (5.9); 2.506 (12.2); 2.502 (16.8); 2.497 (12.7); 2.493 (6.3); 2.073 (0.9); 1.419 (6.3); 1.289 (16.0); 0.008 (0.7); 0.000 (20.2); −0.008 (0.8).

101

Preparation of N-(2-chloro-5-{1-[2,6-dichloro-4-(1,1,1,2,3,3,3-heptafluoropropan-2-yl)phenyl]-1H-pyrazol-4-yl}benzyl)acetamide (Ia-05)

Reaction scheme 17

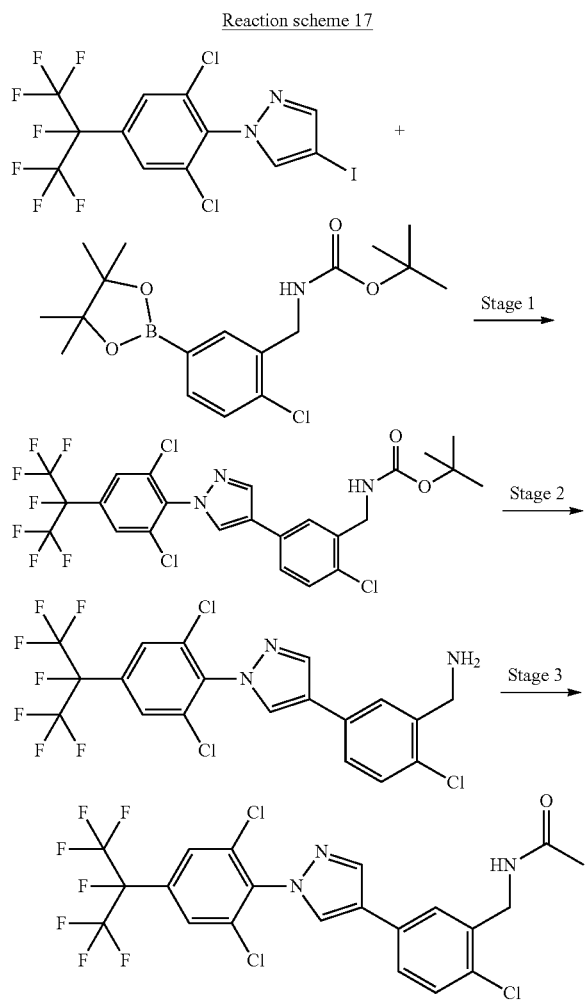

Stage 1: tert-Butyl (2-chloro-5-{1-[2,6-dichloro-4-(1,1,1,2,3,3,3-heptafluoropropan-2-yl)phenyl]-1H-pyrazol-4-yl}benzyl)carbamate To a solution of 1.49 g (2.93 mmol) of 1-[2,6-dichloro-4-(1,1,1,2,3,3,3-heptafluoropropan-2-yl)phenyl]-4-iodo-1H-pyrazole and 1.25 g (3.39 mmol) of tert-butyl [2-chloro-5-(4,4,5,5-tetramethyl-1,3,2-dioxaborolan-2-yl)benzyl]carbamate in 40 mL of 1,4-dioxane were added 20 mL of a saturated aqueous NaHCO$_3$ solution and the reaction mixture was stirred at 80° C. overnight. The organic solvent was then removed under reduced pressure and the aqueous phase extracted exhaustively with ethyl acetate. The combined organic phases were washed with saturated brine, dried with sodium sulfate and filtered. The solvent was removed under reduced pressure. The residue was separated chromatographically by MPLC on silica gel (gradient: ethyl acetate/cyclohexane 0:100→100:0). 1.41 g of tert-butyl (2-chloro-5-{1-[2,6-dichloro-4-(1,1,1,2,3,3,3-heptafluoropropan-2-yl)phenyl]-1H-pyrazol-4-yl}benzyl)carbamate were thus obtained.

102

HPLC-MS$^{a)}$: log P=5.78, mass (m/z)=620 [(M+H)]$^+$ $^1$H-NMR (400 MHz. d$_6$-DMSO): δ=8.608 (3.4); 8.264 (2.7); 8.080 (5.9); 7.589 (1.7); 7.562 (1.3); 7.539 (0.4); 7.475 (2.4); 7.455 (1.7); 7.410 (0.5); 7.395 (0.8); 7.380 (0.5); 4.247 (2.0); 4.233 (1.9); 3.322 (45.3); 2.672 (0.4); 2.502 (60.3); 2.498 (50.3); 2.329 (0.4); 1.988 (0.5); 1.411 (16.0); 1.398 (8.6); 1.309 (0.6); 0.000 (53.2).

Stage 2: 1-(2-Chloro-5-{1-[2,6-dichloro-4-(1,1,1,2,3,3,3-heptafluoropropan-2-yl)phenyl]-1H-pyrazol-4-yl}phenyl)methanamine 25.6 mL of trifluoroacetic added were added to 1.37 g (2.21 mmol) of tert-butyl (2-chloro-5-{1-[2,6-dichloro-4-(1,1,2,3,3,3-heptafluoropropan-2-yl)phenyl]-1H-pyrazol-4-yl}benzyl)carbamate. The reaction mixture was stirred at room temperature for 30 min and then concentrated under reduced pressure. Saturated NaHCO$_3$ solution was added to the residue and the mixture was extracted exhaustively with ethyl acetate. The combined organic phases were dried with sodium sulfate, filtered and the solvent was removed under reduced pressure. 1.06 g of 1-(2-chloro-5-{1-[2,6-dichloro-4-(1,1,1,2,3,3,3-heptafluoropropan-2-yl)phenyl]-1H-pyrazol-4-yl)}phenyl)methanamine were obtained.

HPLC-MS$^{a)}$: log P=2.41, mass (m/z)=522 [(M+H)]$^+$ $^1$H-NMR (400 MHz. d$_6$-DMSO): δ=8.639 (9.6); 8.352 (9.6); 8.315 (0.4); 8.082 (16.0); 7.865 (4.3); 7.861 (4.4); 7.552 (2.3); 7.547 (2.2); 7.532 (3.1); 7.526 (3.1); 7.498 (0.4); 7.478 (0.4); 7.436 (6.4); 7.416 (4.6); 4.057 (0.5); 4.039 (1.6); 4.021 (1.6); 4.003 (0.5); 3.847 (0.7); 3.812 (11.9); 3.320 (12.0); 2.676 (0.4); 2.671 (0.5); 2.667 (0.4); 2.525 (1.4); 2.511 (33.1); 2.507 (66.9); 2.502 (90.6); 2.498 (67.7); 2.493 (33.1); 2.334 (0.5); 2.329 (0.6); 2.325 (0.5); 2.149 (1.4); 1.989 (6.7); 1.193 (1.7); 1.176 (3.5); 1.158 (1.7); 0.146 (0.5); 0.008 (4.4); 0.000 (119.0); −0.008 (4.5); −0.150 (0.5).

Stage 3: N-(2-Chloro-5-{1-[2,6-dichloro-4-(1,1,1,2,3,3,3-heptafluoropropan-2-yl)phenyl]-1H-pyrazol-4-yl}benzyl)acetamide and N-acetyl-N-(2-chloro-5-{1-[2,6-dichloro-4-(1,1,1,2,3,3,3-heptafluoropropan-2-yl)phenyl]-1H-pyrazol-4-yl}benzyl)acetamide To a solution of 1.0 g (1.9 mmol) of 1-(2-chloro-5-{1-[2,6-dichloro-4-(1,1,1,2,3,3,3-heptafluoropropan-2-yl)phenyl]-1H-pyrazol-4-yl}phenyl)methanamine in 50 mL of THF at 0° C. were added 0.55 mL (3.9 mmol) of triethylamine and 309 mg (3.93 mmol) of acetyl chloride. The reaction mixture was stirred at room temperature overnight and then concentrated under reduced pressure. The residue was taken up in ethyl acetate, washed with water and the organic phase dried with sodium sulfate. The solvent was removed under reduced pressure and the residue separated chromatographically by MPLC on RP silica gel (gradient: H$_2$O/acetonitrile). 1.26 g of N-(2-chloro-5-{1-[2,6-dichloro-4-(1,1,1,2,3,3,3-heptafluoropropan-2-yl)phenyl]-1H-pyrazol-4-yl}benzyl)acetamide and 0.45 g of a mixed fraction of the desired product with a secondary product were obtained. This was again separated chromatographically. The separation was effected by HPLC (gradient: H$_2$O/acetonitrile) and gave a further 0.21 g of N-(2-chloro-5-{1-[2,6-dichloro-4-(1,1,1,2,3,3,3-heptafluoropropan-2-yl)phenyl]-1H-pyrazol-4-yl}benzyl)acetamide and 70 mg of N-acetyl-N-(2-chloro-5-{1-[2,6-dichloro-4-(1,1,1,2,3,3,3-heptafluoropropan-2-yl)phenyl]-1H-pyrazol-4-yl}benzyl)acetamide.

N-(2-Chloro-5-{1-[2,6-dichloro-4-(1,1,1,2,3,3,3-heptafluoropropan-2-yl)phenyl]-1H-pyrazol-4-yl}benzyl)acetamide (Ia-05)

HPLC-MS[a)]: log P=4.13, mass (m/z)=564 [(M+H)]+
1H-NMR see Table 1 Example Ia-05

N-Acetyl-N-(2-chloro-5-{1-[2,6-dichloro-4-(1,1,1,2,3,3,3-heptafluoropropan-2-yl)phenyl]-1H-pyrazol-4-yl}benzyl)acetamide (Ia-108)

HPLC-MS[a)]: log P=5.14, mass (m/z)=606 [(M+H)]+
1H-NMR (400 MHz, $d_6$-DMSO): δ=8.730 (2.8); 8.388 (2.8); 8.084 (4.8); 7.642 (0.7); 7.638 (0.7); 7.617 (1.0); 7.541 (1.7); 7.521 (1.2); 7.251 (1.5); 4.946 (3.6); 3.316 (20.5); 2.671 (0.4); 2.501 (63.8); 2.404 (16.0); 2.328 (0.4); 2.073 (0.6); 0.000 (8.7)

Preparation of N-[1-(2-chloro-5-{1-[2,6-dichloro-4-(1,1,1,2,3,3,3-heptafluoropropan-2-yl)phenyl]-1H-pyrazol-4-yl}phenyl)ethyl]propanamide (Ia-47)

organic phase was then dried with sodium sulfate, filtered and the solvent removed under reduced pressure. The residue was separated chromatographically by MPLC on RP silica gel (gradient: H2O/acetonitrile). 22 mg of N-[1-(5-bromo-2-fluorophenyl)ethyl]propanamide were thus obtained.

HPLC-MS[a)]: log P=2.14, mass (m/z)=276 [(M+H)]+
1H-NMR (400 MHz. $d_6$-DMSO): δ=8.310 (1.2); 8.291 (1.2); 7.520 (1.7); 7.514 (2.2); 7.504 (1.7); 7.497 (2.2); 7.482 (1.3); 7.475 (1.0); 7.470 (1.5); 7.464 (1.1); 7.460 (1.5); 7.453 (1.3); 7.449 (1.5); 7.442 (1.1); 7.181 (2.6); 7.160 (2.4); 7.156 (2.8); 7.134 (2.3); 5.123 (0.3); 5.105 (1.3); 5.087 (1.9); 5.069 (1.3); 5.051 (0.3); 3.318 (36.8); 2.671 (0.3); 2.524 (0.7); 2.519 (1.1); 2.511 (19.9); 2.506 (42.9); 2.502 (58.3); 2.497 (41.8); 2.493 (19.7); 2.328 (0.3); 2.157 (2.0); 2.138 (6.7); 2.119 (7.1); 2.101 (2.4); 1.323 (9.9); 1.305 (9.9); 1.001 (7.7); 0.982 (16.0); 0.963 (7.2); 0.000 (5.2).

Reaction scheme 18

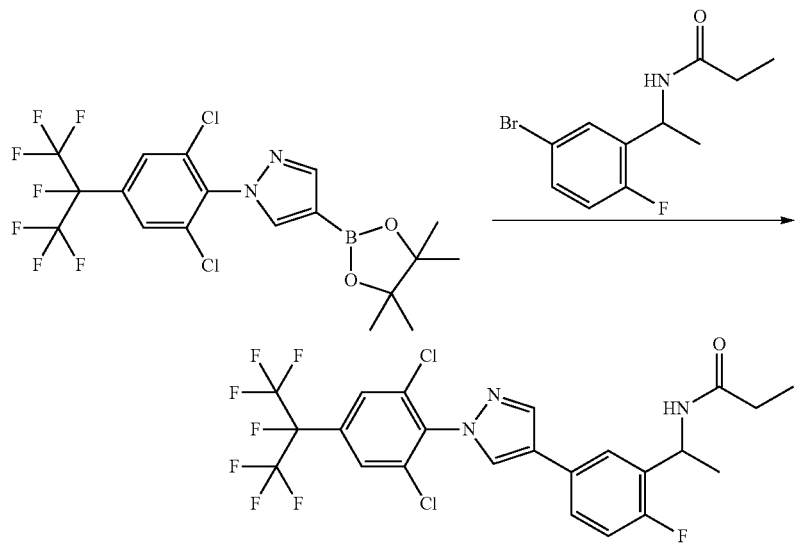

N-[1-(5-Bromo-2-fluorophenyl)ethyl]propanamide

To a solution of 250 mg (1.15 mmol) of 1-(5-bromo-2-fluorophenyl)ethanone and 1.33 g (17.2 mmol) of ammonium acetate at 0° C. were added 362 mg (5.75 mmol) of sodium cyanoborohydride and the reaction mixture was heated under reflux overnight. Water and saturated sodium hydrogencarbonate solution were added to the reaction mixture and the mixture was repeatedly extracted with ethyl acetate. The combined organic phases were washed with saturated sodium chloride solution, dried with sodium sulfate, filtered and the solvent was removed under reduced pressure. 245 mg of crude product were obtained.

To a solution of 80 mg of the crude product of the precursor in CH2Cl2 were added 0.09 mL (0.50 mmol) of N,N-diisopropylethylamine and 24 mg (0.26 mmol) of propionyl chloride. The reaction solution was stirred at room temperature overnight and the solvent then removed under reduced pressure. The residue was taken up in ethyl acetate and washed with 1M hydrochloric acid and water. The 1-[2,6-Dichloro-4-(1,1,1,2,3,3,3-heptafluorpropan-2-yl)phenyl]-4-(4,4,5,5-tetramethyl-1,3,2-dioxaborolan-2-yl)-1H-pyrazole To a solution of 1.27 g (2.50 mmol) of 1-[2,6-dichloro-4-(1,1,1,2,3,3,3-heptafluoropropan-2-yl)phenyl]-4-iodo-1H-pyrazole in THF at −39° C. were added dropwise 2.12 mL of a 1.3M solution of isopropylmagnesium chloride lithium chloride complex and the reaction solution was then stirred at −38° C. for 30 minutes. 0.59 mL (2.9 mmol) of 2-isopropoxy-4,4,5,5-tetramethyl-1,3,2-dioxaborolane was then added dropwise, the cooling bath was removed and the reaction solution stirred at room temperature for 1 h. Saturated ammonium chloride solution was added and the mixture was extracted repeatedly with cyclohexane. The combined organic phases were washed with saturated sodium hydrogen carbonate solution and saturated sodium chloride solution, dried with sodium sulfate, filtered and the solvent removed under reduced pressure. The residue was purified chromatographically by MPLC on silica gel (gradient: ethyl acetate/cyclohexane 0:100→30:70). 270 mg of 1-[2,6-dichloro-4-(1,1,1,2,3,3,3-heptafluoropropan-2-yl)phenyl]-4-(4,4,5,5-tetramethyl-1,3,2-dioxaborolan-2-yl)-1H-pyrazole were thus obtained.

HPLC-MS[a)]: log P=5.55, mass (m/z)=507 [(M+H)]+

$^1$H-NMR (400 MHz. d$_6$-DMSO): δ=8.361 (1.8); 8.045 (2.5); 7.956 (1.8); 3.316 (30.9); 2.523 (1.0); 2.510 (19.5); 2.506 (38.9); 2.501 (51.1); 2.497 (37.6); 2.493 (18.8); 1.398 (3.0); 1.293 (16.0); 0.000 (1.8).

N-[1-(2-Chloro-5-{1-[2,6-dichloro-4-(1,1,1,2,3,3,3-heptafluoropropan-2-yl)phenyl]-1H-pyrazol-4-yl}phenyl)ethyl]propanamide To a solution of 22 mg (80 µmol) of N-[1-(5-bromo-2-fluorophenyl)ethyl]propanamide and 41 mg (80 µmol) of 1-[2,6-dichloro-4-(1,1,1,2,3,3,3-heptafluoropropan-2-yl)phenyl]-4-(4,4,5,5-tetramethyl-1,3,2-dioxaborolan-2-yl)-1H-pyrazole in butanol were added 105 mg (0.32 mmol) of Cs$_2$CO$_3$, water and 2 mg (2 µmol) of Pd(PPh$_3$)$_4$. The reaction solution was stirred at 80° C. for 6 h and at room temperature overnight. Water was then added and the mixture extracted with ethyl acetate. The combined organic phases were washed with saturated sodium chloride solution, dried with sodium sulfate, filtered and the solvent removed under reduced pressure. The residue was separated chromatographically by MPLC on RP silica gel (gradient: H$_2$O/acetonitrile). 5 mg of N-[1-(2-chloro-5-{1-[2,6-dichloro-4-(1,1,1,2,3,3,3-heptafluoropropan-2-yl)phenyl]-1H-pyrazol-4-yl}phenyl)ethyl]propanamide (Ia-47) were thus obtained.

HPLC-MS[a)]: log P=4.41, mass (m/z)=574 [(M+H)]+

$^1$H-NMR (400 MHz. d$_6$-DMSO): δ=8.695 (0.8); 8.564 (8.7); 8.313 (0.4); 8.268 (8.8); 8.245 (2.7); 8.227 (2.4); 8.144 (0.7); 8.138 (0.7); 8.080 (13.9); 8.034 (1.8); 8.017 (0.4); 7.980 (0.3); 7.960 (0.4); 7.852 (0.8); 7.848 (0.8); 7.645 (1.9); 7.640 (2.2); 7.627 (2.1); 7.622 (2.2); 7.572 (1.3); 7.566 (1.3); 7.560 (1.4); 7.551 (1.6); 7.545 (1.4); 7.539 (1.3); 7.533 (1.1); 7.224 (2.3); 7.202 (2.5); 7.198 (2.7); 7.177 (2.1); 6.594 (0.4); 6.588 (0.7); 6.583 (0.4); 5.754 (2.0); 5.186 (0.4); 5.168 (1.5); 5.150 (2.2); 5.131 (1.5); 5.114 (0.4); 3.319 (268.0); 2.675 (0.9); 2.670 (1.2); 2.666 (0.9); 2.523 (2.9); 2.510 (75.5); 2.506 (154.7); 2.501 (205.7); 2.497 (151.1); 2.333 (0.9); 2.328 (1.3); 2.323 (0.9); 2.185 (2.1); 2.166 (6.8); 2.147 (7.3); 2.128 (2.5); 1.384 (10.2); 1.366 (10.2); 1.234 (0.5); 1.225 (0.4); 1.011 (7.8); 0.992 (16.0); 0.973 (7.4); 0.007 (1.4); 0.000 (42.7); −0.008 (1.8).

Preparation of N-(5-{1-[2-bromo-6-chloro-4-(1,1,2,3,3,3-heptafluoropropan-2-yl)phenyl]-1H-pyrazol-4-yl}-2-chlorobenzyl)-2-cyanoacetamide (Ia-137)

Reaction scheme 19

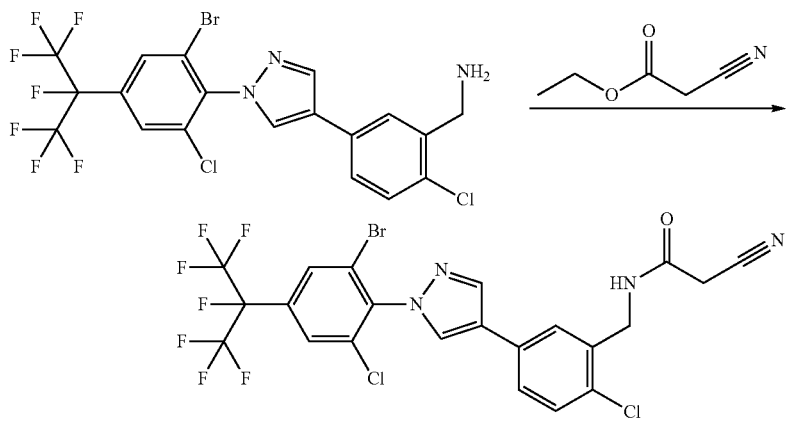

To a solution of 100 mg (177 µmol) of 1-(5-{1-[2-bromo-6-chloro-4-(1,1,1,2,3,3,3-heptafluoropropan-2-yl)phenyl]-1H-pyrazol-4-yl}-2-chlorophenyl)methanamine and 1.3 µL (89 µmol) of 1,8-diazabicyclo[5.4.0]undec-7-ene in 1 mL of THF were added 3.8 µL (0.35 mmol) of ethyl cyanoacetate. The reaction solution was stirred at room temperature overnight. Subsequently, a further 3.8 µL (0.35 mmol) of ethyl cyanoacetate and 1.3 µL (89 µmol) of 1,8-diazabicyclo[5.4.0]undec-7-ene were added and the mixture was stirred at room temperature for two days. 0.1 M hydrochloric acid was added and the reaction mixture extracted with ethyl acetate. The combined organic phases were washed with water, dried with sodium sulfate, filtered and the solvent removed under reduced pressure. The residue was separated chromatographically by HPLC (gradient: H$_2$O/acetonitrile). 47 mg of N-(5-{1-[2-bromo-6-chloro-4-(1,1,1,2,3,3,3-heptafluoropropan-2-yl)phenyl]-1H-pyrazol-4-yl}-2-chlorobenzyl)-2-cyanoacetamide (Ia-137) were thus obtained.

HPLC-MS[a)]: log P=4.28, mass (m/z)=633 [(M+H)]+

$^1$H-NMR (400 MHz. d$_6$-DMSO): δ=8.795 (0.6); 8.773 (1.4); 8.759 (2.8); 8.746 (1.5); 8.663 (8.8); 8.373 (8.9); 8.350 (0.6); 8.315 (0.4); 8.158 (5.1); 8.115 (4.9); 7.669 (0.4); 7.650 (0.8); 7.633 (2.7); 7.614 (10.9); 7.510 (3.9); 7.488

(3.0); 4.399 (6.1); 4.386 (6.4); 3.795 (16.0); 3.319 (30.3); 2.672 (1.3); 2.502 (211.0); 2.499 (188.3); 2.329 (1.2); 2.074 (1.6); 0.002 (29.6); 0.000 (33.8).

Preparation of tert-butyl (2-bromo-5-{1-[2,6-dichloro-4-(1,1,1,2,3,3,3-heptafluoropropan-2-yl)phenyl]-1H-pyrazol-4-yl}benzyl)carbamate Reaction scheme 20

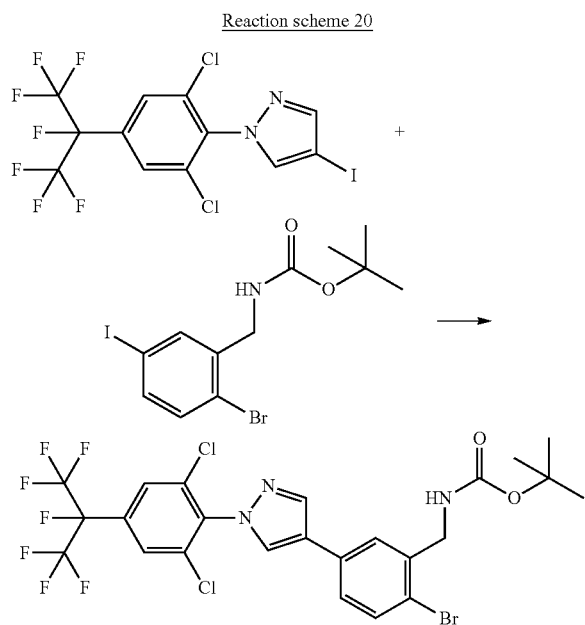

To a solution of 1.50 g (2.96 mmol) of 1-[2,6-dichloro-4-(1,1,1,2,3,3,3-heptafluoropropan-2-yl)phenyl]-4-iodo-1H-pyrazole in THF at −39° C. were added dropwise 2.50 mL of a 1.3 M solution of isopropylmagnesium chloride lithium chloride complex and the reaction solution stirred at −38° C. for 60 minutes. 5.07 mL (3.6 mmol) of a 1.3 M ZnCl₂ solution were then added dropwise, the cooling bath was removed and the reaction solution was stirred at room temperature for 30 minutes. Then, a solution of 1.34 g (3.3 mmol) of tert-butyl (2-bromo-5-iodobenzyl)carbamate, 55 mg (0.24 mmol) of tri-2-furylphosphine and 43 mg (74 µmol) of bis(dibenzylideneacetone)palladium (0) in 3 mL of THF were added and the reaction solution was stirred at room temperature overnight. Saturated ammonium chloride solution was added and the mixture was extracted repeatedly with ethyl acetate. The combined organic phases were dried with sodium sulfate, filtered and the solvent was removed under reduced pressure. The residue was purified chromatographically by MPLC on silica gel (gradient: ethyl acetate/cyclohexane 0:100→20:80). 610 mg of tert-butyl (2-bromo-5-{1-[2,6-dichloro-4-(1,1,1,2,3,3,3-heptafluoropropan-2-yl)phenyl]-1H-pyrazol-4-yl}benzyl)carbamate were thus obtained.

HPLC-MS[a)]: log P=5.93, mass (m/z)=666 [(M+H)]⁺

¹H-NMR (400 MHz. d₆-DMSO): δ=8.618 (1.8); 8.264 (1.4); 8.084 (3.2); 7.641 (1.0); 7.621 (1.3); 7.566 (0.8); 7.505 (0.6); 7.485 (0.5); 7.412 (0.4); 4.213 (1.1); 4.198 (1.1); 3.322 (41.4); 2.671 (0.3); 2.506 (47.9); 2.502 (60.4); 2.498 (44.1); 2.329 (0.3); 1.416 (9.0); 1.398 (16.0); 1.314 (0.35); 1.170 (0.35); 0.008 (2.5); 0.000 (48.6).

Preparation of N-(2-chloro-5-{1-[2,6-dichloro-4-(1,1,1,2,3,3,3-hetafluoropropan-2-yl)phenyl]-1H-pyrazol-4-yl}benzyl)ethanethioamide (Ia-162)

Reaction scheme 21

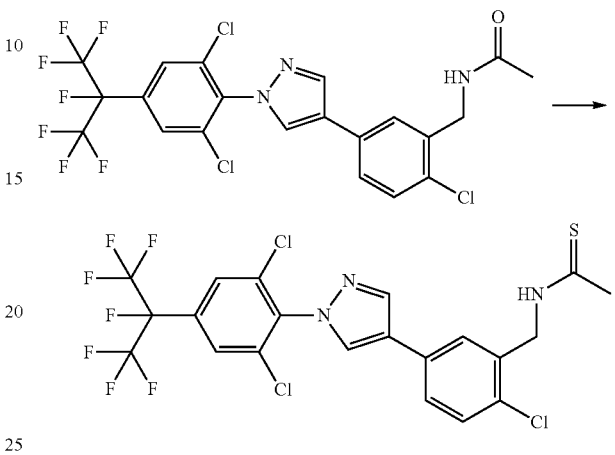

A solution of 100 mg (178 µmol) of N-(2-chloro-5-{1-[2,6-dichloro-4-(1,1,1,2,3,3,3-heptafluoropropan-2-yl)phenyl]-1H-pyrazol-4-yl}benzyl)acetamide and 43 mg (0.11 mmol) of 4-methoxyphenyldithiophosphonic anhydride in 2 mL of THF was heated under reflux for 90 minutes. The reaction mixture was then adsorbed onto silica gel and purified chromatographically by MPLC on silica gel (gradient: ethyl acetate/cyclohexane 0:100→30:70). 68 mg of N-(2-chloro-5-{1-[2,6-dichloro-4-(1,1,1,2,3,3,3-heptafluoropropan-2-yl)phenyl]-1H-pyrazol-4-yl}benzyl)ethanethioamide (Ia-162) were thus obtained.

HPLC-MS[a)]: log P=4.98, mass (m/z)=580 [(M+H)]⁺

¹H-NMR (400 MHz, d₆-DMSO): δ=s. NMR peak list

Preparation of N-(2-chloro-5-{1-[2,6-dichloro-4-(1,1,1,2,3,3,3-heptafluoropropan-2-yl)phenyl]-1H-pyrazol-4-yl}benzyl)-N-methylethanesulfonamide (Ic-03)

Reaction scheme 22

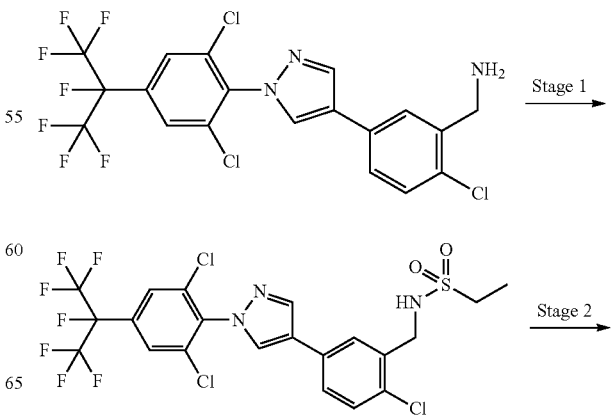

-continued

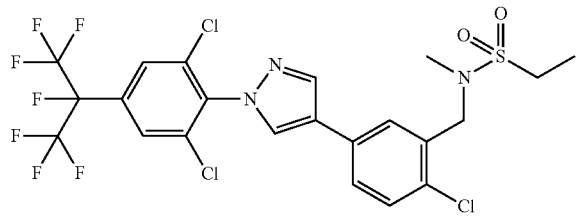

Stage 1: N-(2-Chloro-5-{1-[2,6-dichloro-4-(1,1,1,2,3,3,3-heptafluoropropan-2-yl)phenyl]-1H-pyrazol-4-yl}benzyl)ethanesulfonamid (Ic-02)

To a solution of 80 mg (0.15 mmol) of 1-(2-chloro-5-{1-[2,6-dichloro-4-(1,1,1,2,3,3,3-heptafluoropropan-2-yl)phenyl]-1H-pyrazol-4-yl}phenyl)methanamine and 32 µL (0.23 mmol) of triethylamine in 3 mL of CH$_2$Cl$_2$ at 0° C. were added 17 µL (0.18 mmol) of ethansulfonyl chloride and the mixture was stirred at room temperature overnight. Water was added to the reaction mixture and then extracted repeatedly with CH$_2$Cl$_2$. The combined organic phases were washed with water, dried with sodium sulfate, filtered and the solvent removed under reduced pressure. The residue was separated chromatographically by HPLC (gradient: H$_2$O/acetonitrile). 63 mg of N-(2-chloro-5-{1-[2,6-dichloro-4-(1,1,1,2,3,3,3-heptafluoropropan-2-yl)phenyl]-1H-pyrazol-4-yl}benzyl)ethanesulfonamide (Ic-02) were thus obtained.

HPLC-MS[a)]: log P=4.65, mass (m/z)=612 [(M+H)]$^+$
$^1$H-NMR (400 MHz, d$_6$-DMSO): δ=s. NMR peak list Stage 2: N-(2-Chloro-5-{1-[2,6-dichloro-4-(1,1,1,2,3,3,3-heptafluorpropan-2-yl)phenyl]-1H-pyrazol-4-yl}benzyl)-N-methylethanesulfonamide (Ic-03)

To a solution of 60 mg (90 µmol) of N-(2-chloro-5-{1-[2,6-dichloro-4-(1,1,1,2,3,3,3-heptafluoropropan-2-yl)phenyl]-1H-pyrazol-4-yl}benzyl)ethanesulfonamide in 3 mL of THF at 0° C. were added 9 mg (0.2 mmol) of sodium hydride (55% dispersion in mineral oil). After 30 min at 0° C., 42 mg (0.29 mmol) of iodomethane were added dropwise. The reaction solution was stirred at 0° C. for 1 h and at room temperature for 1 h. Water was subsequently added and the mixture extracted exhaustively with ethyl acetate. The combined organic phases were dried with sodium sulfate, filtered and the solvent was removed under reduced pressure. The residue was separated chromatographically by HPLC (gradient: H$_2$O/acetonitrile). 11 mg of N-(2-chloro-5-{1-[2,6-dichloro-4-(1,1,1,2,3,3,3-heptafluoropropan-2-yl)phenyl]-1H-pyrazol-4-yl}benzyl)-N-methylethanesulfonamide (Ic-03) were thus obtained.

HPLC-MS[a)]: log P=5.21, mass (m/z)=628 [(M+H)]$^+$
$^1$H-NMR (400 MHz, d$_6$-DMSO): δ=s. NMR peak list Preparation of N-(2-chloro-5-{1-[2,6-dichloro-4-(1,1,1,2,3,3,3-heptafluoropropan-2-yl)phenyl]-1H-1,2,3-triazol-4-yl}benzyl)acetamide (I-T7-01)

Reaction scheme 23

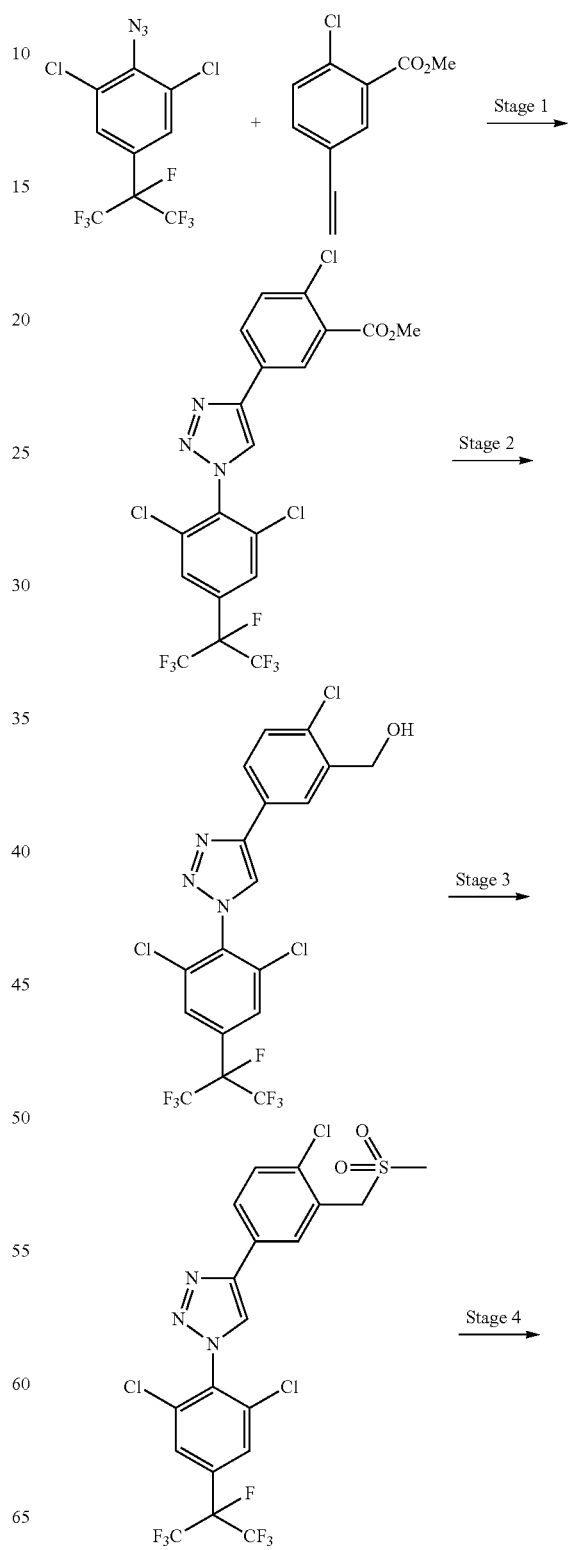

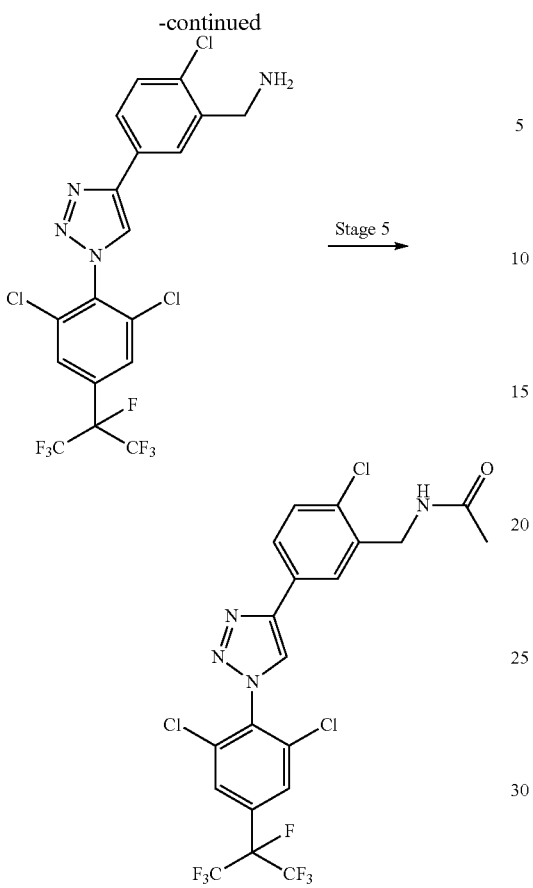

Stage 1: methyl 2-chloro-5-{1-[2,6-dichloro-4-(1,1,2,3,3,3-heptafluoropropan-2-yl)phenyl]-1H-1,2,3-triazol-4-yl}benzoate To a solution of 2-azido-1,3-dichloro-5-(1,1,1,2,3,3,3-heptafluoropropan-2-yl)benzene (1.02 g) and methyl 2-chloro-5-ethynylbenzoate (613 mg) in t-BuOH/H$_2$O 2:1 (3.4 mL) were added CuSO$_4$.7H$_2$O (71.5 mg), sodium ascorbate (56.8 mg) and tris[(1-benzyl-1H-1,2,3-triazol-4-yl)methyl]amine (15.2 mg). The mixture was stirred at room temperature for 5 h. The reaction solution was diluted with EtOAc and filtered. The filtrate was washed with H$_2$O and the aqueous phase extracted with EtOAc. The combined organic phase was dried over MgSO4 and the solvent was removed under reduced pressure. The residue was purified by column chromatography (EtOAc/c-Hex). 812 mg of methyl 2-chloro-5-{1-[2,6-dichloro-4-(1,1,1,2,3,3,3-heptafluoropropan-2-yl)phenyl]-1H-1,2,3-triazol-4-yl}benzoate were obtained.

HPLC-MS$^{a)}$: log P=5.14, mass (m/z)=551 [(M+H)]$^+$
$^1$H-NMR (400 MHz. d$_6$-DMSO): δ=9.24 (s. 1H). 8.38 (d. 1H). 8.21 (s. 2H). 8.11-8.09 (m. 1H). 7.76 (d. 1H). 3.92 (s. 3H)

Stage 2: (2-chloro-5-{1-[2,6-dichloro-4-(1,1,1,2,3,3,3-heptafluoropropan-2-yl)phenyl]-1H-1,2,3-triazol-4-yl}phenyl)methanol To a solution of methyl 2-chloro-5-{1-[2,6-dichloro-4-(1,1,1,2,3,3,3-heptafluoropropan-2-yl)phenyl]-1H-1,2,3-triazol-4-yl}benzoate (1.03 g) in anhydrous toluene at −70° C. was added dropwise DIBAl-H 1M in toluene (9 mL) under an argon atmosphere. After 1 h at −70° C. complete conversion was not achieved. Further DIBAl-H 1M in toluene was added until complete conversion was achieved. The reaction was terminated by addition of aqueous Na—K tartrate solution (20%). Glycerol (0.2 mL/mmol DIBAl-H) was added and the mixture was stirred at room temperature for 1 h. The phases were separated and the aqueous phase was extracted with EtOAc. The combined organic phase was washed with H$_2$O and saturated aqueous NaCl solution and dried over MgSO$_4$. The solvent was removed under reduced pressure. 1.02 g of (2-chloro-5-{1-[2,6-dichloro-4-(1,1,1,2,3,3,3-heptafluoropropan-2-yl)phenyl]-1H-1,2,3-triazol-4-yl}phenyl)methanol were obtained and used without further purification in the following step.

HPLC-MS$^{a)}$: log P=4.27, mass (m/z)=522 [(M+H)]$^+$

Stage 3: 4-{4-chloro-3-[(methylsulfonyl)methyl]phenyl}-1-[2,6-dichloro-4-(1,1,1,2,3,3,3-heptafluoropropan-2-yl)phenyl]-1H-1,2,3-triazole To a solution of (2-chloro-5-{1-[2,6-dichloro-4-(1,1,1,2,3,3,3-heptafluoropropan-2-yl)phenyl]-1H-1,2,3-triazol-4-yl}phenyl)methanol (1.03 g) and N,N-diisopropylamine (1.03 mL) in anhydrous THF at 0° C. was added dropwise methynesulfonyl chloride (0.15 mL). The solution was stirred at room temperature for 1 h. The mixture was diluted with CH$_2$Cl$_2$ and washed with H$_2$O, saturated aqueous NaHCO$_3$ solution and saturated aqueous NaCl solution. The organic phase was dried over MgSO$_4$ and the solvent removed under reduced pressure. 1.13 g of 4-{4-chloro-3-[(methylsulfonyl)methyl]phenyl}-1-[2,6-dichloro-4-(1,1,1,2,3,3,3-heptafluoropropan-2-yl)phenyl]-1H-1,2,3-triazole were obtained and used without further purification in the following step.

HPLC-MS$^{a)}$: log P=4.70, mass (m/z)=600 [(M+H)]$^+$

Stage 4: 1-(2-chloro-5-{1-[2,6-dichloro-4-(1,1,1,2,3,3,3-heptafluoropropan-2-yl)phenyl]-1H-1,2,3-triazol-4-yl}phenyl)methanamine To a mixture of concentrated aqueous ammonia solution (8.8 mL) and ethanol (15 mL) at 0° C. was added dropwise a solution of 4-{4-chloro-3-[(methylsulfonyl)methyl]phenyl}-1-[2,6-dichloro-4-(1,1,1,2,3,3,3-heptafluoropropan-2-yl)phenyl]-1H-1,2,3-triazole (1.13 g) in ethanol. The mixture was stirred at room temperature overnight. IM aqueous sodium hydroxide solution was added to the reaction solution and extracted with CH$_2$Cl$_2$. The organic phase was dried over MgSO$_4$ and the solvent was removed under reduced pressure. 1.00 g of 1-(2-chloro-5-{1-[2,6-dichloro-4-(1,1,1,2,3,3,3-heptafluoropropan-2-yl)phenyl]-1H-1,2,3-triazol-4-yl}phenyl)methanamine was obtained and used without further purification in the following step.

HPLC-MS$^{a)}$: log P=2.21, mass (m/z)=521 [(M+H)]$^+$

Stage 5: N-(2-chloro-5-{1-[2,6-dichloro-4-(1,1,1,2,3,3,3-heptafluoropropan-2-yl)phenyl]-1H-1,2,3-triazol-4-yl}benzyl)acetamide (I-T7-01)

To a solution of 1-(2-chloro-5-{1-[2,6-dichloro-4-(1,1,1,2,3,3,3-heptafluoropropan-2-yl)phenyl]-1H-1,2,3-triazol-4-yl}phenyl)methanamine (150 mg) and triethylamine (0.12 mL) in CH$_2$Cl$_2$ at 0° C. was added dropwise acetyl chloride (23 μL) dissolved in CH$_2$Cl$_2$. The mixture was stirred at room temperature overnight. The solution was diluted with CH$_2$Cl$_2$ and washed with saturated aqueous NaHCO$_3$ solution. The organic phase was dried over MgSO₄ and the solvent was removed under reduced pressure. The residue was separated chromatographically by HPLC (gradient: H₂O/acetonitrile). 24 mg of N-(2-chloro-5-{1-[2,6-dichloro-4-(1,1,1,2,3,3,3-heptafluoropropan-2-yl)phenyl]-1H-1,2,3-triazol-4-yl}benzyl)acetamide (I-T7-01) were obtained.

HPLC-MS$^{a)}$: log P=3.94, mass (m/z)=564 [(M+H)]$^+$ $^1$H-NMR (400 MHz. d$_6$-DMSO): δ=9.16 (s. 1H). 8.47 (t. 1H). 8.21 (s. 2H). 7.88 (d. 1H). 7.83-7.81 (m. 1H). 7.59 (d. 1H). 4.38 (d. 2H). 1.95 (s. 3H).

TABLE 1

(Ia)

$B_1$ is C—$R^6$,
$B_5$ is C—$R^{10}$,
$B_2$, $B_4$, $E_2$, $E_3$ and $A_1$ are CH, $M_1$ is H, $E_1$ is N.

| Example | R⁶ | R⁸ | R¹⁰ | A₁ | A₂ | A₄ | R⁴ | R¹ | M₂ | W | Q | logP$^a$ | Mass [m/z]$^{a,1}$ |
|---|---|---|---|---|---|---|---|---|---|---|---|---|---|
| Ia-01 | Methyl | Heptafluorisopropyl | Methyl | CH | CH | CH | F | H | H | O | Ethyl | 4.19 | 520 |
| Ia-02 | Cl | Heptafluorisopropyl | CHF₂ | CH | CH | CH | H | H | H | O | Methyl | 3.93 | 544 |
| Ia-03 | SMe | Heptafluorisopropyl | Cl | CH | CH | CH | H | H | H | O | Methyl | 3.76 | 540 |
| Ia-04 | Methyl | Heptafluorisopropyl | Methyl | CH | CH | CH | F | H | H | O | Cyclopropyl | 4.38 | 532 |
| Ia-05 | Cl | Heptafluorisopropyl | Cl | CH | CH | CH | Cl | H | H | O | Methyl | 4.13 | 564 |
| Ia-06 | OCF₃ | Heptafluorisopropyl | Cl | CH | CH | CH | F | H | H | O | Methyl | 4.42 | 596 |
| Ia-07 | SMe | Heptafluorisopropyl | Cl | CH | CH | CH | F | H | H | O | Methyl | 3.9 | 558 |
| Ia-08 | Cl | Heptafluorisopropyl | Cl | CH | CH | CH | H | H | H | O | Ethyl | 4.13 | 542 |
| Ia-09 | Cl | Heptafluorisopropyl | Cl | CH | CH | CH | H | H | H | O | Methyl | 3.84 | 528 |
| Ia-10 | SMe | Heptafluorisopropyl | Cl | CH | CH | CH | F | H | H | O | Ethyl | 4.29 | 572 |
| Ia-11 | SO₂Me | Heptafluorisopropyl | Cl | CH | CH | CH | F | H | H | O | Methyl | 3.38 | 590 |
| Ia-12 | SMe | Heptafluorisopropyl | Cl | CH | CH | CH | F | H | H | O | Cyclopropyl | 4.43 | 584 |
| Ia-13 | Methyl | Heptafluorisopropyl | Methyl | CH | CH | CH | F | H | H | O | Methyl | 3.94 | 506 |
| Ia-14 | SO₂Me | Heptafluorisopropyl | Cl | CH | CH | CH | H | H | H | O | Methyl | 3.21 | 572 |
| Ia-15 | Cl | Heptafluorisopropyl | Cl | CH | CH | CH | F | H | H | O | Methyl | 3.93 | 546 |
| Ia-16 | Cl | Heptafluorisopropyl | Cl | CH | CH | CH | Cl | H | H | O | Ethyl | 4.46 | 578 |
| Ia-17 | SOMe | Heptafluorisopropyl | Cl | CH | CH | CH | H | H | H | O | Methyl | 3.04 | 556 |
| Ia-18 | Cl | Heptafluorisopropyl | Cl | CH | N | CH | Cl | H | H | O | Cyclopropyl | 4.08 | 591 |
| Ia-19 | OCF₃ | Heptafluorisopropyl | Cl | CH | CH | CH | F | H | H | O | 2.2.2-Trifluorethyl | 4.77 | 664 |
| Ia-20 | Cl | Heptafluorisopropyl | Cl | CH | CH | CH | Cl | Me | H | O | Methyl | 4.72 | 578 |
| Ia-21 | Cl | Heptafluorisopropyl | Cl | CH | CH | CH | H | H | H | O | 2.2.2-Trifluorethyl | 4.41 | 596 |
| Ia-22 | Cl | Heptafluorisopropyl | Cl | CH | CH | CH | H | Me | H | O | Ethyl | 4.72 | 556 |
| Ia-23 | Cl | Heptafluorisopropyl | CHF₂ | CH | CH | CH | F | H | H | O | Ethyl | 4.27 | 576 |
| Ia-24 | Cl | Heptafluorisopropyl | Cl | CH | CH | CH | Cl | Me | H | O | Cyclopropyl | 5.25 | 602 |
| Ia-25 | Cl | Heptafluorisopropyl | Cl | CH | CH | CH | Cl | H | H | O | Cyclopropyl | 4.8 | 588 |
| Ia-26 | OCF₃ | Heptafluorisopropyl | Cl | CH | CH | CH | F | H | H | O | Ethyl | 4.54 | 610 |
| Ia-27 | OCF₃ | Heptafluorisopropyl | Cl | CH | CH | CH | F | Me | H | O | Ethyl | 5.08 | 624 |
| Ia-28 | Methyl | Heptafluorisopropyl | Methyl | CH | CH | CH | H | H | H | O | Ethyl | 4.12 | 5002 |
| Ia-29 | CF₃ | Heptafluorisopropyl | Cl | CH | CH | CH | Cl | H | H | O | Ethyl | 4.66 | 610 |
| Ia-30 | Cl | Heptafluorisopropyl | Cl | CH | CH | CH | F | H | H | O | Ethyl | 4.25 | 560 |
| Ia-31 | OCF₃ | Heptafluorisopropyl | Cl | CH | CH | CH | F | Cyclopropylcarbonyl | H | O | Cyclopropyl | 5.86 | 690 |
| Ia-32 | Cl | Heptafluorisopropyl | Cl | CH | CH | CH | Cl | Methyl | H | O | Ethyl | 5.19 | 592 |
| Ia-33 | SOMe | Heptafluorisopropyl | Cl | CH | CH | CH | F | H | H | O | Methyl | 3.21 | 574 |
| Ia-34 | Cl | Heptafluorisopropyl | CHF₂ | CH | CH | CH | F | H | H | O | Methyl | 3.99 | 562 |

TABLE 1-continued

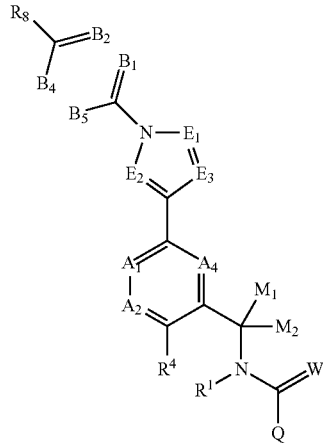

(Ia)

$B_1$ is C—$R^6$,
$B_5$ is C—$R^{10}$,
$B_2$, $B_4$, $E_2$, $E_3$ and $A_1$ are CH, $M_1$ is H, $E_1$ is N.

| Example | $R^6$ | $R^8$ | $R^{10}$ | $A_1$ | $A_2$ | $A_4$ | $R^4$ | $R^1$ | $M_2$ | W | Q | logP$^a$ | Mass [m/z]$^{a,1}$ |
|---|---|---|---|---|---|---|---|---|---|---|---|---|---|
| Ia-35 | Cl | Heptafluorisopropyl | Cl | CH | CH | CH | Cl | H | H | O | 2,2,2-Trifluorethyl | 4.67 | 632 |
| Ia-36 | Cl | Heptafluorisopropyl | Cl | CH | CH | CH | H | H | Methyl | O | Methyl | 3.99 | 542 |
| Ia-37 | Methyl | Heptafluorisopropyl | Methyl | CH | CH | CH | H | H | H | O | Methyl | 3.81 | 488 |
| Ia-38 | OCF$_3$ | Heptafluorisopropyl | Cl | CH | CH | CH | H | H | H | O | Methyl | 4.04 | 578 |
| Ia-39 | CHF$_2$ | Heptafluorisopropyl | Cl | CH | CH | CH | H | H | H | O | Ethyl | 4.18 | 558 |
| Ia-40 | OCF$_3$ | Heptafluorisopropyl | Cl | CH | CH | CH | F | H | H | O | Cyclopropyl | 4.69 | 622 |
| Ia-41 | Cl | Heptafluorisopropyl | Cl | CH | CH | CH | H | H | H | O | Cyclopropyl | 4.27 | 554 |
| Ia-42 | Cl | Heptafluorisopropyl | Cl | CH | CH | CH | H | Methyl | H | O | Methyl | 4.28 | 542 |
| Ia-43 | SOMe | Heptafluorisopropyl | Cl | CH | CH | CH | F | H | H | O | Cyclopropyl | 3.68 | 600 |
| Ia-44 | SO$_2$Me | Heptafluorisopropyl | Cl | CH | CH | CH | F | H | H | O | Cyclopropyl | 3.59 | 616 |
| Ia-45 | SOMe | Heptafluorisopropyl | Cl | CH | CH | CH | F | H | H | O | Ethyl | 3.52 | 588 |
| Ia-46 | SO$_2$Me | Heptafluorisopropyl | Cl | CH | CH | CH | F | H | H | O | Ethyl | 3.65 | 604 |
| Ia-47 | Cl | Heptafluorisopropyl | Cl | CH | CH | CH | H | H | Me | O | Ethyl | 4.32 | 556 |
| Ia-48 | Cl | Heptafluorisopropyl | Cl | CH | CH | CH | H | H | Me | O | Me | 3.99 | 542 |
| Ia-49 | Cl | Heptafluorisopropyl | Cl | CH | CH | CH | F | H | Me | O | Me | 4.13 | 560 |
| Ia-50 | Cl | Heptafluorisopropyl | Cl | CH | CH | CH | F | H | Me | O | Ethyl | 4.41 | 574 |
| Ia-51 | OCHF$_2$ | Heptafluorisopropyl | Cl | CH | CH | CH | Cl | H | H | O | Ethyl | 4.32 | 608 |
| Ia-52 | OCHF$_2$ | Heptafluorisopropyl | Cl | CH | CH | CH | Cl | H | H | O | Cyclopropyl | 4.46 | 620 |
| Ia-53 | OCHF$_2$ | Heptafluorisopropyl | Cl | CH | CH | CH | Cl | H | H | O | Me | 4.08 | 594 |
| Ia-54 | CF$_3$ | Heptafluorisopropyl | Cl | CH | CH | CH | Cl | H | H | O | Cyclopropyl | 4.67 | 622 |
| Ia-55 | CF$_3$ | Heptafluorisopropyl | Cl | CH | CH | CH | Cl | H | H | O | Me | 4.23 | 596 |
| Ia-56 | OCF$_3$ | Heptafluorisopropyl | Cl | CH | CH | CH | Cl | H | H | O | Cyclopropyl | 4.91 | 638 |
| Ia-57 | OCF$_3$ | Heptafluorisopropyl | Cl | CH | CH | CH | Cl | H | H | O | Me | 612 | 4.41 |
| Ia-58 | CHF$_2$ | Heptafluorisopropyl | Cl | CH | CH | CH | F | H | H | O | Cyclopropyl | 4.37 | 588 |
| Ia-59 | CHF$_2$ | Heptafluorisopropyl | Cl | CH | CH | CH | F | H | H | O | n-Butyl | 4.8 | 604 |
| Ia-60 | CHF$_2$ | Heptafluorisopropyl | Cl | CH | CH | CH | F | H | H | O | i-Propyl | 4.5 | 590 |
| Ia-61 | CHF$_2$ | Heptafluorisopropyl | Cl | CH | CH | CH | F | H | H | O | i-Butyl | 4.7 | 604 |
| Ia-62 | CHF$_2$ | Heptafluorisopropyl | Cl | CH | CH | CH | F | H | H | O | t-Butyl | 4.99 | 604 |
| Ia-63 | OCF$_3$ | Heptafluorisopropyl | Cl | CH | CH | CH | F | Me | H | O | Me | 4.75 | 610 |
| Ia-64 | Cl | Heptafluorisopropyl | Cl | CH | CH | CH | F | Me | H | O | Me | 4.46 | 560 |
| Ia-65 | Me | Heptafluorisopropyl | Cl | CH | CH | CH | F | H | H | O | Me | 3.94 | 526 |
| Ia-66 | Me | Heptafluorisopropyl | Cl | CH | CH | CH | F | H | H | O | Ethyl | 4.23 | 540 |
| Ia-67 | Me | Heptafluorisopropyl | Cl | CH | CH | CH | F | H | H | O | Cyclopropyl | 4.37 | 552 |
| Ia-68 | Me | Heptafluorisopropyl | Cl | CH | CH | CH | H | H | H | O | Me | 3.81 | 508 |
| Ia-69 | Me | Heptafluorisopropyl | Cl | CH | CH | CH | H | H | H | O | Ethyl | 4.13 | 522 |
| Ia-70 | Me | Heptafluorisopropyl | Cl | CH | CH | CH | H | H | H | O | Cyclopropyl | 4.32 | 534 |
| Ia-71 | Cl | Heptafluorisopropyl | Cl | CH | CH | CH | F | Me | H | O | Ethyl | 4.92 | 574 |
| Ia-72 | Cl | Heptafluorisopropyl | Cl | CH | CH | CH | CF$_3$ | H | H | O | Ethyl | 4.72 | 610 |
| Ia-73 | Cl | Heptafluorisopropyl | Cl | CH | N | CH | Cl | Me | H | O | Me | 3.99 | 579 |
| Ia-74 | Cl | Heptafluorisopropyl | Cl | CH | CH | CH | CF$_3$ | H | H | O | Me | 4.41 | 596 |
| Ia-75 | Me | Heptafluorisopropyl | Cl | CH | CH | CH | Me | H | H | O | Me | 4.13 | 522 |
| Ia-76 | Me | Heptafluorisopropyl | Cl | CH | CH | CH | Me | H | H | O | Ethyl | 4.44 | 536 |
| Ia-77 | Cl | Heptafluorisopropyl | Cl | CH | CH | CH | CF$_3$ | Me | H | O | Me | 4.94 | 610 |
| Ia-78 | Cl | Heptafluorisopropyl | Cl | CH | CH | CH | CF$_3$ | Me | H | O | Ethyl | 5.38 | 624 |
| Ia-79 | CF$_3$ | Heptafluorisopropyl | Cl | CH | CH | CH | Me | H | H | O | Me | 4.17 | 576 |

TABLE 1-continued

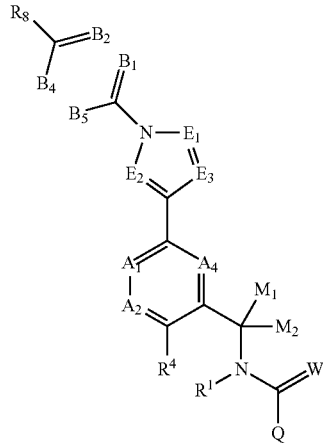

(Ia)

$B_1$ is $C-R^6$, $B_5$ is $C-R^{10}$, $B_2$, $B_4$, $E_2$, $E_3$ and $A_1$ are CH, $M_1$ is H, $E_1$ is N.

| Example | $R^6$ | $R^8$ | $R^{10}$ | $A_1$ | $A_2$ | $A_4$ | $R^4$ | $R^1$ | $M_2$ | W | Q | logP$^a$ | Mass [m/z]$^{a,1}$ |
|---|---|---|---|---|---|---|---|---|---|---|---|---|---|
| Ia-80 | CF$_3$ | Heptafluorisopropyl | Cl | CH | CH | CH | Me | H | H | O | Ethyl | 4.46 | 590 |
| Ia-81 | Cl | Heptafluorisopropyl | Cl | CH | CH | CH | Me | H | H | O | Ethyl | 4.37 | 556 |
| Ia-82 | CF$_3$ | Heptafluorisopropyl | Cl | CH | CH | CH | F | H | H | O | Me | 4.02 | 580 |
| Ia-83 | CF$_3$ | Heptafluorisopropyl | Cl | CH | CH | CH | F | H | H | O | Ethyl | 4.28 | 594 |
| Ia-84 | Me | Heptafluorisopropyl | Cl | CH | CH | CH | Cl | H | H | O | Me | 4.27 | 542 |
| Ia-85 | OCF$_3$ | Heptafluorisopropyl | Cl | CH | CH | CH | Cl | Me | H | O | Me | 4.92 | 626 |
| Ia-86 | OCF$_3$ | Heptafluorisopropyl | Cl | CH | CH | CH | Cl | H | H | O | Ethyl | 4.88 | 626 |
| Ia-87 | OCF$_3$ | Heptafluorisopropyl | Cl | CH | CH | CH | Cl | Me | H | O | Ethyl | 5.46 | 640 |
| Ia-88 | Cl | SO$_2$CF$_3$ | Cl | CH | CH | CH | Cl | H | H | O | Me | 3.41 | 528 |
| Ia-89 | Br | Heptafluorisopropyl | Cl | CH | CH | CH | Cl | H | H | O | Ethyl | 4.51 | 622 |
| Ia-90 | Cl | Heptafluorisopropyl | Cl | CH | CH | CH | Me | H | H | O | Me | 4.08 | 542 |
| Ia-91 | Br | Heptafluorisopropyl | Cl | CH | CH | CH | Cl | H | H | O | Me | 4.26 | 608 |
| Ia-92 | Br | Heptafluorisopropyl | F | CH | CH | CH | Cl | H | H | O | Me | 4.10 | 591 |
| Ia-93 | Me | Heptafluorisopropyl | Me | CH | CH | CH | Cl | H | H | O | Ethyl | 4.51 | 536 |
| Ia-94 | Br | Heptafluorisopropyl | F | CH | CH | CH | Cl | H | H | O | Ethyl | 4.42 | 606 |
| Ia-95 | Me | Heptafluorisopropyl | Me | CH | CH | CH | Cl | H | H | O | Me | 4.18 | 522 |
| Ia-96 | CN | Heptafluorisopropyl | Cl | CH | CH | CH | Me | H | H | O | Me | 3.67 | 533 |
| Ia-97 | CN | Heptafluorisopropyl | Cl | CH | CH | CH | H | H | H | O | Ethyl | 3.71 | 533 |
| Ia-98 | CN | Heptafluorisopropyl | Cl | CH | CH | CH | H | H | H | O | Cyclopropyl | 3.85 | 545 |
| Ia-99 | Br | Heptafluorisopropyl | Cl | CH | CH | CH | Cl | Me | H | O | Me | 4.72 | 622 |
| Ia-100 | Br | Heptafluorisopropyl | F | CH | CH | CH | Cl | Me | H | O | Me | 4.51 | 606 |
| Ia-101 | CN | Heptafluorisopropyl | Cl | CH | CH | CH | Me | H | H | O | Ethyl | 3.95 | 547 |
| Ia-102 | CN | Heptafluorisopropyl | Cl | CH | CH | CH | H | H | H | O | Me | 3.41 | 519 |
| Ia-103 | CN | Heptafluorisopropyl | Cl | CH | CH | CH | F | H | H | O | Ethyl | 3.76 | 551 |
| Ia-104 | CN | Heptafluorisopropyl | Cl | CH | CH | CH | Cl | H | H | O | Me | 3.72 | 553 |
| Ia-105 | CN | Heptafluorisopropyl | Cl | CH | CH | CH | F | H | H | O | Me | 3.5 | 537 |
| Ia-106 | CHF$_2$ | Heptafluorisopropyl | Cl | CH | CH | CH | Cl | H | H | O | Me | 4.32 | 578 |
| Ia-107 | CN | Heptafluorisopropyl | Cl | CH | CH | CH | F | H | H | O | Cyclopropyl | 3.9 | 563 |
| Ia-108 | Cl | Heptafluorisopropyl | Cl | CH | CH | CH | Cl | Acetyl | H | O | Me | 5.14 | 606 |
| Ia-109 | Cl | Heptafluorisopropyl | Cl | CH | CH | CH | Cl | Ethyl | H | O | Me | 5.03 | 592 |
| Ia-110 | Cl | Heptafluorisopropyl | Cl | CF | CH | CH | Cl | Me | H | O | Me | 5.03 | 596 |
| Ia-111 | Cl | Heptafluorisopropyl | Cl | CF | CH | CH | Cl | H | H | O | Ethyl | 4.87 | 596 |
| Ia-112 | Cl | Heptafluorisopropyl | Cl | CH | CH | CH | Cl | Propyl | H | O | Me | 5.40 | 604 |
| Ia-113 | Cl | Heptafluorisopropyl | Cl | CH | CH | CH | Cl | Allyl | H | O | Me | 5.21 | 604 |
| Ia-114 | CN | Heptafluorisopropyl | Cl | CH | CH | CH | Cl | H | H | O | Ethyl | 4.08 | 567 |
| Ia-115 | CHF$_2$ | Heptafluorisopropyl | Cl | CH | CH | CH | Cl | H | H | O | Ethyl | 4.56 | 592 |
| Ia-116 | Cl | Heptafluorisopropyl | Cl | CH | CH | CH | Cl | Cyclopropylmethyl | H | O | Me | 5.46 | 618 |
| Ia-117 | Cl | Heptafluorisopropyl | Cl | CH | CH | CH | Cl | Ethoxymethyl | H | O | Me | 5.27 | 620 |
| Ia-118 | Cl | Heptafluorisopropyl | Cl | CH | CH | CH | Cl | H | H | O | Phenyl | 5.08 | 626 |
| Ia-119 | Cl | Heptafluorisopropyl | Cl | CH | CH | CH | Cl | H | H | O | CHF$_2$ | 4.67 | 600 |
| Ia-120 | Cl | Heptafluorisopropyl | Cl | CH | CH | CH | Cl | H | H | O | CF$_3$ | 5.08 | 618 |
| Ia-121 | Cl | 1-CF$_3$-Cyclopropyl | Cl | CH | CH | CH | Me | H | H | O | Ethyl | 3.89 | 496 |
| Ia-122 | Cl | 1-CF$_3$-Cyclopropyl | Cl | CH | CH | CH | Me | H | H | O | Me | 3.53 | 482 |
| Ia-123 | Cl | 1-CF$_3$-Cyclopropyl | Cl | CH | CH | CH | F | H | H | O | Ethyl | 3.79 | 500 |
| Ia-124 | Cl | 1-CF$_3$-Cyclopropyl | Cl | CH | CH | CH | F | H | H | O | Me | 3.46 | 486 |
| Ia-125 | Cl | 1-CF$_3$-Cyclopropyl | Cl | CH | CH | CH | F | Me | H | O | Me | 3.88 | 500 |

TABLE 1-continued

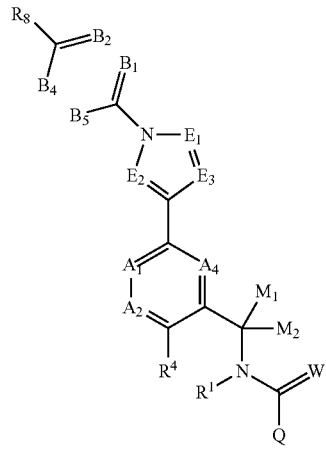

(Ia)

$B_1$ is C—$R^6$,
$B_5$ is C—$R^{10}$,
$B_2$, $B_4$, $E_2$, $E_3$ and $A_1$ are CH, $M_1$ is H, $E_1$ is N.

| Example | $R^6$ | $R^8$ | $R^{10}$ | $A_1$ | $A_2$ | $A_4$ | $R^4$ | $R^1$ | $M_2$ | W | Q | logP$^a$ | Mass [m/z]$^{a,1}$ |
|---|---|---|---|---|---|---|---|---|---|---|---|---|---|
| Ia-126 | Cl | Heptafluorisopropyl | Cl | CH | CH | CH | Cl | H | H | O | 4-Pyridyl | 4.23 | 627 |
| Ia-127 | Cl | 1-CF$_3$-Cyclopropyl | Cl | CH | CH | CH | Cl | H | H | O | Me | 3.76 | 502 |
| Ia-128 | Cl | 1-CF$_3$-Cyclopropyl | Cl | CH | CH | CH | Cl | H | H | O | Ethyl | 4.07 | 516 |
| Ia-129 | Cl | 1-CF$_3$-Cyclopropyl | Cl | CH | CH | CH | Cl | Me | H | O | Me | 4.24 | 516 |
| Ia-130 | Cl | Heptafluorisopropyl | Cl | CH | N | CH | Cl | H | H | O | Me | 3.61 | 563 |
| Ia-131 | OCF$_3$ | Heptafluorisopropyl | Cl | CH | N | CH | Cl | H | H | O | Me | 3.92 | 613 |
| Ia-132 | Cl | Heptafluorisopropyl | Cl | CH | N | CH | Cl | H | H | O | Ethyl | 3.85 | 577 |
| Ia-133 | OCF$_3$ | Heptafluorisopropyl | Cl | CH | N | CH | Cl | H | H | O | Ethyl | 4.23 | 627 |
| Ia-134 | Cl | Heptafluorisopropyl | Cl | CH | N | CH | Cl | Me | H | O | Ethyl | 4.45 | 591 |
| Ia-135 | OCF$_3$ | Heptafluorisopropyl | Cl | CH | N | CH | Cl | Me | H | O | Ethyl | 4.75 | 641 |
| Ia-136 | OCF$_3$ | Heptafluorisopropyl | Cl | CH | N | CH | Cl | Me | H | O | Me | 4.33 | 627 |
| Ia-137 | Br | Heptafluorisopropyl | Cl | CH | CH | CH | Cl | H | H | O | CH$_2$CN | 4.33 | 633 |
| Ia-138 | CF$_3$ | Heptafluorisopropyl | Cl | CH | N | CH | Cl | H | H | O | Ethyl | 3.94 | 611 |
| Ia-139 | CF$_3$ | Heptafluorisopropyl | Cl | CH | N | CH | Cl | H | H | O | Me | 3.73 | 597 |
| Ia-140 | Cl | Heptafluorisopropyl | Cl | CH | CH | COMe | H | H | H | O | Me | 3.95 | 558 |
| Ia-141 | CHF$_2$ | Heptafluorisopropyl | Cl | CH | CH | CF | F | H | H | O | Ethyl | 4.44 | 594 |
| Ia-142 | CHF$_2$ | Heptafluorisopropyl | Cl | CH | CH | CF | F | H | H | O | Me | 4.13 | 580 |
| Ia-143 | CHF$_2$ | Heptafluorisopropyl | Cl | CH | CH | CF | H | H | H | O | Ethyl | 4.39 | 576 |
| Ia-144 | CHF$_2$ | Heptafluorisopropyl | Cl | CH | CH | CF | H | H | H | O | Me | 4.07 | 562 |
| Ia-145 | CHF$_2$ | Heptafluorisopropyl | Cl | CH | N | CH | Cl | H | H | O | Me | 3.72 | 579 |
| Ia-146 | CF$_3$ | Heptafluorisopropyl | Cl | CH | CH | CF | F | H | H | O | Ethyl | 4.46 | 612 |
| Ia-147 | CF$_3$ | Heptafluorisopropyl | Cl | CH | CH | CF | F | H | H | O | Me | 4.15 | 598 |
| Ia-148 | Cl | Heptafluorisopropyl | Cl | CH | CH | CF | F | H | H | O | Ethyl | 4.32 | 578 |
| Ia-149 | Cl | Heptafluorisopropyl | Cl | CH | CH | CF | F | H | H | O | Me | 3.99 | 564 |
| Ia-150 | CF$_3$ | Heptafluorisopropyl | Cl | CH | CH | CF | H | H | H | O | Ethyl | 4.32 | 594 |
| Ia-151 | CF$_3$ | Heptafluorisopropyl | Cl | CH | CH | CF | H | H | H | O | Me | 3.99 | 580 |
| Ia-152 | Cl | Heptafluorisopropyl | Cl | CH | CH | CF | H | H | H | O | Ethyl | 4.27 | 560 |
| Ia-153 | Cl | Heptafluorisopropyl | Cl | CH | CH | CF | H | H | H | O | Me | 3.98 | 546 |
| Ia-154 | CHF$_2$ | Heptafluorisopropyl | Cl | CH | N | CH | Cl | H | H | O | Ethyl | 3.99 | 593 |
| Ia-155 | OCHF$_2$ | Heptafluorisopropyl | Cl | CH | CH | CF | H | H | H | O | Me | 3.85 | 578 |
| Ia-156 | OCHF$_2$ | Heptafluorisopropyl | Cl | CH | N | CH | Cl | H | H | O | Me | 3.59 | 595 |
| Ia-157 | OCHF$_2$ | Heptafluorisopropyl | Cl | CH | CH | CF | F | H | H | O | Ethyl | 4.23 | 610 |
| Ia-158 | OCHF$_2$ | Heptafluorisopropyl | Cl | CH | CH | CF | F | H | H | O | Me | 3.94 | 596 |
| Ia-159 | OCHF$_2$ | Heptafluorisopropyl | Cl | CH | CH | CF | H | H | H | O | Ethyl | 4.17 | 592 |
| Ia-160 | OCHF$_2$ | Heptafluorisopropyl | Cl | CH | N | CH | Cl | H | H | O | Ethyl | 3.87 | 609 |
| Ia-161 | CF$_3$ | Heptafluorisopropyl | Cl | CH | CH | COMe | H | H | H | O | Me | 3.99 | 592 |
| Ia-162 | Cl | Heptafluorisopropyl | Cl | CH | CH | CH | Cl | H | H | S | Me | 4.98 | 580 |
| Ia-163 | Cl | Heptafluorisopropyl | Cl | CH | CH | CH | Cl | Me | H | S | Me | 5.36 | 594 |
| Ia-164 | Cl | Heptafluorisopropyl | Cl | CH | CH | CH | Br | H | H | O | Me | 4.23 | 608 |
| Ia-165 | Cl | Heptafluorisopropyl | Cl | CH | CH | CH | Br | Me | H | O | Me | 4.78 | 622 |
| Ia-166 | Cl | Heptafluorisopropyl | Cl | CH | CH | CH | Br | H | H | O | Ethyl | 4.57 | 622 |
| Ia-167 | Cl | Heptafluorisopropyl | Cl | CH | CH | CH | Br | Me | H | O | Ethyl | 5.25 | 636 |

Me = Methyl

TABLE 2

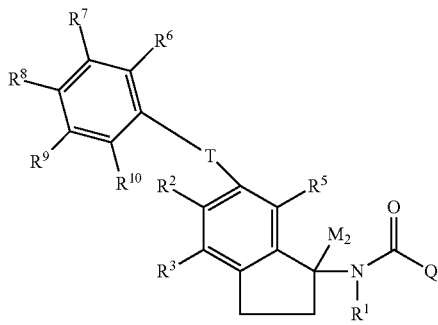

(I-Tc)

$R^8$ is heptafluoroisopropyl,
$R^2$, $R^3$, $R^5$, $R^7$ and $R^9$ are H.
T is T3 with $R^{11}$ = H

| Example | $R^6$ | $R^{10}$ | $R^1$ | $M_2$ | Q | logP$^a$ | Mass [m/z]$^{a,1}$ |
|---|---|---|---|---|---|---|---|
| I-Tc-01 | OCF$_3$ | Cl | H | H | Ethyl | 4.84 | 618 |
| I-Tc-02 | CF$_3$ | Cl | H | H | Ethyl | 4.63 | 602 |
| I-Tc-03 | OCHF$_2$ | Cl | H | H | Ethyl | 4.35 | 600 |

TABLE 3

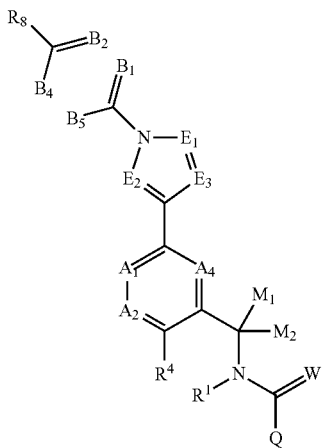

(I-T2)

$B_1$ is C—$R^6$,
$B_5$ is C—$R^{10}$, $R^8$ is heptafluoroisopropyl,
$B_2$, $B_4$, $E_1$, $E_2$, $A_1$, $A_2$ and $A_4$ are CH,
$M_1$ and $M_2$ are H, $E_3$ is N, W is O.

| Example | $R^6$ | $R^{10}$ | $R^4$ | $R^1$ | Q | logP$^a$ | Mass [m/z]$^{a,1}$ |
|---|---|---|---|---|---|---|---|
| I-T2-01 | Cl | Cl | F | H | Me | 3.59 | 546 |
| I-T2-02 | Cl | Cl | Me | H | Me | 3.59 | 542 |
| I-T2-03 | Cl | Cl | F | H | Ethyl | 3.83 | 560 |
| I-T2-04 | Cl | Cl | F | H | Cyclopropyl | 4.03 | 572 |
| I-T2-05 | Cl | Cl | Me | H | Ethyl | 3.89 | 556 |

TABLE 4

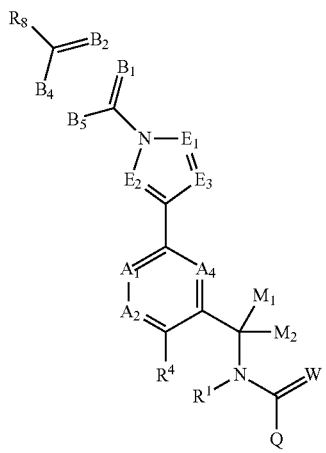

(I-T7)

$B_1$ is C—$R^6$,
$B_5$ is C—$R^{10}$, $R^8$ is heptafluoroisopropyl,
$B_2$, $B_4$, $E_2$, $A_1$, $A_2$ and $A_4$ are CH,
$M_1$ and $M_2$ are H, $E_1$ and $E_3$ are N, W is O.

| Example | $R^6$ | $R^{10}$ | $R^4$ | $R^1$ | Q | logP$^a$ | Mass [m/z]$^{a,1}$ |
|---|---|---|---|---|---|---|---|
| I-T7-01 | Cl | Cl | Cl | H | Me | 3.94 | 563 |
| I-T7-02 | Cl | Cl | Cl | H | Ethyl | 4.23 | 577 |
| I-T7-03 | Cl | Cl | Cl | H | Cyclopropyl | 4.37 | 589 |

TABLE 5

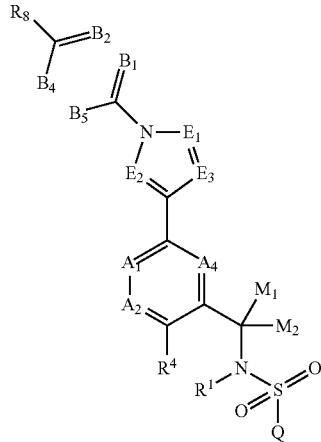

(Ic)

$B_1$ is C—$R^6$,
$B_5$ is C—$R^{10}$, $R^8$ is heptafluoroisopropyl,
$B_2$, $B_4$, $E_2$, $E_3$, $A_1$, $A_2$ and $A_4$ are CH,
$M_1$ and $M_2$ are H, $E_1$ is N.

| Example | $R^6$ | $R^{10}$ | $R^4$ | $R^1$ | Q | logP$^a$ | Mass [m/z]$^{a,1}$ |
|---|---|---|---|---|---|---|---|
| Ic-01 | Cl | Cl | Cl | H | Me | 4.43 | 598 |
| Ic-02 | Cl | Cl | Cl | H | Ethyl | 4.65 | 614 |
| Ic-03 | Cl | Cl | Cl | Me | Ethyl | 5.21 | 628 |

TABLE 5-continued

| Ic-04 | Cl | Cl | Cl | Me | Me | 4.91 | 614 |
| Ic-05 | Cl | Cl | Cl | H | Phenyl | 5.17 | 662 |

[1] unless stated otherwise, the stated mass is the peak of the isotope pattern of the [M+H]$^+$ ion of the highest intensity.
[2] the stated mass is the peak of the isotope pattern of the [M−H]$^-$ ion with the highest intensity.[a] Note regarding the determination of the log P values and mass detection: The determination of the given log P values was carried out in accordance with EEC Directive 79/831 Annex V.A8 by HPLC (High Performance Liquid Chromatography) on a reversed-phase column (C18). Agilent 1100 LC system; 50*4.6 Zorbax Eclipse Plus C18 1.8 micron; mobile phase A: acetonitrile (0.1% formic acid); mobile phase B: water (0.09% formic acid); linear gradient from 10% acetonitrile to 95% acetonitrile in 4.25 min, then 95% acetonitrile for a further 1.25 min; oven temperature 55° C.; flow rate: 2.0 ml/min. Mass detection is effected by means of an Agilend MSD system.

NMR Data of Selected Examples
NMR Peak List Method

The $^1$H NMR data of selected examples are stated in the form of $^1$H NMR peak lists. For each signal peak, first the δ value in ppm and then the signal intensity in round brackets are listed. The pairs of δ value—signal intensity numbers for different signal peaks are listed with separation from one another by semicolons.

The peak list for one example therefore takes the form of:

δ$_1$(intensity$_1$);δ$_2$(intensity$_2$); . . . ;δ$_i$(intensity$_i$); . . . ;δ$_n$(intensity$_n$)

The intensity of sharp signals correlates with the height of the signals in a printed example of an NMR spectrum in cm and shows the true ratios of the signal intensities. In the case of broad signals, several peaks or the middle of the signal and the relative intensity thereof may be shown in comparison to the most intense signal in the spectrum.

For calibration of the chemical shift of $^1$H NMR spectra, we use tetramethylsilane and/or the chemical shift of the solvent, particularly in the case of spectra which are measured in DMSO. Therefore, the tetramethylsilane peak may but need not occur in NMR peak lists.

The lists of the $^1$H NMR peaks are similar to the conventional $^1$H NMR printouts and thus usually contain all peaks listed in a conventional NMR interpretation.

In addition, like conventional $^1$H NMR printouts, they may show solvent signals, signals of stereoisomers of the target compounds which are likewise provided by the invention, and/or peaks of impurities.

In the reporting of compound signals within the delta range of solvents and/or water, our lists of $^1$H NMR peaks show the standard solvent peaks, for example peaks of DMSO in DMSO-D$_6$ and the peak of water, which usually have a high intensity on average.

The peaks of stereoisomers of the target compounds and/or peaks of impurities usually have a lower intensity on average than the peaks of the target compounds (for example with a purity of >90%).

Such stereoisomers and/or impurities may be typical of the particular preparation process. Their peaks can thus help in identifying reproduction of our preparation process with reference to "by-product fingerprints".

An expert calculating the peaks of the target compounds by known methods (MestreC, ACD simulation, but also with empirically evaluated expected values) can, if required, isolate the peaks of the target compounds, optionally using additional intensity filters. This isolation would be similar to the relevant peak picking in conventional 1H NMR interpretation.

Further details of 1H NMR peak lists can be found in the Research Disclosure Database Number 564025.

Example Ia-01: $^1$H-NMR(400.0 MHz, CD$_3$CN): δ = 8.049(2.7); 8.044(6.0); 8.043(5.5); 7.979(2.8); 7.975(6.4); 7.973(5.7); 7.586(0.4); 7.572(2.1); 7.567 (2.0); 7.555(2.3); 7.549(2.6); 7.531(9.4); 7.516(1.5); 7.510(1.5); 7.503(0.9); 7.156(0.8); 7.150(2.0); 7.129(2.5); 7.125(2.1); 7.109(0.7); 7.104(1.7); 6.738(0.9); 5.453(1.6); 5.447(6.3); 4.411(5.1); 4.396(4.7); 2.235(0.9); 2.229(2.2); 2.216(2.4); 2.210(6.4); 2.197(2.7); 2.191(6.8); 2.172(6.5); 2.164 (26.6); 2.148(174.3); 2.120(18.6); 2.115(40.0); 2.107(2.9); 2.101(1.2); 2.095(0.6); 1.971(3.7); 1.964(13.8); 1.958(40.1); 1.952(112.4); 1.946(175.7); 1.940(202.0); 1.934(130.9); 1.927(59.8); 1.915(1.1); 1.781(0.6); 1.774(1.0); 1.768(1.2); 1.762(0.8); 1.756(0.4); 1.443(1.4); 1.437(3.3); 1.272(0.7); 1.222 (0.4); 1.204(0.7); 1.186(0.4); 1.105(2.5); 1.099(8.1); 1.092(1.3); 1.086(4.8); 1.080(16.0); 1.074(1.0); 1.067(2.4); 1.061(7.3); 0.152(0.4); 0.146(1.1); 0.027(0.5); 0.006(78.2); 0.000(287.3); −0.009(9.9); −0.013(1.4); −0.0136(1.3); −0.0144(1.2); −0.015(1.1); −0.016(1.0); −0.0166(0.9); −0.0173(0.8); −0.018(0.7); −0.019(0.7); −0.0195(0.7); −0.0203(0.6); −0.021(0.6); −0.022(0.5); −0.0225(0.5); −0.0232(0.4); −0.024(0.4); −0.0247(0.4); −0.0254(0.4); −0.026(0.4); −0.027(0.4); −0.0276(0.4); −0.0283(0.3); −0.029(0.3); −0.144(0.4); −0.150(1.1)

Example Ia-02: $^1$H-NMR(400.0 MHz, d$_6$-DMSO): δ = 8.879(1.0); 8.662(4.5); 8.361(1.9); 8.345(5.6); 8.323(2.5); 8.314(1.7); 8.071(1.0); 7.976(0.7); 7.956(2.3); 7.601(0.8); 7.568(1.4); 7.550(4.6); 7.404(0.3); 7.388(1.1); 7.368(1.8); 7.349(0.9); 7.182(0.5); 7.170(1.7); 7.150(1.3); 7.039(0.9); 6.905 (2.1); 6.771(1.0); 4.305(1.1); 4.293(4.0); 4.279(3.4); 3.317(308.1); 2.675(2.7); 2.670(3.7); 2.666(2.8); 2.506(456.7); 2.501(589.0); 2.497(449.3); 2.404 (0.4); 2.332(2.8); 2.328(3.8); 2.324(2.9); 1.897(4.6); 1.890(16.0); 0.146(0.3); 0.008(3.0); 0.000(61.6)

Example Ia-03: $^1$H-NMR(400.0 MHz, d$_6$-DMSO): δ = 8.606(0.7); 8.535(3.9); 8.334(0.9); 8.313(1.2); 8.278(4.0); 8.077(1.0); 7.753(1.9); 7.546(1.3); 7.530(3.4); 7.483(1.8); 7.371(1.0); 7.362(0.4); 7.352(1.7); 7.332(1.0); 7.150(1.3); 7.131(1.1); 4.288(3.0); 4.273(2.9); 3.320(68.0); 3.316(57.8); 2.675 (0.6); 2.670(0.8); 2.666(0.6); 2.506(103.7); 2.501(138.8); 2.497(99.0); 2.332(0.6); 2.328(0.8); 2.323(0.6); 1.891(16.0); 0.000(0.8)

Example Ia-04: $^1$H-NMR(400.0 MHz, d$_6$-DMSO): δ = 8.518(0.5); 8.505(0.8); 8.491(0.4); 8.462(3.0); 8.170(3.1); 7.631(0.9); 7.614(1.2); 7.604(0.7); 7.596(0.8); 7.583(4.4); 7.243(0.8); 7.219(1.0); 7.197(0.7); 4.338(2.0); 4.325(2.0); 3.318(72.3); 2.675(0.4); 2.670(0.6); 2.506(73.2); 2.501(96.1); 2.497 (72.8); 2.332(0.4); 2.328(0.6); 2.118(16.0); 1.988(0.9); 1.644(0.4); 1.637(0.4); 1.625(0.8); 1.613(0.5); 1.606(0.5); 1.175(0.4); 0.708(1.0); 0.700(1.9); 0.696(1.8); 0.689(1.7); 0.677(1.1); 0.672(2.0); 0.665(0.9); 0.657(1.1); 0.652(1.7); 0.645(0.8); 0.000(21.9)

Example Ia-05: $^1$H-NMR(400.0 MHz, CDCl$_3$): δ = 8.090(4.6); 7.849(4.8); 7.734(7.5); 7.599(2.7); 7.443(0.5); 7.439(0.4); 7.423(2.7); 7.418(3.3); 7.414 (4.6); 7.393(0.6); 7.261(15.4); 5.955(0.7); 5.300(0.5); 4.567(4.2); 4.552(4.1); 2.034(16.0); 2.007(0.5); 1.601(0.5); 1.576(16.5); 1.541(0.5); 1.255 (0.8); 0.070(1.5); 0.000(4.5)

Example Ia-06: $^1$H-NMR(400.0 MHz, d$_6$-DMSO): δ = 8.619(4.9); 8.339(0.6); 8.317(5.7); 8.203(2.5); 8.200(2.5); 7.930(2.3); 7.613(0.8); 7.606(0.7); 7.600(1.0); 7.592(2.5); 7.579(1.2); 7.574(1.5); 7.257(1.1); 7.232(1.5); 7.211(1.1); 4.318(3.1); 4.304(3.1); 3.321(164.7); 3.319(163.4); 2.671(1.7); 2.506 (222.5); 2.502(281.2); 2.497(201.9); 2.328(1.6); 1.889(16.0); 1.481(1.0); 1.467(1.0); 1.298(0.4); 1.259(0.5); 1.235(1.6); 1.216(0.4); 1.182(0.3); 1.150 (0.6); 1.134(0.6); 0.146(0.4); 0.008(3.0); 0.000(80.6); −0.008(3.1); −0.149(0.4)

Example Ia-07: $^1$H-NMR(400.0 MHz, d$_6$-DMSO): δ = 8.527(4.6); 8.326(0.6); 8.313(1.3); 8.298(0.6); 8.259(4.8); 7.753(2.4); 7.611(0.7); 7.606(0.8); 7.599(0.7); 7.587(2.6); 7.573(2.2); 7.482(2.3); 7.241(0.9); 7.216(1.3); 7.195(0.9); 5.753(0.6); 4.314(2.8); 4.300(2.8); 3.322(123.4); 2.675(0.7); 2.671 (0.9); 2.666(0.6); 2.524(2.3); 2.510(53.8); 2.506(110.3); 2.502(153.8); 2.497(103.1); 2.493(49.3); 2.447(0.4); 2.333(0.6); 2.328(0.8); 2.324(0.7); 1.908 (1.2); 1.891(16.0); 1.259(0.4); 1.236(3.2); 1.154(0.3); 0.854(0.4); 0.008(1.6); 0.000(44.9); −0.008(1.6)

Example Ia-08: $^1$H-NMR(400.0 MHz, CDCl$_3$): δ = 8.045(5.1); 7.786(5.3); 7.775(0.4); 7.665(8.1); 7.426(1.4); 7.409(4.3); 7.337(1.5); 7.318(2.3); 7.303 (0.4); 7.297(1.2); 7.193(16.0); 7.154(1.7); 7.135(1.5); 5.695(0.6); 4.430(4.4); 4.416(4.3); 2.235(1.5); 2.216(4.5); 2.197(4.7); 2.178(1.6); 1.545(15.4); 1.357(0.7); 1.186(0.8); 1.152(5.4); 1.134(10.4); 1.115(5.0); 0.000(3.5); −0.070(3.3)

-continued

Example Ia-09: $^1$H-NMR(400.0 MHz, CDCl$_3$): δ = 8.259(0.4); 8.117(4.3); 8.047(0.4); 7.859(4.4); 7.735(7.3); 7.497(1.4); 7.483(3.6); 7.408(1.3); 7.389(2.1); 7.369(1.1); 7.263(10.7); 7.225(1.6); 7.206(1.3); 5.801(0.5); 4.489(3.9); 4.475(3.8); 2.072(0.3); 2.051(16.0); 1.612(7.7); 1.255(0.5); 0.000(5.6)

Example Ia-10: $^1$H-NMR(400.0 MHz, d$_6$-DMSO): δ = 8.579(0.5); 8.514(9.0); 8.486(1.7); 8.481(1.7); 8.314(0.6); 8.276(0.6); 8.241(10.4); 8.223(1.3); 8.078(0.8); 8.065(0.4); 8.034(2.5); 7.752(5.4); 7.715(1.8); 7.697(2.4); 7.685(1.9); 7.667(2.3); 7.639(0.5); 7.624(1.5); 7.620(1.5); 7.606(2.6); 7.602(2.8); 7.580(6.3); 7.562(5.0); 7.480(4.7); 7.239(2.0); 7.215(2.7); 7.194(1.9); 4.323(5.8); 4.309(5.8); 3.364(0.6); 3.318(156.5); 2.675(1.3); 2.670(1.5); 2.505(206.1); 2.501(277.9); 2.497(195.0); 2.463(0.9); 2.328(1.5); 2.324(1.3); 2.203(2.3); 2.184(7.2); 2.165(7.5); 2.146(2.5); 2.073(11.1); 1.042(7.9); 1.023(16.0); 1.004(7.4); 0.000(35.3)

Example Ia-11: $^1$H-NMR(400.0 MHz, d$_6$-DMSO): δ = 8.610(4.6); 8.515(2.4); 8.510(2.5); 8.356(5.0); 8.345(0.7); 8.331(1.2); 8.317(0.6); 8.243(2.4); 8.239(2.3); 7.629(0.6); 7.623(0.8); 7.617(0.8); 7.611(1.0); 7.598(1.9); 7.580(1.3); 7.259(1.1); 7.234(1.4); 7.213(1.0); 4.321(2.9); 4.307(2.9); 3.368(14.4); 3.317(67.3); 2.679(0.4); 2.674(0.5); 2.670(0.7); 2.666(0.5); 2.506(84.2); 2.501(109.9); 2.497(80.2); 2.328(0.7); 2.324(0.5); 2.073(1.5); 1.889(16.0); 0.008(1.8); 0.000(44.1); −0.008(1.7)

Example Ia-12: $^1$H-NMR(400.0 MHz, d$_6$-DMSO): δ = 8.572(1.6); 8.530(2.2); 8.516(4.0); 8.505(16.0); 8.313(1.3); 8.269(1.6); 8.233(14.7); 8.076(2.4); 8.033(0.6); 7.752(6.9); 7.622(4.3); 7.614(3.9); 7.604(5.7); 7.593(2.9); 7.587(2.2); 7.580(2.5); 7.482(6.6); 7.251(3.5); 7.229(4.0); 7.226(4.2); 7.205(3.0); 4.340(8.9); 4.327(8.8); 3.317(306.1); 2.675(2.2); 2.670(2.9); 2.666(2.2); 2.523(7.4); 2.505(387.9); 2.501(527.4); 2.497(377.3); 2.332(2.1); 2.328(3.0); 2.324(2.4); 1.654(0.9); 1.642(1.8); 1.634(2.1); 1.623(3.7); 1.611(2.3); 1.603(2.2); 1.592(1.0); 1.289(0.4); 0.720(1.1); 0.708(4.6); 0.701(9.0); 0.696(8.1); 0.690(7.3); 0.684(5.1); 0.672(8.7); 0.665(3.9); 0.657(5.0); 0.652(7.5); 0.645(3.8); 0.633(1.3); 0.146(0.4); 0.008(2.6); 0.000(77.3); −0.008(3.2); −0.151(0.4)

Example Ia-13: $^1$H-NMR(400.0 MHz, CD$_3$CN): δ = 19.977(0.7); 8.053(8.6); 7.985(8.8); 7.589(1.3); 7.582(2.1); 7.577(2.7); 7.559(2.6); 7.547(1.7); 7.530(11.3); 7.513(1.9); 7.152(2.7); 7.128(3.1); 7.106(2.4); 6.814(1.0); 4.400(6.7); 4.386(6.8); 4.143(0.5); 4.126(0.5); 2.889(3.2); 2.772(3.0); 2.473(2.4); 2.468(5.0); 2.463(7.1); 2.459(5.3); 2.160(1173.1); 2.116(58.2); 2.108(11.5); 2.101(7.4); 2.095(4.1); 1.964(37.8); 1.958(96.7); 1.952(539.0); 1.946(985.4); 1.940(1339.5); 1.934(945.6); 1.928(503.1); 1.919(66.6); 1.781(3.5); 1.775(6.2); 1.769(8.3); 1.762(5.9); 1.756(3.6); 1.718(0.9); 1.437(8.7); 1.384(1.2); 1.270(16.0); 1.228(2.3); 1.187(1.0); 0.882(3.8); 0.859(3.8); 0.841(2.5); 0.146(17.0); 0.008(127.2); 0.000(3330.2); −0.008(170.6); −0.150(16.5)

Example Ia-14: $^1$H-NMR(400.0 MHz, d$_6$-DMSO): δ = 8.622(4.7); 8.514(2.1); 8.509(2.2); 8.375(4.8); 8.364(0.6); 8.350(1.0); 8.336(0.5); 8.245(2.0); 8.241(2.0); 7.562(1.2); 7.542(4.0); 7.387(0.9); 7.368(1.8); 7.349(0.9); 7.169(1.4); 7.150(1.2); 4.294(3.1); 4.279(3.1); 3.368(13.9); 3.317(59.3); 3.316(57.0); 2.674(0.5); 2.670(0.7); 2.666(0.5); 2.523(1.9); 2.510(41.5); 2.505(83.8); 2.501(111.3); 2.496(81.4); 2.492(40.1); 2.332(0.5); 2.328(0.7); 2.323(0.5); 1.889(16.0); 0.146(0.6); 0.008(4.8); 0.000(121.1); −0.009(4.7); −0.150(0.6)

Example Ia-15: $^1$H-NMR(400.0 MHz, d$_6$-DMSO): δ = 9.101(0.4); 8.725(0.5); 8.593(4.7); 8.339(0.6); 8.326(1.3); 8.313(0.9); 8.294(4.8); 8.269(0.9); 8.154(0.3); 8.077(7.4); 7.854(0.4); 7.611(0.9); 7.605(0.7); 7.598(0.9); 7.587(1.9); 7.569(1.4); 7.253(1.2); 7.231(1.4); 7.228(1.5); 7.207(1.1); 4.320(3.3); 4.306(3.1); 4.057(0.9); 4.039(2.7); 4.021(2.8); 4.003(0.9); 3.321(18.5); 2.507(25.7); 2.502(33.3); 2.498(24.3); 1.989(11.6); 1.894(16.0); 1.236(0.5); 1.193(3.1); 1.176(6.0); 1.158(3.0); 0.008(0.5); 0.000(9.7); −0.008(0.4)

Example Ia-16: $^1$H-NMR(400.0 MHz, CDCl$_3$): δ = 8.016(7.1); 7.775(7.3); 7.665(11.5); 7.524(4.2); 7.370(0.7); 7.348(4.5); 7.341(7.4); 7.320(0.9); 7.194(16.0); 5.900(1.2); 4.504(6.4); 4.489(6.3); 2.221(1.8); 2.202(5.4); 2.183(5.6); 2.164(2.0); 1.565(12.7); 1.215(0.3); 1.186(2.8); 1.152(0.5); 1.146(0.5); 1.131(6.2); 1.112(11.6); 1.093(5.7); 0.000(4.8); −0.070(4.2)

Example Ia-17: $^1$H-NMR(400.0 MHz, d$_6$-DMSO): δ = 8.770(4.5); 8.381(4.6); 8.367(0.6); 8.352(1.0); 8.337(0.6); 8.313(0.4); 8.283(2.3); 8.279(2.4); 8.157(2.2); 7.572(1.3); 7.553(4.5); 7.399(0.9); 7.380(1.8); 7.361(0.9); 7.187(1.5); 7.168(1.3); 5.754(2.5); 4.297(3.4); 4.283(3.4); 3.317(161.2); 2.675(14.7); 2.506(156.0); 2.501(201.9); 2.497(150.4); 2.328(1.2); 2.086(0.6); 1.892(16.0); 0.146(0.3); 0.008(3.1); 0.000(72.1); −0.149(0.3)

Example Ia-18: $^1$H-NMR(400.0 MHz, d$_6$-DMSO): δ = 8.811(0.3); 8.617(0.4); 8.418(10.0); 8.360(0.7); 8.313(0.9); 8.285(10.2); 8.103(0.7); 8.070(16.0); 7.662(8.2); 6.759(0.5); 5.753(1.4); 4.991(0.8); 4.976(0.7); 4.758(0.7); 4.025(0.4); 3.615(0.5); 3.599(0.7); 3.584(0.5); 3.448(0.3); 3.413(13.6); 3.317(224.8); 2.675(1.7); 2.670(2.4); 2.666(1.8); 2.523(5.9); 2.510(148.2); 2.506(301.0); 2.501(397.7); 2.497(287.3); 2.492(138.5); 2.393(0.5); 2.381(1.1); 2.373(1.3); 2.362(2.1); 2.350(1.3); 2.343(1.3); 2.332(2.2); 2.328(2.6); 2.324(1.8); 2.184(0.4); 1.676(0.4); 1.651(0.6); 1.554(0.4); 1.535(1.1); 1.481(5.3); 1.467(5.3); 1.369(0.8); 1.355(2.6); 1.336(1.1); 1.318(0.4); 1.310(1.0); 1.298(1.5); 1.280(1.8); 1.259(2.1); 1.235(7.6); 1.226(2.2); 1.216(1.9); 1.182(1.3); 1.172(0.9); 1.150(3.7); 1.142(0.9); 1.134(3.7); 1.123(1.0); 1.107(1.8); 1.095(2.5); 1.088(4.7); 1.080(3.3); 1.068(4.4); 1.049(2.8); 1.042(4.5); 1.035(5.1); 1.031(5.2); 1.023(3.4); 1.011(1.3); 0.994(0.7); 0.986(0.6); 0.976(0.7); 0.968(0.4); 0.915(0.6); 0.866(0.4); 0.854(0.3); 0.835(0.5); 0.146(1.7); 0.008(13.0); 0.000(364.0); −0.009(13.2); −0.150(1.7)

Example Ia-19: $^1$H-NMR(400.0 MHz, d$_6$-DMSO): δ = 19.945(0.4); 8.765(2.1); 8.751(3.8); 8.738(2.0); 8.592(14.8); 8.313(3.5); 8.298(16.0); 8.204(8.3); 7.933(7.3); 7.639(2.2); 7.634(2.7); 7.626(2.3); 7.620(3.3); 7.613(3.5); 7.602(5.1); 7.585(4.2); 7.285(4.1); 7.261(5.1); 7.239(3.6); 6.630(0.4); 4.440(0.4); 4.384(9.5); 4.370(9.4); 3.985(0.4); 3.891(0.6); 3.534(0.7); 3.505(0.7); 3.476(0.5); 3.395(3.7); 3.367(11.7); 3.338(20.0); 3.319(939.7); 2.675(6.8); 2.670(9.3); 2.666(6.7); 2.586(0.6); 2.523(32.0); 2.510(590.7); 2.506(1161.7); 2.501(1511.1); 2.497(1105.7); 2.493(550.5); 2.403(0.5); 2.332(6.7); 2.328(9.1); 2.324(6.6); 1.297(0.8); 1.236(0.8); 1.183(4.3); 0.856(0.5); 0.146(1.9); 0.008(16.9); 0.000(428.7); −0.009(15.7); −0.149(2.0)

Example Ia-20: $^1$H-NMR(400.0 MHz, CDCl$_3$): δ = 8.086(0.9); 8.077(1.3); 7.851(0.9); 7.834(1.3); 7.742(1.5); 7.733(2.0); 7.456(2.0); 7.405(1.9); 7.402(1.8); 7.266(10.9); 7.235(0.5); 5.301(0.4); 4.772(2.2); 4.635(1.4); 3.026(6.2); 2.199(4.6); 2.146(2.8); 1.658(14.3); 1.427(16.0); 1.255(0.7); 0.000(2.6)

Example Ia-21: $^1$H-NMR(400.0 MHz, CDCl$_3$): δ = 8.037(6.5); 7.781(6.7); 7.667(10.7); 7.441(1.7); 7.421(2.5); 7.406(3.7); 7.347(1.8); 7.328(3.3); 7.309(1.6); 7.195(16.0); 7.142(2.2); 7.123(1.9); 6.232(0.7); 4.473(5.5); 4.458(5.3); 3.109(1.8); 3.082(5.4); 3.055(5.5); 3.029(1.9); 1.602(2.3); 1.578(15.8); 1.186(1.0); 0.000(9.7); −0.070(3.3)

Example Ia-22: $^1$H-NMR(400.0 MHz, CDCl$_3$): δ = 8.115(1.7); 7.860(1.5); 7.740(1.0); 7.734(1.6); 7.465(0.3); 7.444(0.5); 7.370(0.5); 7.268(5.6); 5.302(0.4); 4.641(1.5); 4.584(0.8); 4.131(0.3); 4.113(0.3); 2.996(1.6); 2.958(3.3); 2.456(0.3); 2.437(1.1); 2.419(1.1); 2.400(0.4); 2.045(1.4); 1.714(16.0); 1.427(2.1); 1.277(0.5); 1.259(1.1); 1.255(0.9); 1.242(0.5); 1.229(0.9); 1.211(1.8); 1.202(0.6); 1.192(0.9); 1.184(1.0); 1.165(0.5); 0.070(1.0); 0.000(1.1)

Example Ia-23: $^1$H-NMR(400.0 MHz, d$_6$-DMSO): δ = 8.630(0.6); 8.306(0.6); 4.328(0.4); 4.314(0.4); 4.056(1.3); 4.038(3.9); 4.021(3.9); 4.003(1.3); 3.318(7.4); 2.506(12.4); 2.502(16.0); 2.498(12.1); 2.181(0.5); 2.162(0.5); 1.989(16.0); 1.193(4.3); 1.175(8.4); 1.157(4.2); 1.043(0.5); 1.024(1.1); 1.005(0.5); 0.008(0.3); 0.000(8.4)

Example Ia-24: $^1$H-NMR(400.0 MHz, CDCl$_3$): δ = 8.081(5.1); 8.065(4.9); 7.836(5.1); 7.817(5.0); 7.741(11.0); 7.736(10.5); 7.520(0.4); 7.449(8.0); 7.430(0.5); 7.407(4.4); 7.396(8.6); 7.355(0.3); 7.334(3.4); 7.261(42.8); 6.989(0.3); 5.299(7.6); 4.825(7.9); 4.786(8.7); 3.214(2.5); 3.188(16.0); 3.086(0.8); 3.066(15.4); 1.878(0.3); 1.867(0.7); 1.858(0.9); 1.847(1.4); 1.835(1.0); 1.827(0.8); 1.815(0.4); 1.672(0.5); 1.660(0.8); 1.651(1.1); 1.641(1.6); 1.629(1.1); 1.622(1.0); 1.609(0.8); 1.572(27.0); 1.541(0.5); 1.451(0.5); 1.427(10.1); 1.423(4.5); 1.411(3.4); 1.388(0.7); 1.383(0.6); 1.333(3.6); 1.307(4.0); 1.292(4.7); 1.285(5.3); 1.255(15.6); 1.236(2.6); 1.212(0.8); 1.190(7.6); 1.163(0.4); 1.099(0.5); 1.066(3.8); 1.057(6.1); 1.049(6.2); 1.039(4.1); 1.011(0.4); 0.896(1.0); 0.880(2.1); 0.857(3.3); 0.849(3.4); 0.837(3.5); 0.830(2.9); 0.820(1.2); 0.795(0.4); 0.775(1.2); 0.766(2.5); 0.759(2.6); 0.747(2.7); 0.739(2.2); 0.730(0.8); 0.008(1.0); 0.000(23.1); −0.008(0.9)

Example Ia-25: $^1$H-NMR(400.0 MHz, CDCl$_3$): δ = 8.088(5.0); 7.843(5.1); 7.734(8.3); 7.593(3.1); 7.440(0.4); 7.414(7.3); 7.394(0.4); 7.264(14.9); 7.255(0.9); 6.145(0.9); 5.300(1.0); 4.594(4.6); 4.579(4.5); 1.622(16.0); 1.422(0.5); 1.412(1.5); 1.401(1.0); 1.390(1.5); 1.379(1.0); 1.370(0.9); 1.359(0.5); 1.291(1.2); 1.256(0.8); 1.222(0.8); 1.021(0.8); 1.011(2.7); 1.003(3.2); 1.000(2.7); 0.993(2.8); 0.983(1.0); 0.788(0.9); 0.779(2.5); 0.771(2.6); 0.759(2.7); 0.752(2.2); 0.741(0.8); 0.000(5.7); −0.009(0.5)

Example Ia-26: $^1$H-NMR(400.0 MHz, d$_6$-DMSO): δ = 8.601(8.2); 8.313(0.9); 8.298(8.5); 8.265(1.1); 8.252(2.1); 8.237(1.1); 8.201(4.4); 8.197(4.5); 7.927(3.9); 7.613(1.0); 7.608(1.3); 7.601(1.2); 7.595(1.7); 7.587(1.7); 7.574(3.6); 7.557(2.2); 7.255(2.1); 7.231(2.7); 7.209(1.9); 4.327(5.3); 4.313(5.2); 3.318(200.9); 2.675(1.5); 2.670(2.1); 2.666(1.6); 2.523(5.7); 2.506(255.4); 2.501(338.7); 2.497(250.8); 2.332(1.4); 2.328(2.0); 2.324(1.5); 2.199(2.1); 2.180(6.8); 2.161(7.0); 2.142(2.3); 2.073(3.3); 1.480(0.4); 1.467(0.5); 1.234(0.7); 1.181(0.6); 1.169(1.4); 1.150(0.6); 1.134(0.6); 1.043(7.9); 1.024(16.0); 1.005(7.5); 0.847(0.4); 0.146(0.4); 0.008(3.1); 0.000(85.4); −0.008(3.2); −0.150(0.4)

Example Ia-27: $^1$H-NMR(400.0 MHz, d$_6$-DMSO): δ = 8.678(2.1); 8.632(4.8); 8.343(2.2); 8.324(5.1); 8.199(4.2); 7.926(3.7); 7.669(0.4); 7.662(0.4); 7.654(0.5); 7.647(0.4); 7.641(0.4); 7.636(0.4); 7.622(0.7); 7.616(0.8); 7.610(0.8); 7.602(1.1); 7.595(0.9); 7.589(0.8); 7.583(0.8); 7.477(0.6); 7.464 (0.6); 7.417(1.2); 7.413(1.3); 7.400(1.3); 7.395(1.2); 7.318(0.5); 7.293(0.8); 7.273(1.6); 7.249(1.7); 7.227(1.2); 4.629(3.0); 4.582(6.6); 3.319(50.3); 3.007(16.0); 2.833(6.5); 2.676(0.4); 2.671(0.6); 2.667(0.4); 2.511(34.3); 2.507(71.1); 2.502(96.4); 2.498(73.4); 2.452(1.3); 2.434(3.9); 2.423(1.9); 2.415 (4.1); 2.405(1.8); 2.397(1.5); 2.387(0.6); 2.334(0.4); 2.329(0.6); 2.325(0.4); 2.074(8.1); 1.482(0.3); 1.468(0.3); 1.235(0.6); 1.038(4.3); 1.019(10.5); 1.001(7.6); 0.983(1.8); 0.008(1.9); 0.000(53.6); −0.008(2.5)

Example Ia-28: $^1$H-NMR(400.0 MHz, CD$_3$CN): δ = 8.085(7.9); 8.009(8.4); 7.584(0.3); 7.532(13.2); 7.518(2.6); 7.498(2.8); 7.379(2.3); 7.359(4.5); 7.340(2.2); 7.181(2.6); 7.162(2.1); 6.749(0.7); 4.370(7.5); 4.355(7.3); 2.279(0.5); 2.272(0.3); 2.232(2.5); 2.213(7.4); 2.194(7.7); 2.175(2.9); 2.134(107.6); 2.121(51.9); 2.107(2.6); 2.101(1.7); 2.095(0.9); 2.079(0.3); 2.035(0.4); 1.964(7.8); 1.958(19.1); 1.952(100.0); 1.946(181.0); 1.940(243.4); 1.934(170.0); 1.927(90.6); 1.780(0.5); 1.774(1.0); 1.768(1.3); 1.762(0.9); 1.756(0.6); 1.285(0.4); 1.270(1.0); 1.121(0.3); 1.112(8.2); 1.104(0.8); 1.093 (16.0); 1.074(7.7); 1.050(0.5); 0.146(2.1); 0.008(15.7); 0.000(422.6); −0.008(20.9); −0.150(2.1)

Example Ia-29: $^1$H-NMR(601.6 MHz, CD$_3$CN): δ = 8.206(3.5); 8.146(7.2); 8.101(6.4); 8.056(3.6); 7.579(3.8); 7.575(4.1); 7.520(2.1); 7.516(1.8); 7.506 (2.8); 7.503(2.6); 7.441(5.3); 7.427(3.7); 6.743(0.9); 4.446(7.1); 4.436(7.1); 2.245(2.3); 2.232(7.0); 2.219(7.2); 2.207(2.4); 2.120(115.6); 2.057 (0.9); 2.053(1.6); 2.049(2.2); 2.045(1.5); 2.041(0.8); 1.962(9.9); 1.954(25.3); 1.950(33.2); 1.946(165.7); 1.942(278.1); 1.938(387.6); 1.934(259.7); 1.930 (131.1); 1.832(0.9); 1.827(1.5); 1.823(2.2); 1.819(1.5); 1.815(0.7); 1.285(0.4); 1.271(0.9); 1.107(8.0); 1.095(16.0); 1.082(7.7); 0.097(0.6); 0.005 (5.8); 0.000(142.9); −0.006(5.6); −0.100(0.6)

Example Ia-30: $^1$H-NMR(400.0 MHz, d$_6$-DMSO): δ = 8.578(9.3); 8.313(0.5); 8.276(9.6); 8.264(1.5); 8.250(2.6); 8.236(1.3); 8.076(15.2); 7.609(1.1); 7.604(1.4); 7.598(1.3); 7.591(1.8); 7.584(2.0); 7.572(4.0); 7.555(2.6); 7.251(2.3); 7.227(3.0); 7.205(2.1); 4.326(6.1); 4.312(6.1); 3.317(174.7); 2.671 (1.3); 2.501(222.5); 2.328(1.4); 2.203(2.3); 2.184(7.2); 2.165(7.5); 2.146(2.5); 1.398(12.0); 1.043(8.0); 1.024(16.0); 1.005(7.5); 0.000(44.9)

Example Ia-31: $^1$H-NMR(400.0 MHz, d$_6$-DMSO): δ = 8.620(0.3); 8.606(7.0); 8.314(0.4); 8.299(0.5); 8.283(7.3); 8.199(4.0); 8.195(3.9); 7.926(3.5); 7.630(0.9); 7.624(1.0); 7.618(1.1); 7.610(1.3); 7.603(1.2); 7.597(1.1); 7.591(1.0); 7.419(1.6); 7.413(1.6); 7.401(1.7); 7.396(1.6); 7.285(1.9); 7.263 (2.1); 7.259(2.3); 7.250(0.7); 7.238(1.8); 7.232(0.7); 7.182(0.5); 7.164(0.4); 5.754(8.2); 5.063(8.2); 4.991(0.3); 4.341(0.6); 4.329(0.5); 3.456(0.7); 3.444 (0.7); 3.439(0.8); 3.426(0.7); 3.318(100.6); 2.675(0.8); 2.671(1.0); 2.667(0.7); 2.524(3.0); 2.511(64.5); 2.506(131.7); 2.502(174.8); 2.497(126.8); 2.493(61.9); 2.422(0.9); 2.409(1.8); 2.405(2.0); 2.398(1.5); 2.392(3.6); 2.385(1.4); 2.379(2.0); 2.374(2.1); 2.361(1.0); 2.333(0.8); 2.329(1.0); 2.324 (0.8); 2.300(2.0); 2.182(0.4); 1.535(0.4); 1.481(0.6); 1.467(0.6); 1.356(2.4); 1.236(0.8); 1.151(0.5); 1.135(0.5); 1.074(2.0); 1.056(4.0); 1.044(0.5); 1.039 (2.1); 1.025(0.7); 1.011(0.5); 1.006(0.7); 0.983(16.0); 0.975(11.0); 0.963(8.9); 0.956(3.0); 0.940(0.7); 0.797(0.4); 0.008(2.0); 0.000(55.1); −0.008 (2.1)

Example Ia-32: $^1$H-NMR(400.0 MHz, CDCl$_3$): δ = 8.074(0.7); 8.066(1.0); 7.833(0.7); 7.823(1.0); 7.741(1.1); 7.733(1.6); 7.446(0.9); 7.433(0.6); 7.399 (1.5); 7.261(6.9); 7.207(0.4); 4.779(1.6); 4.638(1.0); 3.042(1.9); 3.017(3.4); 2.462(0.7); 2.444(0.8); 2.378(0.4); 2.360(0.4); 1.573(7.9); 1.427(16.0); 1.255(0.6); 1.237(0.9); 1.219(1.8); 1.200(0.9); 1.184(0.6); 1.165(1.1); 1.147(0.5); 0.000(1.6)

Example Ia-33: $^1$H-NMR(400.0 MHz, d$_6$-DMSO): δ = 8.760(0.5); 8.750(4.6); 8.360(5.1); 8.340(0.7); 8.328(1.2); 8.313(1.0); 8.283(2.4); 8.278(2.5); 8.157(2.4); 7.636(0.9); 7.630(0.8); 7.623(1.0); 7.610(1.9); 7.593(1.4); 7.272(1.1); 7.248(1.4); 7.226(1.0); 5.753(1.7); 4.322(3.1); 4.308(3.1); 3.368 (0.7); 3.317(106.7); 2.679(14.8); 2.506(141.9); 2.501(182.0); 2.497(133.0); 2.333(0.8); 2.328(1.1); 2.324(0.8); 1.891(16.0); 1.236(1.3); 0.008(1.8); 0.000 (47.4); −0.008(1.9)

Example Ia-34: $^1$H-NMR(400.0 MHz, d$_6$-DMSO): δ = 8.850(0.8); 8.645(0.9); 8.333(1.2); 8.323(1.7); 8.076(0.4); 8.062(0.5); 7.976(0.5); 7.956(0.5); 7.660(0.5); 7.645(0.5); 7.607(0.5); 7.540(0.4); 7.258(0.4); 7.235(0.4); 6.902(0.4); 4.321(0.9); 4.314(0.9); 4.308(0.8); 4.056(1.3); 4.039(3.9); 4.021 (4.0); 4.003(1.3); 3.319(7.0); 2.506(15.0); 2.502(19.8); 2.498(15.7); 1.989(16.0); 1.896(3.1); 1.890(3.5); 1.193(4.3); 1.176(8.4); 1.158(4.2); 0.000(4.4)

Example Ia-35: $^1$H-NMR(400.0 MHz, CDCl$_3$): δ = 8.083(9.5); 7.839(9.9); 7.737(16.0); 7.573(5.1); 7.569(5.4); 7.460(1.3); 7.455(1.1); 7.439(5.1); 7.434 (5.2); 7.425(8.7); 7.405(2.6); 7.264(30.2); 6.399(1.4); 4.618(8.7); 4.603(8.5); 3.171(2.6); 3.145(8.1); 3.118(8.2); 3.092(2.8); 1.627(14.8); 1.284 (0.4); 1.255(1.3); 1.216(0.4); 1.201(0.3); 0.000(7.1)

Example Ia-36: $^1$H-NMR(400.0 MHz, d$_6$-DMSO): δ = 8.748(4.1); 8.606(7.5); 8.545(1.2); 8.525(1.5); 8.508(3.3); 8.487(3.9); 8.466(0.9); 8.441(0.4); 8.318(7.6); 8.299(4.5); 8.211(0.4); 8.079(12.3); 8.015(2.2); 7.999(1.7); 7.968(2.2); 7.879(1.3); 7.856(1.0); 7.632(2.4); 7.601(4.2); 7.563(1.3); 7.544 (1.5); 7.531(2.2); 7.512(2.7); 7.486(3.2); 7.429(0.9); 7.424(1.5); 7.418(0.8); 7.408(1.9); 7.402(1.2); 7.388(2.5); 7.369(4.7); 7.350(2.5); 7.338 (0.7); 7.318(3.4); 7.302(12.6); 7.283(2.5); 7.264(0.7); 7.229(3.7); 7.212(3.0); 5.754(5.1); 4.990(1.1); 4.978(2.0); 4.969(1.5); 4.960(2.4); 4.942(2.5); 4.923(2.5); 4.904(2.3); 4.886(1.3); 4.868(0.4); 3.922(2.2); 3.600(0.4); 3.318(264.9); 2.671(2.0); 2.506(251.6); 2.501(324.7); 2.497(237.8); 2.328 (1.9); 1.989(0.5); 1.649(1.3); 1.642(1.7); 1.636(1.8); 1.627(2.8); 1.620(2.6); 1.612(2.9); 1.598(2.2); 1.580(1.0); 1.567(0.5); 1.535(1.4); 1.481(3.0); 1.467 (3.0); 1.432(0.4); 1.405(1.2); 1.388(13.2); 1.356(6.8); 1.347(6.6); 1.338(7.3); 1.330(4.2); 1.299(0.7); 1.259(1.1); 1.236(4.2); 1.216(1.2); 1.175(0.8); 1.150(2.1); 1.142(0.6); 1.135(0.5); 1.124(0.7); 1.107(0.7); 1.069(16.0); 1.013(0.5); 0.995(0.4); 0.975(0.4); 0.854(0.6); 0.836(0.4); 0.808(0.6); 0.789 (0.8); 0.771(0.5); 0.686(2.0); 0.669(6.0); 0.655(10.6); 0.635(13.7); 0.620(7.6); 0.607(3.1); 0.146(0.6); 0.008(5.4); 0.000(126.8); −0.008(4.9); −0.149 (0.6)

Example Ia-37: $^1$H-NMR(400.0 MHz, CD$_3$CN): δ = 8.091(12.1); 8.015(12.8); 7.584(0.4); 7.533(16.0); 7.521(4.1); 7.502(4.2); 7.381(3.7); 7.362(6.9); 7.343(3.5); 7.185(3.8); 7.166(3.1); 6.805(0.9); 4.359(11.0); 4.344(11.0); 2.281(0.5); 2.139(108.1); 2.122(78.1); 2.107(2.7); 2.101(1.7); 2.095(1.0); 2.083(0.6); 2.069(0.5); 1.991(0.3); 1.964(7.1); 1.958(17.6); 1.952(97.1); 1.946(176.4); 1.940(238.5); 1.934(166.8); 1.927(95.7); 1.780(0.6); 1.774 (1.0); 1.768(1.4); 1.762(1.1); 1.756(0.6); 1.301(0.3); 1.285(0.5); 1.271(1.1); 0.146(1.8); 0.022(0.4); 0.008(12.5); 0.000(388.1); −0.008(18.1); −0.150 (1.9)

Example Ia-38: $^1$H-NMR(400.0 MHz, d$_6$-DMSO): δ = 8.636(4.3); 8.361(0.5); 8.346(1.0); 8.337(5.0); 8.313(0.7); 8.202(2.0); 8.198(2.1); 7.928(1.8); 7.551(1.1); 7.535(3.7); 7.387(1.0); 7.366(1.6); 7.347(0.9); 7.169(1.3); 7.150(1.1); 4.292(2.9); 4.278(2.9); 3.323(80.3); 3.318(78.7); 2.675(0.5); 2.671 (0.7); 2.666(0.5); 2.524(1.7); 2.510(44.1); 2.506(90.2); 2.502(119.4); 2.497(85.8); 2.493(41.3); 2.333(0.5); 2.328(0.7); 2.324(0.5); 1.890(16.0); 0.008 (0.4); 0.000(12.3); −0.008(0.4)

Example Ia-39: $^1$H-NMR(400.0 MHz, d$_6$-DMSO): δ = 8.873(1.2); 8.654(8.5); 8.352(1.4); 8.336(9.0); 8.322(4.6); 8.294(1.3); 8.279(2.3); 8.265(1.3); 8.070(1.1); 7.977(0.7); 7.955(4.2); 7.597(1.0); 7.563(2.5); 7.544(8.3); 7.404(0.3); 7.387(2.0); 7.368(3.5); 7.350(1.8); 7.163(3.0); 7.145(2.5); 7.040 (1.7); 6.905(3.8); 6.770(1.9); 4.302(6.9); 4.288(6.3); 3.361(0.4); 3.317(385.4); 2.891(1.0); 2.731(0.9); 2.670(3.9); 2.666(3.1); 2.569(0.4); 2.506(457.4); 2.501(598.8); 2.497(460.2); 2.425(0.4); 2.404(0.3); 2.328(3.8); 2.196(2.3); 2.177(7.2); 2.165(1.7); 2.158(7.4); 2.139(2.6); 1.508(0.5); 1.236(1.4); 1.055 (8.0); 1.036(16.0); 1.017(7.5); 0.146(1.6); 0.008(13.0); 0.000(325.6); −0.150(1.6)

Example Ia-40: $^1$H-NMR(400.0 MHz, d$_6$-DMSO): δ = 10.260(0.7); 8.789(0.6); 8.672(0.8); 8.598(14.5); 8.543(2.1); 8.530(3.8); 8.516(2.0); 8.460(0.6); 8.354(0.9); 8.314(1.1); 8.293(15.3); 8.200(8.1); 8.197(8.0); 7.927(7.3); 7.620(8.3); 7.604(7.4); 7.589(2.9); 7.268(2.7); 7.244(4.9); 7.221(2.8); 5.754 (16.0); 4.963(1.0); 4.346(9.4); 4.332(9.3); 3.358(0.6); 3.317(268.2); 2.675(2.3); 2.671(3.0); 2.666(2.3); 2.506(376.9); 2.502(487.0); 2.497(360.9); 2.399(5.6); 2.328(2.8); 1.652(1.3); 1.640(1.9); 1.633(2.1); 1.621(3.6); 1.609(2.4); 1.602(2.1); 1.590(1.0); 1.535(1.0); 1.481(1.9); 1.467(1.9); 1.413(1.0); 1.371(0.4); 1.337(0.4); 1.299(0.4); 1.279(0.4); 1.259(0.6); 1.235(1.2); 1.216(0.7); 1.171(0.5); 1.150(1.4); 1.135(1.4); 1.124(0.5); 1.107(0.6); 1.056 (0.4); 0.994(0.4); 0.975(0.4); 0.721(1.2); 0.709(4.8); 0.702(9.0); 0.697(8.1); 0.691(7.3); 0.685(5.2); 0.672(8.4); 0.665(4.1); 0.658(5.3); 0.652(7.4); 0.646 (3.7); 0.633(1.3); 0.146(0.6); 0.008(6.0); 0.000(143.1); −0.150(0.6)

Example Ia-41: $^1$H-NMR(400.0 MHz, CDCl$_3$): δ = 8.264(0.3); 8.121(9.8); 8.051(0.3); 7.859(9.9); 7.736(16.0); 7.497(8.5); 7.480(3.9); 7.412(2.4); 7.393 (4.2); 7.372(2.1); 7.261(27.6); 7.242(3.5); 7.223(2.8); 5.919(1.3); 4.517(8.4); 4.503(8.3); 1.570(32.7); 1.404(0.6); 1.393(1.3); 1.384(1.6); 1.373 (2.8); 1.362(1.8); 1.353(1.5); 1.342(0.8); 1.255(0.6); 1.053(1.5); 1.043(5.2); 1.035(5.8); 1.032(5.1); 1.025(5.3); 1.015(1.6); 0.797(1.7); 0.788(4.7); 0.780 (4.9); 0.768(5.0); 0.761(4.1); 0.751(1.3); 0.070(0.5); 0.000(6.0)

Example Ia-42: $^1$H-NMR(400.0 MHz, CDCl$_3$): δ = 8.249(0.3); 8.118(7.4); 8.047(0.3); 7.864(3.2); 7.858(4.8); 7.740(5.1); 7.732(7.5); 7.520(0.9); 7.500 (1.1); 7.489(1.2); 7.470(1.7); 7.454(2.5); 7.444(1.1); 7.425(1.5); 7.405(0.7); 7.392(1.3); 7.373(2.3); 7.354(1.2); 7.341(1.5); 7.261(32.9); 7.182(1.5); 7.163(1.2); 7.115(0.9); 7.096(0.8); 5.299(1.5); 4.629(7.0); 4.576(4.3); 4.149(0.7); 4.131(2.1); 4.113(2.1); 4.095(0.7); 2.986(8.7); 2.967(16.0); 2.189 (9.3); 2.180(15.8); 2.045(9.0); 1.756(0.5); 1.633(0.7); 1.601(3.2); 1.582(3.3); 1.541(2.1); 1.525(0.5); 1.512(0.4); 1.427(2.4); 1.414(0.8); 1.403(0.3);

-continued 1.398(0.4); 1.348(1.5); 1.333(1.1); 1.307(0.5); 1.293(1.4); 1.284(1.7); 1.277(3.4); 1.259(7.8); 1.241(3.2); 1.222(1.2); 1.213(0.4); 1.188(0.4); 0.897(0.4); 0.880(0.7); 0.862(0.4); 0.854(0.4); 0.835(0.3); 0.008(0.5); 0.000(14.5); −0.009(0.6)
Example I-Tc-01: $^1$H-NMR(400.0 MHz, CD$_3$CN): δ = 8.400(0.4); 8.136(7.9); 8.091(7.9); 7.966(3.9); 7.962(3.9); 7.749(3.6); 7.488(2.8); 7.471(9.1); 7.297(3.1); 7.276(2.4); 6.623(1.2); 6.602(1.2); 5.421(0.8); 5.401(2.1); 5.382(2.1); 5.361(0.7); 3.008(0.6); 2.999(0.7); 2.986(0.7); 2.977(0.7); 2.968(1.2); 2.959(1.2); 2.946(1.2); 2.937(1.2); 2.889(1.0); 2.869(1.9); 2.848(1.5); 2.829(1.0); 2.808(0.6); 2.533(0.6); 2.524(0.7); 2.513(1.2); 2.505(1.3); 2.493 (1.2); 2.482(1.4); 2.473(1.3); 2.462(1.0); 2.454(0.7); 2.260(0.4); 2.248(0.5); 2.230(1.5); 2.221(1.3); 2.211(3.7); 2.202(3.7); 2.192(3.9); 2.183(3.9); 2.173 (2.1); 2.152(91.9); 2.127(0.3); 2.113(0.3); 2.106(0.4); 1.963(2.2); 1.957(5.2); 1.951(29.6); 1.945(53.8); 1.939(72.8); 1.933(50.2); 1.927(25.8); 1.860 (0.6); 1.838(1.6); 1.828(0.6); 1.818(1.6); 1.807(1.5); 1.797(0.7); 1.786(1.5); 1.774(0.3); 1.767(0.6); 1.765(0.7); 1.437(5.4); 1.143(0.6); 1.134(8.1); 1.124(1.3); 1.115(16.0); 1.106(0.8); 1.096(7.5); 0.146(1.4); 0.008(15.3); 0.000(266.5); −0.009(13.3); −0.150(1.4)
Example I-Tc-02: $^1$H-NMR(400.0 MHz, CD$_3$CN): δ = 8.201(6.2); 8.130(9.0); 8.064(9.2); 8.051(7.0); 7.488(4.1); 7.471(13.0); 7.296(4.3); 7.276(3.6); 6.609(2.1); 6.591(2.2); 5.419(1.1); 5.399(3.0); 5.379(3.0); 5.360(1.1); 4.068(0.6); 4.050(0.6); 3.682(1.3); 3.008(0.9); 3.000(1.0); 2.985(1.1); 2.977 (1.2); 2.967(1.9); 2.960(2.0); 2.945(1.9); 2.938(1.9); 2.889(1.3); 2.869(2.7); 2.848(2.2); 2.828(1.6); 2.807(0.9); 2.532(0.8); 2.523(0.9); 2.513(1.6); 2.504 (1.9); 2.493(1.8); 2.482(2.0); 2.473(1.9); 2.462(1.5); 2.246(0.6); 2.228(1.9); 2.219(2.0); 2.209(4.4); 2.200(4.7); 2.190(4.9); 2.181(5.2); 2.143(171.5); 2.128(14.4); 1.971(4.3); 1.951(66.5); 1.945(11.5); 1.939(142.2); 1.935(104.1); 1.933(112.1); 1.927(66.5); 1.859(0.7); 1.838(1.9); 1.817(2.1); 1.807 (2.0); 1.786(1.9); 1.767(1.3); 1.271(1.2); 1.221(0.7); 1.204(1.3); 1.186(0.7); 1.131(8.3); 1.112(16.0); 1.094(8.1); 0.859(0.3); 0.146(2.6); 0.052(0.4); 0.000(467.1); −0.015(38.9); −0.150(2.5)
Example I-Tc-03: $^1$H-NMR(601.6 MHz, CD$_3$CN): δ = 19.951(0.4); 8.114(4.6); 8.059(4.8); 7.827(2.5); 7.572(2.5); 7.483(1.6); 7.471(5.8); 7.291(1.7); 7.278(1.5); 6.917(1.5); 6.796(3.0); 6.675(1.5); 6.616(0.7); 5.410(0.5); 5.397(1.3); 5.384(1.3); 5.370(0.4); 2.993(0.4); 2.967(0.6); 2.961(0.7); 2.952 (0.7); 2.947(0.7); 2.877(0.5); 2.863(1.1); 2.849(0.9); 2.836(0.7); 2.822(0.4); 2.520(0.4); 2.514(0.4); 2.507(0.6); 2.501(0.7); 2.494(0.7); 2.486(0.8); 2.480 (0.7); 2.473(0.4); 2.467(0.5); 2.234(0.4); 2.221(0.9); 2.209(2.5); 2.196(3.7); 2.184(2.6); 2.171(1.1); 2.152(35.3); 2.148(31.9); 1.963(1.0); 1.955(2.3); 1.947(19.8); 1.943(35.4); 1.939(52.0); 1.934(35.7); 1.930(18.5); 1.843(0.4); 1.829(1.1); 1.822(0.5); 1.815(1.0); 1.808(0.9); 1.801(0.4); 1.794(0.8); 1.780(0.3); 1.437(16.0); 1.128(4.7); 1.115(9.3); 1.103(4.5); 0.096(0.8); 0.005(5.0); 0.000(170.2); −0.100(0.8)

Biological Results
*Ctenocephalides felis*—In Vitro Contact Tests with Adult Cat Fleas For the coating of the test tubes, 9 mg of active ingredient are first dissolved in 1 ml of acetone p.a. and then diluted to the desired concentration with acetone p.a. 250 µl of the solution are distributed homogeneously on the inner walls and the base of a 25 ml glass tube by turning and rocking on an orbital shaker (rocking rotation at 30 rpm for 2 h). With 900 ppm of active ingredient solution and internal surface area 44.7 cm$^2$, given homogeneous distribution, an area-based dose of 5 µg/cm$^2$ is achieved.

After the solvent has evaporated off, the tubes are populated with 5-10 adult cat fleas (*Ctenocephalides felis*), sealed with a perforated plastic lid and incubated in a horizontal position at room temperature and ambient humidity. After 48 h, efficacy is determined. To this end, the tubes are stood upright and the fleas are knocked to the base of the tube. Fleas which remain motionless at the base or move in an uncoordinated manner are considered to be dead or moribund.

A substance shows good efficacy against *Ctenocephalides felis* if at least 80% efficacy was achieved in this test at an application rate of 5 µg/cm$^2$. 100% efficacy means that all the fleas were dead or moribund. 0% efficacy means that no fleas were harmed.

In this test, for example, the following compounds from the preparation examples show an efficacy of 100% at an application rate of 5 µg/cm$^2$ (=500 g/ha): Ia-01, Ia-05, Ia-07, Ia-08, Ia-10, Ia-13, Ia-15, Ia-16, Ia-20, Ia-23, Ia-25, Ia-30, Ia-32, Ia-51, Ia-52, Ia-56, Ia-60, Ia-63, Ia-64, Ia-65, Ia-66, Ia-69, Ia-71, Ia-73, Ia-75, Ia-76, Ia-79, Ia-80, Ia-82, Ia-83, Ia-90, Ia-93, Ia-95, Ia-104, Ia-107, Ia-108, Ia-113, Ia-115, Ia-116, Ia-117, Ia-130, Ia-131, Ia-134, Ia-136, Ia-137, Ia-139, Ia-142, Ia-147, Ia-149, Ia-158, Ia-162, I-T2-04, I-Tc-03

In this test, for example, the following compounds from the preparation examples show an efficacy of 90% at an application rate of 5 µg/cm$^2$ (=500 g/ha): Ia-53

In this test, for example, the following compounds from the preparation examples show an efficacy of 80% at an application rate of 5 µg/cm$^2$ (=500 g/ha) Ia-54, Ia-67

In this test, for example, the following compounds from the preparation examples show an efficacy of 70% at an application rate of 5 µg/cm$^2$ (=500 g/ha): Ia-55.

*Rhipicephalus sanguineus*—In Vitro Contact Tests with Adult Brown Dog Ticks

For the coating of the test tubes, 9 mg of active ingredient are first dissolved in 1 ml of acetone p.a. and then diluted to the desired concentration with acetone p.a. 250 µl of the solution are distributed homogeneously on the inner walls and the base of a 25 ml glass tube by turning and rocking on an orbital shaker (rocking rotation at 30 rpm for 2 h). With 900 ppm of active ingredient solution and internal surface area 44.7 cm$^2$, given homogeneous distribution, an area-based dose of 5 µg/cm$^2$ is achieved.

After the solvent has evaporated off, the tubes are populated with 5-10 adult dog ticks (*Rhipicephalus sanguineus*), sealed with a perforated plastic lid and incubated in a horizontal position in the dark at room temperature and ambient humidity. After 48 h, efficacy is determined. To this end, the ticks are knocked to the base of the tube and incubated on a hotplate at 45-50° C. for not more than 5 min. Ticks which remain motionless on the base or move in such an uncoordinated manner that they are unable to deliberately avoid the heat by climbing upwards are considered to be dead or moribund.

A substance shows good activity against *Rhipicephalus sanguineus* if, in this test, an efficacy of at least 80% was achieved at an application rate of 5 µg/cm$^2$. An efficacy of 100% means that all the ticks were dead or moribund. 0% efficacy means that none of the ticks were harmed.

In this test, for example, the following compounds from the preparation examples show an efficacy of 100% at an application rate of 5 µg/cm$^2$ (=500 g/ha): Ia-01, Ia-04, Ia-05, Ia-10, Ia-11, Ia-13, Ia-15, Ia-16, Ia-19, Ia-23, Ia-29, Ia-30, Ia-51, Ia-52, Ia-53, Ia-54, Ia-55, Ia-65, Ia-66, Ia-66, Ia-75, Ia-76, Ia-79, Ia-80, Ia-82, Ia-83, Ia-90, Ia-93, Ia-104, Ia-115, Ia-139, Ia-141, Ia-146, Ia-147, Ia-157, Ia-162, I-Tc-01, I-Tc-03

In this test, for example, the following compounds from the preparation examples show an efficacy of 80% at an application rate of 5 µg/cm$^2$ (=500 g/ha): Ia-08, Ia-20, Ia-22, Ia-25, Ia-26, Ia-28, Ia-32, Ia-37, Ia-38, Ia-40, Ia-57, Ia-63, Ia-67, Ia-68, Ia-95, Ia-108, Ia-116, Ia-142, Ia-143, I-Tc-02.

In this text, for example, the following compounds from the preparation examples show on efficacy of 100% at an application rate of 1 µg/cm$^2$ (−100 g/ha): Ia-56, Ia-96.

In this text, for example, the following compounds from the preparation examples show an efficacy of 80% at an application rate of 1 µg/cm² (=100 g/ha): Ia-69.

Amblyomma hebaraeum test
Solvent: dimethyl sulfoxide

To produce a suitable active ingredient formulation, 10 mg of active ingredient are mixed with 0.5 ml of dimethyl sulfoxide, and the concentrate is diluted with water to the desired concentration.

Tick nymphs (Amblyomma hebraeum) are placed into perforated plastic beakers and immersed in the desired concentration for one minute. The ticks are transferred on filter paper into a Petri dish and stored in a climate-controlled cabinet.

After 42 days, the rate of extermination in % is determined. 100% means that all of the ticks have been killed; 0% means that none of the ticks have been killed.

In this test, for example, the following compounds from the preparation examples show an efficacy of 100% at an application rate of 100 ppm: Ia-01, Ia-13

Boophilus microplus—Dip Test
Test animals: cattle ticks (Boophilus microplus) Parkhurst strain, SP-resistant
Solvent: dimethyl sulfoxide 10 mg of active ingredient are dissolved in 0.5 ml of dimethyl sulfoxide. To produce a suitable formulation, the active ingredient solution is diluted with water to the concentration desired in each case.

This active ingredient formulation is pipetted into tubes. 8-10 engorged adult female cattle ticks (Boophilus microplus) are transferred into a further tube with holes. The tube is immersed into the active ingredient formulation, and all the ticks are completely wetted. After the liquid has run out, the ticks are transferred on filter discs into plastic dishes and stored in a climate-controlled room.

Efficacy is assessed after 7 days by laying of fertile eggs. Eggs which are not visibly fertile are stored in a climate-controlled cabinet until the larvae hatch after about 42 days. An efficacy of 100% means that none of the ticks has laid any fertile eggs; 0% means that all the eggs are fertile.

In this test, for example, the following compounds of the preparation examples show an efficacy of 100% at an application rate of 100 ppm: Ia-01, Ia-13, Ia-23, Ia-51, Ia-53, Ia-65, Ia-75, Ia-79, Ia-84, Ia-90, Ia-95, Ia-106, Ia-115, Ia-145, I-T2-04.

In this text, for example, the following compounds of the preparation examples show an efficacy of 95% at an application rate of 100 ppm: Ia-66, Ia-93.

In this text, for example, the following compounds of the preparation examples show an efficacy of 90% at an application rate of 100 ppm: Ia-15, Ia-96.

In this test, for example, the following compounds of the preparation examples show an efficacy of 80% at an application rate of 100 ppm: Ia-28, Ia-83, Ia-91, Ia-142, Ia-162.

Boophilus microplus—Injection Test
Solvent: dimethyl sulfoxide

To produce a suitable active compound preparation, 10 mg of active compound are mixed with 0.5 ml of solvent and the concentrate is diluted to the desired concentration with solvent.

1 µl of the active ingredient solution is injected into the abdomen of 5 engorged adult female cattle ticks (Boophilus microplus). The animals are transferred into dishes and kept in a climate-controlled room.

Efficacy is assessed after 7 days by laying of fertile eggs. Eggs which are not visibly fertile are stored in a climate-controlled cabinet until the larvae hatch after about 42 days. An efficacy of 100% means that none of the ticks has laid any fertile eggs; 0% means that all the eggs are fertile. In this test, for example, the following compounds from the preparation examples show an efficacy of 100% at an application rate of 20 µg/animal: Ia-01, Ia-02, Ia-04, Ia-05, Ia-07, Ia-08, Ia-10, Ia-11, Ia-12, Ia-13, Ia-15, Ia-16, Ia-18, Ia-19, Ia-20, Ia-22, Ia-23, Ia-25, Ia-26, Ia-28, Ia-29, Ia-30, Ia-32, Ia-35, Ia-37, Ia-38, Ia-40, Ia-41, Ia-42, Ia-51, Ia-52, Ia-53, Ia-54, Ia-55, Ia-56, Ia-57, Ia-59, Ia-60, Ia-61, Ia-63, Ia-64, Ia-65, Ia-66, Ia-67, Ia-68, Ia-69, Ia-71, Ia-72, Ia-73, Ia-74, Ia-75, Ia-76, Ia-77, Ia-79, Ia-80, Ia-82, Ia-83, Ia-84, Ia-88, Ia-90, Ia-91, Ia-93, Ia-95, Ia-96, Ia-98, Ia-104, Ia-106, Ia-107, Ia-108, Ia-113, Ia-115, Ia-116, Ia-117, Ia-130, Ia-131, Ia-132, Ia-133, Ia-134, Ia-136, Ia-137, Ia-139, Ia-141, Ia-142, Ia-143, Ia-144, Ia-145, Ia-146, Ia-147, Ia-148, Ia-149, Ia-150, Ia-151, Ia-152, Ia-155, Ia-157, Ia-158, Ia-159, Ia-162, Ic-01, I-T2-04, I-Tc-01, I-Tc-02, I-Tc-03.

Ctenocephalides felis—Oral Test
Solvent: Dimethyl Sulfoxide

To produce a suitable active ingredient formulation, 10 mg of active ingredient are mixed with 0.5 ml of dimethyl sulfoxide. Dilution with citrated cattle blood gives the desired concentration.

About 20 unfed adult cat fleas (Ctenocephalides fells) are placed into a chamber which is closed at the top and bottom with gauze. A metal cylinder whose bottom end is closed with parafilm is placed onto the chamber. The cylinder contains the blood/active ingredient formulation, which can be imbibed by the fleas through the parafilm membrane.

After 2 days, the rate of extermination in % is determined. 100% means that all of the fleas have been killed; 0% means that none of the fleas have been killed.

In this test, for example, the following compounds of the preparation examples show an efficacy of 100% at an application rate of 100 ppm: Ia-01, Ia-02, Ia-04, Ia-05, Ia-07, Ia-08, Ia-10, Ia-11, Ia-12, Ia-13, Ia-15, Ia-16, Ia-18, Ia-19, Ia-20, Ia-22, Ia-23, Ia-25, Ia-26, Ia-28, Ia-29, Ia-30, Ia-32, Ia-35, Ia-37, Ia-38, Ia-40, Ia-41, Ia-42, Ia-51, Ia-52, Ia-53, Ia-54, Ia-55, Ia-56, Ia-57, Ia-59, Ia-60, Ia-61, Ia-63, Ia-64, Ia-65, Ia-66, Ia-67, Ia-68, Ia-69, Ia-71, Ia-72, Ia-73, Ia-74, Ia-75, Ia-76, Ia-77, Ia-79, Ia-80, Ia-82, Ia-83, Ia-84, Ia-88, Ia-90, Ia-91, Ia-93, Ia-95, Ia-96, Ia-98, Ia-104, Ia-106, Ia-107, Ia-108, Ia-113, Ia-115, Ia-116, Ia-117, Ia-128, Ia-130, Ia-131, Ia-132, Ia-133, Ia-134, Ia-136, Ia-137, Ia-139, Ia-141, Ia-142, Ia-143, Ia-144, Ia-145, Ia-146, Ia-147, Ia-148, Ia-149, Ia-150, Ia-151, Ia-152, Ia-155, Ia-157, Ia-158, Ia-159, Ia-162, Ic-01, Ic-04, I-12-04, I-Tc-01, I-Tc-02, I-Tc-03.

Lucilia cuprina Test
Solvent: dimethyl sulfoxide

To produce a suitable active ingredient formulation, 10 mg of active ingredient are mixed with 0.5 ml of dimethyl sulfoxide, and the concentrate is diluted with water to the desired concentration.

About 20 L1 larvae of the Australian sheep blowfly (Lucilia cuprina) are transferred into a test vessel containing minced horsemeat and the active compound preparation of the desired concentration.

After 2 days, the rate of extermination in % is determined. 100% means that all the larvae have been killed; 0% means that no larvae have been killed.

In this test, for example, the following compounds of the preparation examples show an efficacy of 100% at an application rate of 100 ppm:

Ia-01, Ia-02, Ia-04, Ia-05, Ia-07, Ia-08, Ia-10, Ia-11, Ia-12, Ia-13, Ia-15, Ia-16, Ia-18, Ia-19, Ia-20, Ia-22, Ia-23, Ia-25, Ia-26, Ia-28, Ia-29, Ia-30, Ia-32, Ia-35, Ia-37, Ia-38, Ia-40, Ia-41, Ia-42, Ia-51, Ia-52, Ia-53, Ia-54, Ia-55, Ia-56, Ia-57, Ia-59, Ia-60, Ia-61, Ia-63, Ia-64, Ia-65, Ia-66, Ia-67, Ia-68, Ia-69, Ia-71, Ia-72, Ia-73, Ia-74, Ia-75, Ia-76, Ia-77, Ia-79, Ia-80, Ia-82, Ia-83, Ia-84, Ia-88, Ia-90, Ia-91, Ia-93, Ia-95, Ia-96, Ia-98, Ia-104, Ia-106, Ia-107, Ia-108, Ia-113, Ia-115, Ia-116, Ia-117, Ia-128, Ia-130, Ia-131, Ia-132, Ia-133,

Ia-134, Ia-136, Ia-137, Ia-139, Ia-141, Ia-142, Ia-143, Ia-144, Ia-145, Ia-146, Ia-147, Ia-148, Ia-149, Ia-150, Ia-151, Ia-152, Ia-155, Ia-157, Ia-158, Ia-159, Ia-162, Ic-01, Ic-04, I-T2-04, I-Tc-01, I-Tc-02, I-Tc-03.

*Musca domestica* Test

Solvent: dimethyl sulfoxide

To produce a suitable active ingredient formulation, 10 mg of active ingredient are mixed with 0.5 ml of dimethyl sulfoxide, and the concentrate is diluted with water to the desired concentration.

Vessels containing a sponge treated with sugar solution and the active ingredient formulation of the desired concentration are populated with 10 adult houseflies (*Musca domestica*).

After 2 days, the rate of extermination in % is determined. 100% means that all of the flies have been killed; 0% means that none of the flies have been killed.

In this test, for example, the following compounds of the preparation examples show an efficacy of 100% at an application rate of 100 ppm: Ia-01, Ia-02, Ia-04, Ia-05, Ia-07, Ia-10, Ia-11, Ia-12, Ia-13, Ia-15, Ia-16, Ia-18, Ia-19, Ia-23, Ia-25, Ia-26, Ia-28, Ia-29, Ia-30, Ia-35, Ia-37, Ia-38, Ia-40, Ia-41, Ia-51, Ia-52, Ia-53, Ia-54, Ia-55, Ia-56, Ia-57, Ia-59, Ia-60, Ia-63, Ia-64, Ia-65, Ia-66, Ia-67, Ia-68, Ia-69, Ia-71, Ia-72, Ia-73, Ia-74, Ia-75, Ia-76, Ia-79, Ia-80, Ia-82, Ia-83, Ia-84, Ia-90, Ia-91, Ia-93, Ia-95, Ia-104, Ia-106, Ia-107, Ia-108, Ia-113, Ia-115, Ia-116, Ia-117, Ia-128, Ia-130, Ia-131, Ia-132, Ia-133, Ia-134, Ia-136, Ia-137, Ia-139, Ia-141, Ia-142, Ia-143, Ia-144, Ia-145, Ia-146, Ia-147, Ia-148, Ia-149, Ia-150, Ia-151, Ia-152, Ia-155, Ia-157, Ia-158, Ia-159, Ia-162, Ic-04.

In this test, for example, the following compounds from the preparation examples show an efficacy of 90% at an application rate of 100 ppm: Ia-20, Ia-98, Ic-01.

In this test, for example, the following compounds from the preparation examples show an efficacy of 80% at an application rate of 100 ppm: Ia-08, Ia-42, Ia-61.

*Meloidogyne incognita* Test

Solvent: 125.0 parts by weight of acetone

To produce a suitable active compound preparation, 1 part by weight of active compound is mixed with the stated amount of solvent and the concentrate is diluted to the desired concentration with water.

Vessels are filled with sand, active compound solution, an egg/larvae suspension of the southern root-knot nematode (*Meloidogyne incognita*) and lettuce seeds. The lettuce seeds germinate and the plants develop. The galls develop on the roots.

After 14 days, the nematicidal efficacy in % is determined by the formation of galls. 100% means that no galls were found; 0% means that the number of galls on the treated plants corresponds to the untreated control.

In this test, for example, the following compounds from the preparation examples show an efficacy of 100% at an application rate of 20 ppm: Ia-08, Ia-34, Ia-102, Ia-125.

In this text, for example, the following compounds from the preparation examples show an efficacy of 90% at an application rate of 20 ppm: Ia-15, Ia-42, Ia-105, Ia-141.

*Myzus persicae*—Spray Test

Solvent: 78 parts by weight of acetone 1.5 parts by weight of dimethylformamide

Emulsifier: alkylaryl polyglycol ether

To produce a suitable active ingredient formulation, 1 part by weight of active ingredient is dissolved with the specified parts by weight of solvent and made up to the desired concentration with water containing an emulsifier concentration of 1000 ppm. To produce further test concentrations, the formulation is diluted with emulsifier-containing water.

Discs of Chinese cabbage leaves (*Brassica pekinensis*) infested by all stages of the green peach aphid (*Myzus persicae*) are sprayed with an active compound preparation of the desired concentration.

After 6 days, the efficacy in % is determined. 100% means that all the aphids have been killed; 0% means that no aphids have been killed.

In this test, for example, the following compounds from the preparation examples show an efficacy of 100% at an application rate of 100 g/ha: Ia-01, Ia-11, Ia-13, Ia-134, Ia-136, Ia-152.

In this test, for example, the following compounds from the preparation examples show an efficacy of 90% at an application rate of 100 g/ha: Ia-15, Ia-23, Ia-34 Ia-65, Ia-76, Ia-79, Ia-80, Ia-84, Ia-90, Ia-105, Ia-135, Ia-138, Ia-142, Ia-145, Ia-147, Ia-149, Ia-154, Ia-155, Ia-156, Ia-159.

In this text, for example, the following compounds from the preparation examples show an efficacy of 70% at an application rate of 100 g/ha: Ia-58, Ia-66.

*Phaedon cochleariae*—Spray Test

Solvent: 78.0 parts by weight of acetone 1.5 parts by weight of dimethylformamide Emulsifier: alkylaryl polyglycol ether To produce a suitable active ingredient formulation, 1 part by weight of active ingredient is dissolved with the specified parts by weight of solvent and made up to the desired concentration with water containing an emulsifier concentration of 1000 ppm. To produce further test concentrations, the formulation is diluted with emulsifier-containing water.

Discs of Chinese cabbage leaves (*Brassica pekinensis*) are sprayed with an active compound preparation of the desired concentration and, after drying, populated with larvae of the mustard beetle (*Phaedon cochleariae*).

After 7 days, the efficacy in % is determined. 100% means that all the beetle larvae have been killed; 0% means that no beetle larvae have been killed.

In this test, for example, the following compounds from the preparation examples show an efficacy of 100% at an application rate of 100 g/ha: Ia-01, Ia-02, Ia-04, Ia-05, Ia-06, Ia-07, Ia-08, Ia-09, Ia-10, Ia-11, Ia-12, Ia-13, Ia-15, Ia-16, Ia-18, Ia-19, Ia-20, Ia-21, Ia-22, Ia-23, Ia-24, Ia-26, Ia-27, Ia-28, Ia-29, Ia-32, Ia-34, Ia-37, Ia-38, Ia-39, Ia-40, Ia-41, Ia-42, Ia-43, Ia-44, Ia-45, Ia-47, Ia-49, Ia-51, Ia-52, Ia-53, Ia-54, Ia-55, Ia-56, Ia-57, Ia-58, Ia-59, Ia-60, Ia-62, Ia-63, Ia-64, Ia-65, Ia-66, Ia-67, Ia-68, Ia-69, Ia-70, Ia-71, Ia-72, Ia-73, Ia-73, Ia-74, Ia-75, Ia-76, Ia-77, Ia-78, Ia-82, Ia-83, Ia-84, Ia-85, Ia-86, Ia-87, Ia-88, Ia-89, Ia-90, Ia-91, Ia-92, Ia-93, Ia-94, Ia-95, Ia-97, Ia-98, Ia-99, Ia-100, Ia-101, Ia-102, Ia-103, Ia-104, Ia-105, Ia-106, Ia-107, Ia-108, Ia-109, Ia-110, Ia-111, Ia-112, Ia-113, Ia-114, Ia-115, Ia-116, Ia-117, Ia-119, Ia-120, Ia-123, Ia-124, Ia-128, Ia-130, Ia-131, Ia-132, Ia-133, Ia-134, Ia-135, Ia-136, Ia-137, Ia-138, Ia-139, Ia-141, Ia-142, Ia-143, Ia-144, Ia-145, Ia-146, Ia-147, Ia-148, Ia-149, Ia-150, Ia-151, Ia-152, Ia-153, Ia-154, Ia-155, Ia-156, Ia-157, Ia-158, Ia-159, Ia-160, Ia-162, Ia-163, Ia-164, Ia-165, Ia-166, Ia-167, Ic-01, Ic-02, Ic-04, Ic-05, Ic-03, I-T2-01, I-T2-03, I-T2-04, I-T7-01, I-T7-02, I-T7-03.

In this text, for example, the following compounds from the preparation examples show an efficacy of 83% at an application rate of 100 g/ha: Ia-80.

*Spodoptera frugiperda*—Spray Test

Solvent: 78.0 parts by weight of acetone 1.5 parts by weight of dimethylformamide Emulsifier: alkylaryl polyglycol ether To produce a suitable active ingredient formulation, 1 part by weight of active ingredient is dissolved with the specified parts by weight of solvent and made up to the desired concentration with water containing an emulsifier concentration of 1000 ppm. To produce further test concentrations, the formulation is diluted with emulsifier-containing water.

Leaf discs of maize (*Zea mays*) are sprayed with an active ingredient formulation of the desired concentration and, after drying, populated with caterpillars of the armyworm (*Spodoptera frugiperda*).

After 7 days, the efficacy in % is determined. 100% means that all the caterpillars have been killed; 0% means that no caterpillar has been killed.

In this test, for example, the following compounds from the preparation examples show an efficacy of 100% at an application rate of 100 g/ha: Ia-01, Ia-02, Ia-04, Ia-05, Ia-06, Ia-08, Ia-09, Ia-10, Ia-13, Ia-15, Ia-16, Ia-18, Ia-19, Ia-20, Ia-21, Ia-23, Ia-24, Ia-25, Ia-26, Ia-27, Ia-28, Ia-29, Ia-30, Ia-32, Ia-34, Ia-35, Ia-38, Ia-39, Ia-40, Ia-49, Ia-50, Ia-51, Ia-52, Ia-53, Ia-54, Ia-55, Ia-56, Ia-57, Ia-58, Ia-59, Ia-60, Ia-61, Ia-63, Ia-64, Ia-65, Ia-66, Ia-67, Ia-69, Ia-71, Ia-72, Ia-73, Ia-74, Ia-75, Ia-76, Ia-77, Ia-79, Ia-80, Ia-81, Ia-82, Ia-83, Ia-84, Ia-85, Ia-86, Ia-87, Ia-89, Ia-90, Ia-91, Ia-92, Ia-93, Ia-94, Ia-95, Ia-96, Ia-99, Ia-100, Ia-101, Ia-103, Ia-104, Ia-105, Ia-106, Ia-107, Ia-108, Ia-109, Ia-110, Ia-111, Ia-112, Ia-113, Ia-114, Ia-115, Ia-116, Ia-117, Ia-119, Ia-120, Ia-128, Ia-130, Ia-131, Ia-132, Ia-133, Ia-134, Ia-135, Ia-136, Ia-137, Ia-138, Ia-139, Ia-141, Ia-142, Ia-143, Ia-144, Ia-145, Ia-146, Ia-147, Ia-148, Ia-149, Ia-150, Ia-151, Ia-152, Ia-154, Ia-155, Ia-156, Ia-157, Ia-158, Ia-159, Ia-160, Ia-162, Ia-164, Ia-165, Ia-166, Ia-167, Ic-01, Ic-02, Ic-04, Ic-05, Ic-03, I-Tc-01, I-Tc-02, I-Tc-03, I-T7-01, I-T7-02, I-T7-03.

In this test, for example, the following compounds from the preparation examples show an efficacy of 83% at an application rate of 100 g/ha: Ia-07, Ia-12, Ia-37, Ia-47, Ia-68, Ia-88, Ia-123, Ia-163, I-T2-04.

In this text, for example, the following compounds from the preparation examples show an efficacy of 83% at an application rate of 20 g/ha: Ia-43.

*Tetranychus urticae*—Spray Test, OP-Resistant
Solvent: 78.0 parts by weight of acetone
1.5 parts by weight of dimethylformamide
Emulsifier: alkylaryl polyglycol ether To produce a suitable active ingredient formulation, 1 part by weight of active ingredient is dissolved with the specified parts by weight of solvent and made up to the desired concentration with water containing an emulsifier concentration of 1000 ppm. To produce further test concentrations, the formulation is diluted with emulsifier-containing water.

Discs of bean leaves (*Phaseolus vulgaris*) infested with all stages of the greenhouse red spider mite (*Tetranychus urticae*) are sprayed with an active compound preparation of the desired concentration.

After 6 days, the efficacy in % is determined. 100% means that all the spider mites have been killed; 0% means that no spider mites have been killed.

In this test, for example, the following compounds from the preparation examples show an efficacy of 100% at an application rate of 100 g/ha: Ia-01, Ia-02, Ia-04, Ia-07, Ia-10, Ia-11, Ia-12, Ia-13, Ia-15, Ia-20, Ia-23, Ia-27, Ia-28, Ia-32, Ia-34, Ia-37, Ia-39, Ia-42, Ia-44, Ia-58, Ia-59, Ia-60, Ia-63, Ia-64, Ia-65, Ia-66, Ia-67, Ia-68, Ia-71, Ia-72, Ia-73, Ia-74, Ia-75, Ia-76, Ia-79, Ia-80, Ia-81, Ia-82, Ia-84, Ia-85, Ia-87, Ia-88, Ia-90, Ia-91, Ia-92, Ia-93, Ia-95, Ia-96, Ia-99, Ia-100, Ia-104, Ia-105, Ia-106, Ia-107, Ia-109, Ia-111, Ia-115, Ia-116, Ia-119, Ia-120, Ia-134, Ia-135, Ia-136, Ia-137, Ia-141, Ia-142, Ia-145, Ia-147, Ia-149, Ia-154, Ia-156, Ia-158, Ia-160, Ia-162, Ia-163, Ia-164, Ia-166, Ia-167, Ic-01, Ic-04, I-Tc-03.

In this test, for example, the following compounds from the preparation examples show an efficacy of 90% at an application rate of 100 g/ha: Ia-08, Ia-09, Ia-19, Ia-22, Ia-26, Ia-43, Ia-73, Ia-83, Ia-89, Ia-98, Ia-102, Ia-108, Ia-112, Ia-113, Ia-130, Ia-138, Ia-139, Ia-144, Ia-150, Ia-157, Ia-165, I-T7-01.

In this test, for example, the following compounds from the preparation examples show an efficacy of 70% at an application rate of 100 g/ha: Ia-46, Ia-61.

*Myzus persicae*—Spray Test
Solvent: 14 parts by weight of dimethylformamide
Emulsifier: alkylaryl polyglycol ether To produce a suitable active compound formulation, 1 part by weight of the active compound is dissolved in the specified parts by weight of solvent and made up with water, comprising an emulsifier concentration of 1000 ppm, until the desired concentration is reached. To produce further test concentrations, the latter is diluted with emulsifier-containing water. When addition of ammonium salts and/or penetrants is required, these are each added at a concentration of 1000 ppm to the preparation solution.

Bell pepper plants (*Capsicum annuum*), which are heavily infested by the green peach aphid (*Myzus persicae*), are treated by being sprayed with the active compound preparation at the desired concentration.

After 6 days, the kill in % is determined. 100% means that all aphids have been killed; 0% means that no aphids have been killed.

In this test, for example, the following compounds from the preparation examples show an efficacy of 85% at an application rate of 4 ppm: Ia-95.

*Tetranychus Urticae*—Spray Test; OP-Resistant
Solvent: 14 parts by weight of dimethylformamide
Emulsifier: alkylaryl polyglycol ether To produce a suitable active compound formulation, 1 part by weight of the active compound is dissolved in the specified parts by weight of solvent and made up with water, comprising an emulsifier concentration of 1000 ppm, until the desired concentration is reached. To produce further test concentrations, the latter is diluted with emulsifier-containing water. When addition of ammonium salts and/or penetrants is required, these are each added at a concentration of 1000 ppm to the preparation solution.

Bean plants (*Phaseolus vulgaris*), which are heavily infested by all stages of the greenhouse red spider mite (*Tetranychus urticae*), are treated by being sprayed with the active compound preparation at the desired concentration.

After 7 days, the efficacy in % is determined. 100% means that all spider mites have been killed; 0% means that no spider mites have been killed.

In this test, for example, the following compounds from the preparation compounds show an efficacy of 100% at an application rate of 4 ppm: I-T2-04

In this test, for example, the following compounds from the preparation examples show an efficacy of 99% at an application rate of 4 ppm: Ia-51, Ia-53, Ia-55, Ia-57.

*Anopheles* Test (ANPHGB Surface Treatment)
Solvent: acetone+2000 ppm rapeseed oil methyl ester (RME)

To produce a suitable active compound formulation, the active compound is dissolved in the solvent (2 mg/ml). The active compound formulation is pipetted onto a glazed tile and, after it has dried off, adult mosquitoes of the species *Anopheles gambiae* strain RSPH (homozygot kdr) are placed onto the treated tile. The exposure time is 30 minutes.

24 hours after contact with the treated surface, mortality in % is determined. 100% means that all mosquitoes have been killed; 0% means that none of the mosquitoes have been killed.

In this test, for example, the following compounds from the preparation examples show efficacy of 90-100% at an application rate of 100 mg/m²: Ia-05, Ia-06, Ia-20, Ia-24, Ia-27, Ia-32, Ia-38, Ia-40, Ia-91, Ia-108, Ia-112, Ia-113, Ia-116, Ia-163.

In this test, for example, the following compounds from the preparation examples show efficacy of 90-100% at an application rate of 20 mg/m²: Ia-05, Ia-06, Ia-15, Ia-19, Ia-20, Ia-24, Ia-38, Ia-40, Ia-63, Ia-64, Ia-71, Ia-73, Ia-74, Ia-85, Ia-91, Ia-99, Ia-100, Ia-106, Ia-109, Ia-111, Ia-112, Ia-113, Ia-115, Ia-116, Ia-117, Ia-119, Ia-162, Ia-163.

*Anopheles* Test (ANPHFU Surface Treatment)
Solvent: acetone+2000 ppm rapeseed oil methyl ester (RME)

To produce a suitable active compound formulation, the active compound is dissolved in the solvent (2 mg/ml). The active compound formulation is pipetted onto a glazed tile and, after it has dried off, adult mosquitoes of the species *Anopheles funestus* strain FUMOZ-R (Hunt et al., Med Vet Entomol. 2005 September; 19 (3):271-5) are placed onto the treated tile. The exposure time is 30 minutes.

24 hours after contact with the treated surface, mortality in % is determined. 100% means that all mosquitoes have been killed; 0% means that none of the mosquitoes have been killed.

In this test, for example, the following compounds from the preparation examples show efficacy of 90-100% at an application rate of 100 mg/m²: Ia-05, Ia-06, Ia-15, Ia-20, Ia-24, Ia-27, Ia-32, Ia-40, Ia-91, Ia-112, Ia-113, Ia-116, Ia-163

In this test, for example, the following compounds from the preparation examples show efficacy of 90-100% at an application rate of 20 mg/m²: Ia-05, Ia-06, Ia-15, Ia-20, Ia-24, Ia-27, Ia-32, Ia-40, Ia-53, Ia-55, Ia-63, Ia-64, Ia-73, Ia-84, Ia-85, Ia-99, Ia-100, Ia-106, Ia-109, Ia-110, Ia-112, Ia-113, Ia-115, Ia-116, Ia-117, Ia-130, Ia-136, Ia-162, Ia-163.

*Aedes* Test (AEDSAE Surface Treatment)
Solvent: acetone+2000 ppm rapeseed oil methyl ester (RME)

To produce a suitable active compound formulation, the active compound is dissolved in the solvent (2 mg/ml). The active compound formulation is pipetted onto a glazed tile and, after it has dried off, adult mosquitoes of the species *Aedes aegypti* strain MONHEIM are placed onto the treated tile. The exposure time is 30 minutes.

24 hours after contact with the treated surface, mortality in % is determined. 100% means that all mosquitoes have been killed; 0% means that none of the mosquitoes have been killed.

In this test, for example, the following compounds from the preparation examples show efficacy of 90-100% at an application rate of 100 mg/m²: Ia-05, Ia-06, Ia-08, Ia-09, Ia-15, Ia-19, Ia-20, Ia-22, Ia-24, Ia-26, Ia-27, Ia-30, Ia-32, Ia-38, Ia-40, Ia-42, Ia-47, Ia-91, Ia-108, Ia-112, Ia-113, Ia-116, Ia-163

In this test, for example, the following compounds from the preparation examples show efficacy of 90-100% at an application rate of 20 mg/m²: Ia-05, Ia-06, Ia-15, Ia-19, Ia-20, Ia-22, Ia-24, Ia-26, Ia-27, Ia-30, Ia-31, Ia-32, Ia-40, Ia-42, Ia-53, Ia-55, Ia-57, Ia-63, Ia-64, Ia-71, Ia-74, Ia-73, Ia-79, Ia-84, Ia-85, Ia-91, Ia-99, Ia-100, Ia-104, Ia-106, Ia-108, Ia-109, Ia-110, Ia-111, Ia-112, Ia-113, Ia-115, Ia-116, Ia-117, Ia-119, Ia-120, Ia-129, Ia-130, Ia-136, Ia-162, Ia-163.

Biological Examples of Herbicidal Activity

Herbicidal Activity and Plant Tolerance in Pre-Emergent Crops

Seeds of monocotyledonous and dicotyledonous weed plants and crop plants were placed in wood-fibre pots in sandy loam and covered with soil. The compounds according to the invention, formulated as emulsion concentrates (EC), were then applied to the surface of the covering soil as an emulsion at a water application rate equating to 600 to 800 l/ha with addition of 0.2% wetting agent.

After the treatment, the pots were placed in a greenhouse and kept under good growth conditions for the test plants. The damage to the test plants was scored visually after a test period of 3 weeks by comparison with untreated controls (herbicidal activity in percent (%): 100% activity=the plants have died, 0% activity=like control plants). Here, for example, compounds No. Ia-17, Ia-37, Ia-28 and Ia-56 at an application rate of 1280 g/ha each show 100% efficacy against *Amaranthus retroflexus* (AMARE) and with the exception of Ia-56, even against Viola tricolor (VIOTR). Furthermore, compounds no. Ia-17, Ia-37 and Ia-28 at the same application rate show an 80% or better efficacy against *Matricaria inodorae* (MATIN) and Ia-17 and Ia-37 even against *Stellaria media* (STEME).

Herbicidal Activity and Planet Tolerance in Post-Emergent Crops

Seeds of monocotyledonous and dicotyledonous weeds and crop plants were placed in sandy loam in wood-fibre pots, covered with soil and cultivated in a greenhouse under good growth conditions. 2 to 3 weeks after sowing, the test plants are treated at the one-leaf stage. The compounds according to the invention, formulated as emulsion concentrates (EC), were then sprayed onto the green plant parts as an emulsion at a water application rate equating to 600 to 800 l/ha with addition of 0.2% wetting agent. After the test plants have been left to stand in the greenhouse under optimal growth conditions for 3 weeks, the efficacy of the preparations was assessed visually in comparison to untreated controls (herbicidal efficacy in percent (%): 100% activity=the plants have died, 0% activity=like control plants). For example, compounds No. Ia-17, Ia-28 and Ia-37 at an application rate of 1280 g/ha each show at least 100% efficacy against *Amaranthus retroflexus* (AMARE) and Viola tricolor (VOTR). Ia-17 at this application rate additionally shows an 80% or better efficacy against *Abutilon theophrasti* (ABUTH), *Matricaria inodora* (MATIN) and *Stellaria meida* (STEME).

What is claimed is:
1. Compound of formula (I')

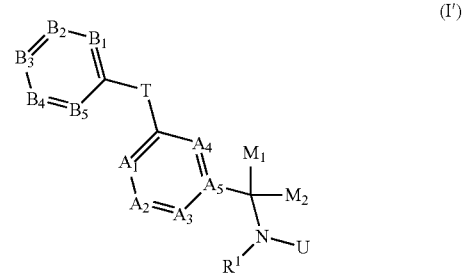

in which

U is —C(=W)-Q or —S(O)$_2$-Q,

R$^1$ is H, in each case optionally substituted C$_1$-C$_6$-alkyl, C$_2$-C$_6$-alkenyl, C$_2$-C$_6$-alkynyl, C$_3$-C$_7$-cycloalkyl, C$_1$-C$_6$-alkylcarbonyl, C$_1$-C$_6$-alkoxycarbonyl, aryl(C$_1$-C$_3$)-alkyl, heteroaryl(C$_1$-C$_3$)-alkyl, or R$^1$ is H, in each case optionally substituted C$_1$-C$_6$-alkyl, C$_2$-C$_6$-alkenyl, C$_2$-C$_6$-alkynyl, C$_3$-C$_7$-cycloalkyl, C$_1$-C$_6$-alkylcarbonyl, C$_1$-C$_6$-alkoxycarbonyl, C$_3$-C$_7$-cycloalkyl(C$_1$-C$_3$)-alkyl, aryl(C$_1$-C$_3$)-alkyl, heteroaryl (C$_1$-C$_3$)-alkyl, the moieties are as follows:

A$_1$ is CR$^2$ or N, $A_2$ is $CR^3$ or N,
$A_3$ is $CR^4$ or N,
$A_4$ is $CR^5$ or N,
$A_5$ is C,
$B_1$ is $CR^6$ or N,
$B_2$ is $CR^7$ or N,
$B_3$ is $CR^8$ or N,
$B_4$ is $CR^9$ or N, and
$B_5$ is $CR^{10}$ or N,
but not more than three of the $A_1$ to $A_4$ moieties are N and not more than three of the $B_1$ to $B_5$ moieties are simultaneously N;

$M_1$, $M_2$ are each independently H, in each case optionally substituted $C_1$-$C_6$-alkyl, $C_2$-$C_6$-alkenyl, $C_2$-$C_6$-alkynyl, $C_3$-$C_7$-cycloalkyl, $C_1$-$C_6$-alkylcarbonyl, $C_1$-$C_6$-alkoxycarbonyl, aryl($C_1$-$C_3$)-alkyl, heteroaryl($C_1$-$C_3$)-alkyl, or $M_1$ and $M_2$ with the carbon atom to which they are attached form an optionally substituted 3-, 4-, 5- or 6-membered ring which optionally contains 0, 1 or 2 nitrogen atoms and/or 0, 1 or 2 oxygen atoms and/or 0, 1 or 2 sulfur atoms, or $M_1$ or $M_2$ with $R^4$ from $A_3$, the carbon atom of $A_3$, and As and D form a 5- or 6-membered ring optionally substituted by F, Cl, Br, I, $C_1$-$C_3$-alkyl, which may contain 0, 1 or 2 nitrogen atoms and/or 0, 1 or 2 oxygen atoms and/or 0, 1 or 2 sulfur atoms, $R^2$, $R^3$, $R^4$, $R^5$, $R^6$, $R^7$, $R^9$ and $R^{10}$ are each independently H, halogen, cyano, nitro, in each case optionally substituted $C_1$-$C_6$-alkyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulfanyl, $C_1$-$C_6$-alkylsulfinyl, $C_1$-$C_6$-alkylsulfonyl, N—$C_1$-$C_6$-alkylamino or N,N-di-$C_1$-$C_6$-alkylamino, if neither of the $A_2$ and $A_3$ moieties is N, $R^3$ and $R^4$ together with the carbon atom to which they are attached may form a 5- or 6-membered ring containing 0, 1 or 2 nitrogen atoms and/or 0 or 1 oxygen atom and/or 0 or 1 sulfur atom, or if neither of the $A_1$ and $A_2$ moieties is N, $R^2$ and $R^3$ together with the carbon atom to which they are attached may form a 6-membered ring containing 0, 1 or 2 nitrogen atoms;

$R^8$ is halogen, cyano, nitro, in each case optionally substituted $C_1$-$C_6$-alkyl, $C_3$-$C_6$-cycloalkyl, $C_1$-$C_6$-alkoxy, N—$C_1$-$C_6$-alkoxyimino-$C_1$-$C_3$-alkyl, $C_1$-$C_6$-alkylsulfanyl, $C_1$-$C_6$-alkylsulfinyl, $C_1$-$C_6$-alkylsulfonyl, N—$C_1$-$C_6$-alkylamino or N,N-di-$C_1$-$C_6$-alkylamino;

W is O or S,

Q is $C_1$-$C_6$-alkyl, $C_3$-$C_6$-cycloalkyl in each case optionally independently substituted by halogen, cyano; or 6-membered aromatic ring selected from phenyl or pyridyl optionally independently substituted by halogen, cyano;

T is one of the 5-membered heteroaromatic systems T2, T3, or T7 shown below, where the bond to the ring (C—B1-B2-B3-B4-B5) is indicated by an asterisk,

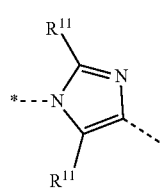

T2

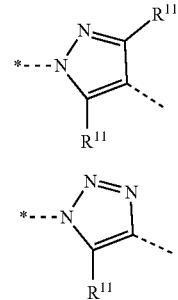

T3

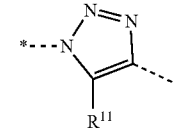

T7 where $R^{11}$ is independently H, optionally halogenated $C_1$-$C_6$-alkyl or halogen, and/or a salt, N-oxide and/or tautomeric form of a compound of the formula (I').

2. Compound according to claim 1, wherein in T is H.

3. Compound according to claim 1, wherein T is T3.

4. Compound according to claim 1, wherein $A_1$ is $CR^2$, $A_2$ is $CR^3$, $A_3$ is $CR^4$, $A_4$ is $CR^5$, As is C and $R^2$, $R^3$ and $R^5$ are in each case H.

5. Compound according to claim 1, wherein $B_1$ is $CR^6$, $B_2$ is $CR^7$, $B_3$ is $CR^8$, $B_4$ is $CR^9$ and $B_5$ is $CR^{10}$.

6. Compound according to claim 1, wherein $B_3$ is $CR^8$ and $R^8$ is halogenated $C_1$-$C_6$-alkyl and $B_2$ is $CR^7$ and $B_4$ is $CR^9$ and $R^7$ and $R^9$ are each H.

7. Compound according to claim 1, wherein $B_1$ is $CR^6$ and $B_5$ is $CR^{10}$ and $R^6$ and $R^{10}$ are each optionally independently halogen, $C_1$-$C_6$-alkyl or $C_1$-$C_6$-alkyl substituted by halogen, $C_1$-$C_6$-alkoxy or $C_1$-$C_6$-alkoxy substituted by halogen.

8. Compound according to claim 1, wherein $A_3$ is $CR^4$ and $R^4$ is H, halogen, or $R^4$ together with the carbon atom of $CR^4$, As and either C-$M_1$ or C-$M_2$ form a 5- or 6-membered ring optionally substituted by F, Cl, Br, I, $C_1$-$C_3$-alkyl, which may contain 0, 1 or 2 nitrogen atoms and/or 0, 1 or 2 oxygen atoms and/or 0, 1 or 2 sulfur atoms.

9. Compound according to claim 1, wherein $M_1$ and $M_2$ are each independently H or $C_1$-$C_6$-alkyl, or C-$M_1$ or C-$M_2$ together with $CR^4$ and As form a 5- or 6-membered ring optionally substituted by F, Cl, Br, I, $C_1$-$C_3$-alkyl, which may contain 0, 1 or 2 nitrogen atoms and/or 0, 1 or 2 oxygen atoms and/or 0, 1 or 2 sulfur atoms.

10. Compound according to claim 1, wherein $R^1$ is H and W is O.

11. Compound according to claim 1, wherein $R^4$ is H, F or Cl or $R^4$ together with the carbon atom of $CR^4$, $A_5$ and either C-$M_1$ or C-$M_2$ form a 5-membered ring optionally substituted by F, Cl, Br, I, $C_1$-$C_3$-alkyl, which may contain 0, 1 or 2 nitrogen atoms and/or 0, 1 or 2 oxygen atoms and/or 0, 1 or 2 sulfur atoms.

12. Compound according to claim 1, wherein $M_1$ and $M_2$ are each independently H or C-$M_1$ or C-$M_2$ together with $CR^4$ and As form a 5-membered ring optionally substituted by F, Cl, Br, I, $C_1$-$C_3$-alkyl, which may contain 0, 1 or 2 nitrogen atoms and/or 0, 1 or 2 oxygen atoms and/or 0, 1 or 2 sulfur atoms.

13. A composition comprising at least one compound according to claim 1 and an extender and/or a surface-active substance.

14. The composition of claim 13, further comprising a fungicide, bactericide, acaricide, molluscicide, nematicide, insecticide, microbiological agent, beneficial organism, herbicide, herbicide, fertilizer, bird repellant, phytotonics, sterilant, safener, semiochemcical, and/or plant growth regulator.

15. A method for protecting transgenic or conventional seed and the plant that arises therefrom from infestation by pests comprising treating seed with at least one compound according to claim 1.

16. A product method of controlling a pest comprising applying a compound according to claim 1 to the pest and/or its habitat.

17. The method according to claim 16, wherein the pest is an insect, arachnid, helminth, nematode, or mollusc.

18. Seed in which a compound according to claim 1 has been applied to the seed as a constituent of a coating or as a further layer or further layers in addition to a coating.

19. A method of controlling a parasite in an animal comprising administering the compound of claim 1 to the animal.

* * * * *